(12) United States Patent
Zegrati et al.

(10) Patent No.: US 11,965,216 B2
(45) Date of Patent: Apr. 23, 2024

(54) DETECTION OF ONE OR MORE PATHOGENS

(71) Applicant: POLYSKOPE LABS, Oklahoma City, OK (US)

(72) Inventors: Cyrus Cody Zegrati, Choctaw, OK (US); Michael Benjamin Centola, Oklahoma City, OK (US); Bobby Alfonso Gramling, Jr., Oklahoma City, OK (US); Paul Simon Smith, Oklahoma City, OK (US)

(73) Assignee: POLYSKOPE LABS, Oklahoma City, OK (US)

( * ) Notice: Subject to any disclaimer, the term of this patent is extended or adjusted under 35 U.S.C. 154(b) by 0 days.

(21) Appl. No.: 15/564,221

(22) PCT Filed: Apr. 6, 2016

(86) PCT No.: PCT/US2016/026140
§ 371 (c)(1),
(2) Date: Oct. 4, 2017

(87) PCT Pub. No.: WO2016/164407
PCT Pub. Date: Oct. 13, 2016

(65) Prior Publication Data
US 2018/0258467 A1  Sep. 13, 2018

Related U.S. Application Data

(60) Provisional application No. 62/239,105, filed on Oct. 8, 2015, provisional application No. 62/144,294, filed on Apr. 7, 2015.

(51) Int. Cl.
| | | |
|---|---|---|
| *C12Q 1/689* | (2018.01) | |
| *C12Q 1/6806* | (2018.01) | |
| *C12Q 1/686* | (2018.01) | |

(52) U.S. Cl.
CPC .......... *C12Q 1/689* (2013.01); *C12Q 1/6806* (2013.01); *C12Q 1/686* (2013.01); *C12Q 2600/16* (2013.01); *C12Q 2600/166* (2013.01)

(58) Field of Classification Search
CPC ...... C12Q 1/689; C12Q 1/6806; C12Q 1/686; C12Q 2600/16; C12Q 2600/166
See application file for complete search history.

(56) References Cited

U.S. PATENT DOCUMENTS

| | | |
|---|---|---|
| 3,687,808 A | 8/1972 | Merigan, Jr. et al. |
| 3,819,158 A | 6/1974 | Sharpe et al. |
| 3,996,345 A | 12/1976 | Ullman et al. |
| 4,351,760 A | 9/1982 | Khanna et al. |
| 4,469,863 A | 9/1984 | Ts'o et al. |
| 4,683,195 A | 7/1987 | Mullis et al. |
| 4,683,202 A | 7/1987 | Mullis |
| 4,851,330 A | 7/1989 | Kohne |
| 4,988,617 A | 1/1991 | Landegren et al. |
| 5,145,786 A | 9/1992 | Bailey et al. |
| 5,185,243 A | 2/1993 | Ullman et al. |
| 5,188,934 A | 2/1993 | Menchen et al. |
| 5,235,033 A | 8/1993 | Summerton et al. |
| 5,242,794 A | 9/1993 | Whiteley et al. |
| 5,494,810 A | 2/1996 | Barany et al. |
| 5,518,894 A | 5/1996 | Berg |
| 5,541,308 A * | 7/1996 | Hogan ................ C12Q 1/6811 536/23.1 |
| 5,573,907 A | 11/1996 | Carrino et al. |
| 5,596,086 A | 1/1997 | Matteucci et al. |
| 5,679,524 A | 10/1997 | Nikiforov et al. |
| 5,750,666 A | 5/1998 | Caruthers et al. |
| 5,846,710 A | 12/1998 | Bajaj |
| 5,888,819 A | 3/1999 | Goelet et al. |
| 6,273,600 B1 | 8/2001 | Sharpe |
| 6,483,303 B2 | 11/2002 | Simmonds et al. |
| 6,582,938 B1 | 6/2003 | Su et al. |
| 6,597,176 B2 | 7/2003 | Simmonds et al. |
| 6,607,922 B2 | 8/2003 | Laborde |
| 6,927,570 B2 | 8/2005 | Simmonds et al. |
| 7,323,139 B2 | 1/2008 | Laborde et al. |
| 7,531,163 B2 | 5/2009 | Samadpour |
| 7,547,526 B2 | 6/2009 | Ladisch et al. |

(Continued)

FOREIGN PATENT DOCUMENTS

| | | |
|---|---|---|
| CN | 101113473 A | 1/2008 |
| CN | 100453638 C | 1/2009 |

(Continued)

OTHER PUBLICATIONS

Garrido (Food Control, 2013, vol. 30, pp. 76-85).*
Omicello (Food Microbiology, 2009, vol. 26, p. 615-622).*
Mafu (J. Food Prot, 2009, vol. 72, No. 6, pp. 1310-1314).*
GenBank accession M24199 (available at ncbi.nlm.nih.gov, printer Jun. 15, 2019, p. 1-3).*
Buck et al (Biotechniques (1999) 27(3):528-536).*

(Continued)

*Primary Examiner* — Sarae L Bausch
(74) *Attorney, Agent, or Firm* — Wilson Sonsini Goodrich & Rosati

(57) ABSTRACT

Provided herein are media, methods, kits, primers and oligonucleotide probes for use in the molecular detection of pathogens. These may be used in combination for the rapid, high-throughput screening PCR-based techniques to simultaneously detect multiple pathogens. The multiplex-detection methods have improved sensitivity and specificity for the detection of multiple pathogens simultaneously. Real-time PCR assaying techniques using such primers include microarrays and multiplex arrays, the latter optionally simultaneously with oligonucleotide TaqMan probes.

17 Claims, 65 Drawing Sheets

Specification includes a Sequence Listing.

(56) References Cited

U.S. PATENT DOCUMENTS

| | | | |
|---|---|---|---|
| 7,943,346 | B2 | 5/2011 | Bergeron et al. |
| 8,206,923 | B2 | 6/2012 | Garza et al. |
| 8,298,758 | B2 | 10/2012 | Horikoshi et al. |
| 8,354,514 | B2 | 1/2013 | Slezak et al. |
| 8,883,488 | B2 | 11/2014 | Abdela et al. |
| 9,434,978 | B2 | 9/2016 | Favier et al. |
| 2003/0219770 | A1 | 11/2003 | Eshleman et al. |
| 2005/0239057 | A1 | 10/2005 | Maes et al. |
| 2006/0177824 | A1 | 8/2006 | Procop |
| 2006/0240442 | A1 | 10/2006 | Vevea |
| 2006/0286625 | A1 | 12/2006 | McIlroy et al. |
| 2007/0141572 | A1* | 6/2007 | Ubalijoro ............... C12Q 1/689 |
| | | | 435/6.13 |
| 2008/0014578 | A1 | 1/2008 | Horikoshi et al. |
| 2008/0107653 | A1 | 5/2008 | Vermeij |
| 2008/0182272 | A1 | 7/2008 | Nagar et al. |
| 2011/0236891 | A1 | 9/2011 | Li et al. |
| 2011/0256584 | A1 | 10/2011 | Matoulkova et al. |
| 2012/0282623 | A1 | 11/2012 | Murakami et al. |
| 2012/0295818 | A1 | 11/2012 | Murakami |
| 2013/0280787 | A1 | 10/2013 | Mueller et al. |
| 2014/0273185 | A1 | 9/2014 | Dineen et al. |
| 2015/0111283 | A1 | 4/2015 | Martinez et al. |

FOREIGN PATENT DOCUMENTS

| | | |
|---|---|---|
| CN | 101412978 A | 4/2009 |
| CN | 101113475 B | 10/2010 |
| CN | 102154497 B | 10/2012 |
| CN | 103160499 A | 6/2013 |
| CN | 103160577 A | 6/2013 |
| CN | 102618662 B | 11/2013 |
| CN | 103484546 A | 1/2014 |
| CN | 104195086 A | 12/2014 |
| CN | 104685047 A | 6/2015 |
| EP | 0320308 B1 | 11/1993 |
| EP | 0336731 B1 | 5/1994 |
| EP | 0439182 B1 | 4/1996 |
| EP | 2558596 A2 | 2/2013 |
| JP | 5502449 B2 | 5/2014 |
| JP | 2015039320 A | 3/2015 |
| WO | WO-8909835 A1 | 10/1989 |
| WO | WO-8912696 A1 | 12/1989 |
| WO | WO-9001069 A1 | 2/1990 |
| WO | WO-9107503 A1 | 5/1991 |
| WO | WO-9513396 A2 | 5/1995 |
| WO | WO-9731256 A2 | 8/1997 |
| WO | WO-03075837 A2 | 9/2003 |
| WO | WO-2004094636 A1 | 11/2004 |
| WO | WO-2009052137 A1 | 4/2009 |
| WO | WO-2009140198 A2 | 11/2009 |
| WO | WO-2010046930 A1 | 4/2010 |
| WO | WO-2011090802 A1 | 7/2011 |
| WO | WO-2011090803 A1 | 7/2011 |
| WO | WO-2011133433 A2 | 10/2011 |
| WO | WO-2011144304 A1 | 11/2011 |
| WO | WO-2012114312 A2 | 8/2012 |
| WO | WO-2013006960 A1 | 1/2013 |
| WO | WO-2013006969 A1 | 1/2013 |
| WO | WO-2013102080 A1 | 7/2013 |
| WO | WO-2013149003 A1 | 10/2013 |
| WO | WO-2014001648 A1 | 1/2014 |
| WO | WO-2014018195 A1 | 1/2014 |
| WO | WO-2016054282 A1 | 4/2016 |
| WO | WO-2016112179 A1 | 7/2016 |
| WO | WO-2016164407 A2 | 10/2016 |

OTHER PUBLICATIONS

Germini (Food Control, 2009, vol. 20, pp. 733-738).*
TSP culture media (CM0129, ThermoFisher, pp. 1-3, printerd Jun. 15, 2019).*
Bhagwat (Int JK Food Microbiology, 2003, 217-224).*
Khan (J Clinical Microbiology, 2004, p. 453-457).*
Kobayashi et al. (Food Sci Technol. Res, 15(4):427-438, 2009).*
Wang (J. Applied Microbiology, 1997, vol. 83:727-736).*
Kawasaki (Foodborne Pathogens and Disease, vol. 7, No. 2010).*
Kim (J Food Protection, 2007, vol. 70, pp. 1656-1662).*
Hyrup et al. Peptide nucleic acids (PNA): synthesis, properties and potential applications. Bioorg Med Chem. Jan. 1996;4(1):5-23.
Jiang et al. Evaluation of Universal Preenrichment Broth for the Recovery of Foodborne Pathogens from Milk and Cheese. Journal of Daily Science. Nov. 1998. vol. 81, Issue 11, pp. 2798-2803.
Pava-Ripoll et al. Detection of foodborne bacterial pathogens from individual filth flies. J Vis Exp. Feb. 13, 2015;(96):e52372.
Sharpe et al. Stomaching: a New Concept in Bacteriological Sample Preparation. Appl Microbiol. Aug. 1972; 24(2): 175-178.
Summerton et al. Morpholino antisense oligomers: design, preparation, and properties. Antisense Nucleic Acid Drug Dev. Jun. 1997;7(3):187-95.
Suo et al. Evaluation of a multiplex selective enrichment broth SEL for simultaneous detection of injured *Salmonella, Escherichia coli* O157:H7 and Listeria monocytogenes. Braz J Microbiol. 2013; 44(3): 737-742.
Hassan, J et al., *Escherichia coil* strain BAUMH1 shiga toxin 1 subunit (stx1) gene, partial cds. NCBI PDB Accession No. KM596779, *Escherichia coil* strain BAU-MH1 shiga toxin 1 subunit (stx1) gene , partial cds., Submitted Sep. 22, 2014, downloaded from the internet https://www.ncbi.nlm.nih.gov/nuccore/850481338 on Oct. 19, 2016, p. 1.
International Search Report dated Nov. 22, 2016 for International Application Serial No. PCT/US2016/026140, (9 pages).
Ogura, Yoshitoshi et al. "Comparative genomics reveal the mechanism of the parallel evolution of O157 and non-O157 enterohemorrhagic *Escherichia coli*." Proceedings of the National Academy of Sciences of the United States of America vol. 106,42 (2009): 17939-44. doi:10.1073/pnas.0903585106.
Ooka T, Seto K, Kawano K, et al. Clinical Significance of *Escherichia albertii*. Emerging Infectious Diseases. 2012;18(3):488-492. doi:10. 3201/eid1803.111401.
Poorafshar, M et al., Ornithorhynchus anatinus coagulation factor X (F10), mRNA, NCBI PDB Accession No. NM_001127614 XM_001515062, Ornithorhynchus anatinus coagulation factor X (F10), mRNA, Submitted Nov. 2000, downloaded from internet, https://www.ncbi.nlm.gov/nuccore/189027043 on Oct. 19, 2016, pp. 1-2.
Post, De, Food Borne Pathogens Monograph 5 *Escherichia coli Shigella* Species, Oxoid Settling Standards, Mar. 1998, pp. 33, 44, 45, 55.
Reischl, U et al. "Rapid identification of methicillin-resistant *Staphylococcus aureus* and simultaneous species confirmation using real-time fluorescence PCR." Journal of clinical microbiology vol. 38,6 (2000): 2429-33.
Van Tongeren, S P et al. "Comparison of three rapid and easy bacterial DNA extraction methods for use with quantitative real-time PCR." European journal of clinical microbiology & infectious diseases : official publication of the European Society of Clinical Microbiology vol. 30,9 (2011): 1053-61. doi:10.1007/s10096-011-1191-4.
Yan, Xianghe et al. "Genome sequencing and comparative genomics provides insights on the evolutionary dynamics and pathogenic potential of different H-serotypes of Shiga toxin-producing *Escherichia coli* O104." BMC microbiology vol. 15 83. Apr. 3, 2015, doi:10. 1186/s12866-015-0413-9.
Yuan, Sanqing et al., "Evaluation of Methods for the Extraction and Purification of DNA from the Human Microbiome", PLoS One, Mar. 23, 2012, vol. 7, No. 3, pp. 1-10, https://doi.org/10.1371/journal.pone.0033865.
Bousquet A et al: "Partition locus-based classification of selected plasmids in Klebsiella pneumoniae, *Escherichia coli* and *Salmonella enterica* spp.: An additional tool", Journal Ofmicrobiological Methods, vol. 110, Jan. 24, 2015 (Jan. 24, 2015), pp. 85-91, XP029165001,ISSN: 0167-7012, DOI: 10.1016/J.MIMET.2015.01. 019.
Communication pursuant to Rule 94(3) EPC in Application No. 16 777 164.1 dated May 12, 2020, 6 pages.

(56) References Cited

OTHER PUBLICATIONS

6th Edition of the Molecular Probes Handbook by Richard P. Haugland. 1996.
Berlman, Handbook of Fluorescence Spectra of Aromatic Molecules, 2nd Edition, Academic Press, New York, (1971).
Bhagwat, AA.: Simultaneous detection of *Escherichia coli* O157:H7, Listeria monocytogenes and *Salmonella* strains by real-time PCR. Int. J. Food Microbiol. Jul. 25, 2003;84(2):217-24 (Abstract).
European Application No. 16777164.1 Annex to the communication dated Sep. 3, 2019.
Extended European Search Report for EP Patent Application No. 16777164.1 dated Aug. 21, 2018.
Extended European Search Report for EP Patent Application No. 20772881.7 dated Oct. 31, 2022.
Glynn et al.: Current and emerging molecular diagnostic technologies applicable to bacterial food safety. International Journal of Dairy Technology 59.2 (2006): 126-139. (Abstract).
International Search Report dated May 27, 2020 for International Application Serial No. PCT/US2020/022831.
Japanese Office Action for JP Application No. 2022-502796 dated Nov. 11, 2022 (in Japanese with English translation).
Marshall, Histochemical J. 7: 299-303 (1975).
Pastinen et al. Minisequencing: a specific tool for DNA analysis and diagnostics on oligonucleotide arrays. Genome Res. 7:606-614 (1997).
PCR Essential Data, J. W. Wiley & sons, Ed. C. R. Newton, 1995.
Pesce et al., editors, Fluorescence Spectroscopy, Marcel Dekker, New York, (1971).
Poorafshar et al.: Identification and structural analysis of four serine proteases in a monotreme, the platypus, Ornithorhynchus anatinus. Immunogenetics. Nov. 2000;52(1-2): 19-28 (abstract).
Quigley L. et al. "A comparison of methods used to extract bacterial DNA from raw milk and raw milk cheese." J Appl Microbiol. Jul. 2012; 113(1):96-105.
Salazar JK et al. "Polymerase chain reaction-based serotyping of pathogenic bacteria in food." J Microbiol Methods. Mar. 2015;110:18-26. Epub Jan. 14, 2015.
Syvanen et al. A primer-guided nucleotide incorporation assay in the genotyping of apolipoprotein E. Genomics 8.4 (1990): 684-692.
U.S. Appl. No. 60/073,011, filed Jan. 29, 1998.
U.S. Appl. No. 60/078,102, filed Mar. 16, 1998.
White et al., Fluorescence Analysis: A Practical Approach, Marcel Dekker, New York, (1970).

* cited by examiner

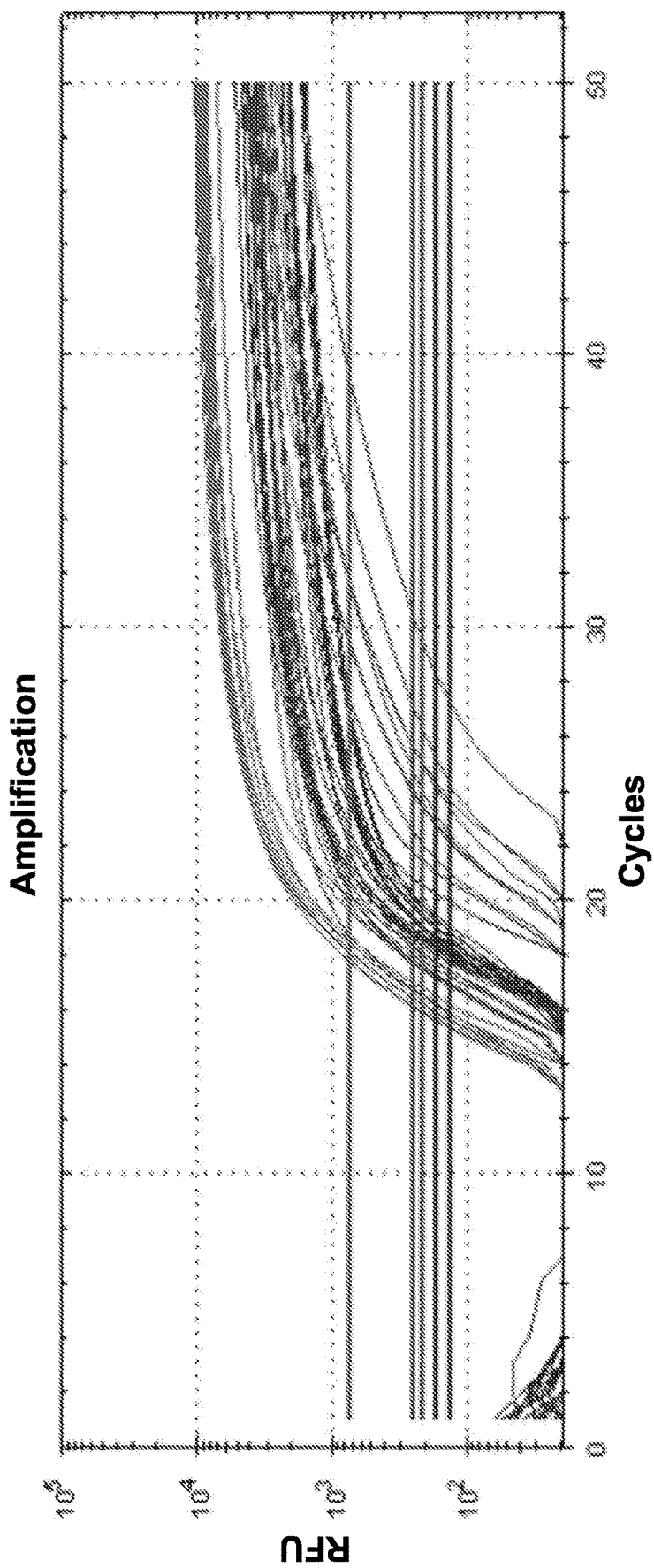
Figure 1. 1CFU/25g – Deli Turkey - All Targets

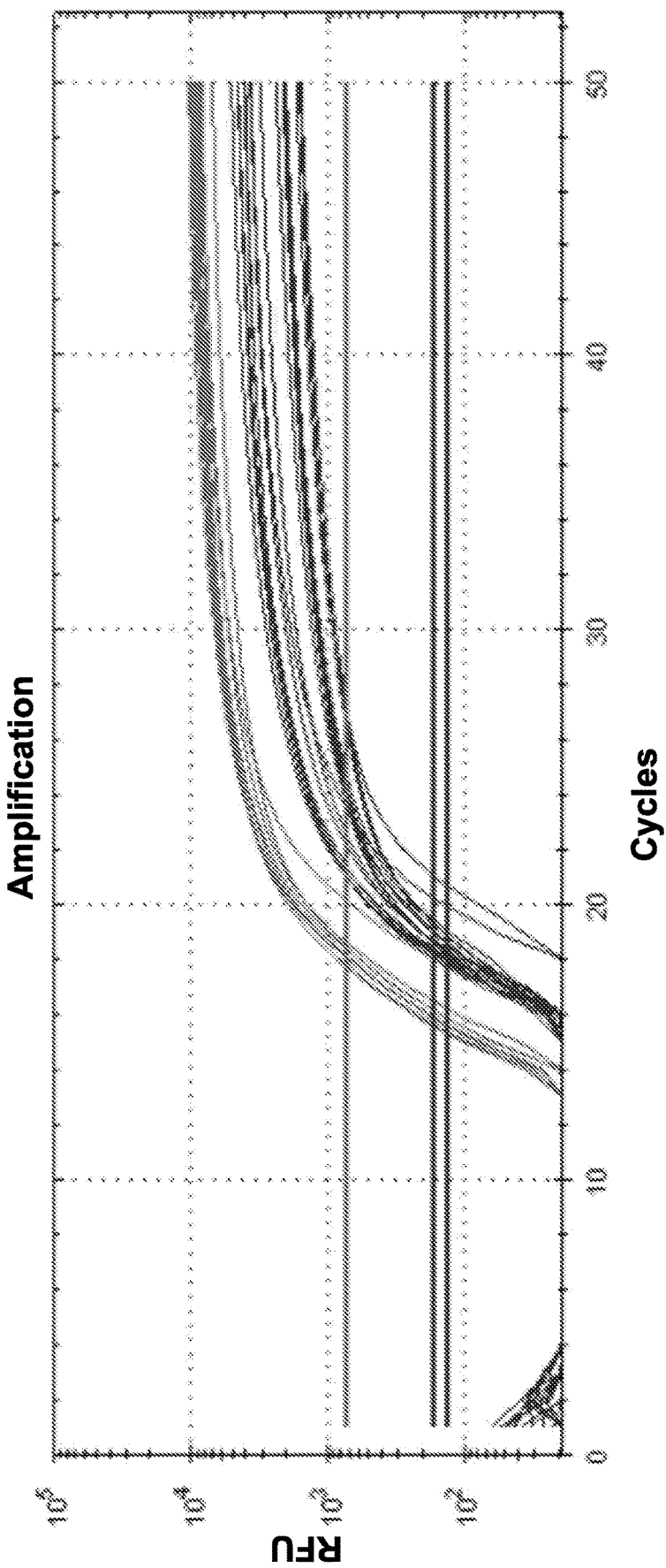
Figure 2. 1CFU/25g – Deli Turkey – STEC Targets

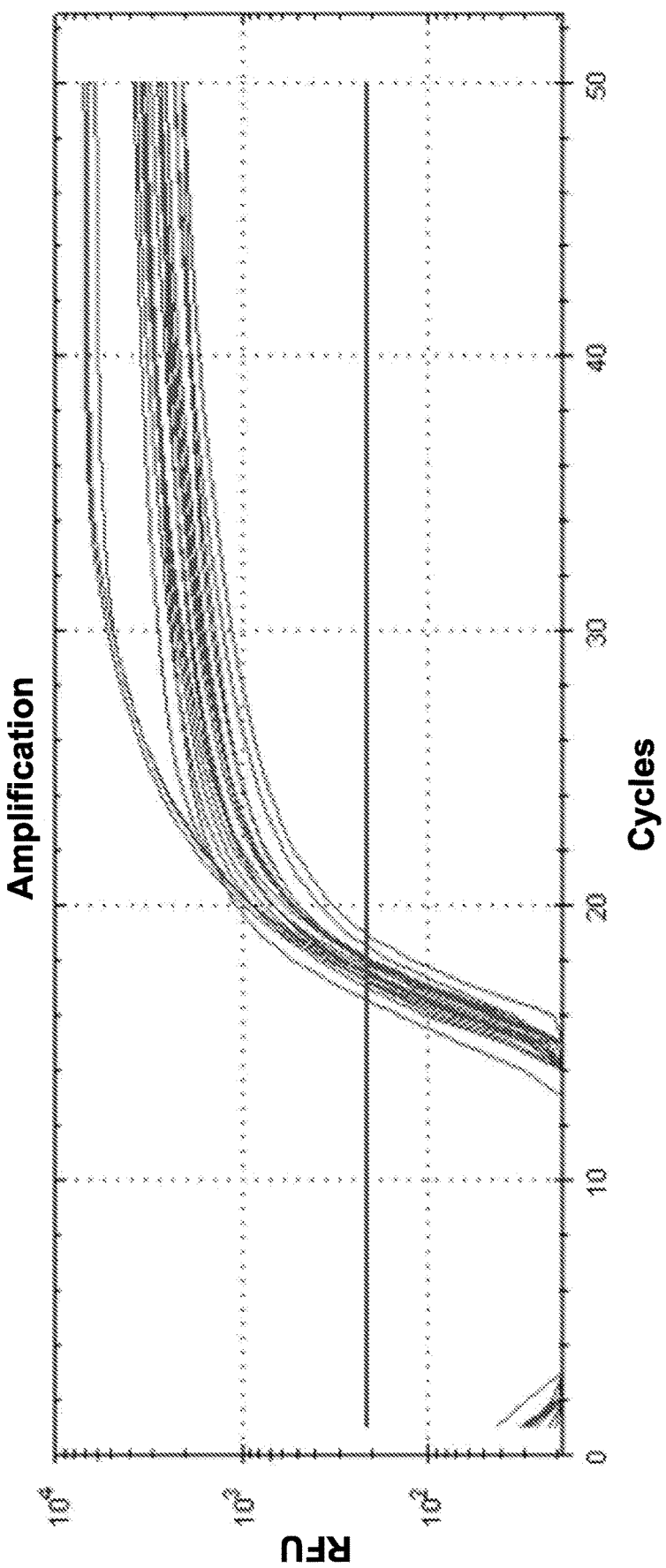
Figure 3. 1CFU/25g – Deli Turkey - *Salmonella* Target

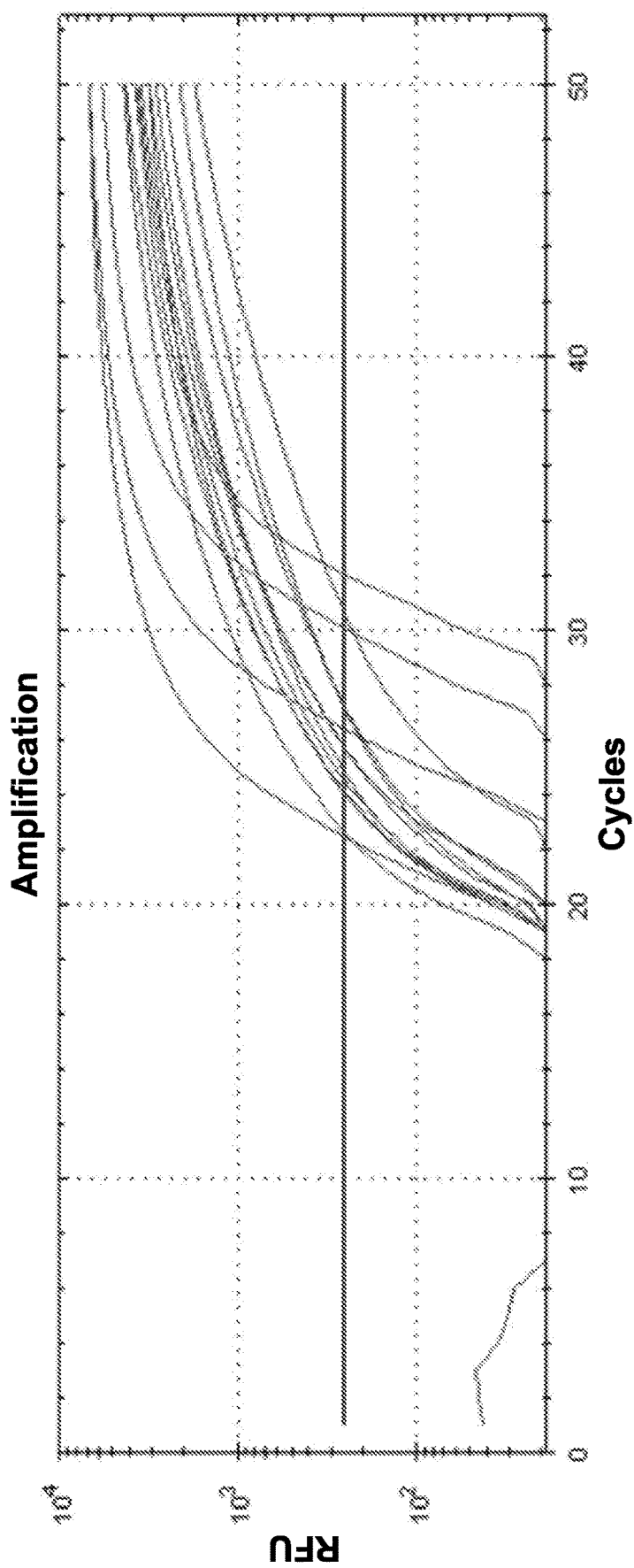
Figure 4. 1CFU/25g – Deli Turkey - *L. monocytogenes* Target

Figure 5. 1CFU/25g – Deli Turkey - Table of Results

| Replicate | EAE "+/-" | EAE Cq | EAE RFU* | STX-1 "+/-" | STX-1 Cq | STX-1 RFU* | STX-2 "+/-" | STX-2 Cq | STX-2 RFU* | Salmonella spp. "+/-" | Salmonella spp. Cq | Salmonella spp. RFU* | L. monocytogenes "+/-" | L. monocytogenes Cq | L. monocytogenes RFU* |
|---|---|---|---|---|---|---|---|---|---|---|---|---|---|---|---|
| 1 | - | N/A | N/A | - | N/A | N/A | - | N/A | N/A | - | N/A | N/A | + | 22 | >10^3 |
| 2 | + | 18 | >10^3 | + | 18 | >10^3 | + | 17 | >10^3 | + | 18 | >10^3 | - | N/A | N/A |
| 3 | + | 20 | >10^3 | + | 20 | >10^3 | + | 20 | >10^3 | + | 17 | >10^3 | + | 25 | >10^3 |
| 4 | + | 18 | >10^3 | + | 18 | >10^3 | + | 17 | >10^3 | + | 18 | >10^3 | - | N/A | N/A |
| 5 | + | 18 | >10^3 | + | 18 | >10^3 | + | 18 | >10^3 | + | 17 | >10^3 | + | 27 | >10^3 |
| 6 | + | 18 | >10^3 | + | 18 | >10^3 | + | 17 | >10^3 | + | 18 | >10^3 | + | 22 | >10^3 |
| 7 | + | 18 | >10^3 | + | 18 | >10^3 | + | 17 | >10^3 | + | 17 | >10^3 | - | N/A | N/A |
| 8 | + | 18 | >10^3 | + | 18 | >10^3 | + | 18 | >10^3 | + | 17 | >10^3 | - | N/A | N/A |
| 9 | + | 19 | >10^3 | + | 18 | >10^3 | + | 18 | >10^3 | + | 16 | >10^3 | + | 24 | >10^3 |
| 10 | + | 18 | >10^3 | + | 18 | >10^3 | + | 18 | >10^3 | + | 17 | >10^3 | + | 23 | >10^3 |
| 11 | + | 18 | >10^3 | + | 18 | >10^3 | + | 17 | >10^3 | + | 17 | >10^3 | + | 30 | >10^3 |
| 12 | + | 18 | >10^3 | + | 18 | >10^3 | + | 18 | >10^3 | + | 18 | >10^3 | + | 25 | >10^3 |
| 13 | - | N/A | N/A | - | N/A | N/A | - | N/A | N/A | + | 17 | >10^3 | + | 32 | >10^3 |
| 14 | - | N/A | N/A | - | N/A | N/A | + | 41 | >10^3 | + | 17 | >10^3 | + | 26 | >10^3 |
| 15 | + | 18 | >10^3 | + | 18 | >10^3 | + | 18 | >10^3 | + | 17 | >10^3 | + | 24 | >10^3 |
| 16 | + | 18 | >10^3 | + | 18 | >10^3 | + | 18 | >10^3 | + | 18 | >10^3 | - | N/A | N/A |
| 17 | + | 18 | >10^3 | + | 18 | >10^3 | + | 18 | >10^3 | + | 17 | >10^3 | + | 27 | >10^3 |
| 18 | + | 18 | >10^3 | + | 18 | >10^3 | + | 18 | >10^3 | + | 18 | >10^3 | + | 24 | >10^3 |
| 19 | - | N/A | N/A | - | N/A | N/A | - | N/A | N/A | + | 17 | >10^3 | + | 30 | >10^3 |
| 20 | + | 18 | >10^3 | + | 18 | >10^3 | + | 17 | >10^3 | + | 17 | >10^3 | - | N/A | N/A |

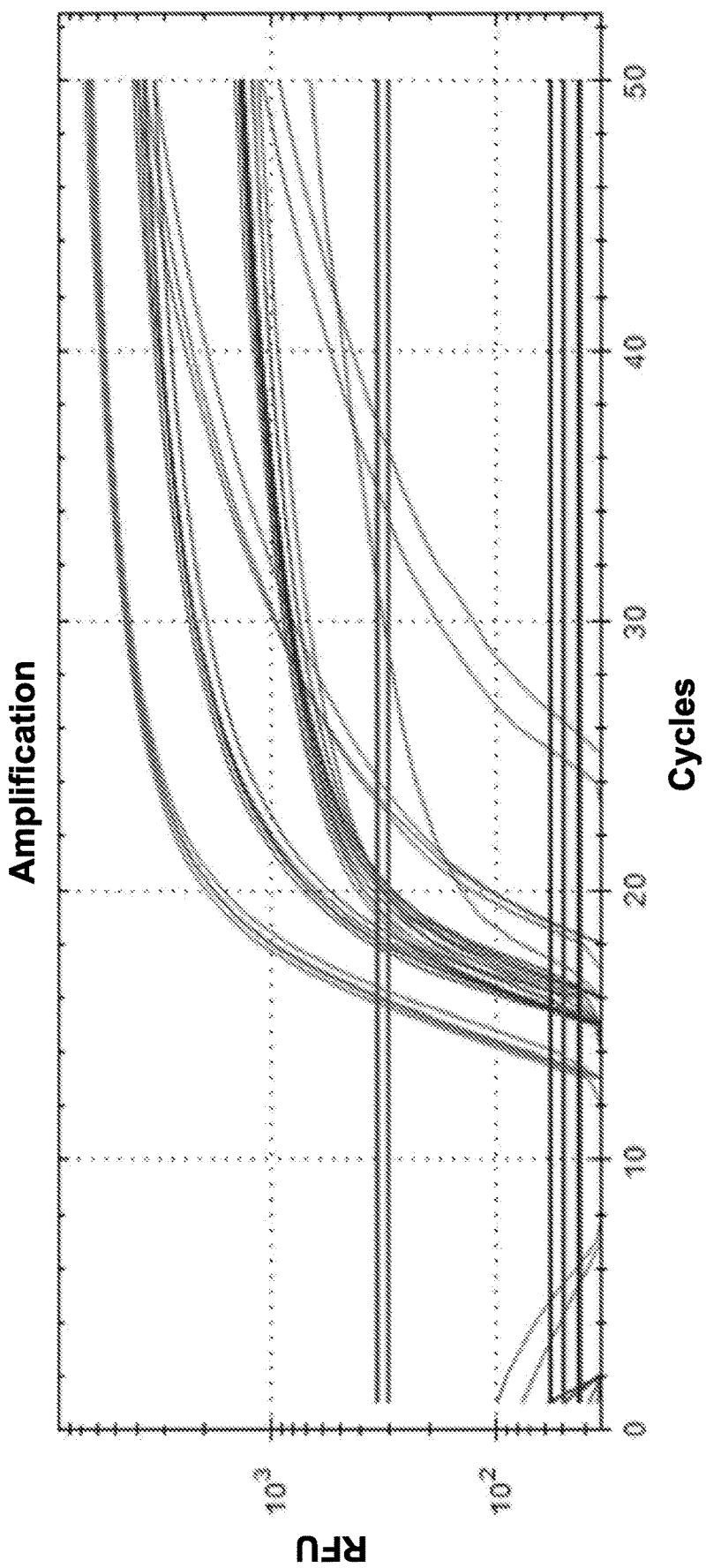
Figure 6. 5 CFU/25g – Deli Turkey – All Targets

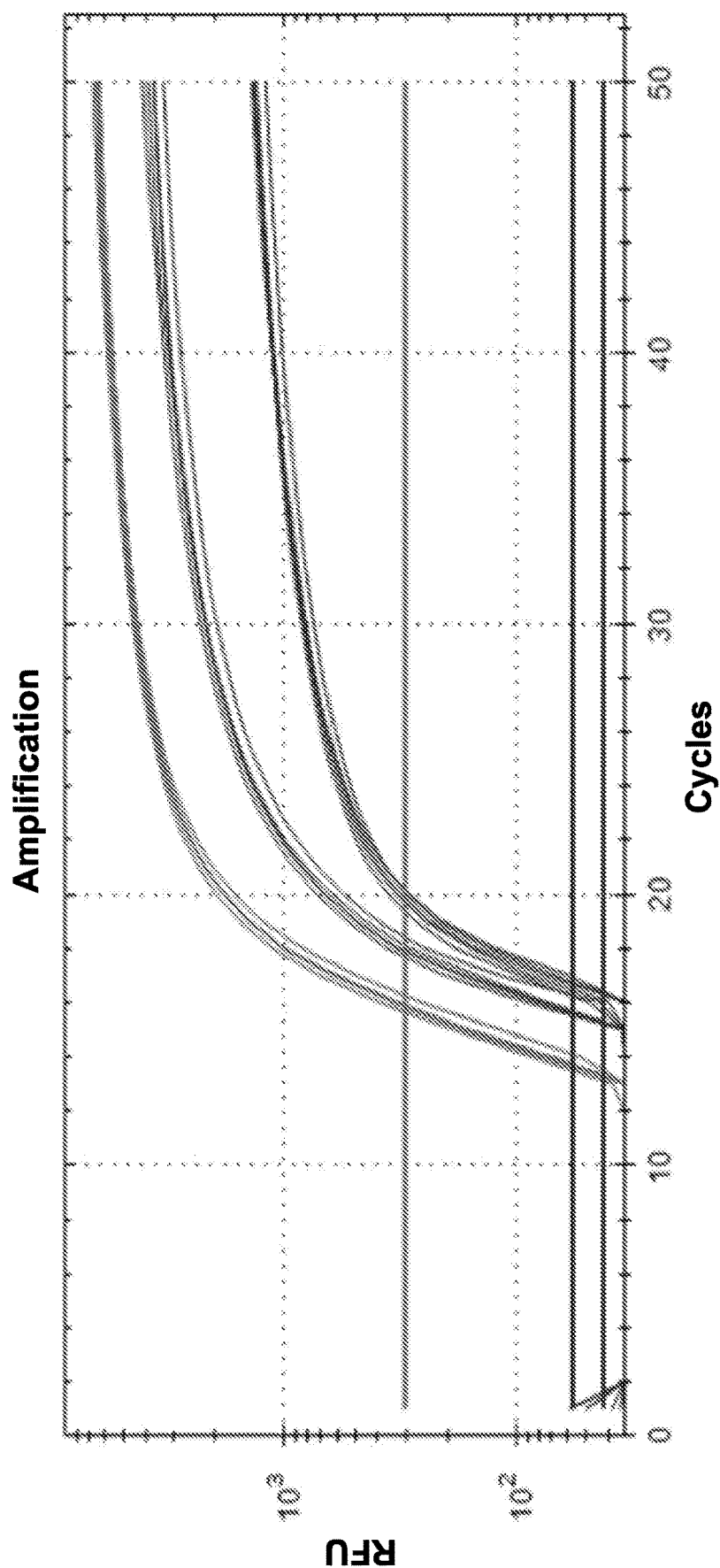
Figure 7. 5 CFU/25g – Deli Turkey – STEC Targets

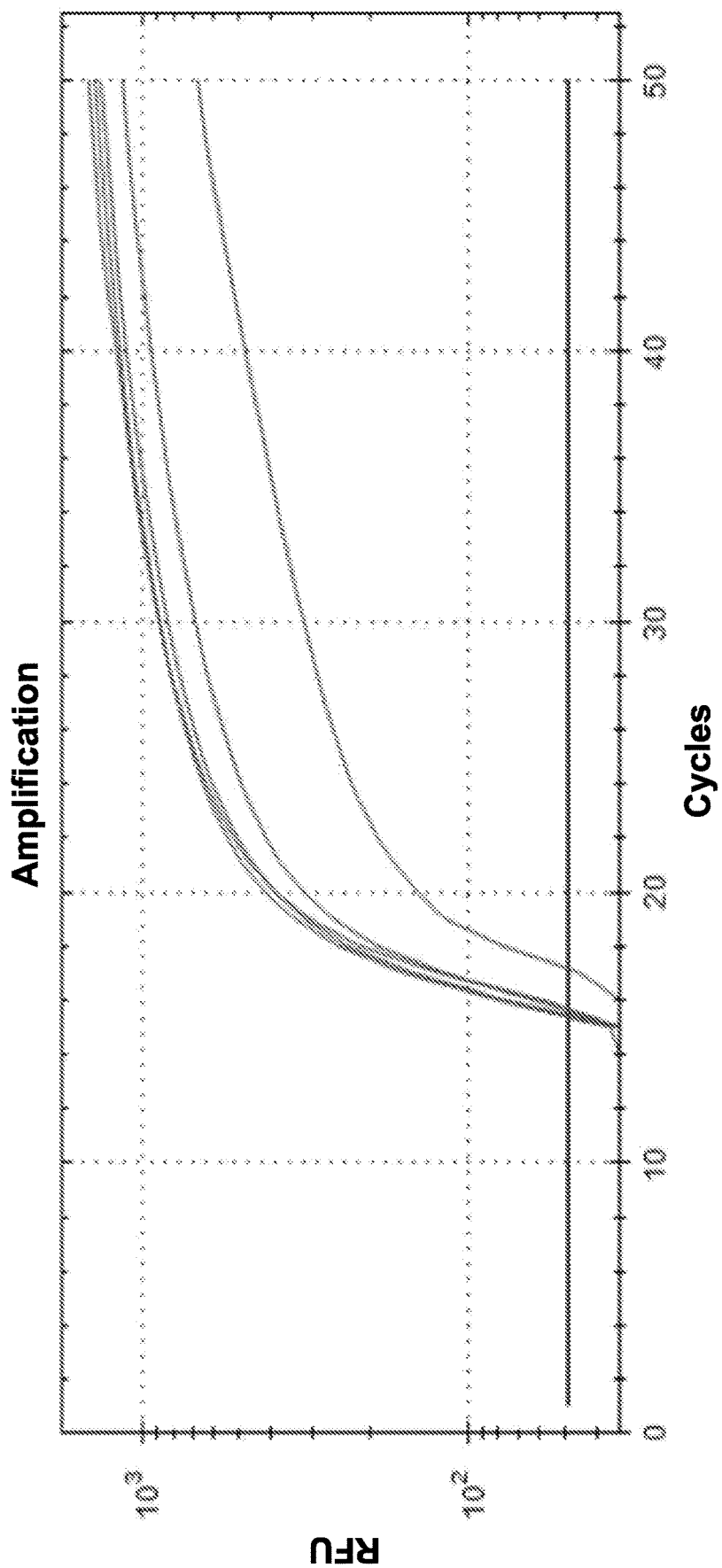
Figure 8. 5 CFU/25g – Deli Turkey – *Salmonella* Target

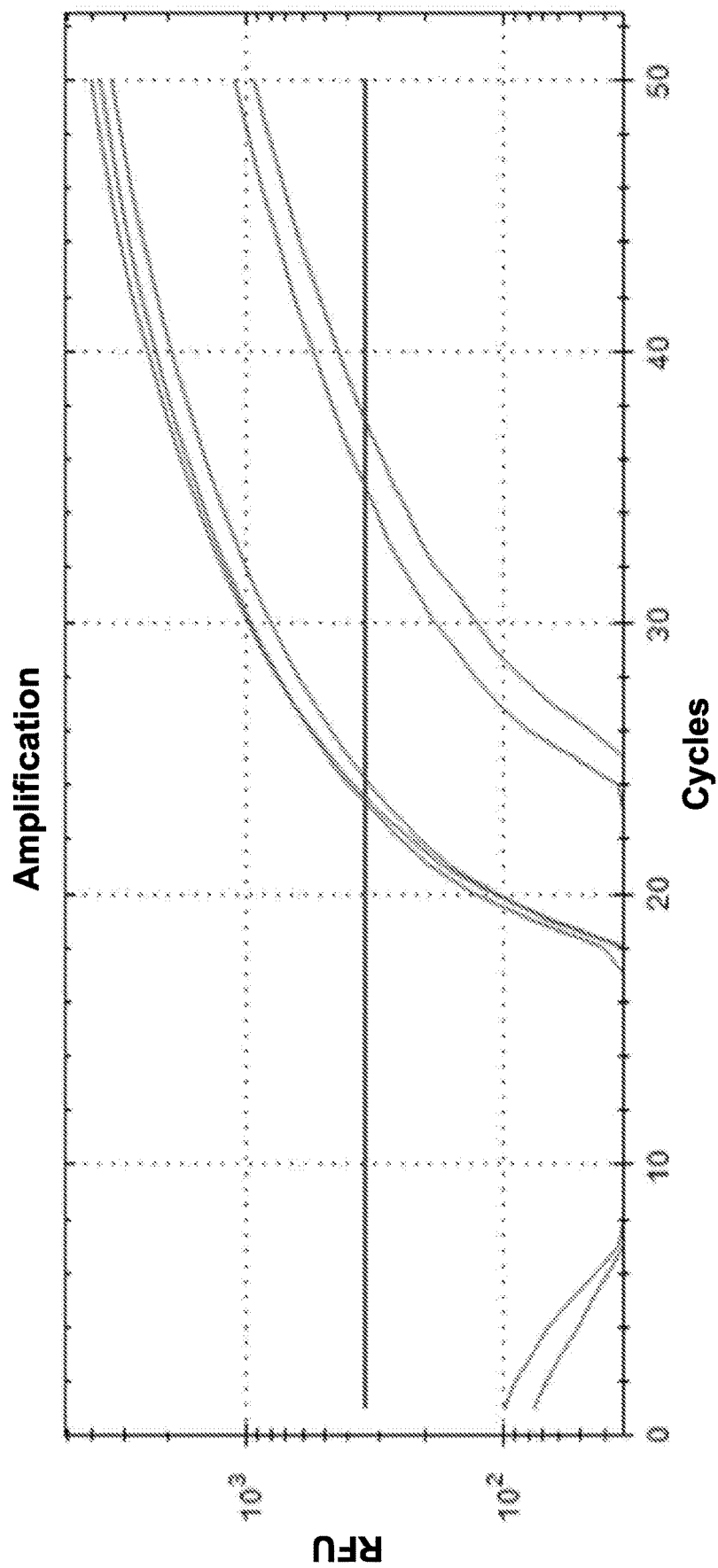
Figure 9. 5 CFU/25g – Deli Turkey – *L. monocytogenes* Target

Figure 10. 5 CFU/25g – Deli Turkey - Table of Results

| Replicate | EAE | | | STX-1 | | | STX-2 | | | Salmonella spp. | | | L. monocytogenes | | |
|---|---|---|---|---|---|---|---|---|---|---|---|---|---|---|---|
| | "+/-" | Cq | RFU* | "+/-" | Cq | RFU* | "+/-" | Cq | RFU* | "+/-" | Cq | RFU* | "+/-" | Cq | RFU* |
| 1 | + | 17 | >10^3 | + | 16 | >10^3 | + | 16 | >10^3 | + | 16 | >10^3 | + | 35 | >10^3 |
| 2 | + | 17 | >10^3 | + | 15 | >10^3 | + | 16 | >10^3 | + | 16 | >10^3 | + | 23 | >10^3 |
| 3 | + | 17 | >10^3 | + | 15 | >10^3 | + | 16 | >10^3 | + | 15 | >10^3 | + | 24 | >10^3 |
| 4 | + | 16 | >10^3 | + | 15 | >10^3 | + | 16 | >10^3 | + | 15 | >10^3 | + | 23 | >10^3 |
| 5 | + | 16 | >10^3 | + | 15 | >10^3 | + | 16 | >10^3 | + | 17 | >10^3 | + | 37 | >10^3 |

Figure 11. 1CFU/25g – Hot Dog – Table of Results

| Replicate | EAE "+/-" | STX-1 "+/-" | STX-2 "+/-" | Salmonella spp. "+/-" | L. monocytogenes "+/-" |
|---|---|---|---|---|---|
| 1 | + | + | + | + | + |
| 2 | + | + | + | + | - |
| 3 | + | + | + | + | - |
| 4 | + | + | + | + | - |
| 5 | + | + | + | + | - |
| 6 | + | + | + | + | + |
| 7 | + | + | + | + | + |
| 8 | + | + | + | + | - |
| 9 | + | + | + | + | + |
| 10 | + | + | + | + | - |
| 11 | + | + | + | + | + |
| 12 | + | + | + | + | - |
| 13 | + | + | + | + | - |
| 14 | + | + | + | + | - |
| 15 | + | + | + | + | + |
| 16 | + | + | + | + | + |
| 17 | + | + | + | + | + |
| 18 | + | + | + | + | - |
| 19 | + | + | + | + | + |
| 20 | + | + | + | + | + |

Figure 12. Hot Dog - 5 CFU/25g – Table of Results

| Replicate | EAE | STX-1 | STX-2 | Salmonella spp. | L. monocytogenes |
|---|---|---|---|---|---|
| | "+/-" | "+/-" | "+/-" | "+/-" | "+/-" |
| 1 | + | + | + | + | + |
| 2 | + | + | + | + | + |
| 3 | + | + | + | + | + |
| 4 | + | + | + | + | + |
| 5 | + | + | + | + | + |

Figure 13. Iceberg Lettuce - 1CFU/25g – Table of Results

| Replicate | EAE "+/-" | STX-1 "+/-" | STX-2 "+/-" | Salmonella spp. "+/-" | L. monocytogenes "+/-" |
|---|---|---|---|---|---|
| 1 | - | - | - | + | + |
| 2 | - | - | - | + | + |
| 3 | - | - | - | + | - |
| 4 | - | - | - | - | + |
| 5 | + | + | + | + | - |
| 6 | - | - | - | + | - |
| 7 | + | + | + | + | + |
| 8 | - | - | - | - | - |
| 9 | + | + | + | - | - |
| 10 | - | - | - | + | + |
| 11 | + | + | + | + | - |
| 12 | + | + | + | + | + |
| 13 | - | - | - | + | - |
| 14 | + | + | + | + | + |
| 15 | + | + | + | + | + |
| 16 | + | + | + | + | - |
| 17 | + | + | + | + | + |
| 18 | - | - | - | + | - |
| 19 | - | - | - | - | - |
| 20 | + | + | + | + | + |

Figure 14. 5 CFU/25g – Iceberg Lettuce - Table of Results

| Replicate | EAE "+/-" | STX-1 "+/-" | STX-2 "+/-" | Salmonella spp. "+/-" | L. monocytogenes "+/-" |
|---|---|---|---|---|---|
| 1 | + | + | + | + | + |
| 2 | + | + | + | + | + |
| 3 | + | + | + | + | + |
| 4 | + | + | + | + | + |
| 5 | + | + | + | + | + |

Figure 15. 1CFU/25g – Raw Ground Beef - Table of Results

| Replicate | EAE "+/-" | STX-1 "+/-" | STX-2 "+/-" | Salmonella spp. "+/-" | L. monocytogenes "+/-" |
|---|---|---|---|---|---|
| 1 | + | - | + | - | - |
| 2 | + | + | + | + | - |
| 3 | - | - | - | - | - |
| 4 | + | + | + | - | - |
| 5 | + | + | + | - | - |
| 6 | + | + | + | + | + |
| 7 | + | + | + | + | + |
| 8 | - | - | - | + | + |
| 9 | + | + | + | + | - |
| 10 | + | + | + | + | + |
| 11 | - | - | - | - | - |
| 12 | - | - | - | + | + |
| 13 | - | - | - | - | - |
| 14 | + | + | + | + | - |
| 15 | + | + | + | + | + |
| 16 | + | + | + | + | + |
| 17 | + | + | + | + | + |
| 18 | + | + | + | + | + |
| 19 | - | - | - | - | + |
| 20 | - | - | - | + | - |

Figure 16. 5 CFU/25g – Raw Ground Beef Table of Results

| Replicate | EAE "+/-" | STX-1 "+/-" | STX-2 "+/-" | Salmonella spp. "+/-" | L. monocytogenes "+/-" |
|---|---|---|---|---|---|
| 1 | + | + | + | + | + |
| 2 | + | + | + | + | + |
| 3 | + | + | + | + | + |
| 4 | + | + | + | + | + |
| 5 | + | + | + | + | + |

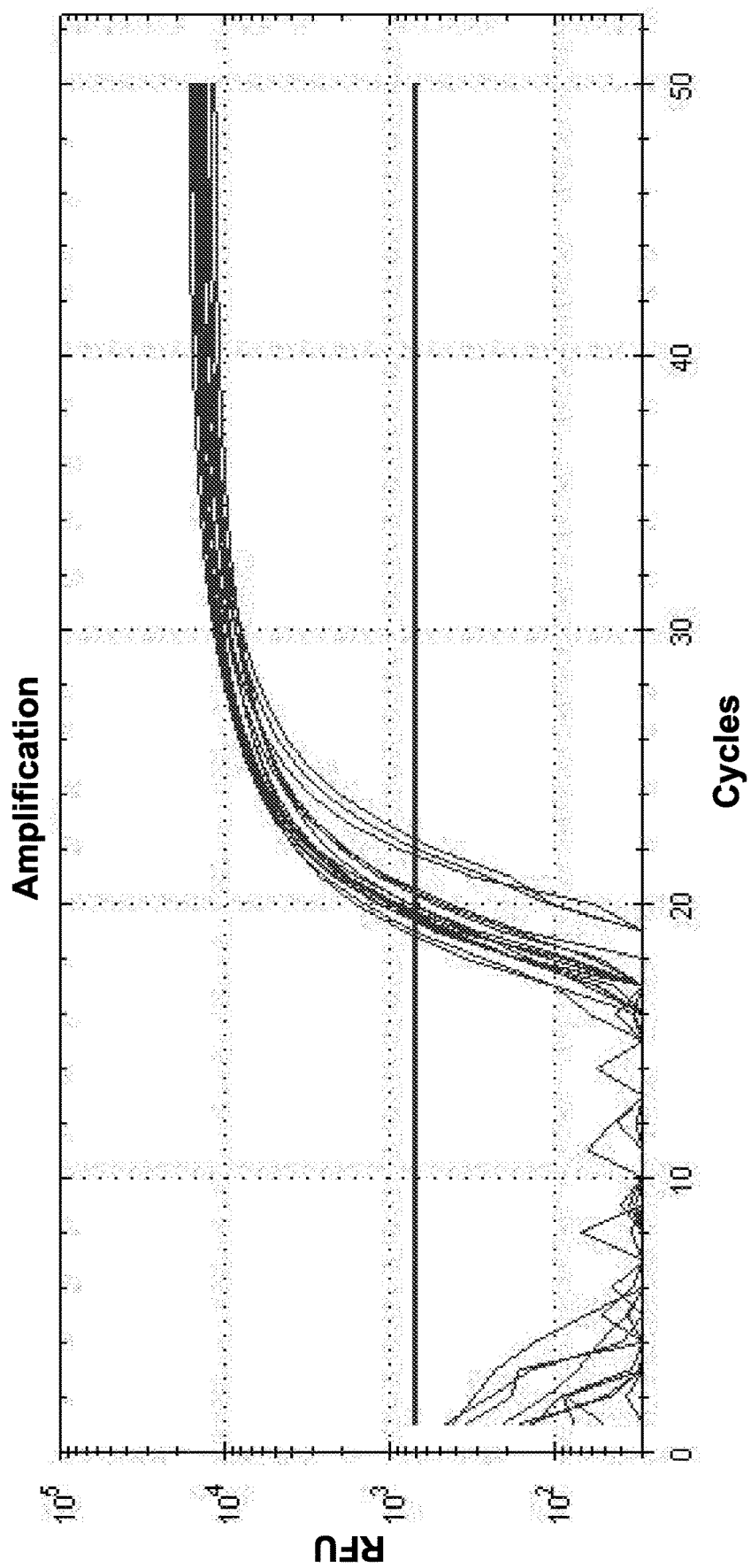
Figure 17. 1 CFU/25g – Deli Turkey – STX-1 and STX-2 – Internal Control

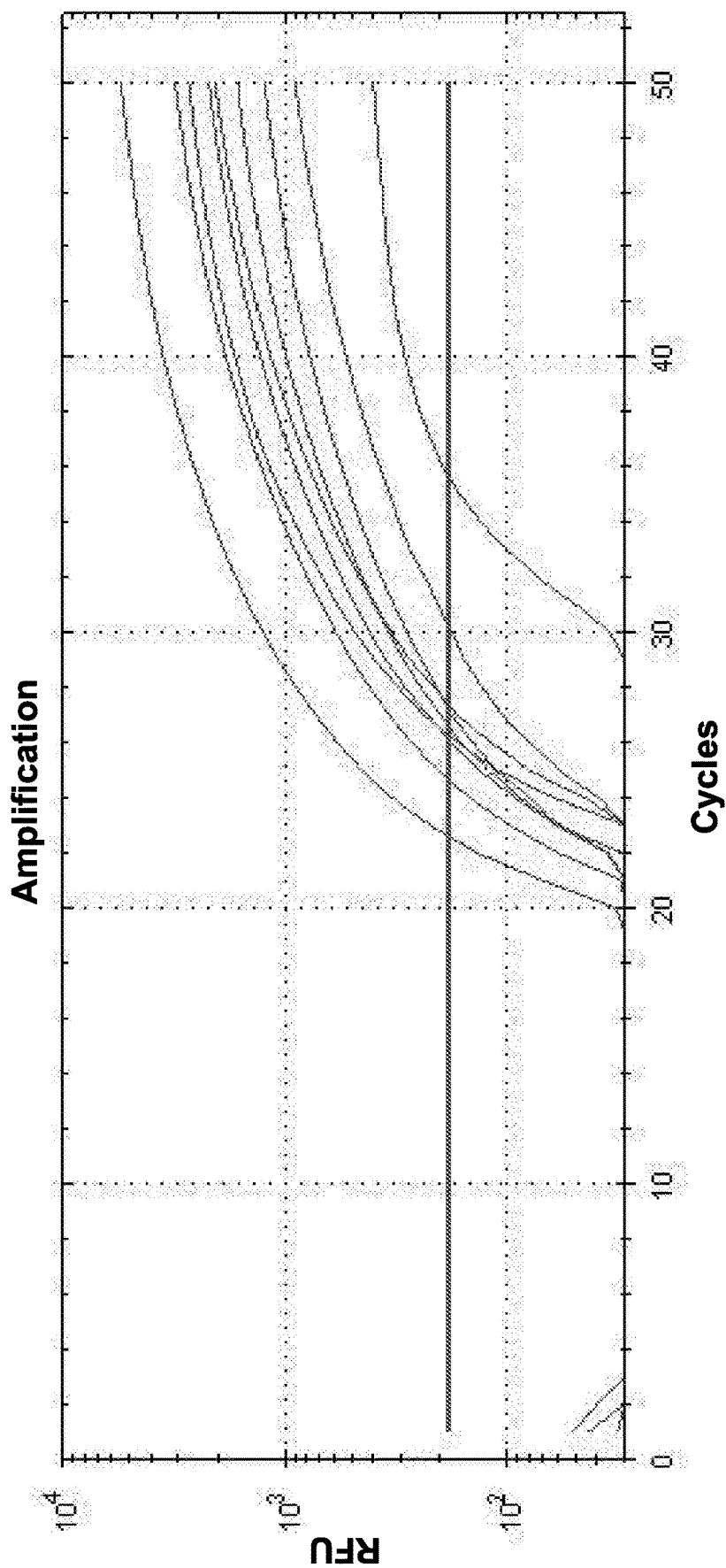
Figure 18. 1 CFU/25g – Deli Turkey - *L. monocytogenes* – Internal Control

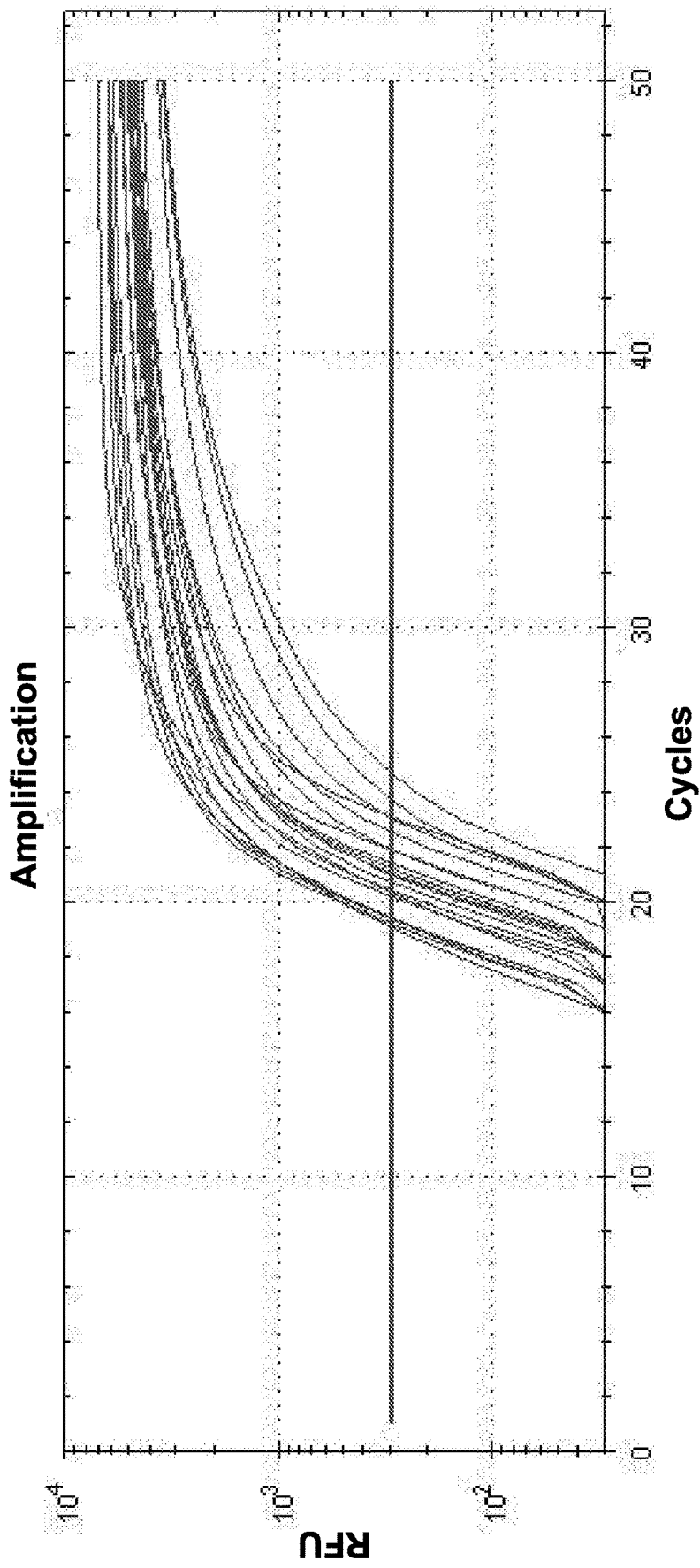
Figure 19. 1 CFU/25g – Deli Turkey - *S. enterica* – Internal Control

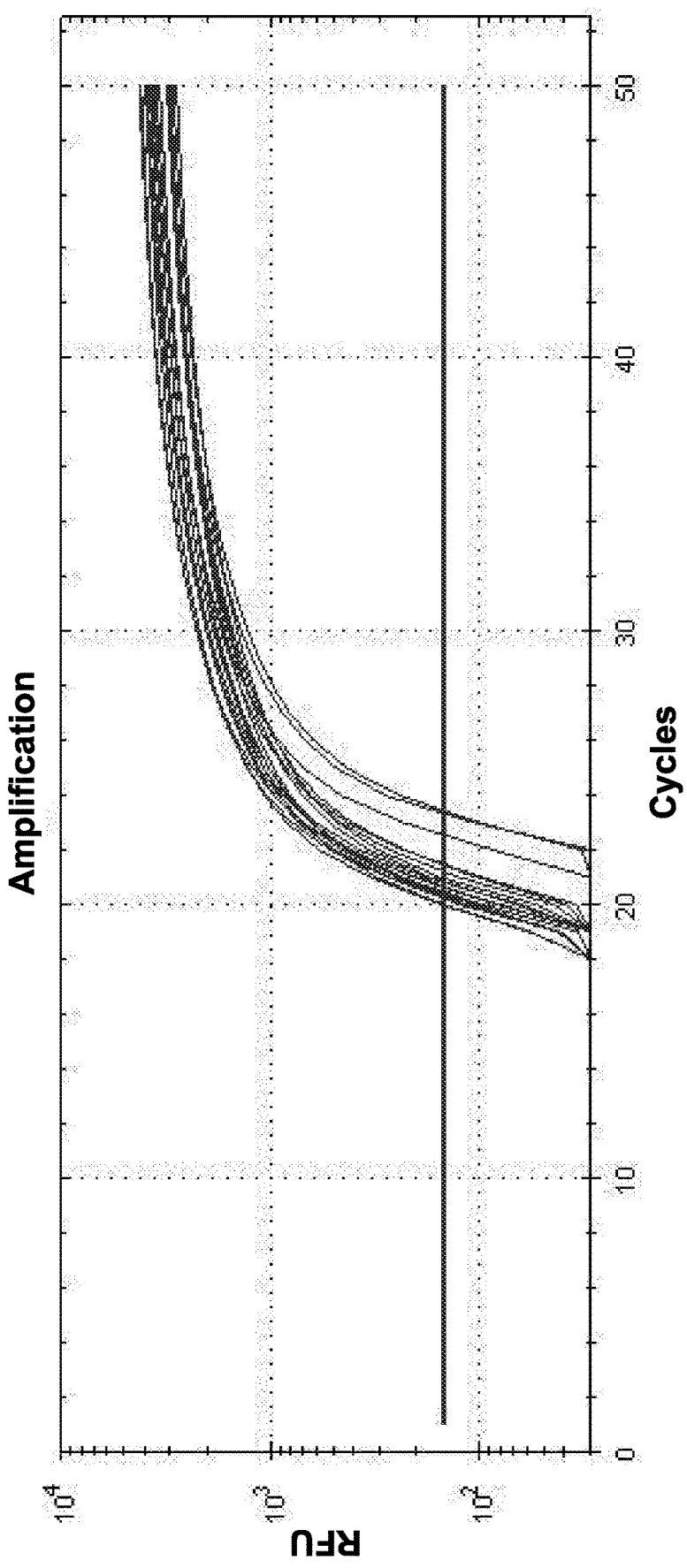
Figure 20. 1 CFU/25g – Deli Turkey - *E. coli* EAE - - Internal Control

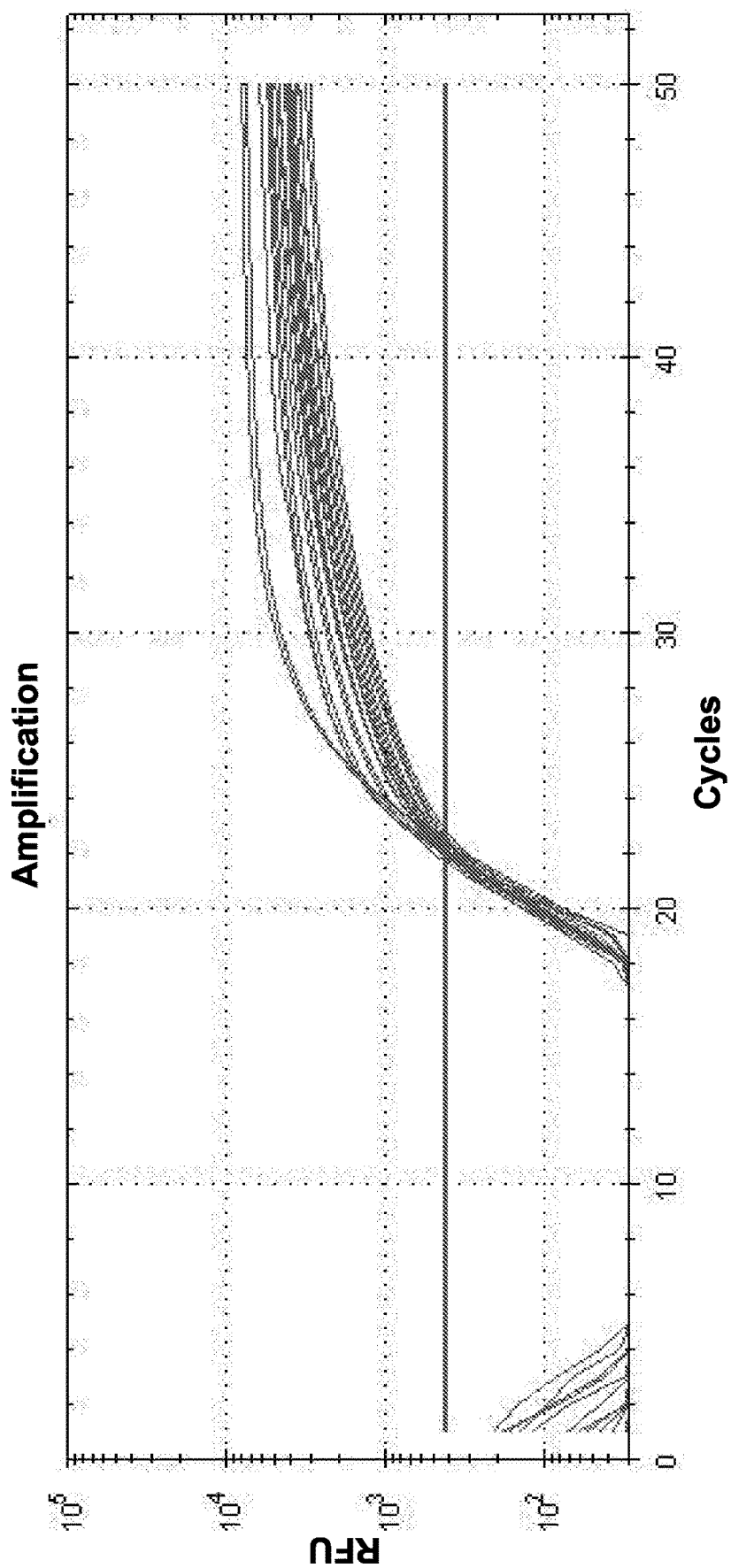
Figure 21. 1 CFU/25g – Deli Turkey - Internal Control

Figure 22. 1 CFU/25g – Deli Turkey - Table of Results – Internal Control

| Replicate | STX-1/ STX-2 "+/-" | L. monocytogenes "+/-" | Salmonella spp. "+/-" | EAE "+/-" | Internal Control "+/-" |
|---|---|---|---|---|---|
| 1 | + | - | + | + | + |
| 2 | + | - | + | + | + |
| 3 | + | - | + | + | + |
| 4 | + | + | + | + | + |
| 5 | + | - | + | + | + |
| 6 | + | + | + | + | + |
| 7 | + | - | + | + | + |
| 8 | + | + | + | + | + |
| 9 | + | - | + | + | + |
| 10 | + | - | + | + | + |
| 11 | + | - | + | + | + |
| 12 | + | + | + | + | + |
| 13 | + | - | + | + | + |
| 14 | - | + | + | - | + |
| 15 | + | + | + | + | + |
| 16 | + | + | + | - | + |
| 17 | + | + | + | + | + |
| 18 | - | - | + | + | + |
| 19 | + | - | - | - | + |
| 20 | + | + | + | + | + |

Figure 23. 5 CFU/25g – Deli Turkey - STX-1 and STX-2 – Internal Control

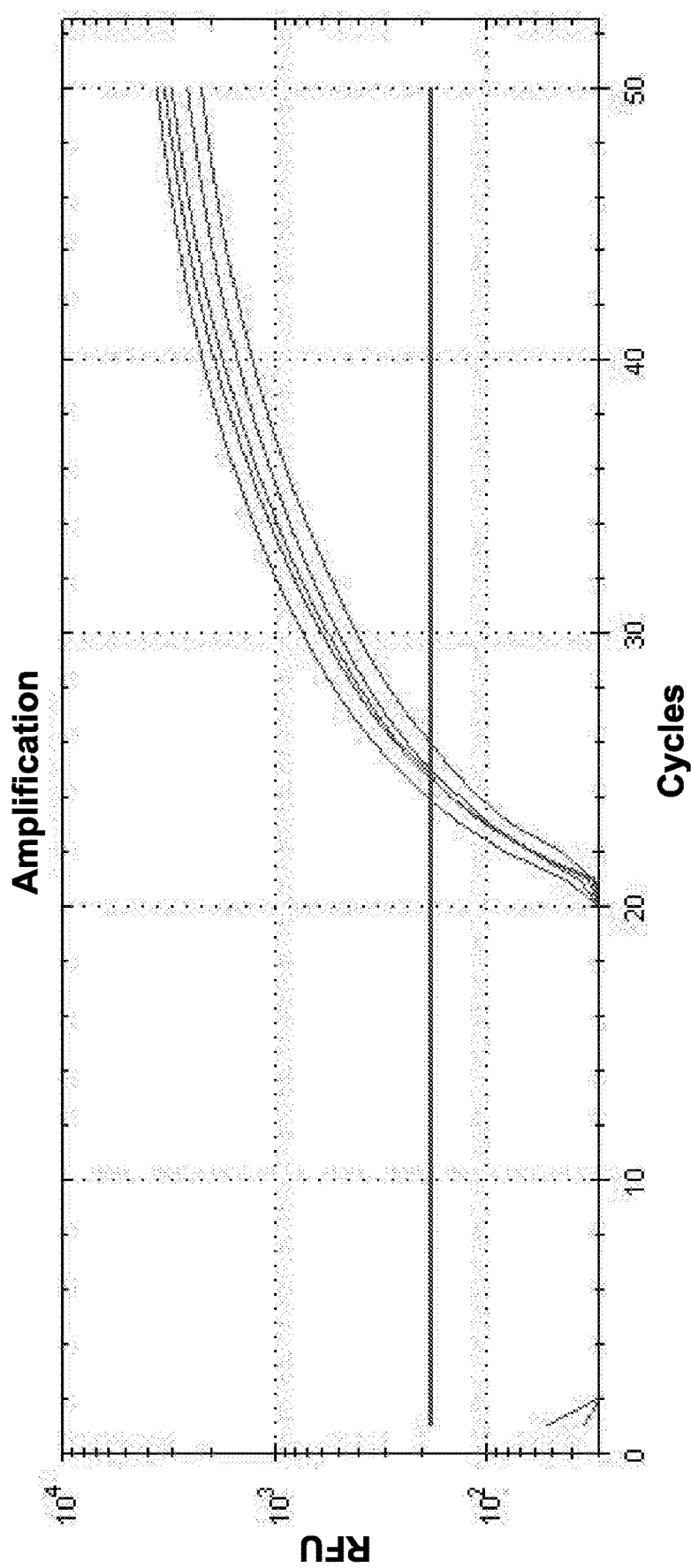
Figure 24. 5 CFU/25g – Deli Turkey – *L. monocytogenes* – Internal Control

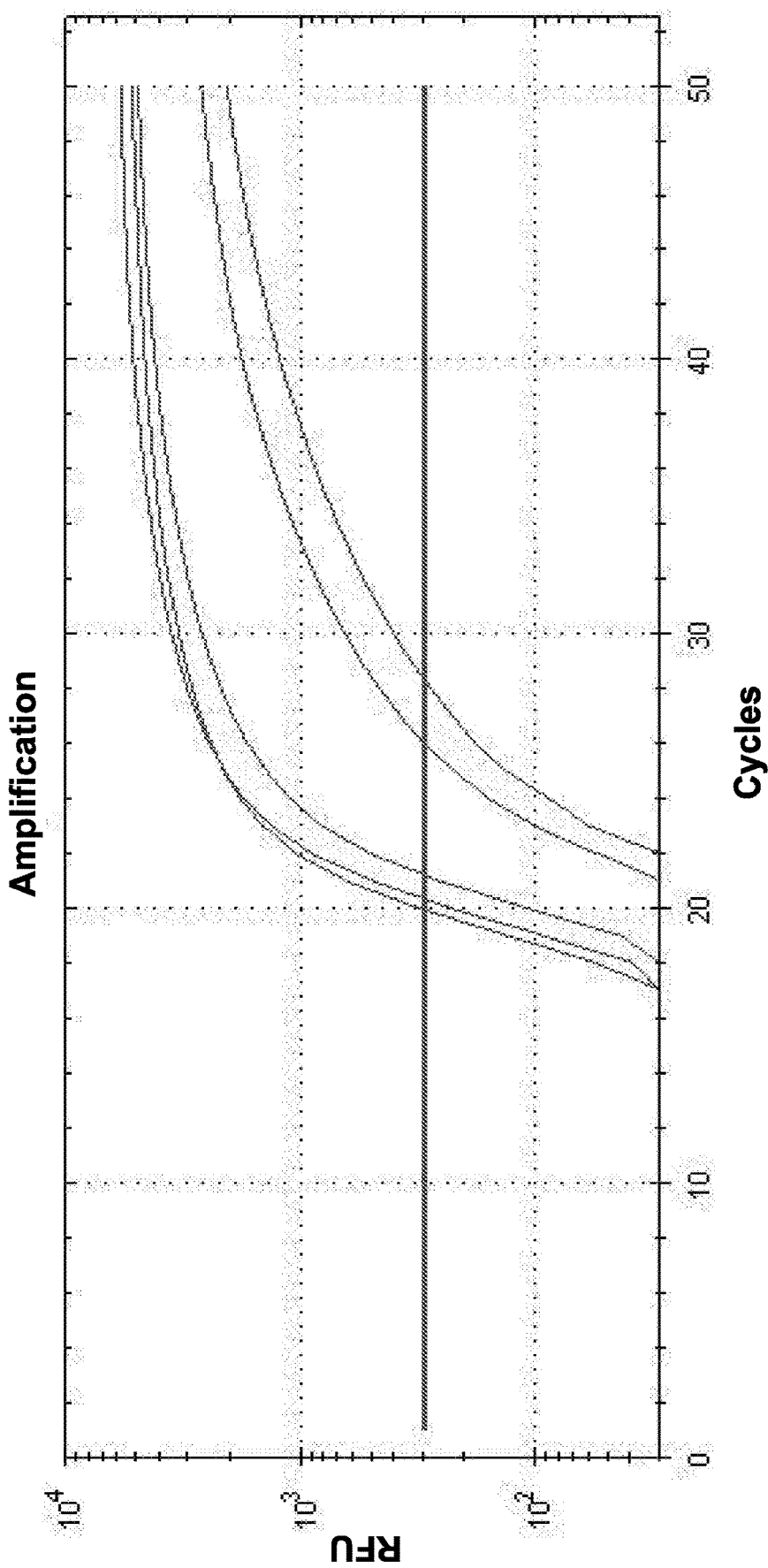
Figure 25. 5 CFU/25g – Deli Turkey - *S. enterica* – Internal Control

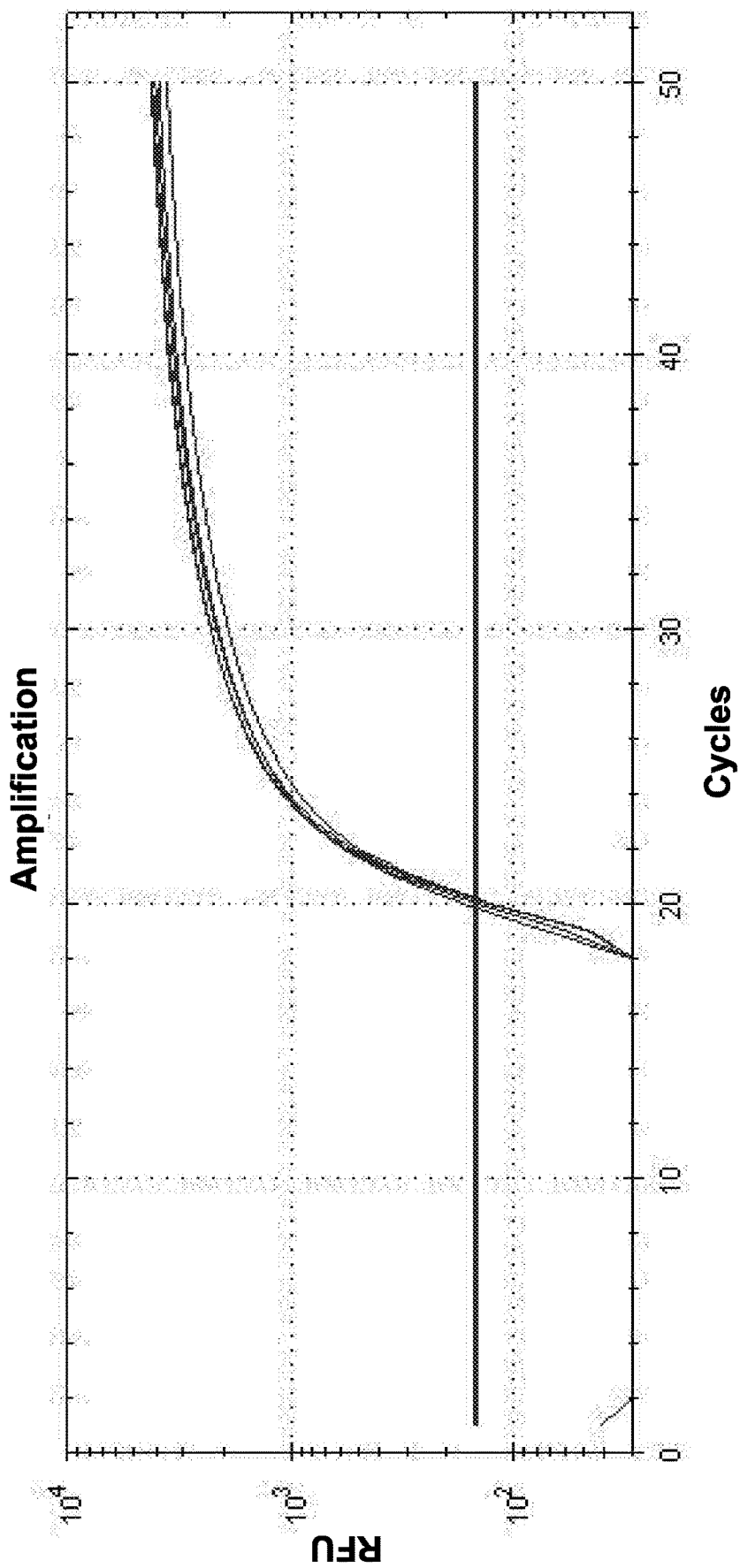
Figure 26. 5 CFU/25g – Deli Turkey – *E. coli* EAE – Internal Control

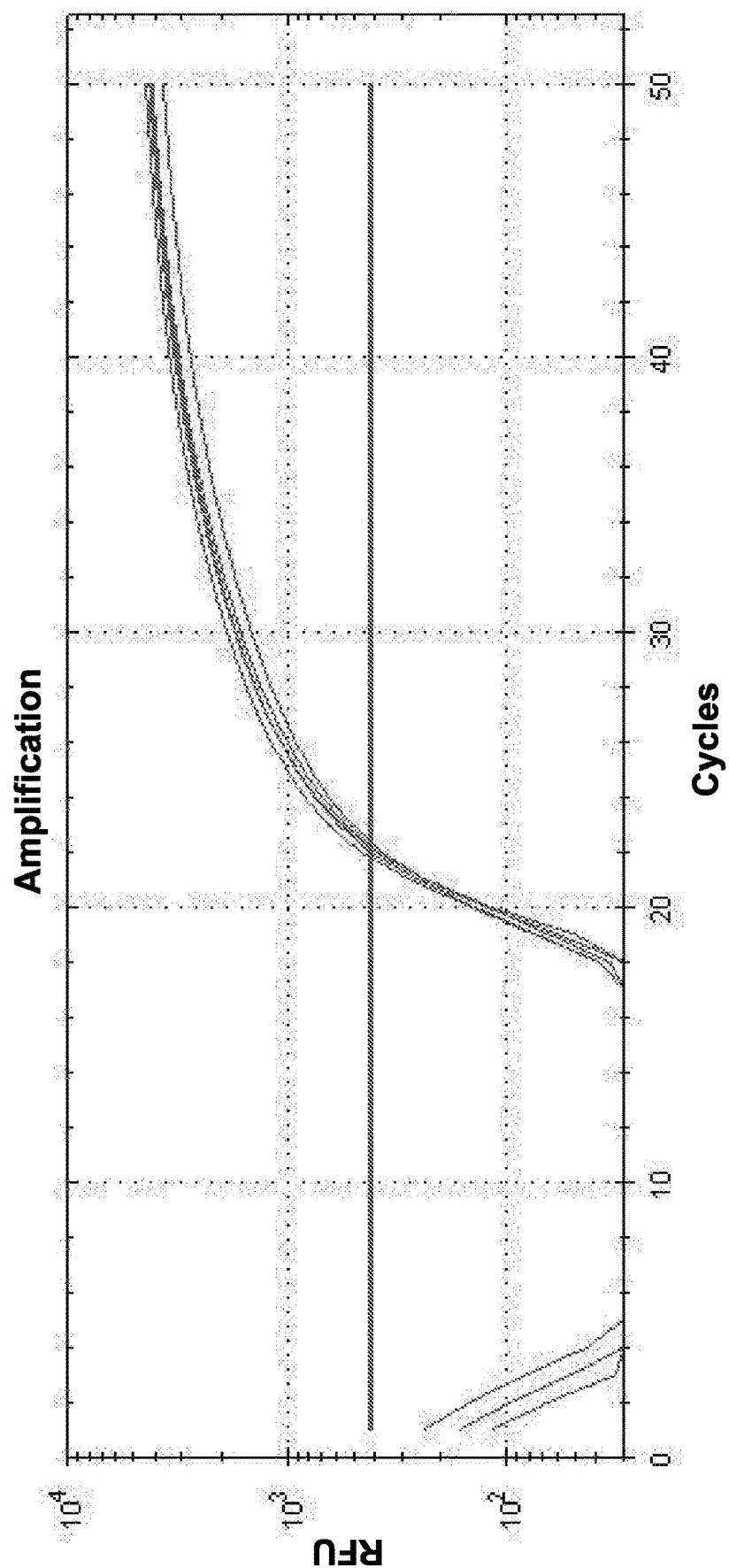
Figure 27. 5 CFU/25g – Deli Turkey - Internal Control

Figure 28. 5 CFU/25g – Deli Turkey - Table of Results – Internal Control

| Replicate | STX-1/ STX-2 | L. monocytogenes | Salmonella spp. | EAE | Internal Control |
|---|---|---|---|---|---|
| | "+/-" | "+/-" | "+/-" | "+/-" | "+/-" |
| 1 | + | + | + | + | + |
| 2 | + | + | + | + | + |
| 3 | + | + | + | + | + |
| 4 | + | + | + | + | + |
| 5 | + | + | + | + | + |

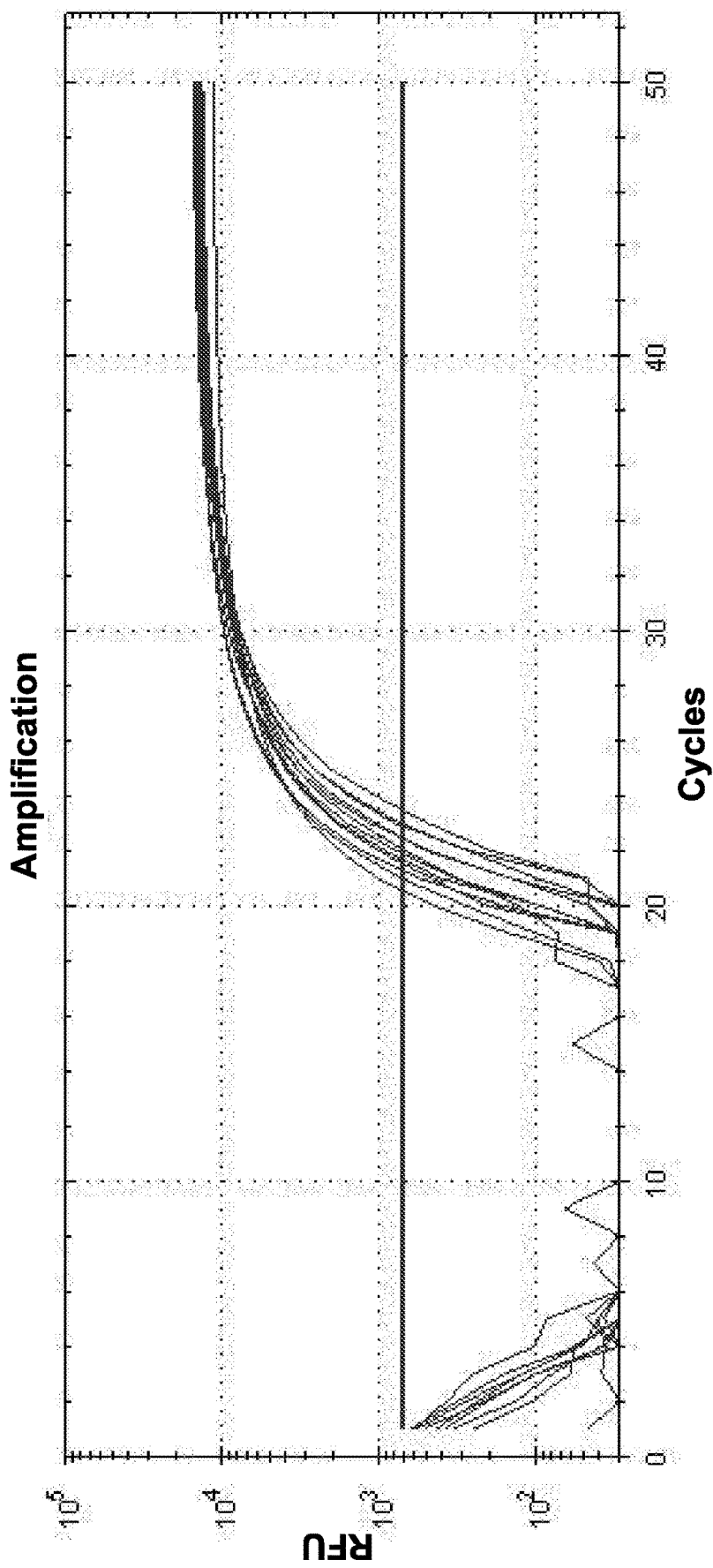
Figure 29. 1 CFU/25g – Lettuce – STX-1 and STX-2 – Internal Control

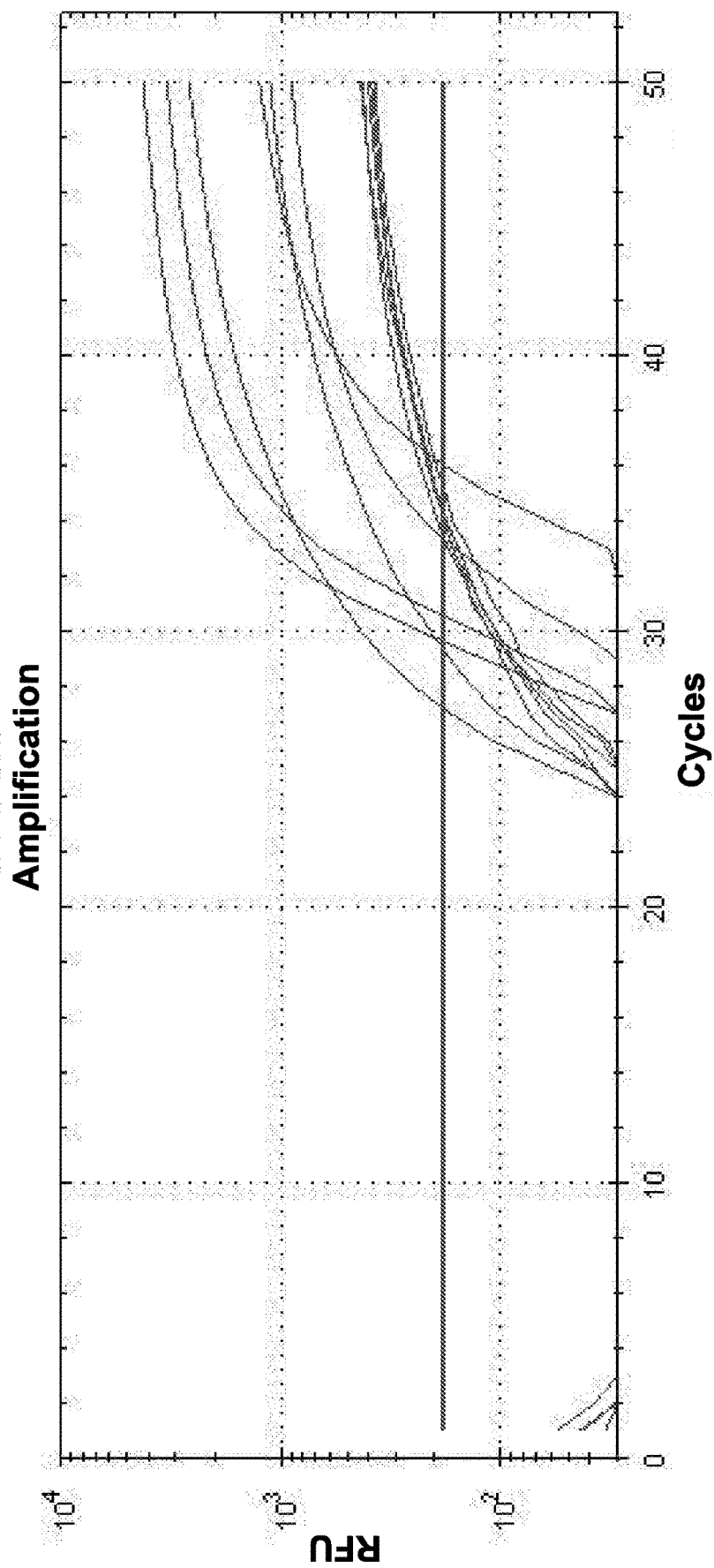
Figure 30. 1 CFU/25g – Lettuce - *L. monocytogenes* – Internal Control

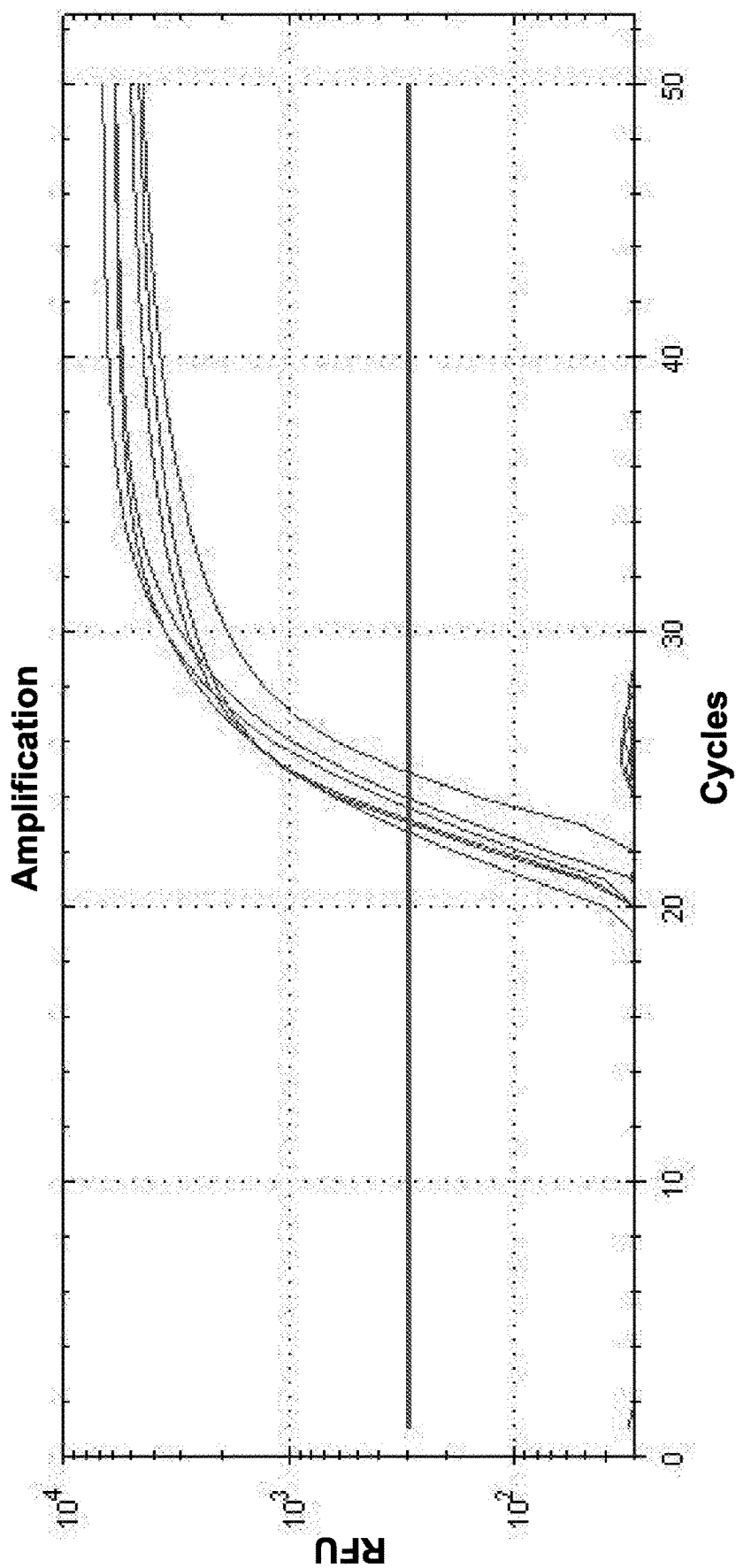
Figure 31. 1 CFU/25g – Lettuce - *S. enterica* – Internal Control

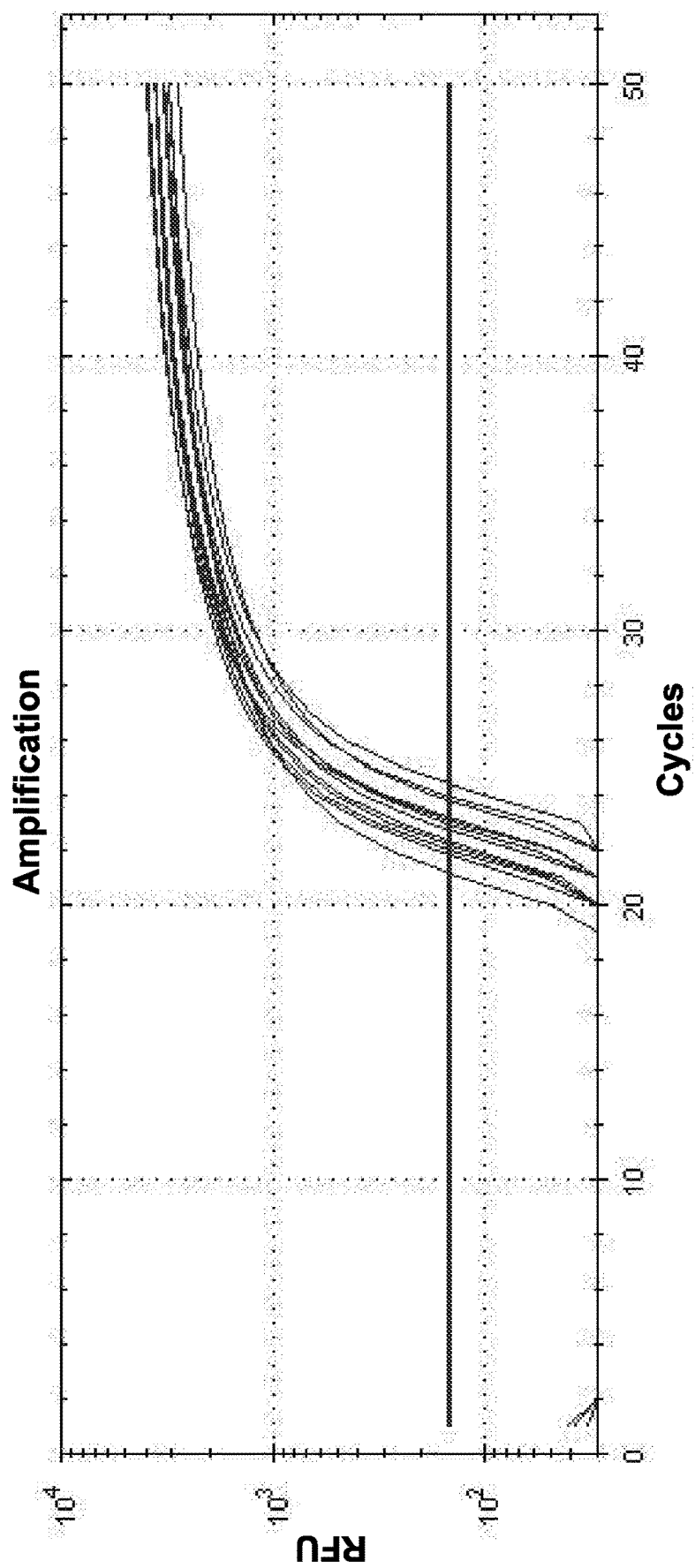
Figure 32. 1 CFU/25g – Lettuce - *E. coli* EAE – Internal Control

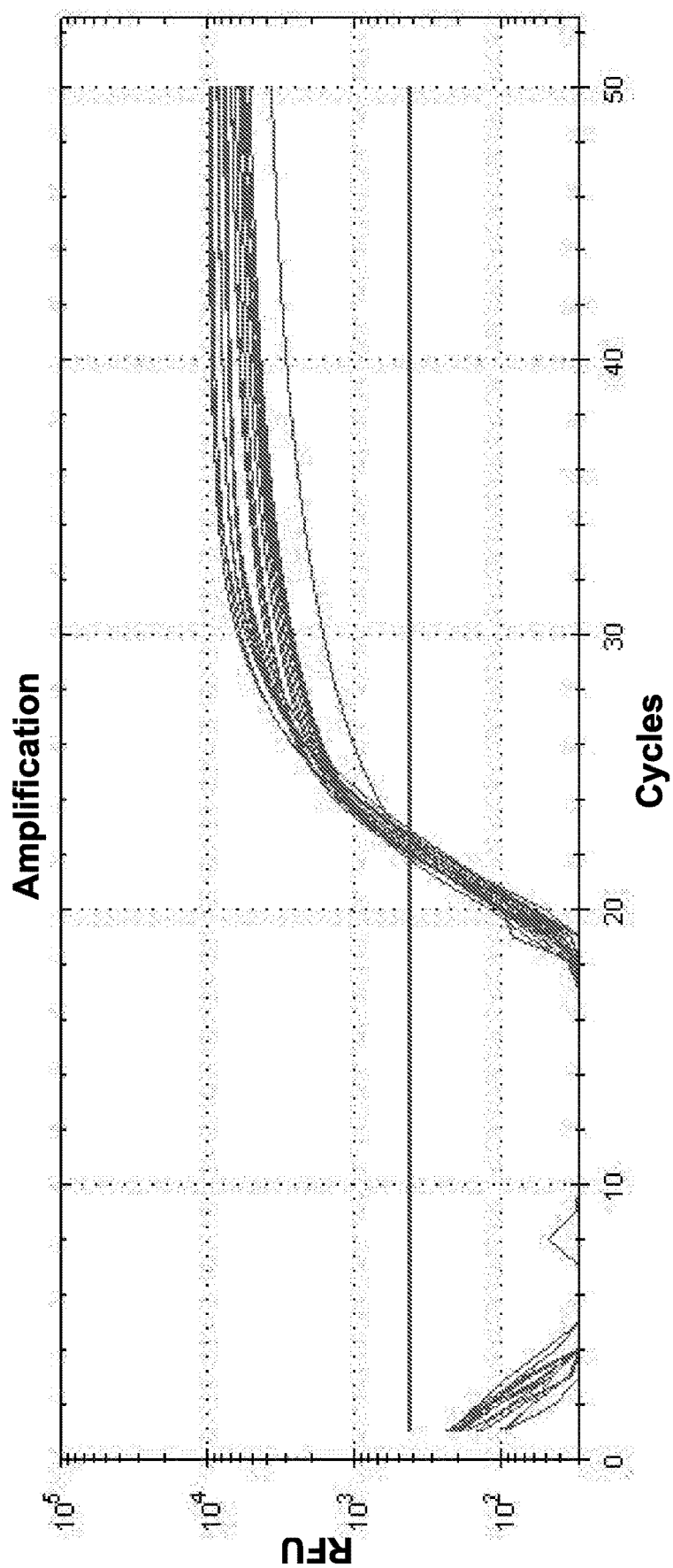
Figure 33. 1 CFU/25g – Lettuce – Internal Control

Figure 34. 1 CFU/25g – Lettuce – Table of Results – Internal Control

| Replicate | STX-1/STX-2 "+/-" | L. monocytogenes "+/-" | Salmonella spp. "+/-" | EAE "+/-" | Internal Control "+/-" |
|---|---|---|---|---|---|
| 1 | - | - | - | - | + |
| 2 | + | + | - | + | + |
| 3 | - | + | - | - | + |
| 4 | - | - | + | - | + |
| 5 | + | + | + | + | + |
| 6 | - | + | - | - | + |
| 7 | - | + | + | - | + |
| 8 | + | - | + | - | + |
| 9 | + | + | + | + | + |
| 10 | + | - | - | + | + |
| 11 | - | + | - | + | + |
| 12 | + | - | - | - | + |
| 13 | + | + | - | + | + |
| 14 | + | - | - | - | + |
| 15 | - | + | - | + | + |
| 16 | + | - | + | - | + |
| 17 | + | + | - | + | + |
| 18 | + | - | - | + | + |
| 19 | - | + | - | + | + |
| 20 | + | - | - | + | + |

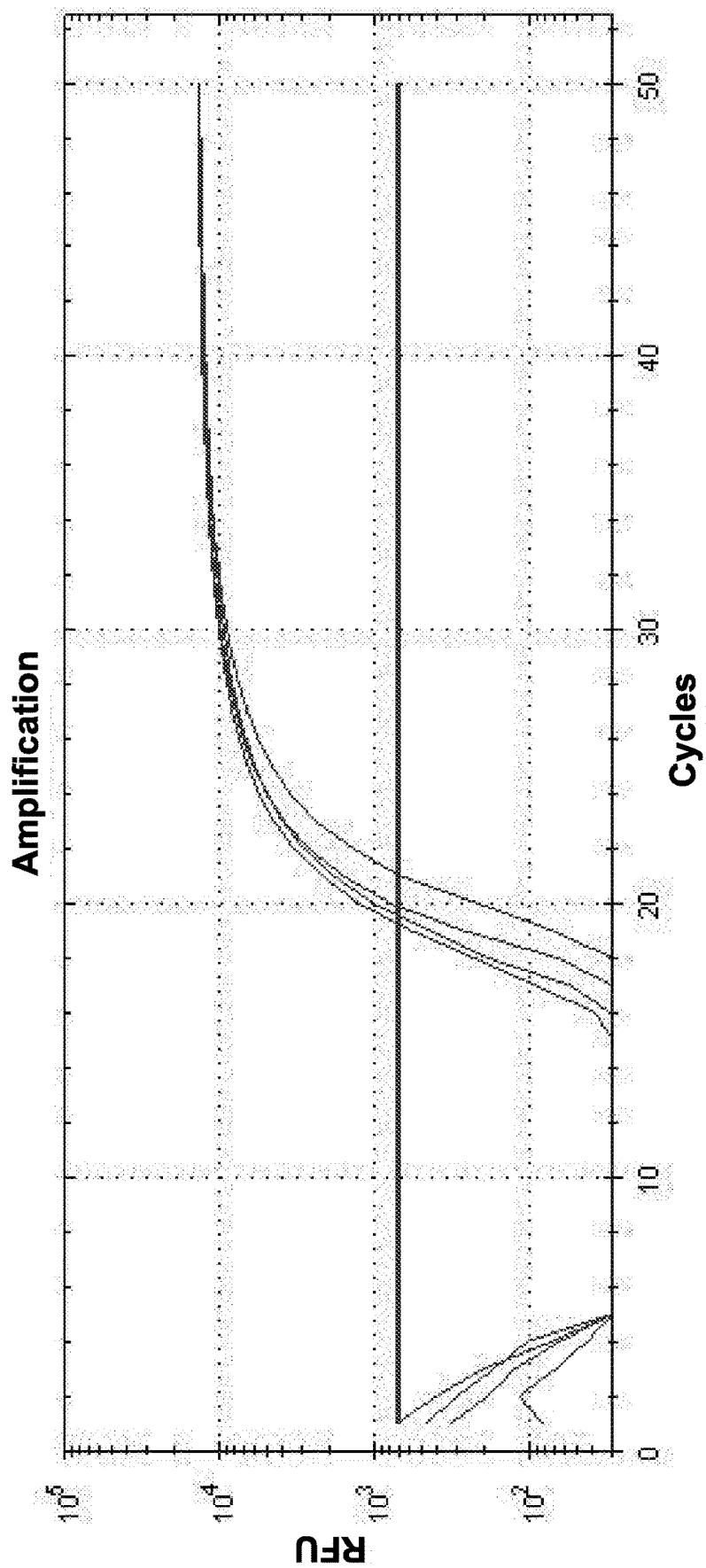
Figure 35. 5 CFU/25g – Lettuce – STX-1 and STX-2 – Internal Control

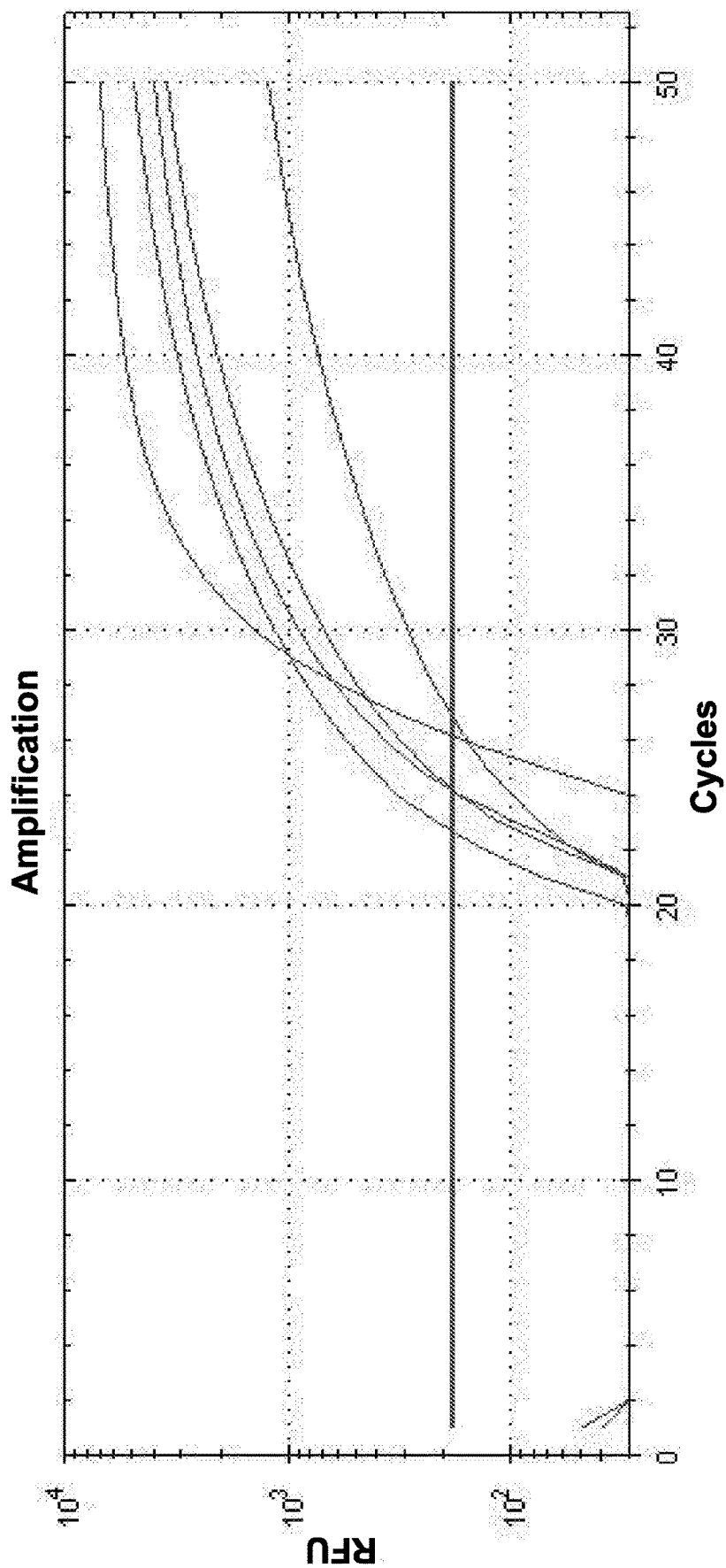
Figure 36. 5 CFU/25g – Lettuce - *L. monocytogenes* – Internal Control

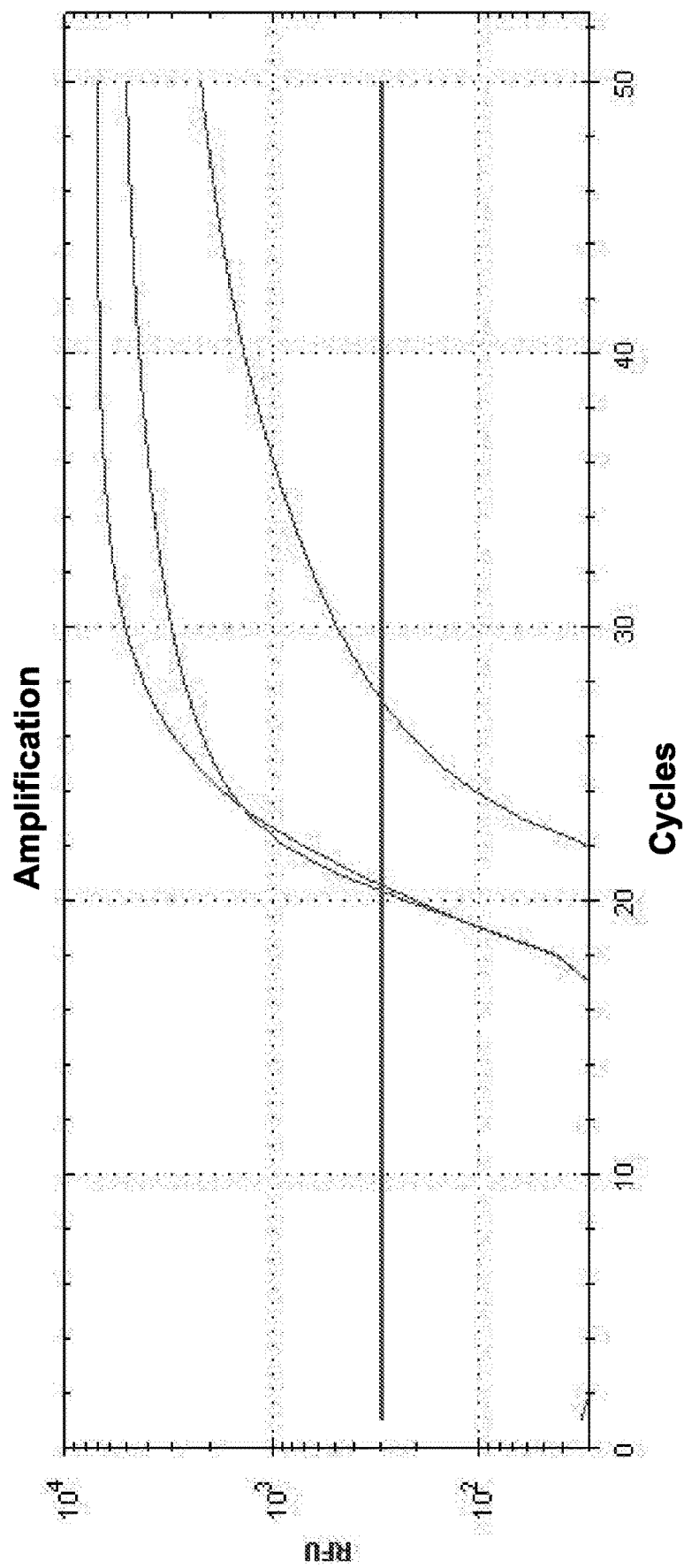
Figure 37. 5 CFU/25g – Lettuce - *S. enterica* – Internal Control

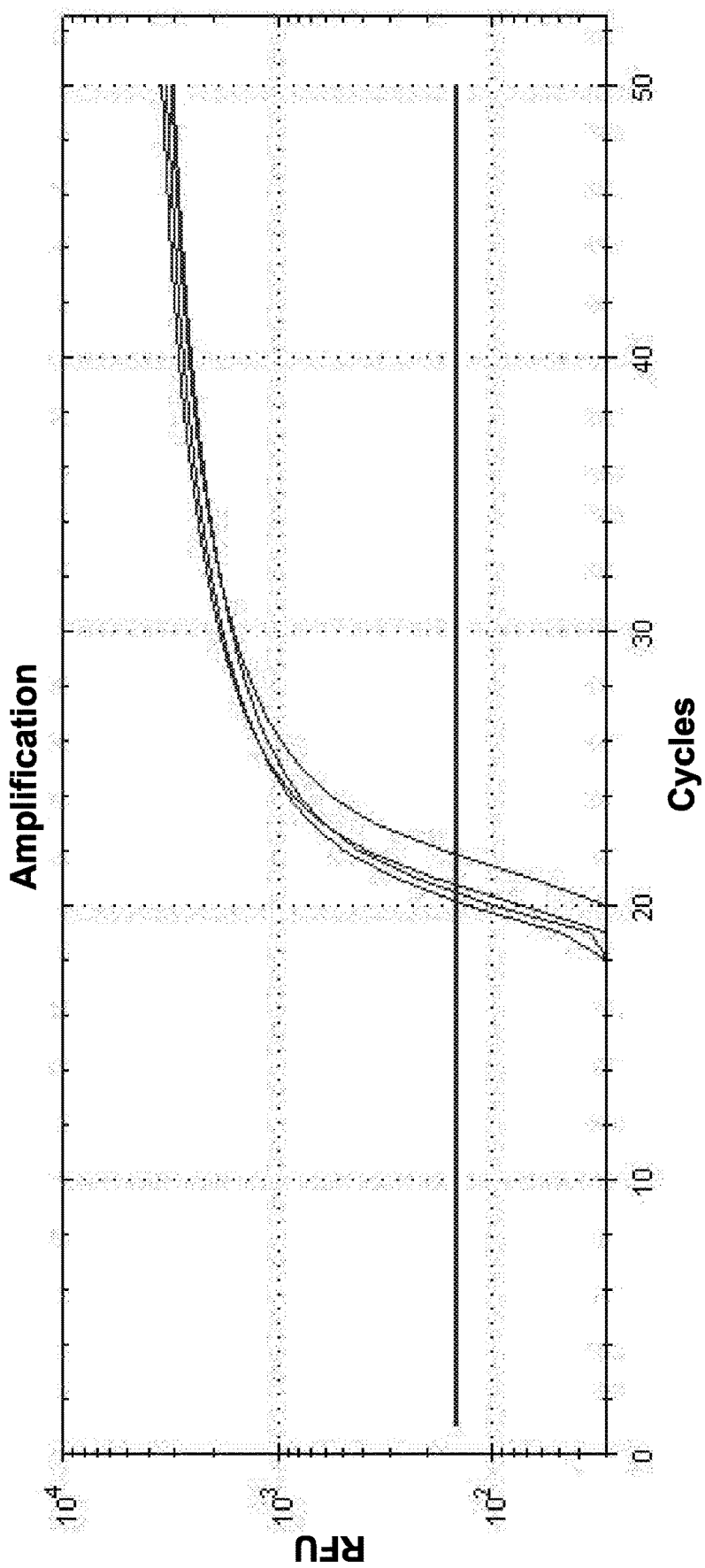
Figure 38. 5 CFU/25g – Lettuce - E. coli EAE – Internal Control

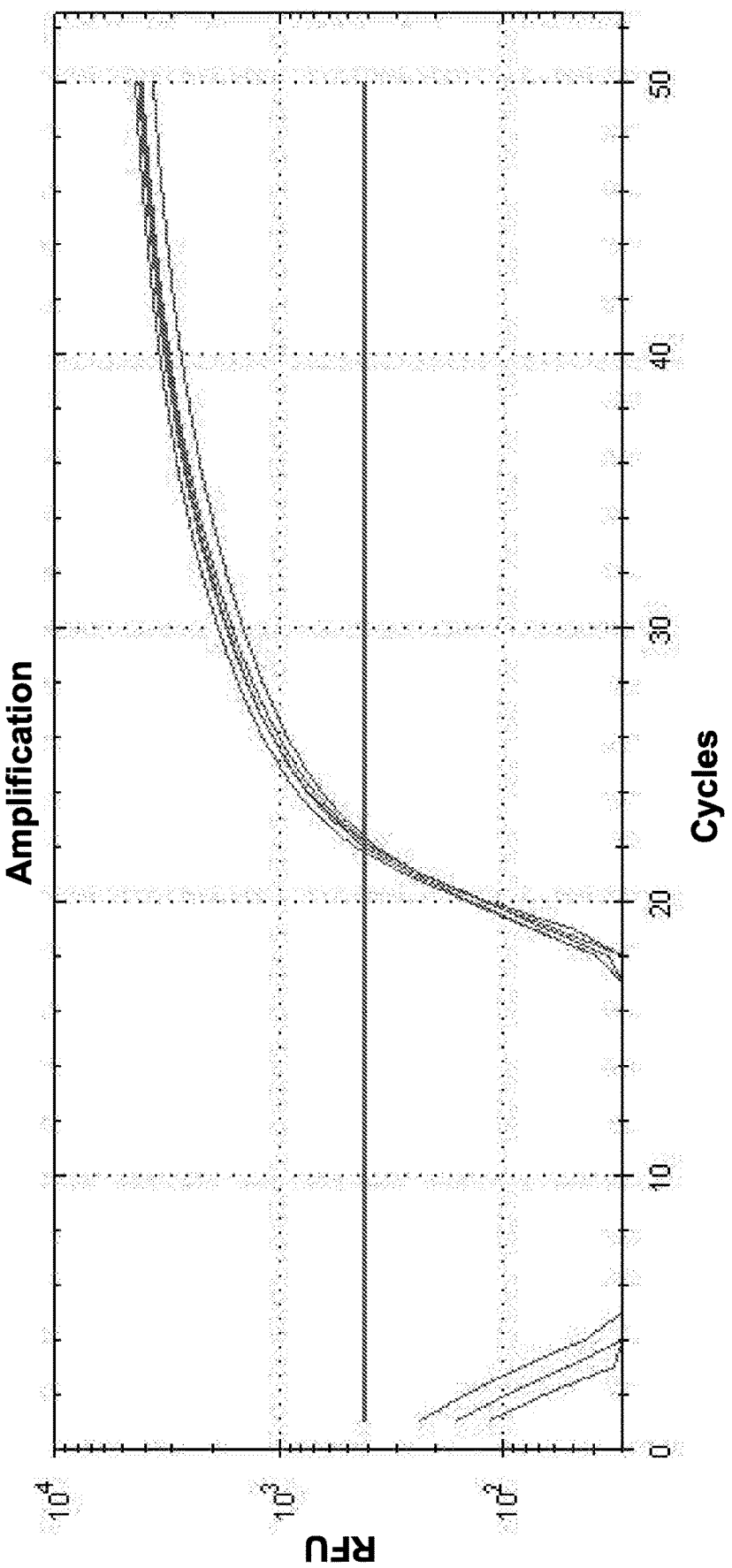
Figure 39. 5 CFU/25g – Lettuce – Internal Control

Figure 40. 5 CFU/25g – Lettuce - Table of Results – Internal Control

| Replicate | STX-1/ STX-2 "+/-" | *L. monocytogenes* "+/-" | *Salmonella* spp. "+/-" | EAE "+/-" | Internal Control "+/-" |
|---|---|---|---|---|---|
| 1 | + | + | - | + | + |
| 2 | + | + | - | + | + |
| 3 | + | + | + | + | + |
| 4 | + | + | + | + | + |
| 5 | - | + | + | - | + |

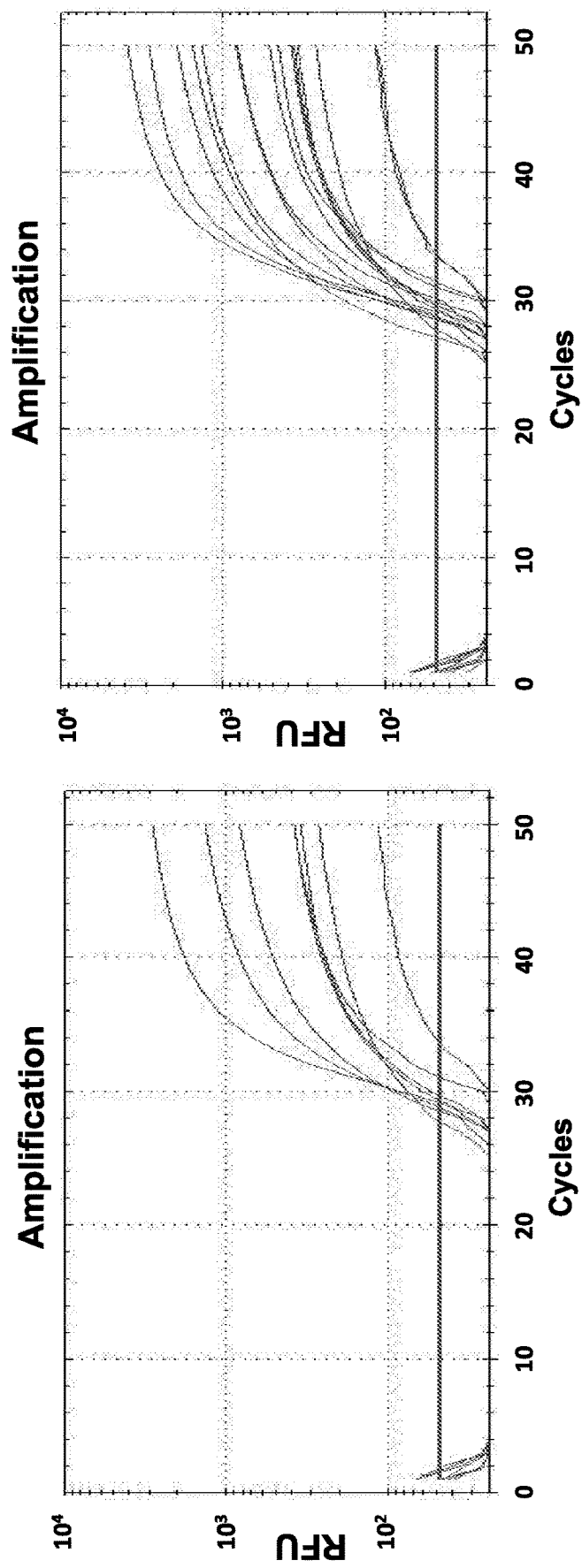
Figure 41. 3 CFU Inoculation of *Listeria Monocytogenes*, *Escherichia Coli O157:H7* and *Salmonella Enterica* Into Raw Beef Trim

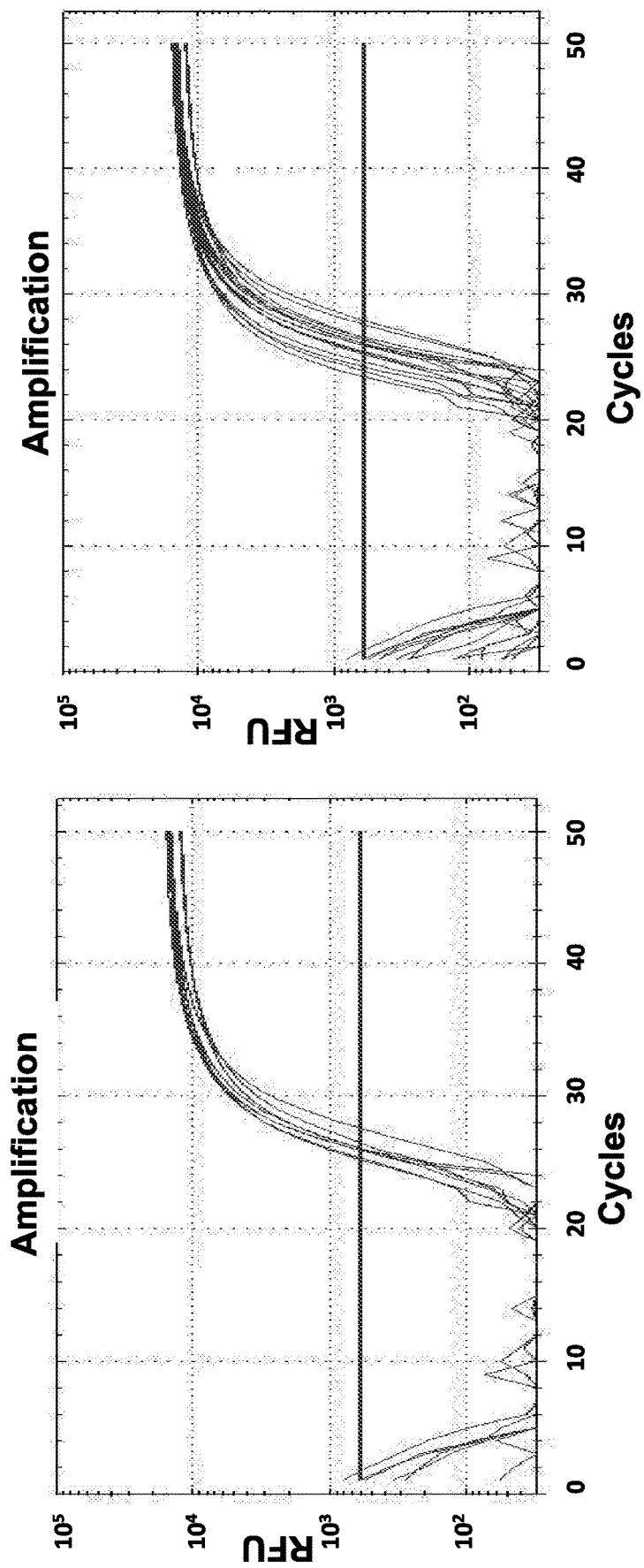
Figure 42. 15 CFU Inoculation of *Escherichia Coli O157:H7* Into Raw Spinach

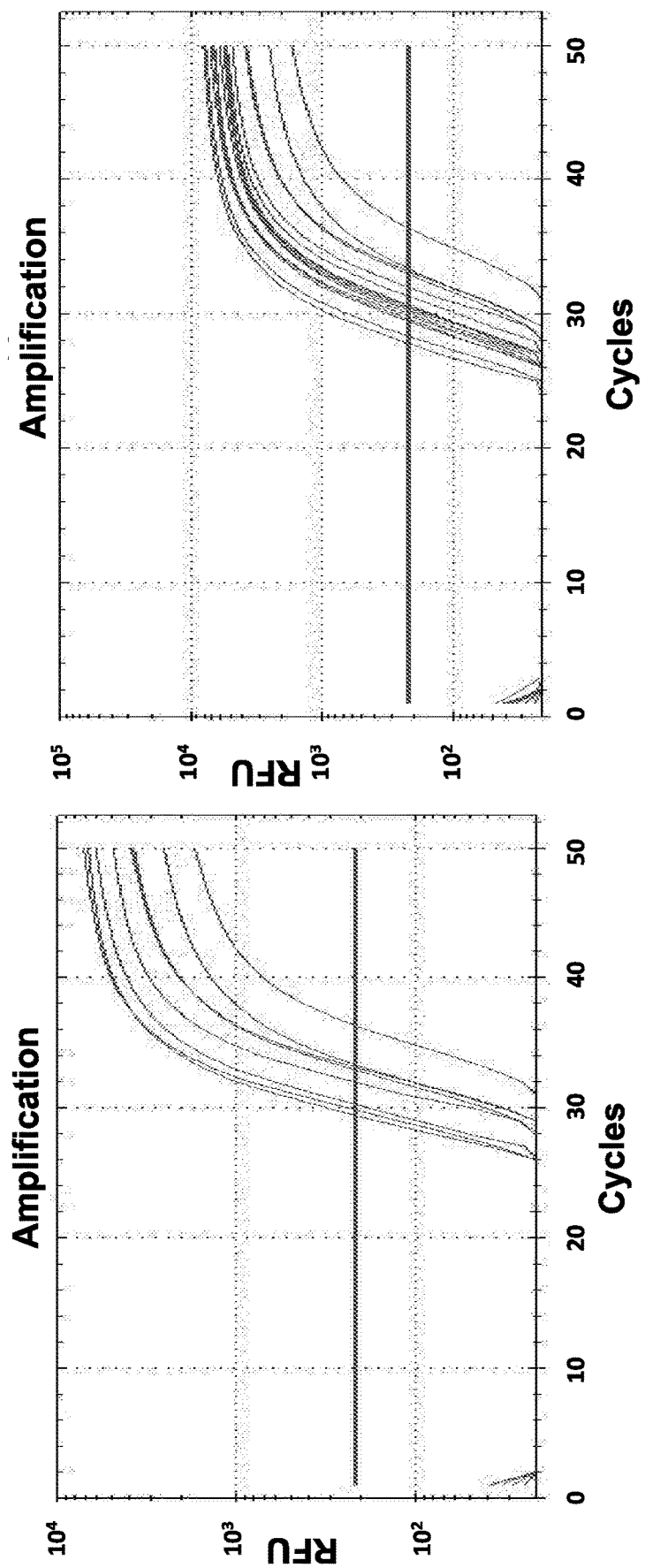
Figure 43. 15 CFU Inoculation of *Escherichia Coli O157:H7* Into Raw Spinach

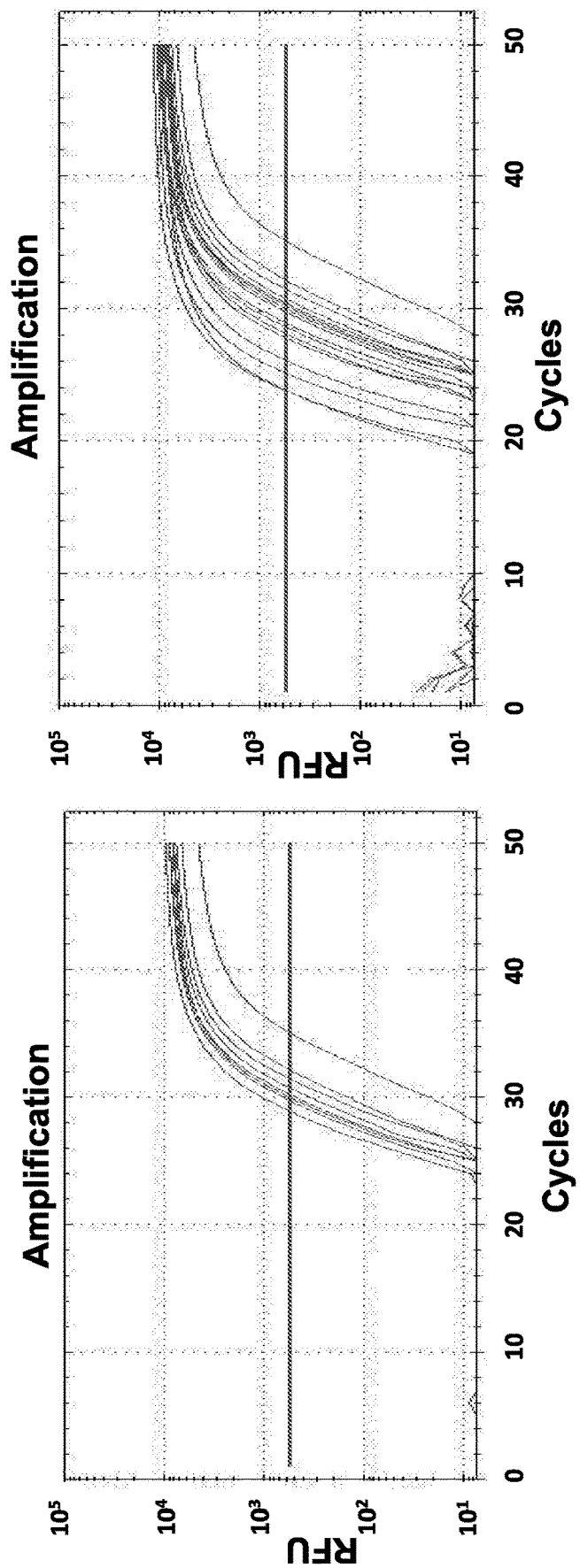
Figure 44. 15 CFU Inoculation of *Listeria Monocytogenes* Into Salmon

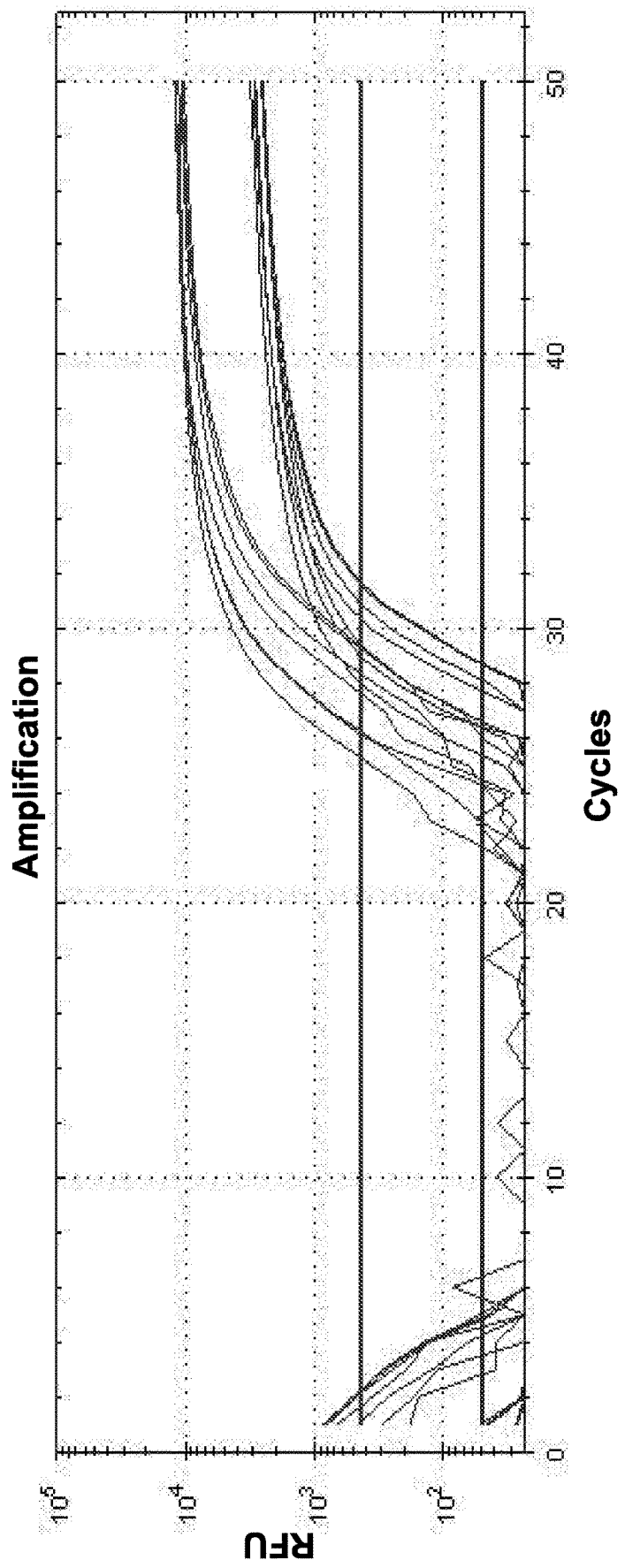
Figure 45. Raw Beef Trim 3 CFU/25 Gram Inoculation *E. Coli* STEC Targets
Polyskope 1.0 detected STX-1, STX-2 and EAE in 7/8 replicates (87.5% recovery)

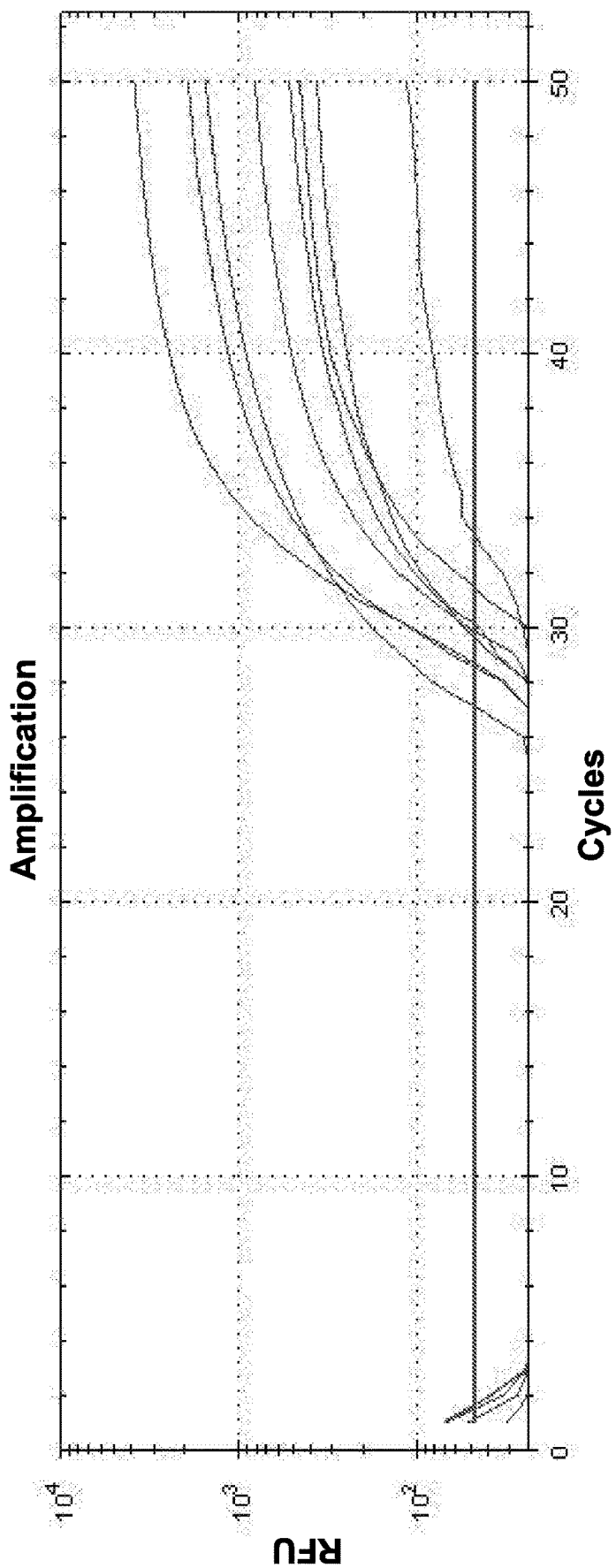
Figure 46. Raw Beef Trim 3 CFU/25 Gram Inoculation *L. monocytogenes* Target
Polyskope 1.0 detected the *L. monocytogenes* target in 8/8 replicates (100% recovery)

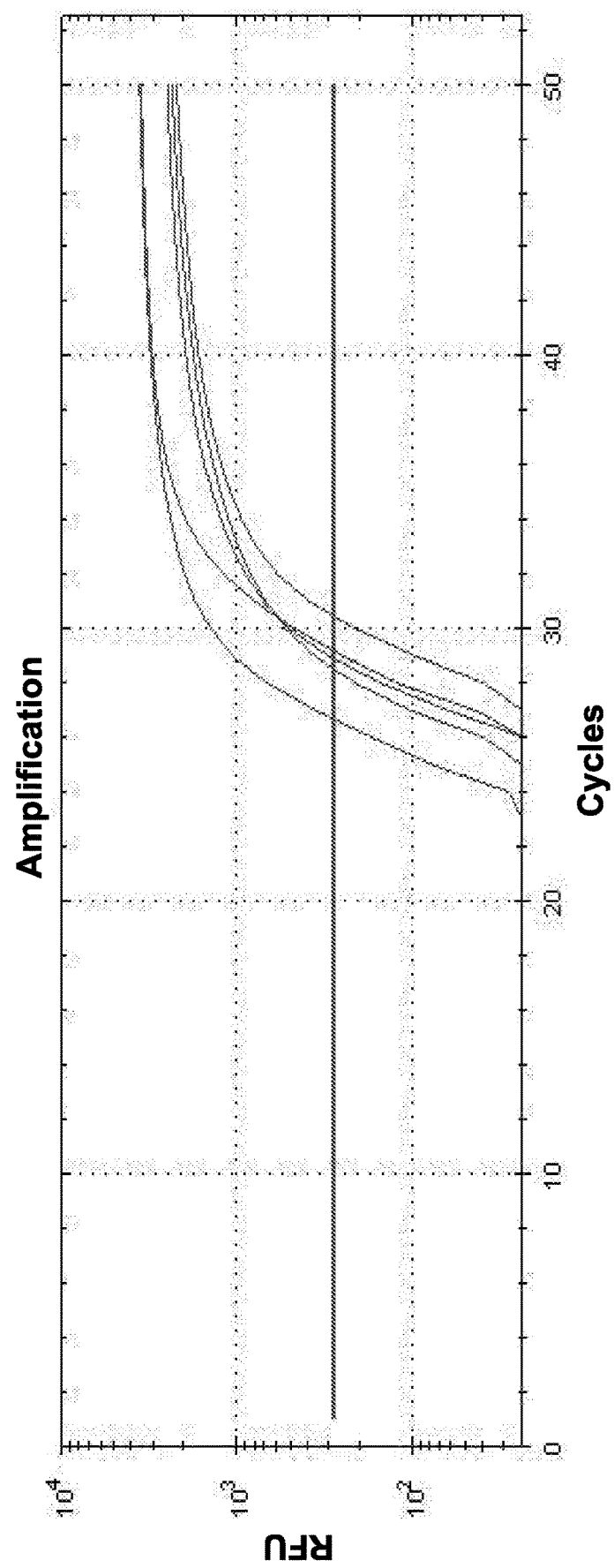
Figure 47. Raw Beef Trim 3 CFU/25 Gram Inoculation S. enterica Target
Polyskope 1.0 detected the S. enterica target in 5/8 replicates (62.5% recovery)

Figure 48. Raw Beef Trim – 3 CFU/25g – Table of Results

| Replicate | STX-1/STX-2 "+/-" | L. monocytogenes "+/-" | S. enterica "+/-" | EAE "+/-" | Internal Control "+/-" |
|---|---|---|---|---|---|
| 1 | + | + | - | + | + |
| 2 | + | + | + | + | + |
| 3 | + | + | + | + | + |
| 4 | + | + | - | + | + |
| 5 | + | + | - | + | + |
| 6 | - | + | + | - | + |
| 7 | + | + | + | + | + |
| 8 | + | + | + | + | + |

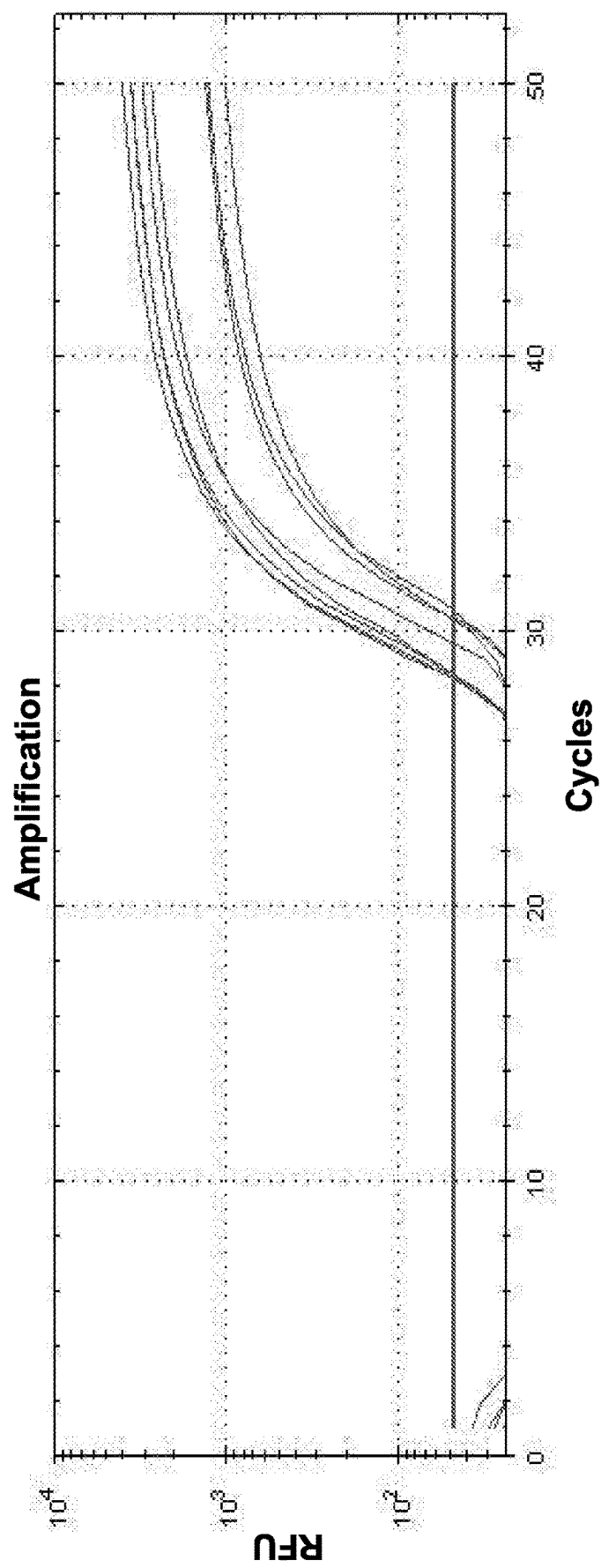
Figure 49. Raw Beef Trim 15 CFU/25 Gram Inoculation *L. monocytogenes* Target
Polyskope 1.0 detected the *L. monocytogenes* target in 8/8 replicates (100% recovery)

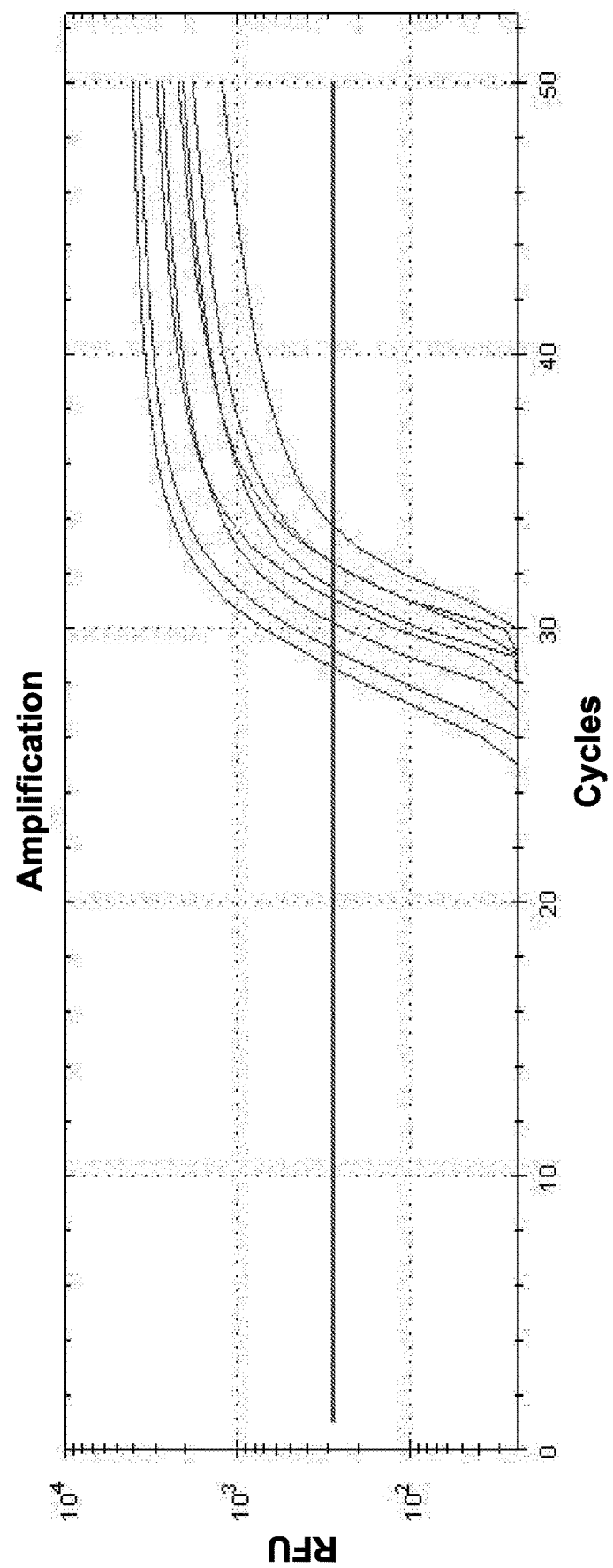
Figure 50. Raw Beef Trim 15 CFU/25 Gram Inoculation *S. enterica* Target Figure 51. Raw Beef Trim – 15 CFU/25g – Table of Results

| Replicate | STX-1/ STX-2 | L. monocytogenes | S. enterica | EAE | Internal Control |
|---|---|---|---|---|---|
| | "+/-" | "+/-" | "+/-" | "+/-" | "+/-" |
| 1 | + | + | + | + | + |
| 2 | + | + | + | + | + |
| 3 | + | + | + | + | + |
| 4 | + | + | + | + | + |
| 5 | + | + | + | + | + |
| 6 | + | + | + | + | + |
| 7 | + | + | + | + | + |
| 8 | + | + | + | + | + |

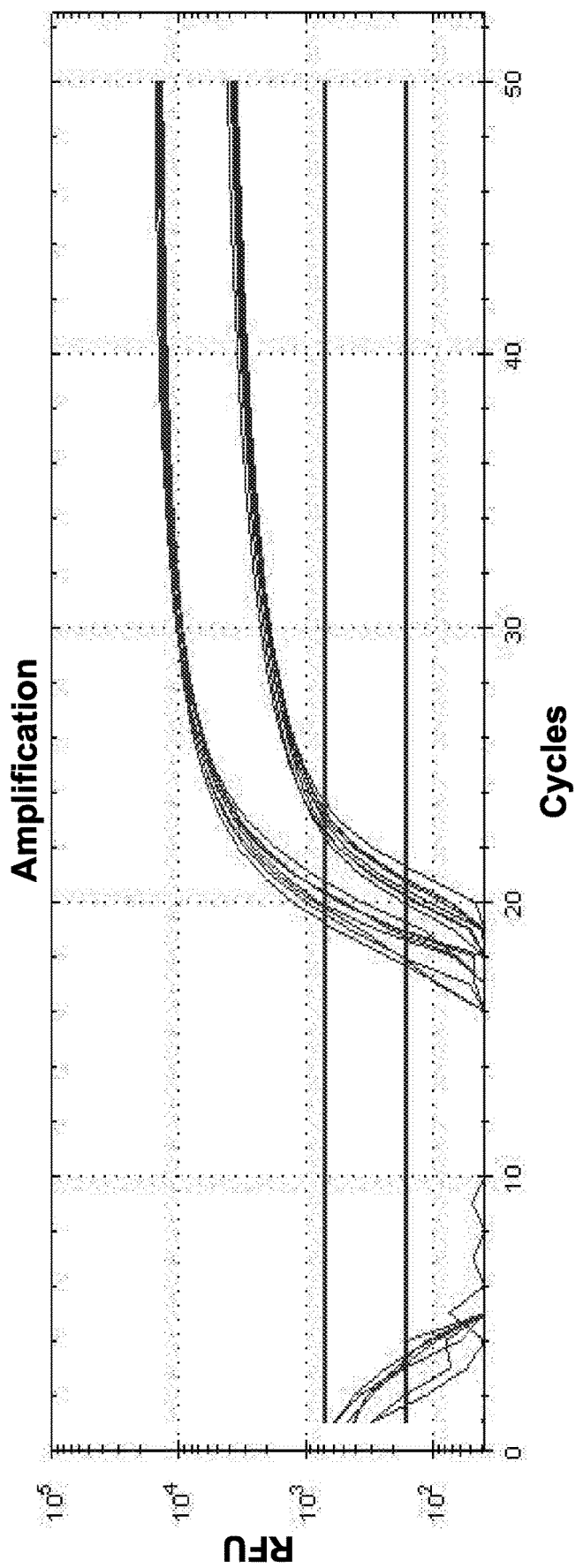
Figure 52. Milk 3 CFU/25 Gram Inoculation E. Coli STEC Targets
Polyskope 1.0 detected STX-1, STX-2 and EAE targets in 8/8 replicates (100% recovery)

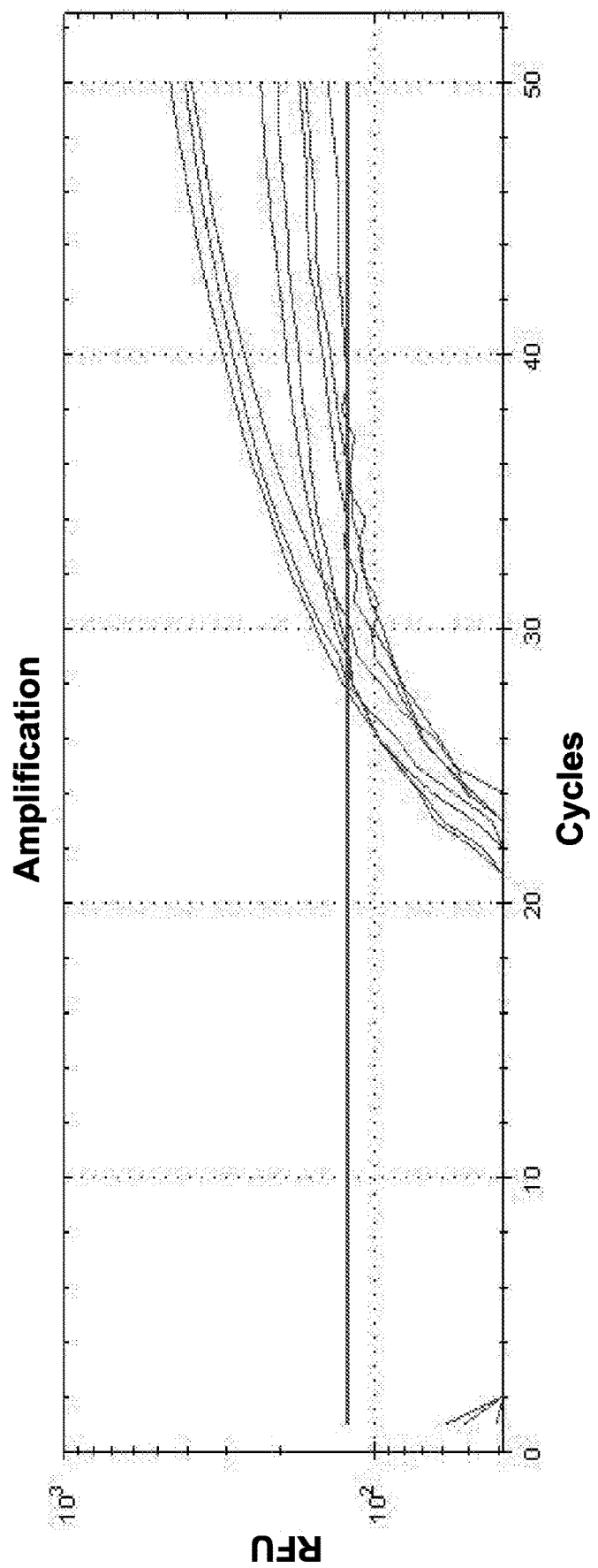

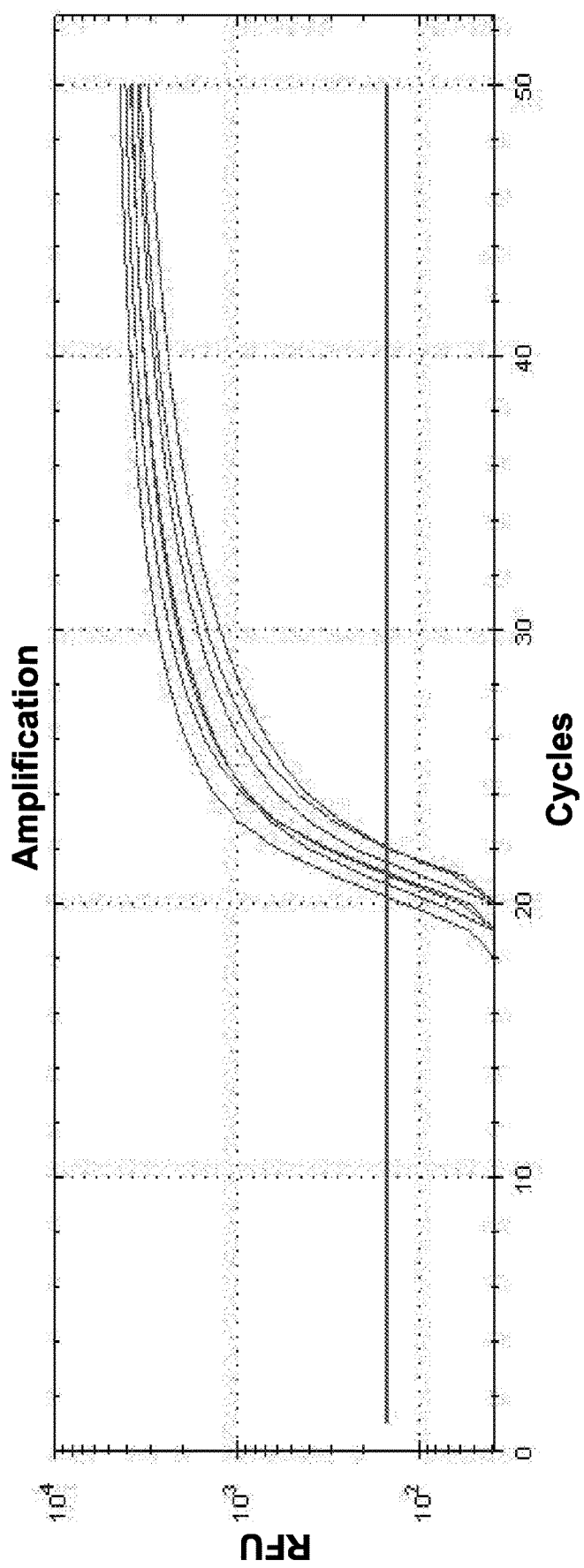
Figure 54. Milk 3 CFU/25 Gram Inoculation *S. enterica* Target

Figure 55. Milk– 3 CFU/25g – Table of Results

| Replicate | STX-1/ STX-2 | L. monocytogenes | S. enterica | EAE | Internal Control |
|---|---|---|---|---|---|
| | "+/-" | "+/-" | "+/-" | "+/-" | "+/-" |
| 1 | + | + | + | + | + |
| 2 | + | + | + | + | + |
| 3 | + | + | + | + | + |
| 4 | + | + | + | + | + |
| 5 | + | + | - | + | + |
| 6 | + | + | + | + | + |
| 7 | + | + | + | + | + |
| 8 | + | + | + | + | + |

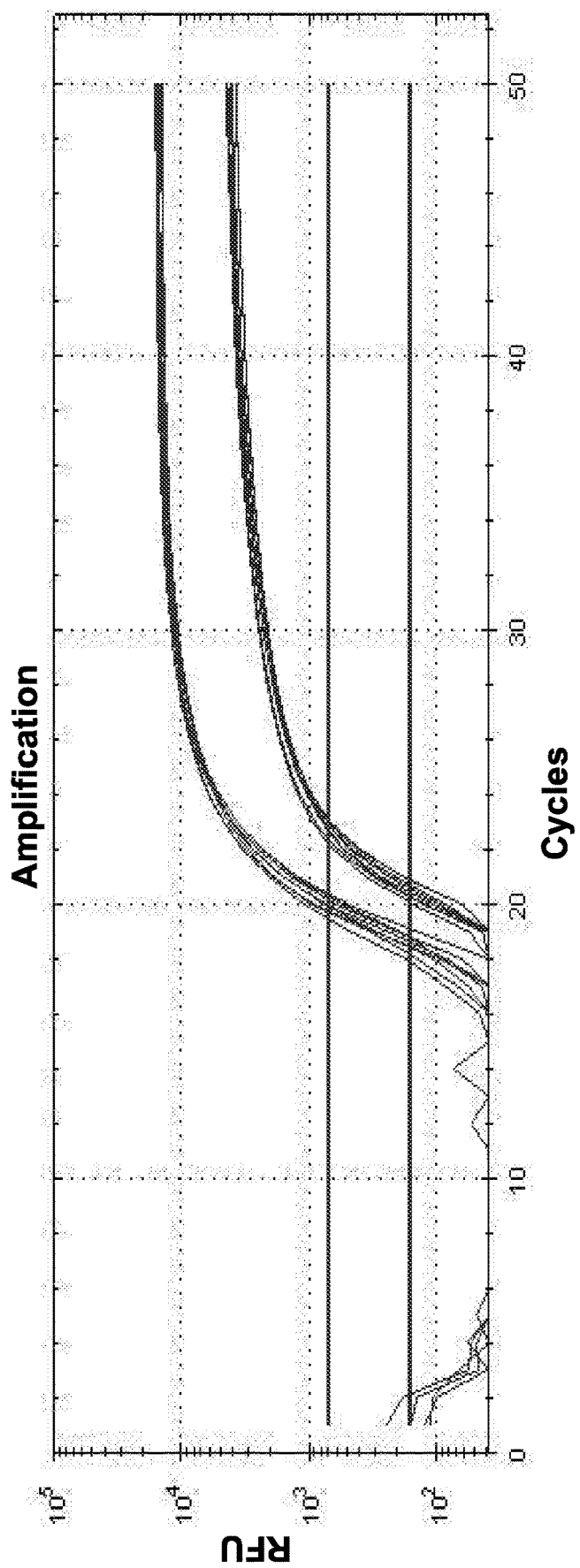
Figure 56. Milk 15 CFU/25 Gram Inoculation
*E. Coli* STEC Targets
Polyskope 1.0 detected the STX-1, STX-2 and EAE targets in 8/8 replicates (100% recovery)

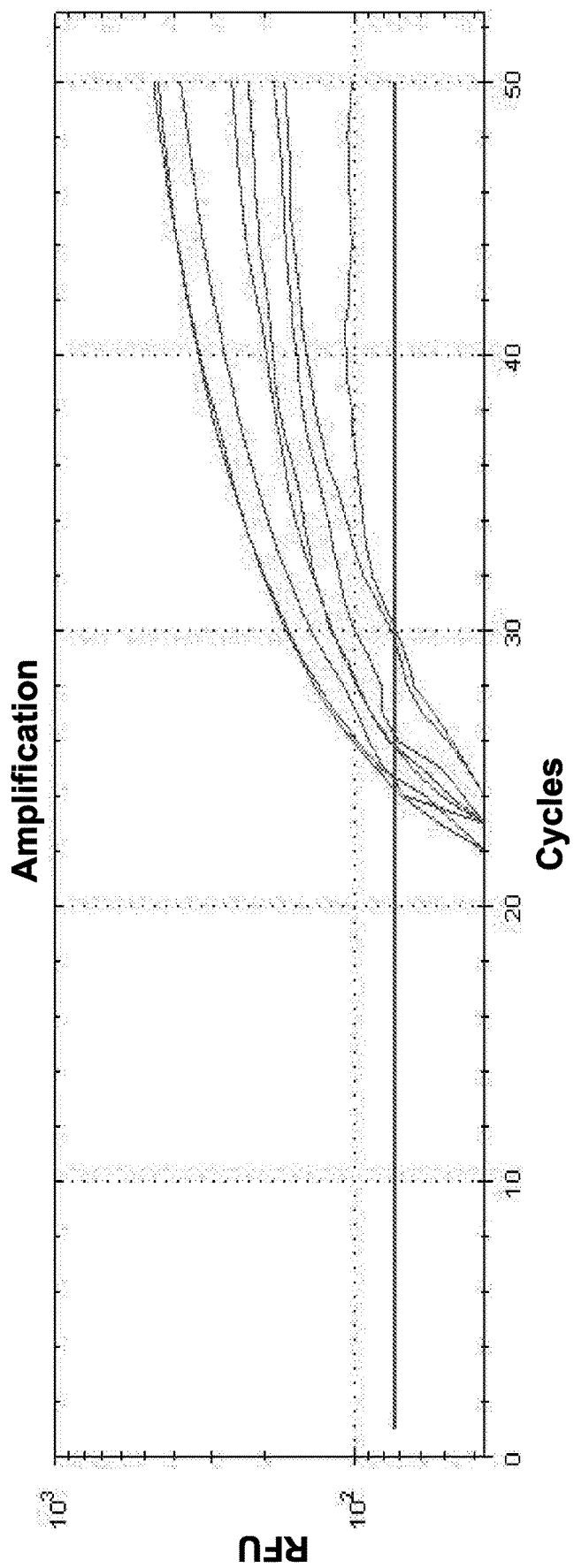
Figure 57. Milk 15 CFU/25 Gram Inoculation *L. monocytogenes* Target
Polyskope 1.0 detected the *L. monocytogenes* target in 8/8 replicates (100% recovery)

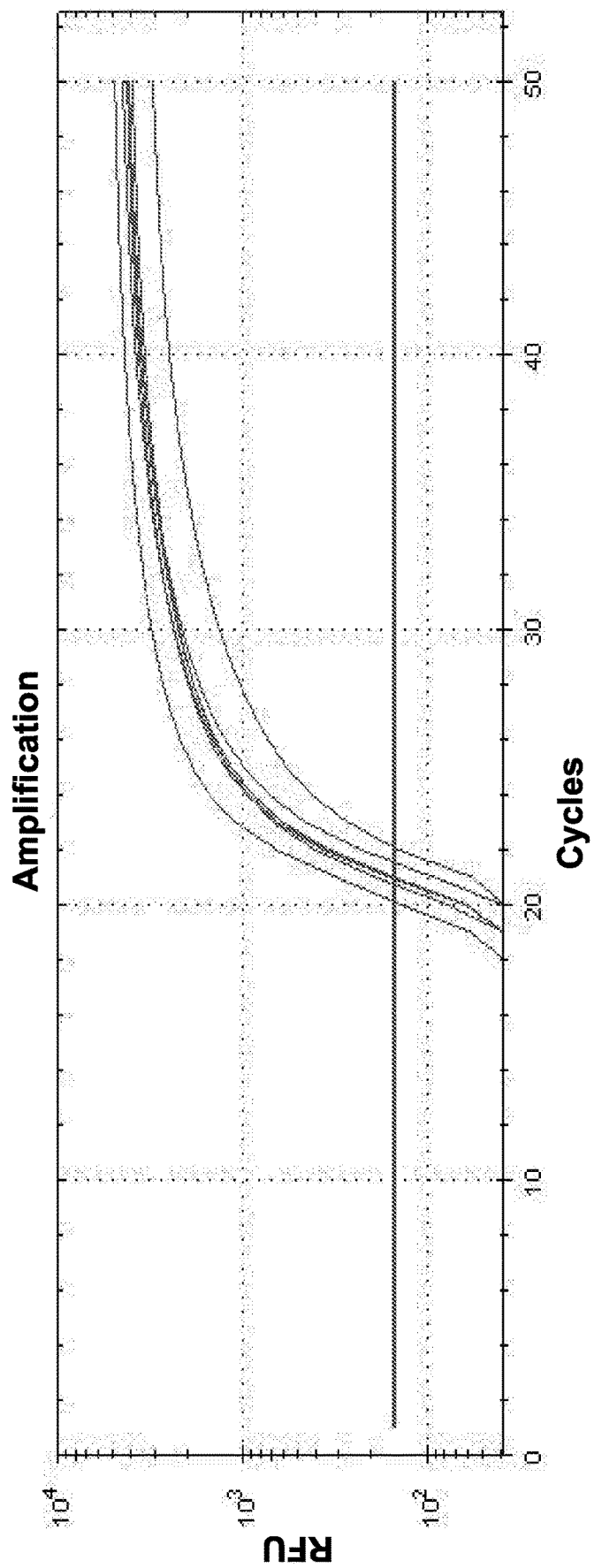
Figure 58. Milk 15 CFU/25 Gram Inoculation S. enterica Target

Figure 59. Milk – 15 CFU/25g – Table of Results

| Replicate | STX-1/STX-2 | L. monocytogenes | S. enterica | EAE | Internal Control |
|---|---|---|---|---|---|
| "+/-" | "+/-" | "+/-" | "+/-" | "+/-" | "+/-" |
| 1 | + | + | + | + | + |
| 2 | + | + | + | + | + |
| 3 | + | + | + | + | + |
| 4 | + | + | + | + | + |
| 5 | + | + | + | + | + |
| 6 | + | + | + | + | + |
| 7 | + | + | + | + | + |
| 8 | + | + | + | + | + |

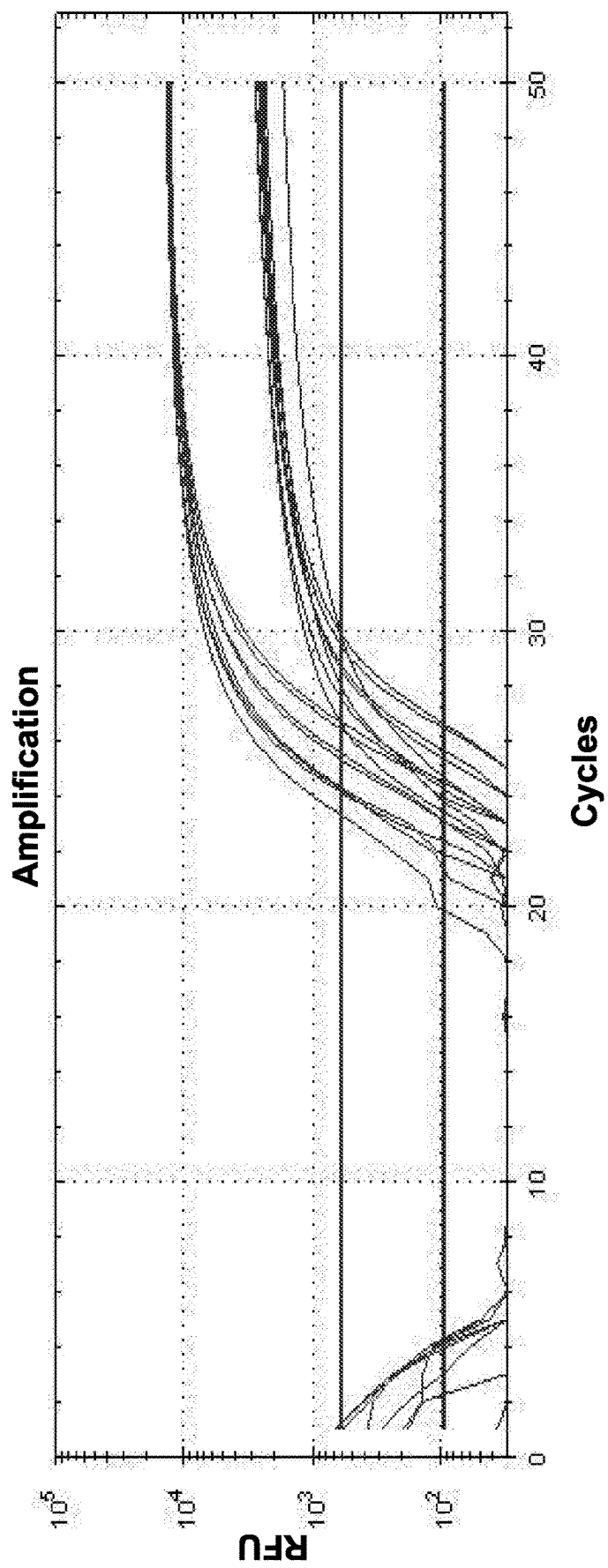
Figure 60. Raw Spinach 15 CFU/25 Gram Inoculation *E. coli* O157 Targets
Polyskope 1.0 detected all *E. coli* O157 targets in 8/8 replicates (100% recovery)

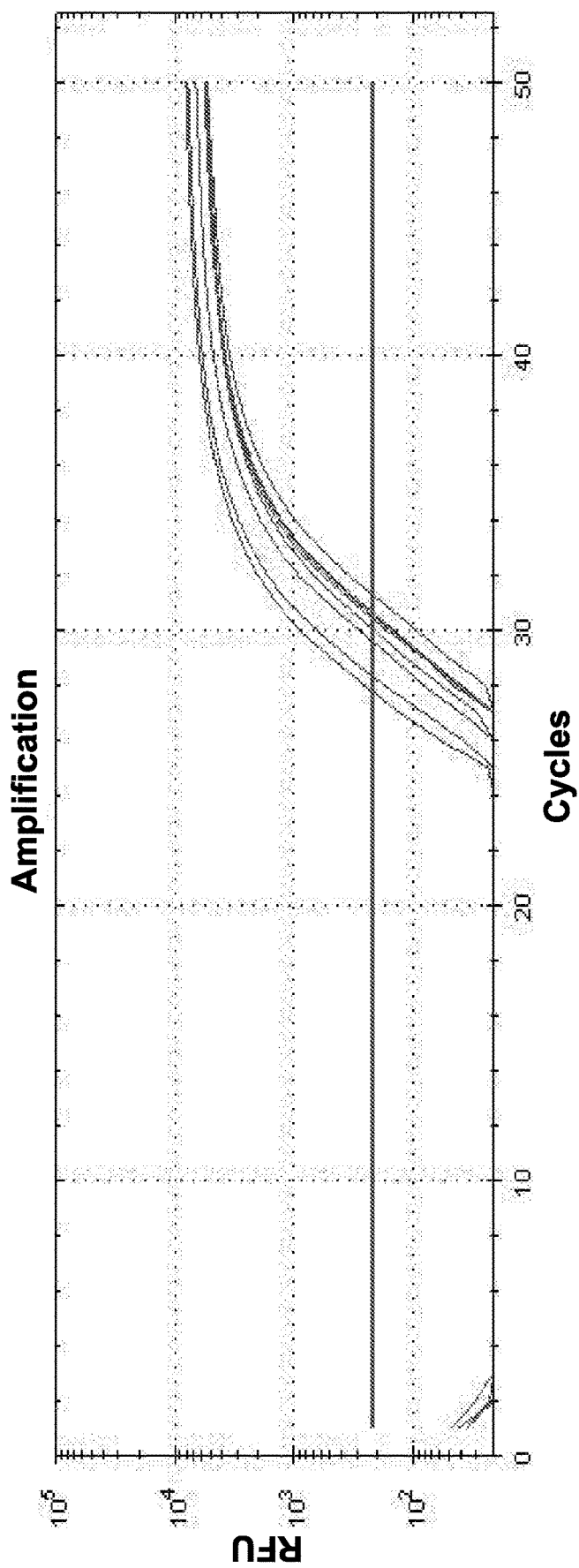
Figure 61. Brie de Meaux 15 CFU/25 Gram Inoculation *L. monocytogenes* Target
Polyskope 1.0 detected the *L. monocytogenes* target in 8/8 replicates (100% recovery)

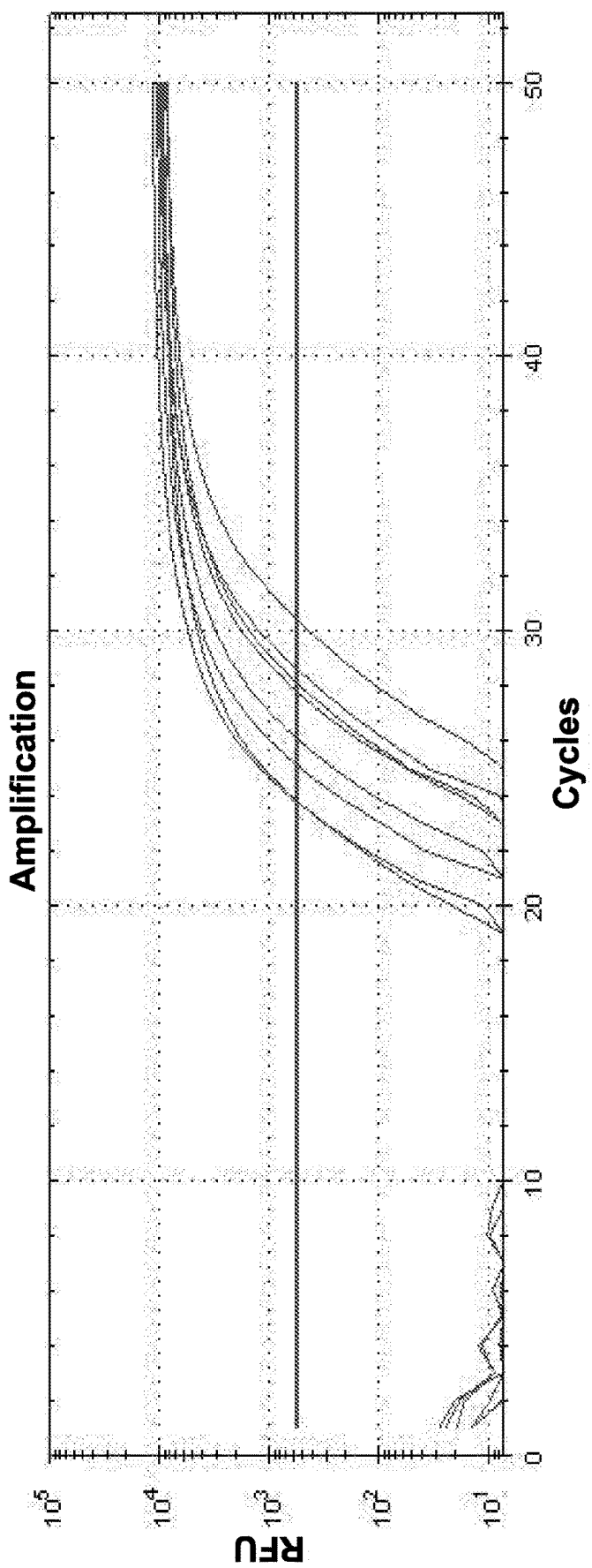
Figure 62. Smoked Salmon 15 CFU/25 Gram Inoculation *L. monocytogenes* Target
Polyskope 1.0 detected the *L. monocytogenes* target in 8/8 replicates (100% recovery)

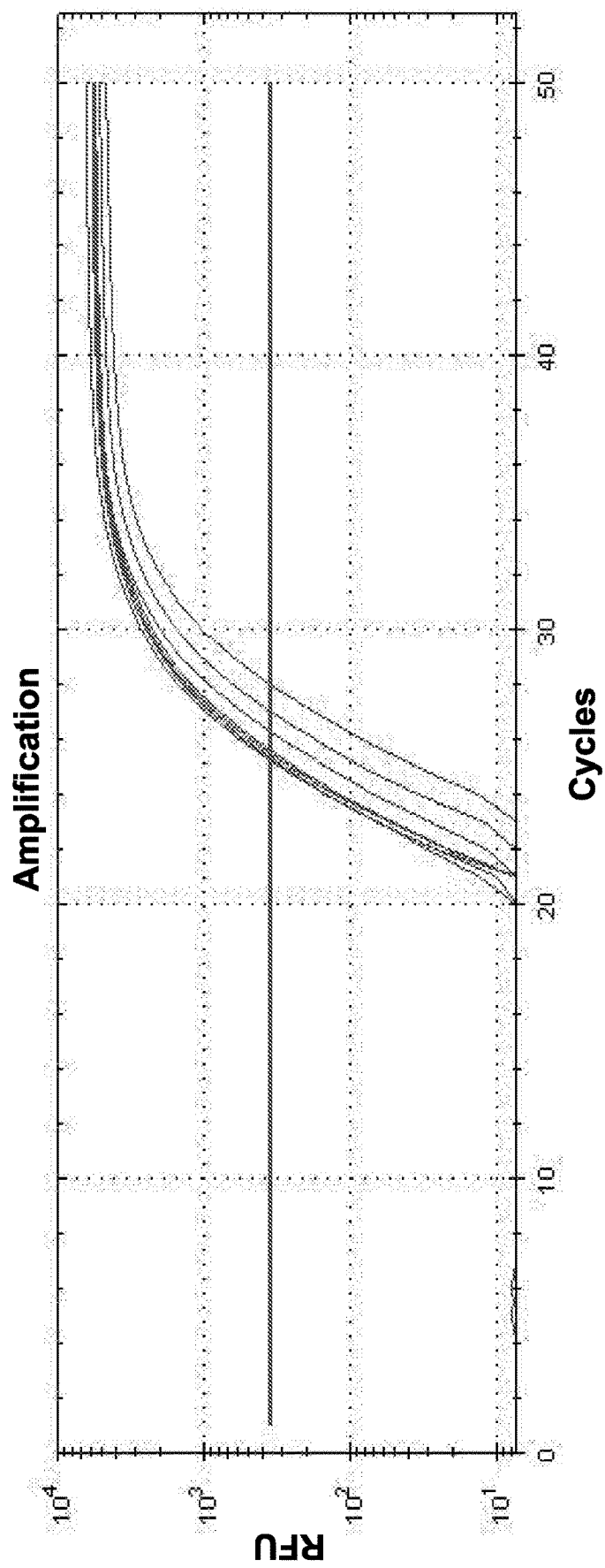

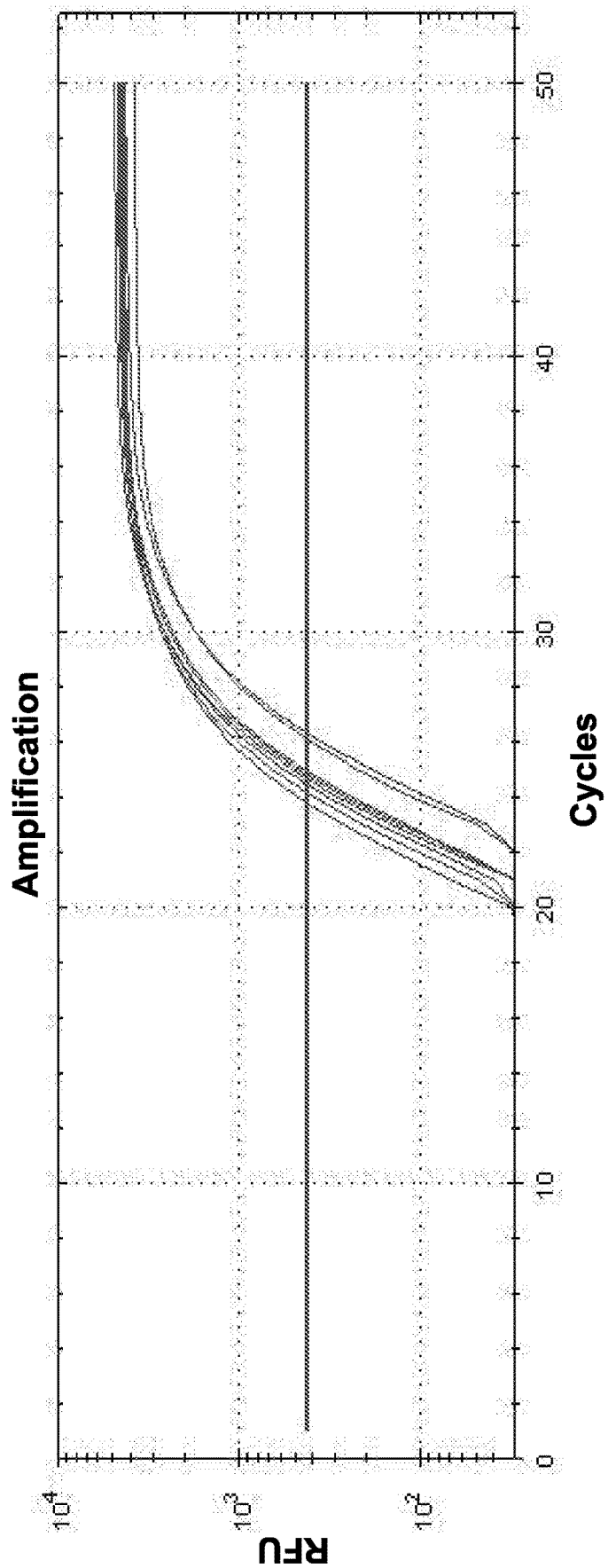
Figure 64. Raw Eggs 15 CFU/25 Gram Inoculation *S. enterica* Target

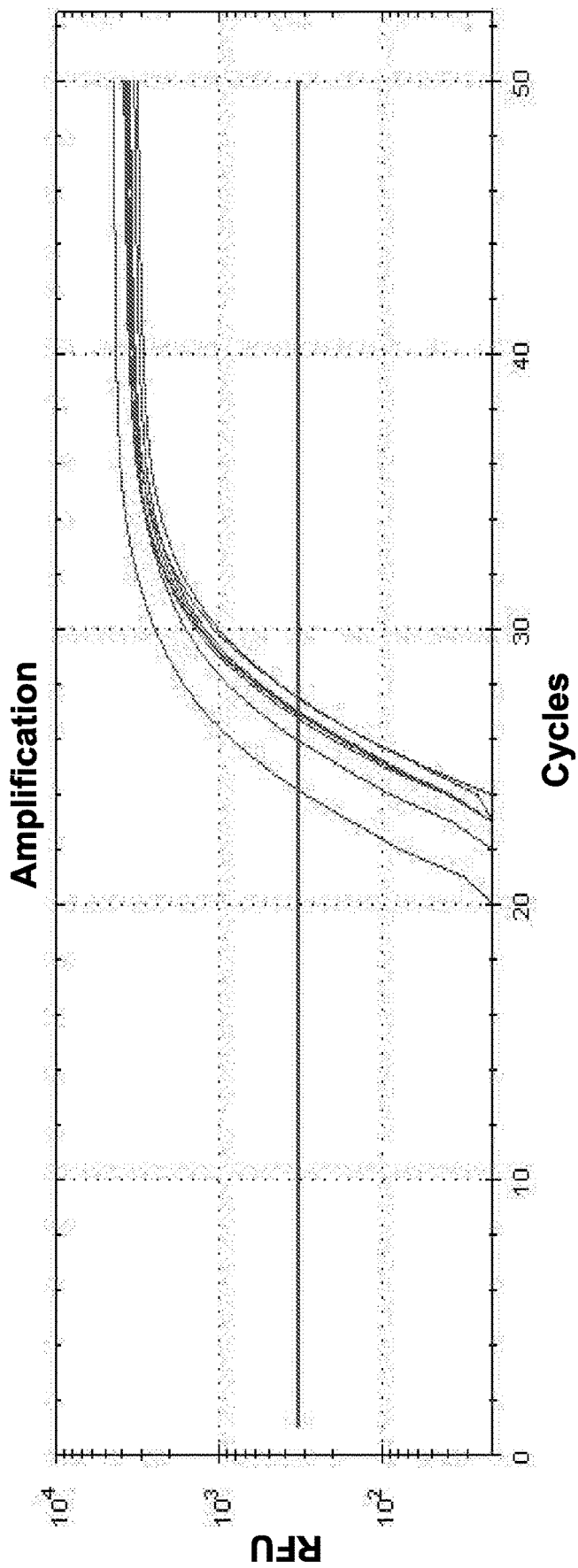
Figure 65. Black Pepper 15 CFU/25 Gram Inoculation *S. enterica* Target

SEQUENCE LISTING

```
<160> NUMBER OF SEQ ID NOS: 19

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agctcatttc acatcgtcca tct                                              23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tccaccattc ccaagctaaa cc                                               22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggcggccaga ttcagcatag                                                  20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 4
gctaccacct tgcacataag c                                        21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcgccattcg ttgactactt c                                        21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acatcgctct tgccacagac t                                        21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cagtgcccgg tgtgacaac                                           19

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gacacgttgc agagtggtat aac                                      23

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgggcatacc atccagagaa                                          20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 10
caccgtggtc cagtttatcg t                                              21

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
ttgccaggta acgcaagaa                                                 19

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
cggaagccaa agcgcac                                                   17

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
tctggattta atgtcgcata gcg                                            23

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
ttccatgaca acggacagc                                                 19

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
atcgggccgc gacttc                                                    16

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 16
tggcgggact attctgaatg ag                                              22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
catctcgctg ctgtctttct tc                                              22

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
actacatcct ctccgcagca cac                                             23

<210> SEQ ID NO 19
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
ttttgtggcg ggactattct gaatgagtac tacatcctct ccgcagcaca ctgcatgcac     60
caagcaaaaa gattcaaagt tagagtaggg gaacgggaca ccgagaagaa agacagcagc    120
gagatggcgc a                                                         131
```

DETECTION OF ONE OR MORE PATHOGENS

CROSS-REFERENCE

This application is a U.S. National Stage filing under 35 U.S.C. § 371 of International Application No. PCT/US2016/026140, filed Apr. 6, 2016, which claims the benefit of U.S. Provisional Patent Application Nos. 62/239,105, filed on Oct. 8, 2015, and 62/144,294 filed on Apr. 7, 2015 which are herein incorporated by reference in their entirety.

SEQUENCE LISTING

The instant application contains a Sequence Listing which has been submitted electronically in ASCII format and is hereby incorporated by reference in its entirety. Said ASCII copy, created on Oct. 29, 2018, is named 48300_701_831_SL.txt and is 8,192 bytes in size.

BACKGROUND

Common pathogens in food are a major cause of food poisoning, and can cause a variety of diseases. These diseases are a serious threat to people's health. Rapid and accurate detection of foodborne pathogens are an effective tool to combat such diseases.

With the development of molecular biology, food inspection, quarantine work and pathogen identification methods have used technological developments such as PCR, and oligonucleotide hybridizing probes, but it remains difficult with current detection methods in molecular biology to simultaneously detect the presence and/or absence and or screen one or more (plurality) pathogens.

No method has been established to sufficiently and reliably detect a plurality of pathogens with the accuracy and precision and within the timeframe of the instant invention. The object of the present invention is to provide methods, kits, and compositions for multiple pathogen detection that can detect contaminating pathogens including but not limited to *Escherichia coli* STEC, *Salmonella* species, and *Listeria monocytogenes*, with high sensitivity comparable, or even superior to official methods, comprising the steps of amplifying a plurality of target genes in a single amplification reaction, and analyzing the same. In other words, the object of the present invention is to provide methods, kits, and compositions for multiple pathogen detection that can detect contaminating pathogens including but not limited to pathogenic *Escherichia coli* STEC, *Salmonella* species, and *Listeria monocytogenes*, by using multiplex PCR with high sensitivity and repeatability.

SUMMARY OF THE DISCLOSURE

Provided herein are methods for detecting the presence and/or absence of the one or more pathogens. In one aspect, the method comprises enriching a sample comprising one or more pathogens in a rich and nonselective media; wherein the rich and nonselective media comprises components to promote the growth of the one or more pathogens; and detecting the presence and/or absence of the one or more pathogens. In some embodiments, the method is performed within a positive total time of about 28 hrs. In some embodiments, the presence and/or absence of at least two pathogens are detected. In some embodiments, the sample comprises a food. In some embodiments, the sample weights a positive amount of less than or equal to about 25 grams by weight. In some embodiments, the sample is suspended in the rich and nonselective media such that the one or more pathogens are isolated from the sample. In some embodiments, the one or more pathogens are isolated from the sample by stomaching. In some embodiments, the sample is stomached for at least about 30 seconds. In some embodiments, the rich and nonselective media comprises *listeria* enrichment broth base with substantially no supplements. In some embodiments, the enrichment media can be media B. In some embodiments, the sample is enriched at a temperature in the range of about 30° C. to about 45° C. In some embodiments, the sample is incubated for a positive amount of time less than or equal to about 24 hours following stomaching. In some embodiments, the one or more pathogen comprises two or more of *Escherichia coli*, *Salmonella*, or *Listeria monocytogenes*. In some embodiments, detecting can comprise one or more of PCR, lectin binding, simple diffusion, lateral diffusion, immunological detection, lateral flow, ELISA or flow through step. In some embodiments, the detecting can be by sequencing. In some embodiments, the nucleic acid is sequenced. In some embodiments, the detecting can be reported by a communication medium. In some embodiment, a result is communicated via a communication medium, for example: an electronic communication medium, email, facsimile, text, video, audio, telegraph, telegram, letter, using a computer processor, or a microprocessor. In some embodiments, the sample is contacted with a lysis buffer at a first temperature and a second temperature, wherein the second temperature is higher than the temperature of the first temperature. In some embodiments, the presence and/or absence of at least two, three, four, five, six, seven, eight, nine, or ten pathogens are detected. In some embodiments, the lysis buffer comprises at least one of: a buffering component; a metal chelating agent; a surfactant; a precipitant; and at least one lysing moiety. In some embodiments, the enriching is performed in less than 1000 ml rich and nonselective media. In some embodiments, the enriching is performed in less than 500 ml rich and nonselective media. In some embodiments, the enriching is performed in 225 ml rich and nonselective media. In some embodiments the rich and nonselective media can comprise, per 1 L of water: between about 5 g/L and about 20 g/L yeast extract; between about 20 g/L and about 50 g/L pancreatic digest of casein; between about 1 g/L and 10 g/L enzymatic digest of soy; between about 1 g/L and about 10 g/L dextrose; between about 1 g/L and about 20 g/L sodium chloride; between about 1 g/L and about 10 g/L dipotassium phosphate; between about 1 g/L and about 10 g/L potassium phosphate; between about 10 g/L and about 30 g/L disodium phosphate; and between about 1 g/L and about 10 g/L sodium pyruvate. In some embodiments the rich and nonselective media can comprise, per 1 L of water between about 5 g/L and about 20 g/L yeast extract. In some embodiments the rich and nonselective media can comprise, per 1 L of water between about 20 g/L and about 50 g/L pancreatic digest of casein. In some embodiments the rich and nonselective media can comprise, per 1 L of water between about 1 g/L and 10 g/L enzymatic digest of soy. In some embodiments the rich and nonselective media can comprise, per 1 L of water between about 1 g/L and about 10 g/L dextrose. In some embodiments the rich and nonselective media can comprise, per 1 L of water between about 1 g/L and about 20 g/L sodium chloride. In some embodiments the rich and nonselective media can comprise, per 1 L of water between about 1 g/L and about 10 g/L dipotassium phosphate. In some embodiments the rich and nonselective media can comprise, per 1 L of water between about 1 g/L and about 10 g/L potassium phosphate. In some embodiments the rich and nonselective media can comprise, per 1 L of water between about 10 g/L and about 30 g/L disodium phosphate. In some embodiments the rich and nonselective media can comprise, per 1 L of water between about 1 g/L and about 10 g/L sodium pyruvate. In some embodiments the rich and nonselective media can comprise, per 1 L of water about 5 g/L of dextrose. In some embodiments the rich and nonselective media can comprise, per 1 L of water about 2.2 g/L of sodium pyruvate. In some embodiments the rich and nonselective media can comprise, per 1 L of water about 12 g/L of yeast extract. In some embodiments the rich and nonselective media can comprise, per 1 L of water about 34 g/L of pancreatic digest of casein. In some embodiments the rich and nonselective media can comprise, per 1 L of water about 6 g/L of enzymatic digest of soy. In some embodiments the rich and nonselective media can comprise, per 1 L of water about 10 g/L sodium chloride. In some embodiments the rich and nonselective media can comprise, per 1 L of water about 5 g/L dipotassium phosphate. In some embodiments the rich and nonselective media can comprise, per 1 L of water about 2.7 g/L potassium phosphate. In some embodiments the rich and nonselective media can comprise, per 1 L of water about 19.2 g/L disodium phosphate.

Provided herein are methods for detecting the presence and/or absence of the one or more pathogens. In one aspect, the method comprises: conducting an amplification with a set of amplification primers on a sample, wherein the amplification primers comprise one or more primer pairs, wherein a first primer of the one or more primer pairs hybridizes to a target nucleic acid sequence of one or more pathogens, and wherein a second primer of the one or more primer pairs hybridizes to a sequence complimentary to the target nucleic acid; and detecting the presence and/or absence of the one or more pathogens. In some embodiments, the method is performed within a positive total time of about 28 hrs. In some embodiments, the presence and/or absence of at least two pathogens are detected. In some embodiments, the sample comprises a food. In some embodiments, the sample weights a positive amount of less than or equal to about 25 grams by weight. In some embodiments, the sample is suspended in the rich and nonselective media such that the one or more pathogens are isolated from the sample. In some embodiments, the one or more pathogens are isolated from the sample by stomaching. In some embodiments, the sample is stomached for at least about 30 seconds. In some embodiments, the rich and nonselective media comprises listeria enrichment broth base with substantially no supplements. In some embodiments, the enrichment media can be media B. In some embodiments, the sample is enriched at a temperature in the range of about 30° C. to about 45° C. In some embodiments, the sample is incubated for a positive amount of time less than or equal to about 24 hours following stomaching. In some embodiments, the nucleic acid is DNA. In some embodiments, the nucleic acid is reverse transcribed from RNA. In some embodiments, the one or more pathogen comprises two or more of *Escherichia coli, Salmonella*, or *Listeria monocytogenes*. In some embodiments, the primer pairs comprise sequences that are at least 80% homologous with the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense; and SEQ ID NO: 9 sense, SEQ ID NO: 10 antisense. In some embodiments, the primer pairs comprise sequences of at least 15 contiguous bases that are at least 80% homologous with the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense; and SEQ ID NO: 9 sense, SEQ ID NO: 10 antisense. In some embodiments, the method further comprises a hybridization of an internal oligonucleotide probe to a sequence within the target sequence or a complement. In some embodiments, wherein the internal oligonucleotide probe does not hybridize to the amplification primers. In some embodiments, the hybridization of the internal oligonucleotide probe to a sequence within the target sequence or a complement thereof is indicative of the presence of the one or more pathogen in the sample. In some embodiments, detecting can comprise one or more of PCR, lectin binding, simple diffusion, lateral diffusion, immunological detection, lateral flow, ELISA or flow through step. In some embodiments, the detecting is by sequencing. In some embodiments, the nucleic acid is sequenced. In some embodiments, the internal oligonucleotide probe comprise sequences that are at least 80/6 homologous with the sequences: SEQ ID NO: 11; SEQ ID NO: 12; SEQ ID NO: 13; SEQ ID NO: 14; and SEQ ID NO: 15. In some embodiments, the internal oligonucleotide probe comprise sequences of at least 15 contiguous bases that are at least 80% homologous with the sequences: SEQ ID NO: 11; SEQ ID NO: 12; SEQ ID NO: 13; SEQ ID NO: 14; and SEQ ID NO: 15. In some embodiments, the internal oligonucleotide probes are labeled at their 5' ends with an energy transfer donor fluorophore and labeled at their 3' ends with an energy transfer acceptor fluorophore. In some embodiments, the detecting is reported by a communication medium. In some embodiment, a result is communicated via a communication medium, for example: an electronic communication medium, email, facsimile, text, video, audio, telegraph, telegram, letter, using a computer processor, or a microprocessor. In some embodiments, the sample is contacted with a lysis buffer at a first temperature and a second temperature, wherein the second temperature is higher than the temperature of the first temperature. In some embodiments, the presence and/or absence of at least two, three, four, five, six, seven, eight, nine, or ten pathogens are detected. In some embodiments, the lysis buffer comprises at least one of: a buffering component; a metal chelating agent; a surfactant; a precipitant; and at least one lysing moiety. In some embodiments, the primer pairs comprise sequences that are at least 80/6 homologous with at least one of the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense, SEQ ID NO: 9 sense; and SEQ ID NO: 10 antisense. In some embodiments, the internal oligonucleotide probe comprises sequences that are at least 80% homologous with at least one of the sequences: SEQ ID NO: 11; SEQ ID NO: 12; SEQ ID NO: 13; SEQ ID NO: 14; and SEQ ID NO: 15. The method of any one of claim 2-50 or 183, wherein a third primer of the one or more primer pairs hybridizes to an internal control nucleic acid sequence, and wherein a fourth primer of the one or more primer pairs hybridizes to a sequence complimentary to the internal control nucleic acid sequence. In some embodiments, the primer pairs further comprise sequences that are at least 80/6 homologous with the sequence SEQ ID NO: 16 sense; and SEQ ID NO: 17 antisense. In some embodiments, the primer pairs comprise sequences of at least 15 contiguous bases that are at least 80/6 homologous with the sequence SEQ ID NO: 16 sense; and SEQ ID NO: 17 antisense. In some embodiments, the internal oligonucleotide probe further comprises sequences that are at least 80/6 homologous with the sequence SEQ ID NO: 18. In some embodiments, the internal oligonucleotide probe comprises sequences of at least 15 contiguous bases that are at least 80% homologous with the sequence SEQ ID NO: 18. In some embodiments, one or more of *Escherichia coli, Salmonella*, or *Listeria monocytogenes* are detected when one or more of *Escherichia coli, Salmonella*, or *Listeria monocytogenes* is inoculated in or on a food product. In some embodiments, the food product is turkey. In some embodiments, the food product is lettuce. In some embodiments, *Escherichia coli* is inoculated at a concentration of at least 0.60 CFU/25 mg. In some embodiments, STX-1 and STX-2 is detected in at least 18/20 replicates. In some embodiments, *E. coli* EAE is detected in at least 18/20 replicates. In some embodiments, *S. enterica* is inoculated at a concentration of at least 0.48 CFU/25 g. In some embodiments, *S. enterica* is detected in at least 20/20 replicates. In some embodiments, *L. monocytogenes* is inoculated at a concentration of at least 1.0 CFU/25 g. In some embodiments, *L. monocytogenes* is detected in at least 9/20 replicates. In some embodiments, *Escherichia coli* is inoculated at a concentration of at least 0.60 CFU/25 mg. In some embodiments, STX-1 and STX-2 is detected in at least 12/20 replicates. In some embodiments, *E. coli* EAE is detected in at least 12/20 replicates. In some embodiments, *S. enterica* is inoculated at a concentration of at least 0.48 CFU/25 g. In some embodiments, *S. enterica* is detected in at least 6/20 replicates. In some embodiments, *L. monocytogenes* is inoculated at a concentration of at least 1.0 CFU/25 g. In some embodiments, *L. monocytogenes* is detected in at least 11/20 replicates. In some embodiments, the enriching is performed in less than 1000 ml rich and nonselective media. In some embodiments, the enriching is performed in less than 500 ml rich and nonselective media. In some embodiments, the enriching is performed in 225 ml rich and nonselective media. In some embodiments the rich and nonselective media can comprise, per 1 L of water: between about 5 g/L and about 20 g/L yeast extract; between about 20 g/L and about 50 g/L pancreatic digest of casein; between about 1 g/L and 10 g/L enzymatic digest of soy; between about 1 g/L and about 10 g/L dextrose; between about 1 g/L and about 20 g/L sodium chloride; between about 1 g/L and about 10 g/L dipotassium phosphate; between about 1 g/L and about 10 g/L potassium phosphate; between about 10 g/L and about 30 g/L disodium phosphate; and between about 1 g/L and about 10 g/L sodium pyruvate. In some embodiments the rich and nonselective media can comprise, per 1 L of water between about 5 g/L and about 20 g/L yeast extract. In some embodiments the rich and nonselective media can comprise, per 1 L of water between about 20 g/L and about 50 g/L pancreatic digest of casein. In some embodiments the rich and nonselective media can comprise, per 1 L of water between about 1 g/L and 10 g/L enzymatic digest of soy. In some embodiments the rich and nonselective media can comprise, per 1 L of water between about 1 g/L and about 10 g/L dextrose. In some embodiments the rich and nonselective media can comprise, per 1 L of water between about 1 g/L and about 20 g/L sodium chloride. In some embodiments the rich and nonselective media can comprise, per 1 L of water between about 1 g/L and about 10 g/L dipotassium phosphate. In some embodiments the rich and nonselective media can comprise, per 1 L of water between about 1 g/L and about 10 g/L potassium phosphate. In some embodiments the rich and nonselective media can comprise, per 1 L of water between about 10 g/L and about 30 g/L disodium phosphate. In some embodiments the rich and nonselective media can comprise, per 1 L of water between about 1 g/L and about 10 g/L sodium pyruvate. In some embodiments the rich and nonselective media can comprise, per 1 L of water about 5 g/L of dextrose. In some embodiments the rich and nonselective media can comprise, per 1 L of water about 2.2 g/L of sodium pyruvate. In some embodiments the rich and nonselective media can comprise, per 1 L of water about 12 g/L of yeast extract. In some embodiments the rich and nonselective media can comprise, per 1 L of water about 34 g/L of pancreatic digest of casein. In some embodiments the rich and nonselective media can comprise, per 1 L of water about 6 g/L of enzymatic digest of soy. In some embodiments the rich and nonselective media can comprise, per 1 L of water about 10 g/L sodium chloride. In some embodiments the rich and nonselective media can comprise, per 1 L of water about 5 g/L dipotassium phosphate. In some embodiments the rich and nonselective media can comprise, per 1 L of water about 2.7 g/L potassium phosphate. In some embodiments the rich and nonselective media can comprise, per 1 L of water about 19.2 g/L disodium phosphate.

Provided herein are methods for detecting the presence and/or absence of the one or more pathogens. In one aspect, the method comprises conducting a first sample lysis and a second sample lysis on a sample or a portion thereof, wherein the second sample lysis is performed at a temperature higher than the temperature of the first sample lysis, thereby forming a lysed sample conducting an amplification with a set of amplification primers on the lysed sample, wherein the amplification primers comprise one or more primer pairs, wherein a first primer of the one or more primer pairs hybridizes to a target nucleic acid sequence of one or more pathogens, and wherein a second primer of the one or more primer pairs hybridizes to a sequence complimentary to the target nucleic acid; and detecting the presence and/or absence of the one or more pathogens. In some embodiments, the method is performed within a positive total time of about 28 hrs. In some embodiments, the presence and/or absence of at least two pathogens are detected. In some embodiments, the sample comprises a food. In some embodiments, the sample weights a positive amount of less than or equal to about 25 grams by weight. In some embodiments, the sample is suspended in the rich and nonselective media such that the one or more pathogens are isolated from the sample. In some embodiments, the one or more pathogens are isolated from the sample by stomaching. In some embodiments, the sample is stomached for at least about 30 seconds. In some embodiments, the rich and nonselective media comprises listeria enrichment broth base with substantially no supplements. In some embodiments, the enrichment media can be media B. In some embodiments, the sample is enriched at a temperature in the range of about 30° C. to about 45° C. In some embodiments, the sample is incubated for a positive amount of time less than or equal to about 24 hours following stomaching. In some embodiments, lysing comprises incubating the sample with a lysis buffer. In some embodiments, the lysis buffer comprises: a buffering component; a metal chelating agent; a surfactant; a precipitant; and/or at least two lysing moieties. In some embodiments, the buffering component comprises tris (hydroxymethyl) aminomethane (TRIS). In some embodiments, tris (hydroxymethyl) aminomethane (TRIS) is present at a concentration in the range of about 60 mM to about 100 mM. In some embodiments, the metal chelating agent comprises ethylenediaminetetraacetic acid (EDTA). In some embodiments, ethylenediaminetetraacetic acid (EDTA) is present at a concentration in the range of about 1 mM to about 18 mM. the surfactant comprises polyethylene glycol p-(1,1,3,3-tetramethylbutyl)-phenyl ether (Triton-X-100). In some embodiments, polyethylene glycol p-(1,1,3,3-tetramethylbutyl)-phenyl ether (Triton-X-100) is present at a concentration in the range of about 0.1% to about 10%. In some embodiments, the precipitant comprises proteinase K. In some embodiments, proteinase K is present at a concentration in the range of about 17.5% to about 37.5%. In some embodiments, the lysing moiety comprises a lysis bead. In some embodiments, the lysis bead comprises 100 µm zirconium lysis beads. In some embodiments, the 100 µm zirconium lysis beads are present at a concentration in the range of about 0.1 grams/ml to about 2.88 grams/ml. In some embodiments, the lysing moiety comprises lysozyme. In some embodiments, the lysozyme is present at a concentration in the range of about 10 mg/ml to about 30 mg/ml. In some embodiments, the first sample lysis the sample is incubated with the lysis buffer in the range of about 5 minutes to about 25 minutes. In some embodiments, the first sample lysis the sample is incubated with the lysis buffer while shaking in the range of about 1200 RPM to about 1400 RPM. In some embodiments, the first sample lysis the sample is incubated with the lysis buffer in the range of about 45° C. to about 85° C. In some embodiments, the second sample lysis the sample is incubated with the lysis buffer in the range of about 5 minutes to about 15 minutes. In some embodiments, the second sample lysis the sample is incubated with the lysis buffer in the range of about 85° C. to about 105° C. In some embodiments, the second sample lysis the sample is incubated with the lysis buffer while shaking in the range of about 1200 RPM to about 1400 RPM. In some embodiments, the nucleic acid is DNA. In some embodiments, the nucleic acid is reverse transcribed from RNA. In some embodiments, the one or more pathogen comprises two or more of *Escherichia coli*, *Salmonella*, or *Listeria monocytogenes*. In some embodiments, the primer pairs comprise sequences that are at least 80/6 homologous with the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense; and SEQ ID NO: 9 sense, SEQ ID NO: 10 antisense. In some embodiments, the primer pairs comprise sequences of at least 15 contiguous bases that are at least 80% homologous with the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense; and SEQ ID NO: 9 sense, SEQ ID NO: 10 antisense. In some embodiments, the method further comprises a hybridization of an internal oligonucleotide probe to a sequence within the target sequence or a complement. In some embodiments, wherein the internal oligonucleotide probe does not hybridize to the amplification primers. In some embodiments, the hybridization of the internal oligonucleotide probe to a sequence within the target sequence or a complement thereof is indicative of the presence of the one or more pathogen in the sample. In some embodiments, detecting can comprise one or more of PCR, lectin binding, simple diffusion, lateral diffusion, immunological detection, lateral flow, ELISA or flow through step. In some embodiments, the detecting is by sequencing, In some embodiments, the nucleic acid is sequenced. In some embodiments, the internal oligonucleotide probe comprise sequences that are at least 80/6 homologous with the sequences: SEQ ID NO: 11; SEQ ID NO: 12; SEQ ID NO: 13; SEQ ID NO: 14; and SEQ ID NO: 15. In some embodiments, the internal oligonucleotide probe comprise sequences of at least 15 contiguous bases that are at least 80% homologous with the sequences: SEQ ID NO: 11; SEQ ID NO: 12; SEQ ID NO: 13; SEQ ID NO: 14; and SEQ ID NO: 15. In some embodiments, the internal oligonucleotide probes are labeled at their 5' ends with an energy transfer donor fluorophore and labeled at their 3' ends with an energy transfer acceptor fluorophore. In some embodiments, the detecting is reported by a communication medium. In some embodiment, a result is communicated via a communication medium, for example: an electronic communication medium, email, facsimile, text, video, audio, telegraph, telegram, letter, using a computer processor, or a microprocessor. In some embodiments, the sample is contacted with a lysis buffer at a first temperature and a second temperature, wherein the second temperature is higher than the temperature of the first temperature. In some embodiments, the presence and/or absence of at least two, three, four, five, six, seven, eight, nine, or ten pathogens are detected. In some embodiments, the lysis buffer comprises at least one of: a buffering component; a metal chelating agent; a surfactant; a precipitant; and at least one lysing moiety. In some embodiments, the primer pairs comprise sequences that are at least 80% homologous with at least one of the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense, SEQ ID NO: 9 sense; and SEQ ID NO: 10 antisense. In some embodiments, the internal oligonucleotide probe comprise sequences that are at least 80/6 homologous with at least one of the sequences: SEQ ID NO: 11; SEQ ID NO: 12; SEQ ID NO: 13; SEQ ID NO: 14; and SEQ ID NO: 15. The method of any one of claim 2-50 or 183, wherein a third primer of the one or more primer pairs hybridizes to an internal control nucleic acid sequence, and wherein a fourth primer of the one or more primer pairs hybridizes to a sequence complimentary to the internal control nucleic acid sequence. In some embodiments, the primer pairs further comprise sequences that are at least 80/6 homologous with the sequence SEQ ID NO: 16 sense; and SEQ ID NO: 17 antisense. In some embodiments, the primer pairs comprise sequences of at least 15 contiguous bases that are at least 80/6 homologous with the sequence SEQ ID NO: 16 sense; and SEQ ID NO: 17 antisense. In some embodiments, the internal oligonucleotide probe further comprise sequences that are at least 80% homologous with the sequence SEQ ID NO: 18. In some embodiments, the internal oligonucleotide probe comprise sequences of at least 15 contiguous bases that are at least 80% homologous with the sequence SEQ ID NO: 18. In some embodiments, one or more of *Escherichia coli*, *Salmonella*, or *Listeria monocytogenes* are detected when one or more of *Escherichia coli*, *Salmonella*, or *Listeria monocytogenes* is inoculated in or on a food product. In some embodiments, the food product is turkey. In some embodiments, the food product is lettuce. In some embodiments, *Escherichia coli* is inoculated at a concentration of at least 0.60 CFU/25 mg. In some embodiments, STX-1 and STX-2 is detected in at least 18/20 replicates. In some embodiments, *E. coli* EAE is detected in at least 18/20 replicates. In some embodiments, *S. enterica* is inoculated at a concentration of at least 0.48 CFU/25 g. In some embodiments, *S. enterica* is detected in at least 20/20 replicates. In some embodiments, *L. monocytogenes* is inoculated at a concentration of at least 1.0 CFU/25 g. In some embodiments, *L. monocytogenes* is detected in at least 9/20 replicates. In some embodiments, *Escherichia coli* is inoculated at a concentration of at least 0.60 CFU/25 mg. In some embodiments, STX-1 and STX-2 is detected in at least 12/20 replicates. In some embodiments, *E. coli* EAE is detected in at least 12/20 replicates. In some embodiments, *S. enterica* is inoculated at a concentration of at least 0.48 CFU/25 g. In some embodiments, *S. enterica* is detected in at least 6/20 replicates. In some embodiments, *L. monocytogenes* is inoculated at a concentration of at least 1.0 CFU/25 g. In some embodiments, *L. monocytogenes* is detected in at least 11/20 replicates. In some embodiments, the enriching is performed in less than 1000 ml rich and nonselective media. In some embodiments, the enriching is performed in less than 500 ml rich and nonselective media. In some embodiments, the enriching is performed in 225 ml rich and nonselective media. In some embodiments the rich and nonselective media can comprise, per 1 L of water: between about 5 g/L and about 20 g/L yeast extract; between about 20 g/L and about 50 g/L pancreatic digest of casein; between about 1 g/L and 10 g/L enzymatic digest of soy; between about 1 g/L and about 10 g/L dextrose; between about 1 g/L and about 20 g/L sodium chloride; between about 1 g/L and about 10 g/L dipotassium phosphate; between about 1 g/L and about 10 g/L potassium phosphate; between about 10 g/L and about 30 g/L disodium phosphate; and between about 1 g/L and about 10 g/L sodium pyruvate. In some embodiments the rich and nonselective media can comprise, per 1 L of water between about 5 g/L and about 20 g/L yeast extract. In some embodiments the rich and nonselective media can comprise, per 1 L of water between about 20 g/L and about 50 g/L pancreatic digest of casein. In some embodiments the rich and nonselective media can comprise, per 1 L of water between about 1 g/L and 10 g/L enzymatic digest of soy. In some embodiments the rich and nonselective media can comprise, per 1 L of water between about 1 g/L and about 10 g/L dextrose. In some embodiments the rich and nonselective media can comprise, per 1 L of water between about 1 g/L and about 20 g/L sodium chloride. In some embodiments the rich and nonselective media can comprise, per 1 L of water between about 1 g/L and about 10 g/L dipotassium phosphate. In some embodiments the rich and nonselective media can comprise, per 1 L of water between about 1 g/L and about 10 g/L potassium phosphate. In some embodiments the rich and nonselective media can comprise, per 1 L of water between about 10 g/L and about 30 g/L disodium phosphate. In some embodiments the rich and nonselective media can comprise, per 1 L of water between about 1 g/L and about 10 g/L sodium pyruvate. In some embodiments the rich and nonselective media can comprise, per 1 L of water about 5 g/L of dextrose. In some embodiments the rich and nonselective media can comprise, per 1 L of water about 2.2 g/L of sodium pyruvate. In some embodiments the rich and nonselective media can comprise, per 1 L of water about 12 g/L of yeast extract. In some embodiments the rich and nonselective media can comprise, per 1 L of water about 34 g/L of pancreatic digest of casein. In some embodiments the rich and nonselective media can comprise, per 1 L of water about 6 g/L of enzymatic digest of soy. In some embodiments the rich and nonselective media can comprise, per 1 L of water about 10 g/L sodium chloride. In some embodiments the rich and nonselective media can comprise, per 1 L of water about 5 g/L dipotassium phosphate. In some embodiments the rich and nonselective media can comprise, per 1 L of water about 2.7 g/L potassium phosphate. In some embodiments the rich and nonselective media can comprise, per 1 L of water about 19.2 g/L disodium phosphate.

Provided herein are methods for detecting the presence and/or absence of the one or more pathogens. In one aspect, the method comprises: enriching a sample comprising one or more pathogens in a rich and nonselective media; wherein the rich and nonselective media comprises components to promote the growth of the one or more pathogens; conducting a first sample lysis and a second sample lysis on the enriched sample or a portion thereof, wherein the second sample lysis is performed at a temperature higher than the temperature of the first sample lysis, thereby forming a lysed sample; conducting an amplification with a set of amplification primers on the lysed sample, wherein the amplification primers comprise one or more primer pairs, wherein a first primer of the one or more primer pairs hybridizes to a target nucleic acid sequence of the one or more pathogens, and wherein a second primer of the one or more primer pairs hybridizes to a sequence complimentary to the target nucleic acid; and detecting the presence and/or absence of the one or more pathogens. In some embodiments, the method is performed within a positive total time of about 28 hrs. In some embodiments, the presence and/or absence of at least two pathogens are detected. In some embodiments, the sample comprises a food. In some embodiments, the sample weights a positive amount of less than or equal to about 25 grams by weight. In some embodiments, the sample is suspended in the rich and nonselective media such that the one or more pathogens are isolated from the sample. In some embodiments, the one or more pathogens are isolated from the sample by stomaching. In some embodiments, the sample is stomached for at least about 30 seconds. In some embodiments, the rich and nonselective media comprises *listeria* enrichment broth base with substantially no supplements. In some embodiments, the enrichment media can be media B. In some embodiments, the sample is enriched at a temperature in the range of about 30° C. to about 45° C. In some embodiments, the sample is incubated for a positive amount of time less than or equal to about 24 hours following stomaching. In some embodiments, lysing comprises incubating the sample with a lysis buffer. In some embodiments, the lysis buffer comprises: a buffering component; a metal chelating agent; a surfactant; a precipitant; and/or at least two lysing moieties. In some embodiments, the buffering component comprises tris (hydroxymethyl) aminomethane (TRIS). In some embodiments, tris (hydroxymethyl) aminomethane (TRIS) is present at a concentration in the range of about 60 mM to about 100 mM. In some embodiments, the metal chelating agent comprises ethylenediaminetetraacetic acid (EDTA). In some embodiments, ethylenediaminetetraacetic acid (EDTA) is present at a concentration in the range of about 1 mM to about 18 mM. the surfactant comprises polyethylene glycol p-(1,1,3,3-tetramethylbutyl)-phenyl ether (Triton-X-100). In some embodiments, polyethylene glycol p-(1,1,3,3-tetramethylbutyl)-phenyl ether (Triton-X-100) is present at a concentration in the range of about 0.1% to about 10%. In some embodiments, the precipitant comprises proteinase K. In some embodiments, proteinase K is present at a concentration in the range of about 17.5% to about 37.5%. In some embodiments, the lysing moiety comprises a lysis bead. In some embodiments, the lysis bead comprises 100 μm zirconium lysis beads. In some embodiments, the 100 μm zirconium lysis beads are present at a concentration in the range of about 0.1 grams/ml to about 2.88 grams/ml. In some embodiments, the lysing moiety comprises lysozyme. In some embodiments, the lysozyme is present at a concentration in the range of about 10 mg/ml to about 30 mg/ml. In some embodiments, the first sample lysis the sample is incubated with the lysis buffer in the range of about 5 minutes to about 25 minutes. In some embodiments, the first sample lysis the sample is incubated with the lysis buffer while shaking in the range of about 1200 RPM to about 1400 RPM. In some embodiments, the first sample lysis the sample is incubated with the lysis buffer in the range of about 45° C. to about 85° C. In some embodiments, the second sample lysis the sample is incubated with the lysis buffer in the range of about 5 minutes to about 15 minutes. In some embodiments, the second sample lysis the sample is incubated with the lysis buffer in the range of about 85° C. to about 105° C. In some embodiments, the second sample lysis the sample is incubated with the lysis buffer while shaking in the range of about 1200 RPM to about 1400 RPM. In some embodiments, the nucleic acid is DNA. In some embodiments, the nucleic acid is reverse transcribed from RNA. In some embodiments, the one or more pathogen comprises two or more of *Escherichia coli, Salmonella,* or *Listeria monocytogenes*. In some embodiments, the primer pairs comprise sequences that are at least 80/6 homologous with the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense; and SEQ ID NO: 9 sense, SEQ ID NO: 10 antisense. In some embodiments, the primer pairs comprise sequences of at least 15 contiguous bases that are at least 80% homologous with the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense; and SEQ ID NO: 9 sense, SEQ ID NO: 10 antisense. In some embodiments, the method further comprises a hybridization of an internal oligonucleotide probe to a sequence within the target sequence or a complement. In some embodiments, wherein the internal oligonucleotide probe does not hybridize to the amplification primers. In some embodiments, the hybridization of the internal oligonucleotide probe to a sequence within the target sequence or a complement thereof is indicative of the presence of the one or more pathogen in the sample. In some embodiments, detecting can comprise one or more of PCR, lectin binding, simple diffusion, lateral diffusion, immunological detection, lateral flow, ELISA or flow through step. In some embodiments, the detecting is by sequencing, In some embodiments, the nucleic acid is sequenced. In some embodiments, the internal oligonucleotide probe comprise sequences that are at least 80/6 homologous with the sequences: SEQ ID NO: 11; SEQ ID NO: 12; SEQ ID NO: 13; SEQ ID NO: 14; and SEQ ID NO: 15. In some embodiments, the internal oligonucleotide probe comprise sequences of at least 15 contiguous bases that are at least 80% homologous with the sequences: SEQ ID NO: 11; SEQ ID NO: 12; SEQ ID NO: 13; SEQ ID NO: 14; and SEQ ID NO: 15. In some embodiments, the internal oligonucleotide probes are labeled at their 5' ends with an energy transfer donor fluorophore and labeled at their 3' ends with an energy transfer acceptor fluorophore. In some embodiments, the detecting is reported by a communication medium. In some embodiment, a result is communicated via a communication medium, for example: an electronic communication medium, email, facsimile, text, video, audio, telegraph, telegram, letter, using a computer processor, or a microprocessor. In some embodiments, the sample is contacted with a lysis buffer at a first temperature and a second temperature, wherein the second temperature is higher than the temperature of the first temperature. In some embodiments, the presence and/or absence of at least two, three, four, five, six, seven, eight, nine, or ten pathogens are detected. In some embodiments, the lysis buffer comprises at least one of: a buffering component; a metal chelating agent; a surfactant; a precipitant; and at least one lysing moiety. In some embodiments, the primer pairs comprise sequences that are at least 80% homologous with at least one of the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense, SEQ ID NO: 9 sense; and SEQ ID NO: 10 antisense. In some embodiments, the internal oligonucleotide probe comprise sequences that are at least 80/6 homologous with at least one of the sequences: SEQ ID NO: 11; SEQ ID NO: 12; SEQ ID NO: 13; SEQ ID NO: 14; and SEQ ID NO: 15. The method of any one of claim 2-50 or 183, wherein a third primer of the one or more primer pairs hybridizes to an internal control nucleic acid sequence, and wherein a fourth primer of the one or more primer pairs hybridizes to a sequence complimentary to the internal control nucleic acid sequence. In some embodiments, the primer pairs further comprise sequences that are at least 80/6 homologous with the sequence SEQ ID NO: 16 sense; and SEQ ID NO: 17 antisense. In some embodiments, the primer pairs comprise sequences of at least 15 contiguous bases that are at least 80/6 homologous with the sequence SEQ ID NO: 16 sense; and SEQ ID NO: 17 antisense. In some embodiments, the internal oligonucleotide probe further comprise sequences that are at least 80% homologous with the sequence SEQ ID NO: 18. In some embodiments, the internal oligonucleotide probe comprise sequences of at least 15 contiguous bases that are at least 80% homologous with the sequence SEQ ID NO: 18. In some embodiments, one or more of *Escherichia coli, Salmonella,* or *Listeria monocytogenes* are detected when one or more of *Escherichia coli, Salmonella,* or *Listeria monocytogenes* is inoculated in or on a food product. In some embodiments, the food product is turkey. In some embodiments, the food product is lettuce. In some embodiments, *Escherichia coli* is inoculated at a concentration of at least 0.60 CFU/25 mg. In some embodiments, STX-1 and STX-2 is detected in at least 18/20 replicates. In some embodiments, *E. coli* EAE is detected in at least 18/20 replicates. In some embodiments, *S. enterica* is inoculated at a concentration of at least 0.48 CFU/25 g. In some embodiments, *S. enterica* is detected in at least 20/20 replicates. In some embodiments, *L. monocytogenes* is inoculated at a concentration of at least 1.0 CFU/25 g. In some embodiments, *L. monocytogenes* is detected in at least 9/20 replicates. In some embodiments, *Escherichia coli* is inoculated at a concentration of at least 0.60 CFU/25 mg. In some embodiments, STX-1 and STX-2 is detected in at least 12/20 replicates. In some embodiments, *E. coli* EAE is detected in at least 12/20 replicates. In some embodiments, *S. enterica* is inoculated at a concentration of at least 0.48 CFU/25 g. In some embodiments, *S. enterica* is detected in at least 6/20 replicates. In some embodiments, *L. monocytogenes* is inoculated at a concentration of at least 1.0 CFU/25 g. In some embodiments, *L. monocytogenes* is detected in at least 11/20 replicates. In some embodiments, the enriching is performed in less than 1000 ml rich and nonselective media. In some embodiments, the enriching is performed in less than 500 ml rich and nonselective media. In some embodiments, the enriching is performed in 225 ml rich and nonselective media. In some embodiments the rich and nonselective media can comprise, per 1 L of water: between about 5 g/L and about 20 g/L yeast extract; between about 20 g/L and about 50 g/L pancreatic digest of casein; between about 1 g/L and 10 g/L enzymatic digest of soy; between about 1 g/L and about 10 g/L dextrose; between about 1 g/L and about 20 g/L sodium chloride; between about 1 g/L and about 10 g/L dipotassium phosphate; between about 1 g/L and about 10 g/L potassium phosphate; between about 10 g/L and about 30 g/L disodium phosphate; and between about 1 g/L and about 10 g/L sodium pyruvate. In some embodiments the rich and nonselective media can comprise, per 1 L of water between about 5 g/L and about 20 g/L yeast extract. In some embodiments the rich and nonselective media can comprise, per 1 L of water between about 20 g/L and about 50 g/L pancreatic digest of casein. In some embodiments the rich and nonselective media can comprise, per 1 L of water between about 1 g/L and 10 g/L enzymatic digest of soy. In some embodiments the rich and nonselective media can comprise, per 1 L of water between about 1 g/L and about 10 g/L dextrose. In some embodiments the rich and nonselective media can comprise, per 1 L of water between about 1 g/L and about 20 g/L sodium chloride. In some embodiments the rich and nonselective media can comprise, per 1 L of water between about 1 g/L and about 10 g/L dipotassium phosphate. In some embodiments the rich and nonselective media can comprise, per 1 L of water between about 1 g/L and about 10 g/L potassium phosphate. In some embodiments the rich and nonselective media can comprise, per 1 L of water between about 10 g/L and about 30 g/L disodium phosphate. In some embodiments the rich and nonselective media can comprise, per 1 L of water between about 1 g/L and about 10 g/L sodium pyruvate. In some embodiments the rich and nonselective media can comprise, per 1 L of water about 5 g/L of dextrose. In some embodiments the rich and nonselective media can comprise, per 1 L of water about 2.2 g/L of sodium pyruvate. In some embodiments the rich and nonselective media can comprise, per 1 L of water about 12 g/L of yeast extract. In some embodiments the rich and nonselective media can comprise, per 1 L of water about 34 g/L of pancreatic digest of casein. In some embodiments the rich and nonselective media can comprise, per 1 L of water about 6 g/L of enzymatic digest of soy. In some embodiments the rich and nonselective media can comprise, per 1 L of water about 10 g/L sodium chloride. In some embodiments the rich and nonselective media can comprise, per 1 L of water about 5 g/L dipotassium phosphate. In some embodiments the rich and nonselective media can comprise, per 1 L of water about 2.7 g/L potassium phosphate. In some embodiments the rich and nonselective media can comprise, per 1 L of water about 19.2 g/L disodium phosphate.

Provided herein are methods for detecting the presence and/or absence of one or more pathogens. In one aspect, the method comprises conducting a sample enrichment protocol on a sample in a media, wherein the media comprises a component to promote the growth of one or more pathogens, thereby forming a sample that has undergone the enrichment protocol; conducting a lysing protocol on the sample that has undergone the enrichment protocol, or a portion thereof, at a first temperature and a second temperature, wherein the second temperature is higher than the first temperature, thereby forming a sample or portion thereof that has undergone the lysing protocol; and conducting an amplification protocol on the sample or portion thereof that has undergone the lysing protocol. In some embodiments, the sample comprises one or more pathogens. In some embodiments, the method is performed within a positive total time of about 28 hrs. In some embodiments, the presence and/or absence of at least two pathogens are detected. In some embodiments, the sample comprises a food. In some embodiments, the sample weights a positive amount of less than or equal to about 25 grams by weight. In some embodiments, the sample is suspended in the rich and nonselective media such that the one or more pathogens are isolated from the sample.

In some embodiments, the one or more pathogens are isolated from the sample by stomaching. In some embodiments, the rich and nonselective media comprises *listeria* enrichment broth base with substantially no supplements. In some embodiments, the enrichment media can be media B. In some embodiments, the sample is enriched at a temperature in the range of about 30° C. to about 45° C. In some embodiments, the sample is incubated for a positive amount of time less than or equal to about 24 hours following stomaching. In some embodiments, lysing comprises incubating the sample with a lysis buffer. In some embodiments, the lysis buffer comprises: a buffering component; a metal chelating agent; a surfactant; a precipitant; and/or at least two lysing moieties. In some embodiments, the buffering component comprises tris (hydroxymethyl) aminomethane (TRIS). In some embodiments, tris (hydroxymethyl) aminomethane (TRIS) is present at a concentration in the range of about 60 mM to about 100 mM. In some embodiments, the metal chelating agent comprises ethylenediaminetetraacetic acid (EDTA). In some embodiments, ethylenediaminetetraacetic acid (EDTA) is present at a concentration in the range of about 1 mM to about 18 mM. In some embodiments, the surfactant comprises polyethylene glycol p-(1,1,3,3-tetramethylbutyl)-phenyl ether (Triton-X-100). In some embodiments, polyethylene glycol p-(1,1,3,3-tetramethylbutyl)-phenyl ether (Triton-X-100) is present at a concentration in the range of about 0.1% to about 10%. In some embodiments, the precipitant comprises proteinase K. In some embodiments, proteinase K is present at a concentration in the range of about 17.5% to about 37.5%. In some embodiments, the lysing moiety comprises a lysis bead. In some embodiments, the lysis bead comprises 100 μm zirconium lysis beads. In some embodiments, the 100 μm zirconium lysis beads are present at a concentration in the range of about 0.1 grams/ml to about 2.88 grams/ml. In some embodiments, the lysozyme is present at a concentration in the range of about 10 mg/ml to about 30 mg/ml. In some embodiments, the media is a rich media. In some embodiments, the media is non selective media. In some embodiments, the amplification protocol is performed with a set of amplification primers. In some embodiments, the amplification primers comprise one or more primer pairs. In some embodiments, a first primer pair of the one or more primer pair hybridizes to a target nucleic acid sequence of one or more pathogens. In some embodiments, a second primer of the one or more primer pairs hybridizes to a sequence complimentary to the target nucleic acid. In some embodiments, the sample is incubated with a lysis buffer in the range of about 5 minutes to about 25 minutes according to the lysing protocol at the first temperature. In some embodiments, the sample is incubated with the lysis buffer while shaking in the range of about 1200 RPM to about 1400 RPM according to the lysing protocol at the first temperature. In some embodiments, the first temperature comprises a range of about 45° C. to about 85° C. In some embodiments, the sample is incubated with a lysis buffer in the range of about 5 minutes to about 15 minutes according to the lysing protocol at the first temperature. In some embodiments, the second temperature comprises a range of about 85° C. to about 105° C. In some embodiments, the sample is incubated with a lysis buffer in a range of about 5 minutes to about 25 minutes according to the lysing protocol at the second temperature. In some embodiments, the method further comprising detecting a presence and/or absence of the one or more pathogens. In some embodiments, the nucleic acid is DNA. In some embodiments, the nucleic acid is reverse transcribed from RNA. In some embodiments, the one or more pathogen comprises two or more of *Escherichia coli*, *Salmonella*, or *Listeria monocytogenes*. In some embodiments, the primer pairs comprise sequences that are at least 80/6 homologous with the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense; and SEQ ID NO: 9 sense, SEQ ID NO: 10 antisense. In some embodiments, the primer pairs comprise sequences of at least 15 contiguous bases that are at least 80% homologous with the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense; and SEQ ID NO: 9 sense, SEQ ID NO: 10 antisense. In some embodiments, the method further comprises a hybridization of an internal oligonucleotide probe to a sequence within the target sequence or a complement. In some embodiments, wherein the internal oligonucleotide probe does not hybridize to the amplification primers. In some embodiments, the hybridization of the internal oligonucleotide probe to a sequence within the target sequence or a complement thereof is indicative of the presence of the one or more pathogen in the sample. In some embodiments, the internal oligonucleotide probe comprise sequences that are at least 80/6 homologous with the sequences: SEQ ID NO: 11; SEQ ID NO: 12; SEQ ID NO: 13; SEQ ID NO: 14; and SEQ ID NO: 15. In some embodiments, the internal oligonucleotide probe comprise sequences of at least 15 contiguous bases that are at least 80% homologous with the sequences: SEQ ID NO: 11; SEQ ID NO: 12; SEQ ID NO: 13; SEQ ID NO: 14; and SEQ ID NO: 15. In some embodiments, the internal oligonucleotide probes are labeled at their 5' ends with an energy transfer donor fluorophore and labeled at their 3' ends with an energy transfer acceptor fluorophore. In some embodiments, the detecting is reported by a communication medium. In some embodiment, a result is communicated via a communication medium, for example: an electronic communication medium, email, facsimile, text, video, audio, telegraph, telegram, letter, using a computer processor, or a microprocessor. In some embodiments, the sample is contacted with a lysis buffer at a first temperature and a second temperature, wherein the second temperature is higher than the temperature of the first temperature. In some embodiments, the presence and/or absence of at least two, three, four, five, six, seven, eight, nine, or ten pathogens are detected. In some embodiments, the lysis buffer comprises at least one of: a buffering component; a metal chelating agent; a surfactant; a precipitant; and at least one lysing moiety. In some embodiments, the primer pairs comprise sequences that are at least 80% homologous with at least one of the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense, SEQ ID NO: 9 sense; and SEQ ID NO: 10 antisense. In some embodiments, the internal oligonucleotide probe comprise sequences that are at least 80/6 homologous with at least one of the sequences: SEQ ID NO: 11; SEQ ID NO: 12; SEQ ID NO: 13; SEQ ID NO: 14; and SEQ ID NO: 15. The method of any one of claim 2-50 or 183, wherein a third primer of the one or more primer pairs hybridizes to an internal control nucleic acid sequence, and wherein a fourth primer of the one or more primer pairs hybridizes to a sequence complimentary to the internal control nucleic acid sequence. In some embodiments, the primer pairs further comprise sequences that are at least 80/6 homologous with the sequence SEQ ID NO: 16 sense; and SEQ ID NO: 17 antisense. In some embodiments, the primer pairs comprise sequences of at least 15 contiguous bases that are at least 80/6 homologous with the sequence SEQ ID NO: 16 sense; and SEQ ID NO: 17 antisense. In some embodiments, the internal oligonucleotide probe further comprise sequences that are at least 80% homologous with the sequence SEQ ID NO: 18. In some embodiments, the internal oligonucleotide probe comprise sequences of at least 15 contiguous bases that are at least 80% homologous with the sequence SEQ ID NO: 18. In some embodiments, one or more of *Escherichia coli*, *Salmonella*, or *Listeria monocytogenes* are detected when one or more of *Escherichia coli*, *Salmonella*, or *Listeria monocytogenes* is inoculated in or on a food product. In some embodiments, the food product is turkey. In some embodiments, the food product is lettuce. In some embodiments, *Escherichia coli* is inoculated at a concentration of at least 0.60 CFU/25 mg. In some embodiments, STX-1 and STX-2 is detected in at least 18/20 replicates. In some embodiments, *E. coli* EAE is detected in at least 18/20 replicates. In some embodiments, *S. enterica* is inoculated at a concentration of at least 0.48 CFU/25 g. In some embodiments, *S. enterica* is detected in at least 20/20 replicates. In some embodiments, *L. monocytogenes* is inoculated at a concentration of at least 1.0 CFU/25 g. In some embodiments, *L. monocytogenes* is detected in at least 9/20 replicates. In some embodiments, *Escherichia coli* is inoculated at a concentration of at least 0.60 CFU/25 mg. In some embodiments, STX-1 and STX-2 is detected in at least 12/20 replicates. In some embodiments, *E. coli* EAE is detected in at least 12/20 replicates. In some embodiments, *S. enterica* is inoculated at a concentration of at least 0.48 CFU/25 g. In some embodiments, *S. enterica* is detected in at least 6/20 replicates. In some embodiments, *L. monocytogenes* is inoculated at a concentration of at least 1.0 CFU/25 g. In some embodiments, *L. monocytogenes* is detected in at least 11/20 replicates. In some embodiments, the enriching is performed in less than 1000 ml rich and nonselective media. In some embodiments, the enriching is performed in less than 500 ml rich and nonselective media. In some embodiments, the enriching is performed in 225 ml rich and nonselective media. In some embodiments the rich and nonselective media can comprise, per 1 L of water: between about 5 g/L and about 20 g/L yeast extract; between about 20 g/L and about 50 g/L pancreatic digest of casein; between about 1 g/L and 10 g/L enzymatic digest of soy; between about 1 g/L and about 10 g/L dextrose; between about 1 g/L and about 20 g/L sodium chloride; between about 1 g/L and about 10 g/L dipotassium phosphate; between about 1 g/L and about 10 g/L potassium phosphate; between about 10 g/L and about 30 g/L disodium phosphate; and between about 1 g/L and about 10 g/L sodium pyruvate. In some embodiments the rich and nonselective media can comprise, per 1 L of water between about 5 g/L and about 20 g/L yeast extract. In some embodiments the rich and nonselective media can comprise, per 1 L of water between about 20 g/L and about 50 g/L pancreatic digest of casein. In some embodiments the rich and nonselective media can comprise, per 1 L of water between about 1 g/L and 10 g/L enzymatic digest of soy. In some embodiments the rich and nonselective media can comprise, per 1 L of water between about 1 g/L and about 10 g/L dextrose. In some embodiments the rich and nonselective media can comprise, per 1 L of water between about 1 g/L and about 20 g/L sodium chloride. In some embodiments the rich and nonselective media can comprise, per 1 L of water between about 1 g/L and about 10 g/L dipotassium phosphate. In some embodiments the rich and nonselective media can comprise, per 1

L of water between about 1 g/L and about 10 g/L potassium phosphate. In some embodiments the rich and nonselective media can comprise, per 1 L of water between about 10 g/L and about 30 g/L disodium phosphate. In some embodiments the rich and nonselective media can comprise, per 1 L of water between about 1 g/L and about 10 g/L sodium pyruvate. In some embodiments the rich and nonselective media can comprise, per 1 L of water about 5 g/L of dextrose. In some embodiments the rich and nonselective media can comprise, per 1 L of water about 2.2 g/L of sodium pyruvate. In some embodiments the rich and nonselective media can comprise, per 1 L of water about 12 g/L of yeast extract. In some embodiments the rich and nonselective media can comprise, per 1 L of water about 34 g/L of pancreatic digest of casein. In some embodiments the rich and nonselective media can comprise, per 1 L of water about 6 g/L of enzymatic digest of soy. In some embodiments the rich and nonselective media can comprise, per 1 L of water about 10 g/L sodium chloride. In some embodiments the rich and nonselective media can comprise, per 1 L of water about 5 g/L dipotassium phosphate. In some embodiments the rich and nonselective media can comprise, per 1 L of water about 2.7 g/L potassium phosphate. In some embodiments the rich and nonselective media can comprise, per 1 L of water about 19.2 g/L disodium phosphate.

Provided herein are kits for simultaneous detecting the presence and/or absence of one or more pathogen. In one aspect, the kit comprises: a lysis buffer comprising: a buffering component; a metal chelating agent; a surfactant; a precipitant; and at least two lysing moieties; and a set of amplification primers, wherein the amplification primers comprise one or more primer pairs, wherein a first primer of the one or more primer pairs hybridizes to a target nucleic acid sequence of the one or more pathogen, and wherein a second primer of the one or more primer pairs hybridizes to a sequence complimentary to the target nucleic acid. In some embodiments, the kit further comprises an internal oligonucleotide probe, wherein the internal oligonucleotide probe is complementary to a sequence within the target sequence or compliment thereof, of the one or more primer pairs. In some embodiments, the buffering component comprises tris (hydroxymethyl) aminomethane (TRIS). In some embodiments, tris (hydroxymethyl) aminomethane (TRIS) is present at a concentration in the range of about 60 mM to about 100 mM. In some embodiments, tris (hydroxymethyl) aminomethane (TRIS) is present at a concentration of about 80 mM. In some embodiments, the metal chelating agent comprises ethylenediaminetetraacetic acid (EDTA). In some embodiments, ethylenediaminetetraacetic acid (EDTA) is present at a concentration in the range of about 1 mM to about 18 mM. In some embodiments, ethylenediaminetetraacetic acid (EDTA) is present at a concentration of about 8 mM. In some embodiments, the surfactant comprises polyethylene glycol p-(1,1,3,3-tetramethylbutyl)-phenyl ether (Triton-X-100). In some embodiments, polyethylene glycol p-(1,1,3,3-tetramethylbutyl)-phenyl ether (Triton-X-100) is present at a concentration in the range of about 0.1% to about 10%. In some embodiments, polyethylene glycol p-(1,1,3,3-tetramethylbutyl)-phenyl ether (Triton-X-100) is present at a concentration of about 4.8%. In some embodiments, the precipitant comprises proteinase K. In some embodiments, proteinase K is present at a concentration in the range of about 17.5% to about 37.5%. In some embodiments, proteinase K is present at a concentration of about 27.5%. In some embodiments, the lysing moiety comprises a lysis bead. In some embodiments, the lysis bead comprises 100 µm zirconium lysis beads. In some embodiments, the 100 µm zirconium lysis beads are present at a concentration in the range of about 0.1 grams/ml to about 2.88 grams/ml. In some embodiments, the lysing moiety comprises lysozyme. In some embodiments, the lysozyme is present at a concentration in the range of about 10 mg/ml to about 30 mg/ml. In some embodiments, the primer pairs comprise sequences that are at least 80/6 homologous with the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense; and SEQ ID NO: 9 sense, SEQ ID NO: 10 antisense. In some embodiments, the primer pairs comprise sequences of at least 15 contiguous bases that are at least 80% homologous with the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense; and SEQ ID NO: 9 sense, SEQ ID NO: 10 antisense. In some embodiments, the internal oligonucleotide probe comprise sequences that are at least 80/6 homologous with the sequences: SEQ ID NO: 11; SEQ ID NO: 12; SEQ ID NO: 13; SEQ ID NO: 14; and SEQ ID NO: 15. In some embodiments, the internal oligonucleotide probe comprise sequences of at least 15 contiguous bases that are at least 80% homologous with the sequences: SEQ ID NO: 11; SEQ ID NO: 12; SEQ ID NO: 13; SEQ ID NO: 14; and SEQ ID NO: 15. In some embodiments, the probes are labeled at their 5' ends with an energy transfer donor fluorophore and labeled at their 3' ends with an energy transfer acceptor fluorophore. In some embodiments, the kit further comprises an amplification mix. In some embodiments, the kit further comprises a negative PCR control. In some embodiments, the kit further comprises a positive PCR control. In some embodiments, the kit further comprises instructions for use. In some embodiments, the lysis buffer comprises at least one of: a buffering component; a metal chelating agent; a surfactant; a precipitant; and at least one lysing moiety. In some embodiments, the primer pairs comprise sequences that are at least 80% homologous with at least one of the sequences: SEQ ID NO: 1 sense, SEQ ID NO: 2 antisense; SEQ ID NO: 3 sense, SEQ ID NO: 4 antisense; SEQ ID NO: 5 sense, SEQ ID NO: 6 antisense; SEQ ID NO: 7 sense, SEQ ID NO: 8 antisense, SEQ ID NO: 9 sense; and SEQ ID NO: 10 antisense. In some embodiments, the internal oligonucleotide probe comprise sequences that are at least 80% homologous with at least one of the sequences: SEQ ID NO: 11; SEQ ID NO: 12; SEQ ID NO: 13; SEQ ID NO: 14; and SEQ ID NO: 15. In some embodiments, the primer pairs further comprise sequences that are at least 80/6 homologous with the sequence SEQ ID NO: 16 sense; and SEQ ID NO: 17 antisense. In some embodiments, wherein the primer pairs comprise sequences of at least 15 contiguous bases that are at least 80% homologous with the sequence SEQ ID NO: 16 sense; and SEQ ID NO: 17 antisense. In some embodiments, wherein the internal oligonucleotide probe further comprise sequences that are at least 80% homologous with the sequence SEQ ID NO: 18. In some embodiments, wherein the internal oligonucleotide probe comprise sequences of at least 15 contiguous bases that are at least 80% homologous with the sequence SEQ ID NO: 18. In some embodiments, the kit may comprise one or more media disclosed herein. In some embodiments, the media can be a rich and nonselective media. In some embodiments the rich and nonselective media can comprise, per 1 L of water: between about 5 g/L and about 20 g/L yeast extract; between about 20 g/L and about 50 g/L pancreatic digest of casein; between about 1 g/L and 10 g/L enzymatic digest of soy;

between about 1 g/L and about 10 g/L dextrose; between about 1 g/L and about 20 g/L sodium chloride; between about 1 g/L and about 10 g/L dipotassium phosphate; between about 1 g/L and about 10 g/L potassium phosphate; between about 10 g/L and about 30 g/L disodium phosphate; and between about 1 g/L and about 10 g/L sodium pyruvate. In some embodiments the rich and nonselective media can comprise, per 1 L of water between about 5 g/L and about 20 g/L yeast extract. In some embodiments the rich and nonselective media can comprise, per 1 L of water between about 20 g/L and about 50 g/L pancreatic digest of casein. In some embodiments the rich and nonselective media can comprise, per 1 L of water between about 1 g/L and 10 g/L enzymatic digest of soy. In some embodiments the rich and nonselective media can comprise, per 1 L of water between about 1 g/L and about 10 g/L dextrose. In some embodiments the rich and nonselective media can comprise, per 1 L of water between about 1 g/L and about 20 g/L sodium chloride. In some embodiments the rich and nonselective media can comprise, per 1 L of water between about 1 g/L and about 10 g/L dipotassium phosphate. In some embodiments the rich and nonselective media can comprise, per 1 L of water between about 1 g/L and about 10 g/L potassium phosphate. In some embodiments the rich and nonselective media can comprise, per 1 L of water between about 10 g/L and about 30 g/L disodium phosphate. In some embodiments the rich and nonselective media can comprise, per 1 L of water between about 1 g/L and about 10 g/L sodium pyruvate. In some embodiments the rich and nonselective media can comprise, per 1 L of water about 5 g/L of dextrose. In some embodiments the rich and nonselective media can comprise, per 1 L of water about 2.2 g/L of sodium pyruvate. In some embodiments the rich and nonselective media can comprise, per 1 L of water about 12 g/L of yeast extract. In some embodiments the rich and nonselective media can comprise, per 1 L of water about 34 g/L of pancreatic digest of casein. In some embodiments the rich and nonselective media can comprise, per 1 L of water about 6 g/L of enzymatic digest of soy. In some embodiments the rich and nonselective media can comprise, per 1 L of water about 10 g/L sodium chloride. In some embodiments the rich and nonselective media can comprise, per 1 L of water about 5 g/L dipotassium phosphate. In some embodiments the rich and nonselective media can comprise, per 1 L of water about 2.7 g/L potassium phosphate. In some embodiments the rich and nonselective media can comprise, per 1 L of water about 19.2 g/L disodium phosphate.

Provided herein are lysis buffer compositions. In one aspect, the composition comprises: A buffering component selected from the group consisting of tris (hydroxymethyl) aminomethane (TRIS), 4-(2-hydroxyethyl)-1-piperazineethanesulfonic acid (HEPES), 3-(N-morpholino) propanesulfonic acid (MOPS), sodium dihydrogen phosphate (NaH2P04), disodium hydrogen phosphate (a2HPO4), and combinations thereof; a metal chelating agent selected from the group consisting of ethylenediaminetetraacetic acid (EDTA), ethylene glycol tetraacetic acid (EGTA), and combinations thereof; a surfactant selected from the group consisting of sodium dodecyl sulfate (SDS), nonyl phenoxypolyoxyethanol (NP-40), polyethylene glycol p-(1,1,3,3-tetramethylbutyl)-phenyl ether (Triton-X-100), polyoxyethylene (20) sorbitan monooleate (Tween-20), and combinations thereof; a precipitant selected from the group consisting of glycerol, dimethyl sulfoxide (DMSO), acetonitrile (ACN), bovine serum albumin (BSA), proteinase K, acetate salts, and combinations thereof; and at least two lysing moieties. In some embodiments, the buffering component comprises tris (hydroxymethyl) aminomethane (TRIS). In some embodiments, tris (hydroxymethyl) aminomethane (TRIS) is present at a concentration in the range of about 60 mM to about 100 mM. In some embodiments, the metal chelating agent comprises ethylenediaminetetraacetic acid (EDTA). In some embodiments, ethylenediaminetetraacetic acid (EDTA) is present at a concentration in the range of about 1 mM to about 18 mM. In some embodiments, the surfactant comprises polyethylene glycol p-(1,1,3,3-tetramethylbutyl)-phenyl ether (Triton-X-100). In some embodiments, polyethylene glycol p-(1,1,3,3-tetramethylbutyl)-phenyl ether (Triton-X-100) is present at a concentration in the range of about 0.1% to about 10%. In some embodiments, the precipitant comprises proteinase K. In some embodiments, proteinase K is present at a concentration in the range of about 17.5% to about 37.5%. In some embodiments, the lysing moiety comprises a lysis bead. In some embodiments, the lysis bead comprises 100 µm zirconium lysis beads. In some embodiments, the 100 µm zirconium lysis beads are present at a concentration in the range of about 0.1 grams/ml to about 2.88 grams/ml. In some embodiments, the lysing moiety comprises lysozyme. In some embodiments, the lysozyme is present at a concentration in the range of about 10 mg/ml to about 30 mg/ml.

Provided herein are methods for the isolation of nucleic acid from a sample. In one aspect, the method comprises: a first sample lysis comprising: combining the sample and the lysis buffer composition as defined in any one of claims 78-91, thereby forming a sample/lysis buffer mixture; agitating the sample/lysis buffer mixture, thereby lysing the sample and forming a lysed sample mixture; a second sample lysis comprising: continuing to agitate the lysed sample mixture at a temperature higher than the temperature of the first sample lysis; and separating the lysed sample mixture into a mixture comprising a solids fraction comprising sample and a supernatant comprising nucleic acid; and recovering the nucleic acid supernatant from the lysed sample mixture. In some embodiments, agitating comprises shaking. In some embodiments, the first sample lysis the sample is incubated with the lysis buffer in the range of about 5 minutes to about 25 minutes. In some embodiments, the first sample lysis the sample is incubated with the lysis buffer while shaking in the range of about 1200 RPM to about 1400 RPM. In some embodiments, the first sample lysis the sample is incubated with the lysis buffer in the range of about 45° C. to about 85° C. In some embodiments, the second sample lysis the sample is incubated with the lysis buffer in the range of about 5 minutes to about 15 minutes. In some embodiments, the second sample lysis the sample is incubated with the lysis buffer in the range of about 85° C. to about 105° C. In some embodiments, the second sample lysis the sample is incubated with the lysis buffer while shaking in the range of about 1200 RPM to about 1400 RPM. In some embodiments, the lysed sample mixture is separated into a mixture comprising a solids fraction comprising sample and a supernatant comprising nucleic acid by centrifugation.

Provided herein is a pair of single-stranded DNA primers for determination of a nucleotide sequence of *Listeria monocytogenes* gene Listeriolysin O (HlyA) by a polymerase chain reaction, wherein the use of the primers in a polymerase chain reaction results in the synthesis of DNA having all or part of the sequence of *Listeria monocytogenes* gene Listeriolysin O (HlyA), wherein the pair comprises sequences that are at least 80/6 homologous with the sequences: SEQ ID NO: 1 sense; and SEQ ID NO: 2 antisense. Provided herein is an oligonucleotide probe which is complementary across its entire length to a sequence amplified by the primer pair, wherein the oligonucleotide probe comprises sequences that are at least 80/6 homologous with the sequence: SEQ ID NO: 11.

Provided herein is a pair of single-stranded DNA primers for determination of a nucleotide sequence of Shiga Toxin-Producing *Escherichia coli* gene intimin (eaeA) by a polymerase chain reaction, wherein the use of the primers in a polymerase chain reaction results in the synthesis of DNA having all or part of the sequence of Shiga Toxin-Producing *Escherichia coli* gene intimin (eaeA), wherein the pair comprises sequences that are at least 80% homologous with the sequences: SEQ ID NO: 3 sense; and SEQ ID NO: 4 antisense. Provided herein is an oligonucleotide probe which is complementary across its entire length to a sequence amplified by the primer pair, wherein the oligonucleotide probe comprises sequences that are at least 80% homologous with the sequence: SEQ ID NO: 12.

Provided herein is a pair of single-stranded DNA primers for determination of a nucleotide sequence of Shiga Toxin-Producing *Escherichia coli* gene Shiga toxin 1 (stx1) by a polymerase chain reaction, wherein the use of the primers in a polymerase chain reaction results in the synthesis of DNA having all or part of the sequence of Shiga Toxin-Producing *Escherichia coli* gene Shiga toxin 1 (stx1), wherein the pair comprises sequences that are at least 80% homologous with the sequences: SEQ ID NO: 5 sense; and SEQ ID NO: 6 antisense. Provided herein is an oligonucleotide probe which is complementary across its entire length to a sequence amplified by the primer pair, wherein the oligonucleotide probe comprises sequences that are at least 80% homologous with the sequence: SEQ ID NO: 13.

Provided herein is a pair of single-stranded DNA primers for determination of a nucleotide sequence of Shiga Toxin-Producing *Escherichia coli* gene Shiga toxin 2 (stx2) by a polymerase chain reaction, wherein the use of the primers in a polymerase chain reaction results in the synthesis of DNA having all or part of the sequence of Shiga Toxin-Producing *Escherichia coli* gene Shiga toxin 1 (stx2), wherein the pair comprises sequences that are at least 80% homologous with the sequences: SEQ ID NO: 7 sense; and SEQ ID NO: 8 antisense. Provided herein is an oligonucleotide probe which is complementary across its entire length to a sequence amplified by the primer pair of, wherein the oligonucleotide probe comprises sequences that are at least 80% homologous with the sequence: SEQ ID NO: 14.

Provided herein is a pair of single-stranded DNA primers for determination of a nucleotide sequence of *Salmonella* Invasion Gene A (InvA) by a polymerase chain reaction, wherein the use of the primers in a polymerase chain reaction results in the synthesis of DNA having all or part of the sequence of *Salmonella* Invasion Gene A (InvA), wherein the pair comprises sequences that are at least 80/6 homologous with the sequences: SEQ ID NO: 9 sense; and SEQ ID NO: 10 antisense. Provided herein is an oligonucleotide probe which is complementary across its entire length to a sequence amplified by the primer pair, wherein the oligonucleotide probe comprises sequences that are at least 80/6 homologous with the sequence: SEQ ID NO: 15.

Provided herein are methods for lysing a sample. In one aspect, the method comprises a first sample lysis comprising: combining the sample and a lysis buffer composition, thereby forming a sample/lysis buffer mixture, wherein the lysis buffer composition comprises: a buffering component; a metal chelating agent; a surfactant; a precipitant; and at least two lysing moieties; agitating the sample/lysis buffer mixture, thereby lysing the sample and forming a lysed sample mixture; a second sample lysis comprising: continuing to agitate the lysed sample mixture at a temperature higher than the temperature of the first sample lysis, thereby lysing the sample. In some embodiments, agitating comprises shaking. In some embodiments, the first sample lysis the sample is incubated with the lysis buffer in the range of about 5 minutes to about 25 minutes. In some embodiments, the first sample lysis the sample is incubated with the lysis buffer while shaking in the range of about 1200 RPM to about 1400 RPM. In some embodiments, the first sample lysis the sample is incubated with the lysis buffer in the range of about 45° C. to about 85° C. In some embodiments, the second sample lysis the sample is incubated with the lysis buffer in the range of about 5 minutes to about 15 minutes. In some embodiments, the second sample lysis the sample is incubated with the lysis buffer in the range of about 85° C. to about 105° C. In some embodiments, the second sample lysis the sample is incubated with the lysis buffer while shaking in the range of about 1200 RPM to about 1400 RPM. In some embodiments, the buffering component comprises tris (hydroxymethyl) aminomethane (TRIS). In some embodiments, tris (hydroxymethyl) aminomethane (TRIS) is present at a concentration in the range of about 60 mM to about 100 mM. In some embodiments, the metal chelating agent comprises ethylenediaminetetraacetic acid (EDTA). In some embodiments, ethylenediaminetetraacetic acid (EDTA) is present at a concentration in the range of about 1 mM to about 18 mM. In some embodiments, the surfactant comprises polyethylene glycol p-(1,1,3,3-tetramethylbutyl)-phenyl ether (Triton-X-100). In some embodiments, polyethylene glycol p-(1,1,3,3-tetramethylbutyl)-phenyl ether (Triton-X-100) is present at a concentration in the range of about 0.1% to about 10%. In some embodiments, the precipitant comprises proteinase K. In some embodiments, proteinase K is present at a concentration in the range of about 17.5% to about 37.5%. In some embodiments, the lysing moiety comprises a lysis bead. In some embodiments, the lysis bead comprises 100 μm zirconium lysis beads. In some embodiments, the 100 μm zirconium lysis beads are present at a concentration in the range of about 0.1 grams/ml to about 2.88 grams/ml. In some embodiments, the lysing moiety comprises lysozyme. In some embodiments, the lysozyme is present at a concentration in the range of about 10 mg/ml to about 30 mg/ml.

Provided herein are a pair of single-stranded DNA primers for determination of a nucleotide sequence of an internal control by a polymerase chain reaction, wherein the use of the primers in a polymerase chain reaction results in the synthesis of DNA having all or part of the sequence of the internal control template, wherein the pair comprises sequences that are at least 80% homologous with the sequences: SEQ ID NO: 16 sense; and SEQ ID NO: 17 antisense. In some embodiments, the internal control template comprises a sequence of: SEQ ID NO: 19. In some embodiments, the internal control template comprises a sequence at least 80% homologous with the sequence SEQ ID NO: 19. In some embodiments, Provided herein is an oligonucleotide probe which is complementary across its entire length to a sequence amplified by the primer pair wherein the oligonucleotide probe comprises sequences that are at least 80/6 homologous with the sequence: SEQ ID NO: 18.

In some aspects, the methods of the present invention may achieve these and other objects via the use of primers in combination for the rapid, high-throughput screening PCR-based techniques to simultaneously detect multiple pathogens. The multiplex-detection methods performed in some aspects of the present invention have improved sensitivity and specificity for the detection of multiple pathogens simultaneously.

In some aspects, the methods described herein comprises primers that detect with high specificity and sensitivity to certain pathogens, and thus the primers described herein may be used in reliable detection techniques as described herein to identify pathogens in the human food supply before the pathogens reach the consumer. Various aspects of the present invention utilize amplifiable PCR product sizes, allowing the methods to also be useful in the identification of pathogens and their closely related variants for the purpose of classifying and tracing the origin of contamination.

In some aspects, organisms for which the method can detect include but is not limited to relevant species, subspecies, serovars, and/or strains of for example, *Escherichia coli* O157:H7, *Shigella dysenteriae, Salmonella enterica* ssp. *enterica* (including serovars *Typhi, Typhimurium*, and Saintpaul) *Francisella tularensis* ssp. *tularensis, Francisella tularensis* ssp. *novicida, Vibrio cholerae, Vibrio parahaemolyticus, Shigella sonnei, Yersinia pestis, Listeria monocytogenes* and *Yersinia pseudotuberculosis*. In some aspects, the methods described herein identifies PCR conditions that are suitable for the amplification of all pathogens under the same reaction conditions, thus making the primers thus identified suitable for combined use under those reaction conditions in multiple simultaneous PCR to detect and identify those food pathogens.

In some aspects, sets of multiplex PCR primers and TaqMan probes may be designed using commercial software and genomic DNA sequences. In some aspects, specificity of resulting sequences may be assessed in silico against the nr database using Blast. In some aspects, optimal PCR conditions may be identified for each of the multiplex sets. In some aspects, selection of a final set of primers and probes may be done in a step-wise manner. In some aspects, compatibility, sensitivity, and specificity may be assessed using purified genomic DNA from target organisms and with non-target bacteria DNA. In some aspects, sets of primers and probes with optimal performance in with non-target bacteria DNA may then be further tested using DNA prepared from cultured bacteria. In some aspects, sets of primers and probes may be tested using DNA prepared from bacteria cultured in the presence of various food matrices.

In some aspects, the methods described herein can identify primers for pathogens that may be readily combined into common assays for the rapid and accurate detection of pathogens, wherein the assays are capable of discriminating a broad range of pathogens or related bacteria.

In some aspects, the methods described herein can identify various primers may be used alone to detect and identify a selected pathogen, or may be used in combination and/or tandem to detect and identify whether any of a plurality of pathogens are present in a sample.

In some aspects, when used in tandem or combination, the primers and or oligonucleotide probes described herein may comprise using primer pairs or oligonucleotide probes designed for detecting two or more different pathogens in a common PCR-microplate array or, alternatively, in a multiplex PCR. In some aspects, the various different primer pairs and or oligonucleotide probes are selected such that all utilized pairs can operate under the same conditions (e.g., melting temperatures) such that the PCR process can be run in simultaneously on the microarray or one-tube array, or together in an assay. In some aspects, the microarrays and/or multiplex arrays contain primer pairs and or oligonucleotide probes sufficient to detect and identify two, three, four, five, six or more pathogens simultaneously. In some aspects, particularly with respect to multiplex PCR, such embodiments can optionally use different probes specific to the target gene containing different dyes of different emission capacity to assist in multiplex detection.

Further disclosed herein include system and device for detecting one or more pathogens. The device and system can be a computer system. The device and system can comprise a memory that stores executable instructions and a processor to execute the executable instructions to perform any methods for detecting one or more pathogens. In some cases, the device and system can detect one or more pathogens in a sample using the oligonucleotide probes, primers, and lysis buffers in the kits disclosed herein. In some aspects, the device and system can detect the presence or absence of one or more pathogens.

INCORPORATION BY REFERENCE

All publications, patents, and patent applications mentioned in this specification are herein incorporated by reference in their entirety for all purposes, to the same extent as if each individual publication, patent, or patent application is specifically and individually indicated to be incorporated by reference in their entireties.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 1 depicts a graph showing 1CFU/25 g—Deli Turkey—All Targets.

FIG. 2 depicts a graph 1CFU/25 g—Deli Turkey—STEC Targets.

FIG. 3 depicts a graph showing 1CFU/25 g—Deli Turkey—*Salmonella* Target

FIG. 4 depicts a graph showing 1CFU/25 g—Deli Turkey—*L. monocytogenes* Target FIG. 5 depicts a chart showing 1CFU/25 g—Deli Turkey—Table of Results FIG. 6 depicts a graph showing 5 CFU/25 g—Deli Turkey—All Targets FIG. 7 depicts a graph showing 5 CFU/25 g—Deli Turkey—STEC Targets FIG. 8 depicts a graph showing 5 CFU/25 g—Deli Turkey—*Salmonella* Target FIG. 9 depicts a graph showing 5 CFU/25 g—Deli Turkey—*L. monocytogenes* Target FIG. 10 depicts a chart showing 5 CFU/25 g—Deli Turkey—Table of Results FIG. 11 depicts a chart showing 1CFU/25 g—Hot Dog—Table of Results FIG. 12 depicts a chart showing Hot Dog—5 CFU/25 g—Table of Results FIG. 13 depicts a chart showing Iceberg Lettuce—1CFU/25 g—Table of Results FIG. 14 depicts a chart showing 5 CFU/25 g—Iceberg Lettuce—Table of Results FIG. 15 depicts a chart showing 1CFU/25 g—Raw Ground Beef—Table of Results FIG. 16 depicts a chart showing 5 CFU/25 g—Raw Ground Beef Table of Results FIG. 17 depicts a graph showing 1 CFU/25 g—Deli Turkey—STX-1 and STX-2—Internal Control.

FIG. 18 depicts a graph showing 1 CFU/25 g—Deli Turkey—*L. monocytogenes*—Internal Control.

FIG. 19 depicts a graph showing 1 CFU/25 g—Deli Turkey—*S. enterica*—Internal Control.

FIG. 20 depicts a graph showing 1 CFU/25 g—Deli Turkey—*E. coli* EAE—Internal Control.

FIG. 21 depicts a graph showing 1 CFU/25 g—Deli Turkey—Internal Control.

FIG. 22 depicts a chart showing 1 CFU/25 g—Deli Turkey—Table of Results—Internal Control.

FIG. 23 depicts a graph showing 5 CFU/25 g—Deli Turkey—STX-1 and STX-2—Internal Control.

FIG. 24 depicts a graph showing 5 CFU/25 g—Deli Turkey—*L. monocytogenes*—Internal Control.

FIG. 25 depicts a graph showing 5 CFU/25 g—Deli Turkey—*S. enterica*—Internal Control.

FIG. 26 depicts a graph showing 5 CFU/25 g—Deli Turkey—*E. coli* EAE—Internal Control.

FIG. 27 depicts a graph showing 5 CFU/25 g—Deli Turkey—Internal Control.

FIG. 28 depicts a chart showing 5 CFU/25 g—Deli Turkey—Table of Results—Internal Control.

FIG. 29 depicts a graph showing 1 CFU/25 g—Lettuce—STX-1 and STX-2—Internal Control.

FIG. 30 depicts a graph showing 1 CFU/25 g—Lettuce—*L. monocytogenes*—Internal Control.

FIG. 31 depicts a graph showing 1 CFU/25 g—Lettuce—*S. enterica*—Internal Control.

FIG. 32 depicts a graph showing 1 CFU/25 g—Lettuce—*E. coli* EA—Internal Control.

FIG. 33 depicts a graph showing 1 CFU/25 g—Lettuce—Internal Control.

FIG. 34 depicts a chart showing 1CFU/25 g—Lettuce—Table of Results—Internal Control.

FIG. 35 depicts a graph showing 5 CFU/25 g—Lettuce—STX-1 and STX-2—Internal Control.

FIG. 36 depicts a graph showing 5 CFU/25 g—Lettuce—*L. monocytogenes*—Internal Control.

FIG. 37 depicts a graph showing 5 CFU/25 g—Lettuce—*S. enterica*—Internal Control.

FIG. 38 depicts a graph showing 5 CFU/25 g—Lettuce—*E. coli* EE—Internal Control.

FIG. 39 depicts a graph showing 5 CFU/25 g—Lettuce—Internal Control.

FIG. 40 depicts a chart showing 5 CFU/25 g—Lettuce—Table of Results—Internal Control.

FIG. 41 depicts a graph showing 3 CFU inoculation of *Listeria monocytogenes*, into raw beef trim. FIG. 41A depicts a graph showing amplification results following enrichment in Media A.

FIG. 41B depicts a graph showing amplification results following enrichment in Media A versus Media B.

FIG. 42 depicts a graph showing 15 CFU inoculation of *Escherichia Coli* O157:H7 into raw spinach. FIG. 42A depicts a graph showing amplification results following enrichment in Media A.

FIG. 42B depicts a graph showing amplification results following enrichment in Media A versus Media B.

FIG. 43 depicts a graph showing 15 CFU inoculation of *Escherichia Coli* O157:H7 into raw spinach. FIG. 43A depicts a graph showing amplification results following enrichment in Media A.

FIG. 43B depicts a graph showing amplification results following enrichment in Media A versus Media B.

FIG. 44 depicts a graph showing 15 CFU inoculation of *Listeria Monocytogenes* into salmon. FIG. 44A depicts a graph showing amplification results following enrichment in Media A.

FIG. 44B depicts a graph showing amplification results following enrichment in Media A versus Media B.

FIG. 45 depicts a graph showing Raw Beef Trim 3 CFU/25 Gram Inoculation *E. Coli* STEC Targets.

FIG. 46 depicts a graph showing Raw Beef Trim 3 CFU/25 Gram Inoculation *L. monocytogenes* Target.

FIG. 47 depicts a graph showing Raw Beef Trim 3 CFU/25 Gram Inoculation *S. enterica* Target.

FIG. 48 depicts a table showing Raw Beef Trim—3 CFU/25 g—Table of Results

FIG. 49 depicts a graph showing Raw Beef Trim 15 CFU/25 Gram Inoculation *L. monocytogenes* Target.

FIG. 50 depicts a graph showing Raw Beef Trim 15 CFU/25 Gram Inoculation *S. enterica* Target.

FIG. 51 depicts a table showing Raw Beef Trim—15 CFU/25 g—Table of Results.

FIG. 52 depicts a graph showing Milk 3 CFU/25 Gram Inoculation *E. Coli* STEC Targets.

FIG. 53 depicts a graph showing Milk 3 CFU/25 Gram Inoculation *L. monocytogenes* Target.

FIG. 54 depicts a graph showing Milk 3 CFU/25 Gram Inoculation *S. enterica* Target.

FIG. 55 depicts a table showing Milk—3 CFU/25 g—Table of Results.

FIG. 56 depicts a graph showing Milk 15 CFU/25 Gram Inoculation *E. Coli* STEC Targets.

FIG. 57 depicts a graph showing Milk 15 CFU/25 Gram Inoculation *L. monocytogenes* Target.

FIG. 58 depicts a graph showing Milk 15 CFU/25 Gram Inoculation *S. enterica* Target.

FIG. 59 depicts a graph showing Milk—15 CFU/25 g—Table of Results.

FIG. 60 depicts a graph showing Raw Spinach 15 CFU/25 Gram Inoculation *E. coli* 0157 Targets.

FIG. 61 depicts a graph showing Brie de Meaux 15 CFU/25 Gram Inoculation *L. monocytogenes* Target.

FIG. 62 depicts a graph showing Smoked Salmon 15 CFU/25 Gram Inoculation *L. monocytogenes* Target.

FIG. 63 depicts a graph showing Peanut Butter 15 CFU/25 Gram Inoculation *S. enterica* Target.

FIG. 64 depicts a graph showing Raw Eggs 15 CFU/25 Gram Inoculation *S. enterica* Target.

FIG. 65 depicts a graph showing Black Pepper 15 CFU/25 Gram Inoculation *S. enterica* Target.

DETAILED DESCRIPTION OF THE DISCLOSURE

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Definitions

In this disclosure the term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and within 2-fold, of a value. Where particular values are described in the application and claims, unless otherwise stated the term "about" meaning within an acceptable error range for the particular value should be assumed.

In this disclosure the term "media", "medium", "broth", "culture broth" and the like all refer to a nutrient mixture suitable to culture a desired pathogen which may be a bacteria or microbe strain or species, or virus or infectious agent or biological agent that causes disease or illness to its host.

In this disclosure the term "pathogen" and the like all refer to bacteria, or microbe strain, or species, or virus, or infectious agents, or biological agents that can cause disease or illness to its host.

In this disclosure the term "microorganism" is encompassed in the term "pathogen".

In this disclosure "detecting" a microorganism or pathogen, means any process of observing the presence of a pathogen, or a change in the presence of a pathogen, in a sample, whether or not the pathogen or the change in the pathogen is actually detected.

In this disclosure the term "enriched media," "enrichment media" "rich media" and the like all refer to media that have been supplemented with highly nutritious materials such as but not limited to blood, serum or yeast extract for the purpose of cultivating fastidious organisms.

In this disclosure "enrichment" of a media refers to the addition of selected components to promote the growth or other characteristics of one or more desired pathogen. An "enrichment solution" refers to a solution comprising these additional components.

In this disclosure the term "selective agent" means a chemical or culture condition which serves to favor the growth of a desired pathogen or to inhibit the growth of an undesired pathogen.

In this disclosure the term "non-selective media" and the like all refer to media that is substantially free, or free of antibiotics.

In this disclosure the term "selective enrichment supplement" is equivalent to the term "selective agent".

In this disclosure the term "hybridizing probe" or "internal oligonucleotide probe" can be equivalent to the term "oligonucleotide probe".

In this disclosure a "supplement" for a culture media refers to a solution, liquid, solid or other material for addition to a culture medium.

In this disclosure "substantially free" refers to less about 10% by weight, or less than about 9% by weight, or less than about 8% by weight, or less than about 7% by weight, or less than about 6% by weight, or less than about 5% by weight, or less than about 4% by weight, or less than about 3% by weight, or less than about 2% by weight, or less than about 1.5% by weight, such as less than about 1% by weight of the ingredient to which it refers.

In this disclosure "amplicon" refers to the amplified product of a nucleic acid amplification reaction, e.g., the product of amplification of a sequence.

In this disclosure the terms "sample" and "biological sample" have the same and broadest possible meaning consistent with their context and refer generally and without limitation to anything desired to be tested for the presence of one or more pathogens of interest, and include all such subject matter whether or not it actually contains any pathogens, or any pathogens of interest and whether or not it contains Noroviruses (Norwalk-like viruses), *Campylobacter* species, *Giardia lamblia, Salmonella, Shigella, Cryptosporidium parvum, Clostridium* species, *Toxoplasma gondii, Staphylococcus aureus,* Shiga toxin-producing *Escherichia coli* (STEC), *Yersinia enterocolitica, Bacillus cereus, Bacillus anthracis, Cyclospora cayetanensis, Listeria monocytogenes, Vibrio parahemolyticus* or *V. vulnificus*.

In this disclosure the term "chelating agent" refers to a "polydentate ligand". The terms "chelating agent", "chelator", "chelant", and "sequestering agent" are used interchangeably. The chelating agent is capable of forming multiple bindings to a single atom such as a metal ion, e.g., $Mg^{2+}$ or $Ca^{2+}$.

The term "detergent" as used herein means "surfactant".

In this disclosure the term "beads" refers to particles, which are of a size in the range of 50 μm to 2 mm, in some aspects 100 μm to 800 μm.

In this disclosure the terms "polynucleotide" when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes DNAs and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

In this disclosure the terms "oligonucleotide" refers to a relatively short polynucleotide, including, without limitation, single-stranded deoxyribonucleotides, single- or double-stranded ribonucleotides, RNA, DNA hybrids and double-stranded DNAs. Oligonucleotides, such as single-stranded DNA oligonucleotide probes, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

In this disclosure the term "primary label" refers to a label that can be directly detected, such as a fluorophore.

In this disclosure the "secondary label" refers to a label that is indirectly detected.

Briefly, and as described in more detail below, disclosed and claimed herein are kits, compositions and methods for determining the presence and/or absence of one or more pathogens in a sample.

Pathogen

In some aspects, the organisms for which the method can detect include but is not limited to relevant species, subspecies, serovars, and/or strains of for example, *Escherichia coli* O157:H7, *Shigella dysenteriae*, *Salmonella enterica* ssp. *enterica* (including serovars *Typhi*, *Typhimurium*, and Saintpaul) *Francisella tularensis* ssp. *tularensis*, *Francisella tularensis* ssp. *novicida*, *Vibrio cholerae*, *Vibrio parahaemolyticus*, *Shigella sonnei*, *Yersinia pestis*, *Listeria monocytogenes* and *Yersinia pseudotuberculosis*.

In some aspects, the invention concerns rapid and accurate methods for detecting food-borne pathogens, including without limitation relevant species, subspecies, serovars, and/or strains of for example, parasites and their eggs, Noroviruses (Norwalk-like viruses), *Campylobacter* species, *Giardia lamblia*, *Salmonella*, *Shigella*, *Cryptosporidium parvum*, *Clostridium* species, *Toxoplasma gondii*, *Staphylococcus aureus*, Shiga toxin-producing *Escherichia coli* (STEC), *Yersinia enterocolitica*, *Bacillus cereus*, *Bacillus anthracis*, *Cyclospora cayetanensis*, *Listeria monocytogenes*, *Vibrio parahemolyticus* and *V. vulnificus*, *Helicobactor*, *Mycobacterium*, *Streptococcus*, *Pseudomonas*, *Aeromonas hydrophila*; *Citrobacter freundi*, *Enterobacter cloacae*, *Enter o. faecalis*, *E. coli* non-VTEC, *Hafnia alvei*, *Klebsiella pneumoniae*, *Proteus vulgaris*, *Pseudomonas aeroginosa*.

Pathogenic viruses may be detected in combination with a pathogen detection method as disclosed herein. Examples of pathogenic virus families include, but are not limited to, Adenoviridae, Picornaviridae, Herpesviridae, Hepadnaviridae, Flaviviridae, Retroviridae, Orthomyxoviridae, Paramyxoviridae, Papovaviridae, Rhabdoviridae, and Togaviridae. The term "microorganism" as used in this disclosure includes a virus, bacterium, parasite or parasite's egg.

Time

In some aspects, the one or more pathogens are detected within a positive total time of about 28 hrs or less. In some aspects, the disclosure provides detecting one or more pathogens within a positive total time of about 1 hrs, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 16 hrs, 17 hrs, 18 hrs, 19 hrs, 20 hrs, about 21 hrs, about 22 hrs, about 23 hrs, about 24 hrs, about 25 hrs, about 26 hrs, about 27 hrs, about 28 hrs, about 29 hrs, about 30 hrs, about 31 hrs, about 32 hrs, about 33 hrs, about 34 hrs, about 35 hrs, about 36 hrs, about 37 hrs, about 38 hrs, about 39 hrs, about 40 hrs, about 41 hrs, about 42 hrs, about 43 hrs, about 44 hrs, about 45 hrs, about 46 hrs, about 47 hrs, about 48 hrs, about 49-72 hrs, or about 72-96 hrs. In some aspects, the disclosure provides detecting 2 to 10 pathogens. In some embodiments, the disclosure provides detecting 1, 2, 3, 4, 5, 6, 7, 8, 9, 10, 11, 12, 13, 14, 15, 16, 17, 18, 19, or 20 pathogens. In some aspects, the disclosure provides detecting simultaneously 2, 3, 4, 5, 6, 7, 8, 9, 10, 11, 12, 13, 14, 15, 16, 17, 18, 19, 20 pathogens simultaneously. In some aspects, the disclosure provides detecting simultaneously 20 or more pathogens.

Sample

In some embodiments, as will be appreciated by those of skill in the art, the sample may comprise any number of things, including, but not limited to, bodily fluids (including, but not limited to, blood, nasopharyngeal secretions, urine, serum, lymph, saliva, milk, anal and vaginal secretions, and semen) of virtually any organism, with mammalian samples, including livestock, (e.g. sheep, cow, horse, pig, goat, lama, emu, ostrich or donkey), poultry (e.g. chicken, turkey, goose, duck, or game bird), fish (e.g. salmon or sturgeon), laboratory animal (e.g. rabbit, guinea pig, rat or mouse) companion animal (e.g. dog or cat) or a wild animal in captive or free state, environmental samples (including, but not limited to, air, agricultural, water and soil samples); biological warfare agent samples; research samples; purified samples, such as purified genomic DNA, RNA, proteins, etc.; and raw samples (bacteria, virus, genomic DNA, etc.).

In some embodiments, the sample may be a food, comprising, meats, poultry, fish, seafood, fruits, and vegetables. In some embodiments, the disclosure provides a sample comprising raw food products, cooled or frozen food products, or products that are generally heated prior to consumption. In some embodiments, the sample is not a food product. In some embodiments, the sample may not be a food product In some embodiments, the food products are raw. In some embodiments, the food product could be partially cooked. In some embodiments, the food product could be cooked but may require additional heating prior to consumption. In some embodiments, food products may include meats (beef, pork, lamb, rabbit and/or goat), poultry, wild game (pheasant, partridge, boar and/or bison), fish, vegetables (veggie-patties, veggie hamburgers), combinations of vegetables and meat, egg products (quiches, custards, cheesecakes) and/or baked goods (batters, doughs, cakes, breads, muffins, biscuits, cupcakes, pancakes and the like whether baked, raw or partially baked).

In some embodiments, the sample may be obtained by taking a piece or portion, or by use of a swab, wipe, filter, smear, or any other suitable method, all of which will be readily understood and implemented and selected among by those skilled in the art. In some embodiments, a sample is or comprises food material or is or comprises plant or animal material or is or comprises meat, seafood, fish, vegetables, fruit, salads, premade meals, eggs, dairy produce, combined and uncombined food materials, canned goods, or any other form of fresh, raw, cooked, uncooked, frozen, refrigerated, ground, chopped, canned, heat treated, dried, preserved, refined, or preserved foodstuffs whatsoever. In some embodiments a sample may be taken from an environment, surface, container or location wherein it is desired to determine whether a pathogen of interest is present, for example and without limitation kitchen surfaces, cooking surfaces, food storage containers, eating utensils, refrigerators, freezers, display containers, wrapping materials, live plants and animals and any other environment, location, surface, or material whatsoever that may be of interest to a user. In some embodiments, the sample may be wash solutions of food samples, drinking water, ocean/river water, environment water, mud, or soil. Those skilled in the art will understand and implement suitable methods for selecting, obtaining and handling any sample for use in embodiments. In selected embodiments samples may comprise meat, fish, seafood, vegetables, eggs or dairy produce.

In some embodiments, the sample may be less than or equal to about 25 grams by weight. In some aspects, the sample is about 1 gram, about 2 grams, about 3 grams, about 4 grams, about 5 grams, about 6 grams, about 7 grams, about 8 grams, about 9 grams, about 10 grams, about 11 grams, about 12 grams, about 13 grams, about 14 grams, about 15 grams, about 16 grams, about 17 grams, about 18 grams, about 19 grams, about 20 grams, about 21 grams, about 22 grams, about 23 grams, about 24 grams, or about 25 grams. In some embodiments, the sample may be less than 1 gram.

In some embodiments, the sample may be greater than or equal to about 25 grams by weight. In some embodiments the sample is about 26 grams, about 27 grams, about 28 grams, about 29 grams, about 30 grams, about 31 grams, about 32 grams, about 33 grams, about 34 grams, about 35 grams, about 36 grams, about 37 grams, about 38 grams, about 39 grams, about 40 grams, about 41 grams, about 42 grams, about 43 grams, about 44 grams, about 45 grams, about 46 grams, about 47 grams, about 48 grams, about 49 grams, about 50 grams, about 51 grams, about 52 grams, about 53 grams, about 54 grams, or about 55 grams. In some aspects, the sample is greater than 55 grams by weight.

Enrichment

In some aspects, the sample may be enriched. In some aspects, the sample may be enriched in media. In some aspects, enrichment comprises suspending the sample in the media. In some aspects, the media is a nonselective media, selective media, rich and non-selective media, rich and selective media, or a combination thereof. In some aspects, selective media may contain combinations of selective agents such as antibiotic to inhibit growth of competing microorganisms. In some aspects, selectivity of selective media may be controlled by concentration of the selective agents. In some embodiments, the sample is suspended in a rich and nonselective media. In some embodiments, the sample is suspended in Buffered Listeria Enrichment Broth Base (no supplements).

In some aspects, the media may comprise one or more of water, agar, proteins or peptides, growth factors, amino acids, caesein hydrolysate, salts, lipids, carbohydrates, minerals, vitamins, and pH buffers, and may contain extracts such as meat extract, yeast extract, tryptone, phytone, peptone, and malt extract, and may comprise luria bertani (LB) medium. In some aspects, the media may contain extracts such as meat extract, yeast extract, tryptone, phytone, peptone, or malt extract. In some aspects, the media may comprise luria bertani (LB) medium. In some aspects, the media may be simple, complex or defined media and may be enriched media and may be supplemented in a wide variety of ways, all of which will be readily understood by those skilled in the art. In some aspects, the media may comprise MOPS buffer, an Iron (III) salt such as ferric citrate, a magnesium salt such as Magnesium sulphate, a lithium salt such as lithium chloride, and may contain pyruvate. In some embodiments, the media may comprise or consist of any core media as defined herein.

In some aspects, media may contain a pH buffer which may be a non-Magnesium chelating buffer. In some aspects, the pH buffer is a mixture of MOPS sodium salt and MOPS free acid, but a range of other buffers such as Carbonate and Phosphate buffers may be useable in alternative embodiments and will be readily selected amongst and implemented by those skilled in the art, to achieve a desired pH for the medium.

In some aspects, the media may be provided in the form of a powder or concentrate, also generally referred to as "powdered medium", "medium powder", "medium concentrate", "concentrated medium" or the like, comprising a plurality of components and suitable to be combined with a predetermined volume of water to provide a liquid medium with desired concentrations of the particular components. Such a powdered medium or concentrated medium may be complete, meaning that it need only be dissolved in suitable water, normally sterile water, before use. Alternatively, in some aspects, a powdered or concentrated medium may be partial, meaning that additional components need to be added to provide a complete medium suitable for use. In embodiments a powdered or concentrated medium also includes medium that is at least partly hydrated in concentrated form suitable for dilution to produce the medium for actual use in culturing. It will be understood that term "medium" or "media" as used herein, unless otherwise required by the context, includes both the final media having components at concentrations suitable for culturing pathogens, and powdered or concentrated media suitable for dilution.

In some aspects, the components included in an enrichment solution include one or more of MOPS, Fe(111) salt, Lithium salt, pyruvate. In some aspects a selective enrichment supplement comprises one or more selective agents such as nalidixic acid, cycloheximide, and acriflavine hydrochloride. In some aspects, the enriched broth contains one or more of Magnesium sulphate, Lithium Chloride, Ferric Citrate, Sodium pyruvate and enrichment supplement.

In some aspects, the media may comprise one or more of Brain Heart Infusion Broth, Tryptic Soy Broth, Brucella Agar, Buffered Listeria Enrichment Broth Base, Carbohydrate Consumption Broth, Fraser Broth, Base, Fraser secondary enrichment broth base, HiCrome™ Listeria Agar Base, LPM Agar, Listeria Enrichment Broth according to FDA/IDF-FIL, Listeria Motility Medium, Listeria Selective Agar, Listeria mono Confirmatory Agar (Base), Listeria mono Differential Agar (Base), Nutrient Agar, Nutrient Broth No. 1, Nutrient Broth No. 2, Nutrient Broth No. 4, Oxford Agar, PALCAM Listeria Selective Agar, PALCAM Listeria Selective Enrichment Broth, Plate Count Agar, Plate Count Agar, Plate Count MUG Agar, Plate Count Skim Milk Agar, Rhamnose Broth, Tryptone Soya Yeast Extract Agar, UVM Listeria Selective Enrichment Broth, Universal Pre-Enrichment or a combination thereof.

In some aspects, the media may comprise one or more of Andrade Peptone Water, Andrade peptone water, Blood Agar (Base), Bromcresol Purple Broth, China Blue Lactose Agar, Christensen's Urea Agar, CLED Agar, Decarboxylase Broth Base, Moeller, DEV Lactose Broth, DEV Lactose Peptone Broth, DEV Tryptophan Broth, Glucose Bromcresol Purple Agar, HiCrome™ ECC Agar, HiCrome™ MM Agar, HiCrome™ UTI Agar, modified, Kligler Agar, Lactose Broth, Lactose Broth, Lactose Broth, Vegitone, Lysine Iron Agar, Malonate Broth, Methyl Red Voges Proskauer Broth, Methyl Red Voges Proskauer Saline Broth, Mineral-modified Glutamate Broth (Base), Motility Test Medium, Mucate Broth, MUG Tryptone Soya Agar, Nitrate Broth, OF Test Nutrient Agar, Simmons Citrate Agar, Triple Sugar Iron Agar, Tryptone Medium, Tryptone Water, Tryptone Water, Vegitone, Urea Broth Selective media for differentiation, BRILA MUG Broth, DEV ENDO Agar, ECD MUG Agar, EMB Agar, Endo Agar, ENDO Agar (Base), Gassner Agar, HiCrome™ Coliform Agar, HiCrome™ E. coli Agar B, HiCrome™ ECC Selective Agar, HiCrome™ ECD Agar with MUG Selective media for differentiation, HiCrome™ Mac Conkey Sorbitol Agar, HiCrome™ M-TEC Agar, HiCrome™ Rapid Coliform Broth, Lactose TTC Agar with Tergitol®-7, Levine EMB Agar, LST-MUG Broth, Mac Conkey Agar No. 1, Mac Conkey Agar No. 1, Vegitone, MacConkey Agar with Crystal Violet, Sodium Chloride and 0.15% Bile Salts, MacConkey Agar with Crystal Violet, Sodium Chloride and 0.15% Bile Salts, MacConkey Broth, MacConkey Broth purple, MacConkey MUG Agar, Mac-Conkey-Agar (without salt), MacConkey-Sorbitol Agar, Membrane Lactose Glucuronide Agar, m-Endo Agar LES, M-FC Agar, m-FC Agar Plates (55 mm diameter), M-FC Agar, Vegitone, M-Lauryl Sulphate Broth, MUG EC Broth, TBX Agar, Tergitol®-7 Agar, Violet Red Bile Agar, Violet Red Bile Agar, Vegitone, Violet Red Bile Glucose Agar, Violet Red Bile Glucose Agar without Lactose, Violet Red Bile Glucose Agar without Lactose, Vegitone, Violet Red Bile Lactose Dextrose Agar, VRB MUG Agar, WL Differential Agar, XLT4 Agar (Base) Selective media, A1 Broth, Brilliant Green Bile Lactose Broth, EC Broth, ECD Agar, Lauryl sulphate Broth, Lauryl sulphate Broth, M Endo Broth, M HD Endo Broth with Brilliant Green, M-Lauryl Sulphate Broth, Vegitone, Mossel Broth or a combination thereof.

In some aspects, the media comprises one or more of Bismuth sulfite Agar, BPL Agar, Brilliant Green Agar, modified, Brilliant Green Phenol Red Lactose Sucrose Agar, Purple Broth, DCLS Agar, DCLS Agar No. 2, Deoxycholate Citrate Agar, Glucose Hektoen Enteric Agar, Kligler Agar Fluka, Leifson Agar, Lysine Decarboxylase Broth, Muller-Kauffmann Tetrathionate Broth, Base (ISO), Pril® Mannitol Agar, Rappaport Vassiliadis Broth, Rappaport Vassiliadis Broth, modified, Rappaport Vassiliadis Medium, Rappaport Vassiliadis medium (base), modified, semi-solid, Salmonella Agar, Salmonella Enrichment Broth, Selenite Broth (Base), Selenite Cystine Broth, SIM Medium, SS-Agar, TBG Broth, Tetrathionate Broth, Tetrathionate Enrichment Broth, Triple Sugar Iron Agar, Urea Broth, XLD Agar or a combination thereof.

In some aspects, the media may comprise an oxygen scavenger. In some aspects, the oxygen scavenger may be selected from at least one of a pyruvate salt, catalase, a thioglycolate salt, cysteine, Oxyrase™, $Na_2S$, or FeS. In some aspects, the media may comprise from about 1.0 to about 20.0 g/L sodium pyruvate. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 24.0, 25 or more than about 25.0 g/L oxygen scavenger. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 24.0, 25 or more than about 25.0 g/L sodium pyruvate. In some aspects, the media may further comprise carbohydrate such as dextrose, esculin, maltose, amygdalin, cellobiose, fructose, mannose, salicin, dextrin, (x-methyl-D-glucoside and mixtures thereof. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 24.0, 25, 26, 27, 28, 29, 30 or more than about 30.0 g/L carbohydrate. In some aspects, the media may comprise from about 1.0 to about 20.0 g/L dextrose. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5 or more than about 20.0 g/L dextrose. In some aspects, the media may comprise Yeast Extract. In some aspects, the media may comprise from about 1.0 to about 30.0 g/L Yeast Extract. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0, 4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6, 4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 24.0, 25, 26, 27, 28, 29, 30 or more than about 30.0 g/L Yeast Extract. In some aspects, the media may comprise salts such as sodium, potassium, or calcium salts of chloride. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 24.0, 25, 26, 27, 28, 29, 30 or more than about 30.0 g/L salts. In some aspects, the media may comprise from about 1.0 to about 30.0 g/L sodium chloride. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 24.0, 25, 26, 27, 28, 29, 30 or more than about 30.0 g/L sodium chloride. In some aspects, the media further comprises a protein, which may be provided from a variety of sources. For example, the protein may be provided from sources such as Tryptone, Tryptose, Soytone, Peptone, Pantone, Bitone, Proteose Peptone, pancreatic digest of gelatin, pancreatic digest of casein, enzymatic digest of soy and mixtures thereof. In some aspects, the media comprises from about 1.0 to about 70.0 g/L protein. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9, 4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 24.0, 25, 26, 27, 28, 29, 30, 31, 32, 33, 34, 35, 36, 37, 38, 39, 40, 45, 50, 60, 70 or more than about 70.0 g/L protein. In some aspects, the media comprises from about 1.0 to about 60.0 g/L pancreatic digest of casein. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7, 4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 1.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 24.0, 25, 26, 27, 28, 29, 30, 31, 32, 33, 34, 35, 36, 37, 38, 39, 40, 45, 50, 60 or more than about 60.0 g/L pancreatic digest of casein. In some aspects, the media comprises from about 1.0 to about 40.0 g/L enzymatic digest of soy. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0, 4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5.3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 24.0, 25, 26, 27, 28, 29, 30, 31, 32, 33, 34, 35, 36, 37, 38, 39, 40, or more than about 40.0 g/L pancreatic digest of casein. In some aspects, may further comprise buffers, which are effective for maintaining the pH in a desired range. For example, buffers that may be used include buffers such as potassium phosphate monobasic, potassium phosphate dibasic, sodium phosphate dibasic, and mixtures thereof. In some aspects, the media comprises from about 1.0 to about 50.0 g/L buffer. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 24.0, 25, 26, 27, 28, 29, 30, 31, 32, 33, 34, 35, 36, 37, 38, 39, 40, 45, 50, or more than about 50.0 g/L buffers. In some aspects, the media may comprise from about 1 to about 20 g/L potassium phosphate. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9.8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0 or more than about 20.0 g/L potassium phosphate. In some aspects, the media comprises from about 1 to about 40 g/L disodium phosphate. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0, 4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9, 4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 24.0, 25, 26, 27, 28, 29, 30, 31, 32, 33, 34, 35, 36, 37, 38, 39, 40, or more than about 40.0 g/L disodium phosphate. In some aspects, the media comprises from about 1 to about 20 g/L dipotassium phosphate. In some aspects, the media comprises about 0.0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.5, 14.0, 14.5, 15.0, 15.5, 16.0, 16.5, 17.0, 17.5, 18.0, 18.5, 19.0, 19.5, 20.0 or more than about 20.0 g/L dipotassium phosphate.

In some aspects, the media may comprise essential ions such as magnesium and/or iron. In some embodiments, magnesium may be selected from the group of magnesium sulfate, magnesium chloride, and mixtures thereof. In some embodiments, iron may be selected from the group of ferric ammonium citrate, ferrous sulfate, ferric sulfate, ferric citrate, ferrous ammonium sulfate, ferric chloride, and mixtures thereof.

In this disclosure the term "pyruvate salt" means and includes all salts of pyruvic acid (also known as 2-oxopropanoic acid) and any compounds comprising a pyruvate anion, and any biologically effective isomers or substituted forms thereof. In embodiments the pyruvate salt is sodium or potassium pyruvate. Those skilled in the art will readily identify and avoid salts which are not biologically effective or desirable, for example due to toxicity. In embodiments a salt is soluble and may be organic or inorganic, and by way of example may be chloride, phosphate, nitrate, hydrogen carbonate, pyruvate, ethanoate.

In some embodiments, the yeast extract may be yeast autolysate or yeast hydrolysate. For example, the yeast extract may include the water-soluble compounds of yeast autolysate. In this regard autolysis of the yeast cells may be carefully controlled to preserve natural vitamin B complexes. The yeast extract may be obtainable by growing *Saccharomyces* spp. in carbohydrate-rich plant media. The yeast may be harvested, washed and resuspended in the water, and then self-digested with its own enzymes ("autolysis") in the water. The autolytic activities of the enzymes may be lost by heating. The resulting yeast extract is filtered until it becomes clear, and the filtrate is spray-dried into powder form. The yeast extract may supply vitamins, nitrogen, amino acids, and carbon to the medium. The yeast extract may be commercially available from, for example, DIFCO™ Laboratories Inc., and ACUMEDIA™ Inc.

In some embodiments, the media may comprise suitable carbon sources. Among the suitable carbon sources are, for example, glucose, fructose, xylose, sucrose, maltose, lactose, mannitol, sorbitol, glycerol, corn syrup and corn syrup solids. Examples of suitable nitrogen sources include organic and inorganic nitrogen-containing substances such as peptone, corn steep liquor, meat extract, yeast extract, casein, urea, amino acids, ammonium salts, nitrates, enzymatic digest of soy, and mixtures thereof.

Those skilled in the art will readily understand that the growth of a desired microorganism will be best promoted at selected temperatures suited to the microorganism in question. In particular embodiments culturing may be carried out at about 39° C. and the media to be used may be pre-warmed to this temperature. In embodiments disclosed herein, enrichment may be carried out at any temperature between 33° C. and 43° C. and may be carried out at about 33° C., 34° C. 35° C., 36° C., 37° C., 38° C., or 39° C., or 40° C., or 41° C. or 42° C. or 43° C. or between 33° C. and 34° C., 34° C. and 35° C., 35° C. and 36° C., 36° C. and 37° C., 37° C. and 38° C., 38° C. and 39° C. 39° C. and 40° C. 40° C. and 41° C., 41° C. and 42° C. or 42° C. and 43° C. or at a temperature of between 34° C. and 43° C., or between 35° C. and 42° C. or between 36° C. and 42° C., 38° C. and 42° C. or between 39° C. and 41° C. or between 39° C. and 40° C. or between 38° C. and 39° C., or between 39° C. and 40° C., or between 40° C. and 41° C., or between 41° C. and 42° C. or between 42° C. and 43° C.

In some embodiments, the kits described herein can comprise a media disclose herein. In some embodiments, the kits disclosed herein can comprise Media A or a derivative thereof. In some embodiments, the kits disclosed herein can comprise Media B or a derivative thereof. In some embodiments, Media A comprise: yeast extract 6 g/L, pancreatic digest of casein 17 g/L, enzymatic digest of soy 3 g/L, dextrose 2.5 g/L, NaCl 5 g/L, dipotassium phosphate 2.5 G/L, potassium phosphate 1.35 g/L, disodium phosphate 9.6 g/L, sodium pyruvate 1.1 g/L. In some embodiments, Media A can have a pH within the range of 7.2-7.4. In some embodiments, Media B comprise: yeast extract 12 g/L, pancreatic digest of casein 34 g/L, enzymatic digest of soy 6 g/L, dextrose 5 g/L, NaCl 10 g/L, dipotassium phosphate 5 g/L, potassium phosphate 2.7 g/L, disodium phosphate 19.2 g/L, sodium pyruvate 2.2 g/L. In some embodiments, Media B can have a pH was within the range of 7.2-7.4.

Supplement

In some embodiments, the media comprises supplements.

In some embodiments, a supplement comprises one or more of a magnesium salt, a lithium salt, an iron(111) salt, a pyruvate and a selective agent, or comprises precursors or modified forms that may be readily converted or metabolized to form any of the foregoing. In some embodiments, a supplement is a supplement for promoting the growth of one or more pathogen. In some embodiments, a supplement is a supplement for promoting the growth of *Listeria* spp. In some embodiments, selective agents include antibiotics, sulphanamides or antiseptics. In some embodiments, a selective agent is or comprises one, two or all three of nalidixic acid, cycloheximide and acriflavine hydrochloride or includes suitable equivalents or alternatives thereto. In some embodiments, the working concentration of cycloheximide is about 33.75 mg per liter of culture medium, and in alternative embodiments is between 15 and 50 mg/liter of culture medium, or may be greater than 5, 0, 15, 20, 25, 30, 35, 40, 45, 50, 55, 60, 65, 70, 75, 80, 85, 90, 95, 100 or more mg/liter of culture medium. In some embodiments the working concentration of nalidixic acid is about 27 mg per liter of culture medium, or is between 10 and 50 mg/liter of culture medium or is greater than 5, 10, 15, 20, 25, 30, 35, 40, 45, 50, 55, 60, 65, 70, 75, 80, 85, 90, 95, 100 or more mg/liter of culture medium. In some embodiments, the working concentration of acriflavine hydrochloride is about 10, 25 mg/liter, or is between 6000 and 15,000 mg/liter, or is greater than 1000, 2000, 3000, 4000, 5000, 6000, 7000, 8000, 9000, 10000, 11000, 12000, 13000, 14000, 15000, 16000, 17000, 18000, 19000, 20000 or more mg/liter of culture medium. Those skilled in the art will, however, recognize that a wide variety of concentrations of selective agents may be employed and will make suitable adjustments for particular purposes.

In some embodiments, the media is free of supplements.

In some embodiments, the media is substantially free of supplements.

PH

In some aspects, the pH of culture medium is generally set at between 7 and 8 and for example in particular embodiments may be about 7.0, 7.1, 7.2, 7.3, 7.4, 7.5, 7.6, 7.7, 7.8, 7.9 or 8.0 or is in a range delimited by any two of the foregoing values. It will be understood that a pH outside of the range pH7-8 may still be useable in embodiments, but that the efficiency and selectivity of the culture may be adversely affected. Therefore in some embodiments, the pH can be 1-7 or 8-14.

Volume

In some embodiments, the sample may be enriched by suspension in media at a volume in the range of about 10 ml to about 1000 ml. In some embodiments, the sample maybe enriched by suspension in media at a volume of about 10 ml, 20 ml, 30 ml, 40 ml, 50 ml, 60 ml, 70 ml, 80 ml, 90 ml, 100 ml, 110 ml, 120 ml, 130 ml, 140 ml, 150 ml, 160 ml, 170 ml, 180 ml, 190 ml, 200 ml, 210 ml, 220 ml, 225 ml, 230 ml, 240 ml, 250 ml, 300 ml, 350 ml, 400 ml, 450 ml, 500 ml, 550 ml, 600 ml, 650 ml, 700 ml, 800 ml, 900 ml, or about 1000 ml, in some embodiments a volume above 50 ml, in some embodiments the volume is about 225 f 10 ml, in some embodiments about 225 ml.

Homogenizing

In some embodiments, the sample may be homogenized or otherwise finely divided in order to separate the pathogen from the sample by techniques know to one of skill in the art. For example, stirring, mixing, agitating, blending, or vortexing. In some embodiments, samples may be homogenized by hand mixing, stomaching, or blending. In some embodiments, the sample is stomached. A stomaching device can be used that mixes a source and diluents in a bag through the use of two paddles in a kneading-type action. See, for example, U.S. Pat. No. 3,819,158. An oscillating device known as the PULSIFIER® is described in U.S. Pat. No. 6,273,600, which employs a bag placed inside an agitating metal ring. Another technique, vortexing for analyte suspension, has been described in U.S. Pat. No. 6,273,600. See also U.S. Patent.

In some embodiments, the sample may be homogenized for about 1, 2, 3, 4, 5, 6, 7, 8, 9, 10, 15, 20, 25, 26, 27, 28, 29, 30, 31, 32, 33, 34, 35, 40, 45, 50, 55, 60, 70, 80, 90, 100, 110, 120, 130, 140, 150, 160, 170, 180, 190, 200, 210, 220, 225, 230, 240, 250, 300, 350, 400, 450, 500, 550, 600, 650, 700, 800, 900, or 1000 seconds, in some embodiments above 15 seconds, in some embodiments 30 f 5 seconds, in some embodiments about 30 seconds.

Following homogenization, in some embodiments, the sample may be incubated. For example, incubation following homogenization may occur at a temperature of about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80° C., or to any other temperature above 80° C. In some embodiments, the incubation temperature is in the range of about 25 to about 80° C., in some embodiments about 25 to about 45° C., in some embodiments the temperature is about 37f 5° C. In some embodiments, incubation following homogenization can be for a time period in the range of about 1 minute to about 48 hours, e.g., 1, 5, 10, 15, 20, 25, 30, 40, 50, 60, 70, 80, 90, 100, 110, 120, 130, 140, 150, 160, 170, 180, 190, 200, 210, 220, 230, 240, 250, 260, 270, 280, 290, 300, 400, 500, 600, 700, 800, 900, 1000, 1500, 2000, 2500, 3000 minutes, in some embodiments 60 minutes. In some embodiments, the sample is incubated following homogenization while being agitated. In some embodiments, the sample is incubated following homogenization and is agitated at a speed in the range of 20 to 3500 rpm, e.g., 20, 50, 100, 150, 200, 300, 400, 500, 700, 1000, 1100, 1200, 1300, 1350, 1400, 1450, 1500, 1550, 1600, 1750, 2000, 2250, 2500, 2750, 3000, 3250, 3500 rpm. In some embodiments, the sample can be incubated following homogenization while substantially free of being agitated. In some embodiments, the sample can be incubated following homogenization free of being agitated.

Lysis

Cell lysis is a process of releasing materials in a cell by disrupting the cell membrane, and in particular, a process of extracting intracellular materials from a cell to isolate DNA or RNA before amplification, such as a polymerase chain reaction (PCR). In some embodiments, cell lysis may be performed to isolate DNA or RNA before amplification, such as a polymerase chain reaction (PCR).

In some aspects, lysis may be by mechanical methods include ultrasonication, disruption using a homogenizer, pressing mechanism, for example, a French press, etc., decompression, pulverization, etc. Non-mechanical lysis methods include chemical methods, thermal methods, enzymatic methods, etc.

In some aspects, nucleic acid from the sample may be isolated using known techniques. For example, the sample may be treated to lyse the cells, using known lysis buffers, sonication, electroporation, etc., with purification occurring as needed, as will be appreciated by those in the art. In addition, the reactions outlined herein may be accomplished in a variety of ways, as will be appreciated by those in the art. Components of the lysis reaction may be added simultaneously, or sequentially, in any order, with some embodiments outlined below. In some aspects, the lysis reaction may include a variety of other reagents that may be included in assays to be performed following cell lysis. In some aspects, these reagents include salts, buffers, neutral proteins, e.g. albumin, detergents, etc., which may be used to facilitate optimal hybridization and detection, and/or reduce non-specific or background interactions. In some aspects, reagents that otherwise improve the efficiency of an assay, such as protease inhibitors, nuclease inhibitors, anti-microbial agents, etc., may be used, depending on the sample preparation methods and purity of the target.

In some aspects, lysis may be by a lysis buffer. In some aspects, the lysis buffer has a pH that is approximately neutral. In some aspects, the lysis buffer has a pH in the range of 5.5 to 8, i.e., a pH of 5.5, 6, 6.5, 7, 7.5, or 8, in some aspects a pH of about 7. It will be understood that a pH outside of the range pH7-8 may still be useable in embodiments. Therefore in some aspects, the pH can be about 1-7 or about 8-14.

Recovery of DNA and/or RNA utilizing a lysis buffer of the present invention may proceed by combining the lysis buffer sample, agitating the mixture of the cells and lysis buffer to provide a mixture including a supernatant including DNA and/or RNA to be recovered and a solids fraction, and recovering the DNA-containing supernatant.

In some aspects, a portion of the sample may be combined with the lysis buffer and forms a sample/lysis buffer mixture. In some aspects, formation of the sample/lysis buffer mixture includes dilution of the lysis buffer with an aqueous medium (e.g., deionized water). In some aspects, an aqueous medium is combined with the lysis buffer at a volumetric ratio (aqueous medium:lysis buffer) of about 1:1, 1:2, 1:3, 1:4, 1:5, 1:6, 1:10, 1:20, 20:1, 10:1, 6:1, 5:1, 4:1, 3:1, or about 2:1 for dilution. After the sample and lysis buffer have been combined, the mixture is treated to provide breakdown of the sample cell walls and release of DNA and/or RNA. In some aspects, this treatment includes agitation of the sample/lysis buffer mixture, which generally includes placing samples of the mixture into a suitable container (e.g., a multi-well plate, deep-well block) and shaking of the samples.

In some aspects, the agitation for breakdown of cell walls and release of DNA and/or RNA includes contacting the sample with particulate matter for facilitating breakdown of the cell walls. In some aspects, this contact generally includes placing suitable particulate matter in each well of the multi-well plate/deep-well block so that the particulate matter and sample come into mutually abrading contact during agitation (e.g., shaking) of the sample/lysis buffer mixture. The particulate matter is generally spherical and constructed of suitable material (e.g., stainless steel). In some aspects, the particulate matter may not be spherical.

In some aspects, after a suitable period of agitation of the sample/lysis buffer mixture, the resulting mixture generally comprises a lysed sample mixture including a solids fraction and a supernatant comprising nucleic acid to be recovered. In some aspects, the lysed sample may be treated for purposes of separating the solids fraction and supernatant. In some aspects, this treatment generally comprises centrifuging the samples (i.e., the multi-well plate, deep-well block) under suitable conditions. Typically, the samples are subjected to treatment by centrifuging at from about 1000 to about 3500 revolutions per minute (rpm) for from about 5 to about 10 minutes.

In some aspects, prior to agitation of the sample/lysis buffer mixture, the mixture may be subjected to an incubation period. In some aspects, the incubation period proceeds for at least about 5 minutes, at least about 10 minutes, or at least about 15 minutes. In some aspects, during the incubation period, the sample/lysis mixture may be subjected to temperatures of room temperature, or even higher. In some aspects, the sample/lysis mixture may be subjected to temperatures of up to about 25° C., up to about 35° C., or up to about 45° C., or up to about 55° C., or up to about 65° C., or up to about 75° C. The precise combination of time/temperature incubation conditions is not narrowly critical, however, in various embodiments, the incubation proceeds for a up to about 15 minutes while the sample/lysis buffer mixture is subjected to a temperature of from about 20° C. to about 30° C. (e.g., about 25° C.).

In some aspects, separation of the lysed sample mixture (e.g., by centrifuging) forms a lysed sample mixture including a nucleic acid supernatant that is then recovered from the lysed sample mixture. In some aspects, the nucleic acid is then subjected to analysis by any method known in the art, including but not limited to those listed below. In some aspects, the DNA content of the lysed sample mixture and/or the nucleic acid supernatant is at least about 50%, at least about 60%, at least about 70%, at least about 80%, at least about 90%, at least about 95%, or at least about 99% of the DNA present in the sample prior to lysing the sample.

In some aspects, the lysis buffer comprises a buffering component. In some aspects, the lysis buffer according to the present invention may comprise buffering components that may, for example, be used to adjust the pH of the lysis buffer. In some aspects, buffering components include, for example, 3-{[tris(hydroxymethyl)methyl]amino}propanesulfonic acid (TAPS), N,N-bis(2-hydroxy-ethyl)glycine (Bicine), tris (hydroxymethyl)methylamine (TRIS), N-tris(hydroxylmethyl)-methylglyxine (Tricine), 4-2-hydroxyethyl-1-piperazineethanesulfonic acid (HEPES), 2-{[tris(hydroxymethyl) methyl]amino}ethanesulfonic acid (TES), 3-(N-morpholino)propane-sulfonic acid (MOPS), piperazine-N,N'-bis(2-ethanesulfonic acid) (PIPES), dimethylarsinic acid (Cacodylate), saline sodium citrate (SSC), 2-(N-morpholino)ethanesulfonic acid (MES), and combination thereof. In some aspects, the lysis buffer according to the present invention may comprise buffering components present at a concentration in the range of about 0.01 to about 300 mM. In some aspects, the buffering components can be present at about 0.01 mM, 0.05 mM, 0.1 mM, 0.5 mM 1.0 mM, 5.0 mM, 10 mM, 20 mM, 30 mM, 40 mM, 50 mM, 60 mM, 70 mM, 80 mM, 90 mM, 110 mM, 120 mM, 130 mM, 140 mM, 150 mM, 160 mM, 170 mM, 180 mM, 190 mM, or 200 mM, 250 mM, or about 300 mM. In some aspects, the buffering components can be present at a concentration above about 20 mM. In some aspects, the concentration is above 20 mM, in some aspects, the concentration is about 80 f 10 mM, in some aspects, the concentration is about 80 mM. In some aspects, the lysis buffer is substantially free of a buffering component.

In some aspects, the lysis buffer according to the present invention may comprise chelating agents. In some aspects, the chelating agents include, for example, acetylacetone, ethylenediamine, diethylenetriamine, iminodiacetate, triethylenetetramine, triaminotriethylamine, nitrilotriacetate, ethylenediaminotriacetate, ethylenediaminotetraacetic acid (EDTA), ethylene glycol tetraacetic acid (EGTA), diethylene triamine pentaacetic acid (DTP A), 1,4,7,10-tetraazacyclododecane-1,4,7,10-tetraacetic acid (DOTA), and combination thereof. In some embodiments, the lysis buffer according to the present invention, contain one or more chelating agents, for example, one or more of the above chelating agents. In some aspects, the lysis buffer may contain one or more chelating agents in a concentration in the range of about 0.5 to about 100 mM, in some aspects, about 5 to about 10 mM, such as in a concentration of about 1, 2, 5, 6, 7, 8, 9, 10, 15, 20, 25, 30, 35, 40, 45, 50, 60, 70, 80, 90, or 100 mM. In some aspects, the lysis buffer is substantially free of a metal chelating agent.

In some aspects, the lysis buffer may comprise a surfactant. In some aspects, the surfactants include, for example, alkyl sulfate salts, such as sodium dodecyl sulfate (SDS) or ammonium lauryl sulfate, non-ionic surfactants, such as Triton X-100, octyl glucoside, Genapol X-100, or polysorbates, e.g., Tween 20 or Tween 80, and sarkosyl (N-lauroylsarcosine) and combinations thereof. In some aspects, surfactant of the present invention may also include nonyl phenoxypolyoxyletthanol (NP-40). In some aspects, the lysis buffer according to the present invention may contain one or more chelating agents, for example, one or more of the above surfactants. In some aspects, the lysis buffer according to the present invention may contain one or more surfactants in a concentration in the range of about 0.2% to about 20% (w/v), in some aspects, about 0.5% to 10% (w/v), such as about 0.5, 1.0, 1.5, 2.0, 2.5, 3.0, 3.5, 4.0, 4.5, 4.8, 5.0, 5.5, 6.0, 6.5, 7.0, 7.5, 8.0, 8.5, 9.0, 9.5, or about 10% (w/v). In some aspects, the lysis buffer according to the present invention is substantially free of surfactants.

In some aspects, the lysis buffer may comprise a precipitant. In some aspects, precipitants include, for example, glycerol, dimethyl sulfoxide (DMSO), acetonitrile (ACN), bovine serum albumin (BSA), proteinase K, acetate salts, and combinations thereof. In some aspects, the lysis buffer can comprise proteinase K. In some aspects, the lysis buffer according to the present invention may contain one or more precipitants in a concentration in the range of about 2% to about 50% (w/v), in some aspects, about 15% to about 35% (w/v), such as about 2, 5, 10, 15, 20, 21, 22, 23, 24, 25, 26, 27, 28, 29, 30, 35, 40, 45, 48, 50, 55, or about 60/6 (w/v). In some aspects, the lysis buffer according to the present invention is substantially free of precipitants.

In some aspects, the lysis buffer may comprise a lysing moiety. In some aspects, the lysis buffer comprises at least two lysing moieties. In some aspects, the lysing moiety is a bead. In some aspects, the beads may exhibit any shape, for example, the bead may be ball-shaped, cube-shaped, triangular-shaped, or they may exhibit any irregular shape. In some aspects, the beads are made of a solid inert material. In some aspects, the beads exhibit a firm consistency and do not react chemically with biological substances such as proteins or nucleic acids to a significant extent. In some aspects, the beads do not bind nucleic acids to a significant extent. In some aspects, the beads are made of glass, ceramics, plastics, or metal such as steel. In some aspects, bead surfaces may be made to a variety of bead types including, but not limited to, beads made with silica (e.g., manufactured as fused quartz, crystal, fumed silica or pyrogenic silica, colloidal silica, silica gel, aerogel, glass, fiber (e.g., optical fiber), cement and ceramics (e.g., earthenware, stoneware, and porcelain), zirconium, zirconium silica, zirconium yttrium, and all other related glass oxide and mixtures of glasses and oxides. In some aspects, the term "beads" does not refer beads used for nucleic acid isolation. In some aspects the term "beads" as described herein and are present in the lysis reaction mixture in a concentration in the range of about 0.50 to about 1.5 g/ml, in some aspects, in the range of about 0.100 to about 0.900 g/ml, in some aspects, in the range of about 0.150 to about 0.950 g/ml, in some aspects, in the range of about 0.250 to about 0.950 g/ml. In some embodiments, beads may be present in the lysis buffer mixture in a concentration of about 0.50, 0.100, 0.150, 0.200, 0.250, 0.300, 0.350, 0.400, 0.450, 0.500, 0.600, 0.700, 0.800, 0.850, 0.88, 0.900, 1, 1.1, 1.2, 1.3, 1.4, or about 1.5 g/ml, in some aspects, in a concentration of about 0.8f 0.1 g/ml, in some aspects, in a concentration of about 0.88±0.05 g/ml.

In some aspects, the lysing moiety may be a lysing enzyme. In some aspects, the lysing moiety may be β-glucuronidase, Mutanolysin, lysozyme, Achromopeptidase, Lysostaphin, Labiase, combination thereof and/or other lytic enzymes know by one of skill in the art. In some aspect, the lysing moiety may be lysozyme. In some aspects, lysozyme as described herein are present in the lysis buffer in a concentration in the range of about 5 to about 150 mg/ml, in some aspects, in the range of about 15 to about 25 mg/ml, in some aspects, in the range of about 18 to about 25 mg/ml, in some aspects, in the range of about 20 to about 25 mg/ml. In some aspects, lysozyme may be present in the lysis buffer in a concentration of about 5, 10, 15, 20, 0.25, 30, 35, 40, 45, 50, 60, 70, 80, 85, 90, 100, 110, 120, 130, 140, or about 150 mg/ml, in some aspects, in a concentration of about 20f 3 mg/ml, in some aspects, in a concentration of about 20±0.05 mg/ml.

In some aspects, the lysis buffer further comprises a mineral salt selected from the group consisting of sodium chloride (NaCl), potassium chloride (KCl), diammonium sulfate ($NH_4SO_4$), and combinations thereof.

In some aspects, the lysis buffer may further comprise sodium chloride (NaCl). In some aspects, the lysis buffer may further comprise potassium chloride (KCl). In some aspects, the lysis buffer may further comprise diammonium sulfate ($NH_4SO_4$).

In some aspects, the lysis buffer may further comprise an alkali metal hydroxide selected from the group consisting of sodium hydroxide, potassium hydroxide, and combinations thereof. In some aspects, the lysis buffer may further comprise sodium hydroxide. In some aspects, the lysis buffer may further comprise potassium hydroxide.

In some aspects, cell lysis can occur in one step.

In some aspects, cell lysis may occur in two or more steps. In some aspects, cell lysis can occur in two steps. In some aspects, the first sample lysis may comprise combining the sample and the lysis buffer composition thereby forming a sample/lysis buffer mixture, agitating the sample/lysis buffer mixture, thereby lysing the sample and forming a lysed sample mixture. In some aspects, a second sample lysis comprising continuing to agitate the lysed sample mixture is performed at a temperature higher than the temperature of the first sample lysis. In some aspects, the first sample lysis may be performed at a first temperature, for example, the sample/lysis buffer mixture is heated from room temperature to about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80° C., or to any other temperature above about 80° C. In some aspects, the first temperature is in the range of about 25 to about 80° C., in some aspects, about 40 to about 70° C., in some aspects, the first temperature is about 65±5° C. In some aspects, the second sample lysis may be performed wherein the sample/lysis buffer mixture/lysed sample mixture is heated to a second temperature. In some aspects, the second temperature is higher than the first temperature. In some aspects, the second temperature is in the range of about 50 to about 120° C., in some aspects, about 60 to about 100° C., in some aspects, about 80 to about 100° C. In some aspects, the second temperature may be about 80, 81, 82, 83, 84, 85, 86, 87, 88, 89, 90, 91, 92, 93, 94, 95, 96, 97, 98, 99, or about 100° C., in some aspects, about 95 f 5° C. In some aspects, the difference between the first temperature and the second temperature may be about 1, 5, 10, 15, 20, 25, 30, 35, 40, 45, 50, 60, 70, 80, 90, or 100° C. In some aspects, the difference between the first temperature and the second temperature may be in the range of about 1-5, 5-10, 10-15, 15-20, 20-25, 25-30, 30-35, 35-40, 40-45, 45-50, 50-60, 60-70, 70-80, 80-90, or 90-100° C. In some aspects, following the second sample lysis, the temperature is reduced to about room temperature.

In some aspects, the first sample lysis may occur for a time period in the range of about 1 minute to about 1 hour, e.g., about 1, 5, 10, 15, 20, 25, 30, 40, 50, or about 60 minutes, in some aspects, about 15 minutes. In some aspects, the second sample lysis may occur for a time period in the range of about 1 minute to about 1 hour, e.g., about 1, 5, 10, 15, 20, 25, 30, 40, 50, or about 60 minutes, in some aspects, about 10 minutes. In some aspects, the first sample lysis and the second sample lysis is agitated at a speed in the range of about 1000 to about 3500 rpm, e.g., about 1000, 1100, 1200, 1300, 1350, 1400, 1450, 1500, 1550, 1600, 1750, 2000, 2250, 2500, 2750, 3000, 3250, or about 3500 rpm, in some aspects, at a speed of about 1350 f 100 rpm.

Reverse Transcription

In some embodiments, nucleic acid recovered following sample lysis may be DNA or RNA.

In some embodiments, nucleic acid is prepared from RNA by reverse transcription. In some embodiments, the nucleic acids are prepared from DNA by primer extension, such as using a polymerase.

In some embodiments, the methods described herein can be used in coupled reverse transcription-PCR (reverse transcription-PCR). In some embodiments, reverse transcription and PCR can be carried out in two distinct steps. In some embodiments, a cDNA copy of the sample mRNA can be synthesized using either a polynucleotide dT primer, a sequence specific primer, a universal primer, or any primer described herein.

In some embodiments, reverse transcription and PCR can be carried out in a single closed vessel reaction. For example, three primers can be employed, one for reverse transcription and two for PCR. In some embodiments, the primer for reverse transcription can bind to the mRNA 3' to the position of the PCR amplicon. In some embodiments, the reverse transcription primer can include RNA residues or modified analogs such as 2'-O-methyl RNA bases, which will not form a substrate for RNase H when hybridized to the mRNA.

The temperature to carry out the reverse transcription reaction depends on the reverse transcriptase being used. In some embodiments, a thermostable reverse transcriptase is used and the reverse transcription reaction is carried out at about 37° C. to about 75° C., at about 37° C. to about 50° C., at about 37° C. to about 55° C., at about 37° C. to about 60° C., at about 55° C. to about 75° C., at about 55° C. to about 60° C., at about 37° C., or at about 60° C. In some embodiments, a reverse transcriptase that transfers 3 or more non-template terminal nucleotides to an end of the transcribed product is used.

In some embodiments, a reverse transcription reaction and the PCR reaction described herein can be carried out in various formats known in the art, such as in tubes, microtiter plates, microfluidic devices, or droplets.

In some embodiments, a reverse transcription reaction can be carried out in volumes ranging from about 5 µL to 500 µL, or in 10 µL to about 20 µL reaction volumes. In droplets, reaction volumes can range from about 1 µL to 100 nL, or 10 µL to about 1 nL. In some embodiments, the reverse transcription reaction is carried out in a droplet having a volume that is about or less than 1 nL.

In some embodiments, target polynucleotides, such as RNA, can be reverse transcribed into cDNA using one or more reverse transcription primers. In some embodiments, one or more reverse transcription primers can comprise a region complementary to a region of the RNA. In some embodiments, the reverse transcription primers can comprise a first reverse transcription primer with a region complementary to a region of a first RNA, and a second reverse transcription primer with a region complementary to a region of a second RNA. In some embodiments, the reverse transcription primers can comprise a first reverse transcription primer with a region complementary to a region of a first RNA, and one or more reverse transcription primers with a region complementary to a region of one or more RNAs, respectively.

In some embodiments, reverse transcription primers can further comprise a region that is not complementary to a region of the RNA. In some embodiments, the region that is not complementary to a region of the RNA is 5' to a region of the primers that is complementary to the RNA. In some embodiments, the region that is not complementary to a region of the RNA is 3' to a region of the primers that is complementary to the RNA. In some embodiments, the region that is not complementary to a region of the RNA is a 5' overhang region. In some embodiments, the region that is not complementary to a region of the RNA comprises a priming site for amplification and/or a sequencing reaction. Using the one or more primers described herein, the RNA molecules are reverse transcribed using suitable reagents known in the art.

In some embodiments, the forward/reverse primers in the plurality of forward/reverse primers may further comprise a region that is not complementary to a region of the RNA. In some embodiments, the region that is not complementary to a region of the RNA is 5' to a region of the forward/reverse primers that is complementary to the RNA. In some embodiments, the region that is not complementary to a region of the RNA is 3' to a region of the forward/reverse primers that is complementary to the RNA. In some embodiments, the region that is not complementary to a region of the RNA is a 5' overhang region. In some embodiments, the region that is not complementary to a region of the RNA comprises a priming site for amplification and/or a second sequencing reaction. In some embodiments, the region that is not complementary to a region of the RNA comprises a priming site for amplification and/or a third sequencing reaction. In some embodiments, the region that is not complementary to a region of the RNA comprises a priming site for a second and a third sequencing reaction. In some embodiments, the sequence of the priming site for the second and the third sequencing reaction are the same. In some embodiments, using the one or more forward/reverse primers and a reverse primer as described herein, the cDNA molecules are amplified using suitable reagents known in the art.

Amplification

In some aspects, the nucleic acid recovered following cell lysis or the sample containing the one or more pathogens comprises fragments thereof, which can be amplified. In some aspects, the average length of the mRNA, or fragments thereof, can be less than about 100, 200, 300, 400, 500, or about 800 base pairs, or less than about 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, about 100 kilobases. In some aspects, a target sequence may be from a relative short template, such as a sample containing a template that is about 40, 45, 50, 55, 60, 65, 70, 75, 80, 85, 90, 95, or about 100 bases, is amplified.

In some aspects, an amplification reaction can comprise one or more additives. In some aspects, the one or more additives are dimethyl sulfoxide (DMSO), glycerol, betaine (mono)hydrate (N,N,N-trimethylglycine=[caroxy-methyl] trimethylammonium), trehalose, 7-Deaza-2'-deoxyguanosine triphosphate (dC7GTP or 7-deaza-2'-dGTP), BSA (bovine serum albumin), formamide (methanamide), tettrmethylammonium chloride (TMAC), other tetraalkylammonium derivatives (e.g., tetraethyammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some aspects, an amplification reaction can comprise 0, 1, 2, 3, 4, 5, 6, 7, 8, 9, or 10 different additives. In some aspects, an amplification reaction can comprise 10 or more different additives.

In some embodiments, thermocycling reactions can be performed on samples contained in reaction volumes.

In some aspects, the nucleic acid recovered following cell lysis or the sample containing the one or more pathogens can comprise cDNA, DNA, or fragments thereof, which can be amplified. In some aspects, the average length of the DNA, cDNA, or fragments thereof, can be less than about 100, 200, 300, 400, 500, or about 800 base pairs, or less than about 5, 10, 20, 30, 40, 50, 60, 70, 80, 90, 100, 110, 120, 130, 140, 150, 160, 170, 180, 190, or about 200 nucleotides, or less than about 1, 2, 5, 10, 20, 30, 40, 50, 60, 70, 80, 90, or about 100 kilobases. In some cases, a target sequence from a relative short template, such as a sample containing a template that is about 40, 45, 50, 55, 60, 65, 70, 75, 80, 85, 90, 95, or about 100 bases, is amplified.

In some aspects, any DNA polymerase that catalyzes primer extension can be used, including but not limited to E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, REDTaq™, Genomic DNA polymerase, or sequenase. In some aspects, a thermostable DNA polymerase is used. In some aspects, a hot start PCR can also be performed wherein the reaction is heated to about 95° C. for two minutes prior to addition of the polymerase or the polymerase can be kept inactive until the first heating step in cycle 1. In some aspects, hot start PCR can be used to minimize nonspecific amplification. In some aspects, any number of PCR cycles can be used to amplify the DNA, e.g., about, more than about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 100 cycles. The number of amplification cycles can be about 1-45, 10-45, 20-45, 30-45, 35-45, 10-40, 10-30, 10-25, 10-20, 10-15, 20-35, 25-35, 30-35, or about 35-40.

In some aspects, amplification of target nucleic acids can be performed by any means known in the art. In some aspects, target nucleic acids can be amplified by polymerase chain reaction (PCR) or isothermal DNA amplification. In some aspects, the amplification technique may be PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference.

In some aspects, examples of PCR techniques that can be used include, but are not limited to, quantitative PCR, quantitative fluorescent PCR (QF-PCR), multiplex PCR, multiplex fluorescent PCR (MF-PCR), real time PCR (reverse transcription-PCR), single cell PCR, restriction fragment length polymorphism PCR (PCR-RFLP), PCR-RFLP/ reverse transcription-PCR-RFLP, hot start PCR, nested PCR, nested multiplex PCR, in situ polony PCR, in situ rolling circle amplification (RCA), digital PCR (dPCR), droplet digital PCR (ddPCR), bridge PCR, picotiter PCR and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate polynucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938, as well as include Q beta replicase mediated RNA amplification.

In some aspects, amplification can be isothermal amplification, e.g., isothermal linear amplification.

In some aspects, examples of PCR that can be use in the invention include, but is not limited to "quantitative competitive PCR" or "QC-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR", "panhandle PCR", and "PCR select cDNA subtraction", "allele-specific PCR", among others. In some aspects, the amplification technique is signal amplification. See generally Sylvanen et al., Genomics 8:684-692 (1990); U.S. Pat. Nos. 5,846,710 and 5,888,819; Pastinen et al., Genomics Res. 7(6):606-614 (1997); all of which are expressly incorporated herein by reference. See generally U.S. Pat. Nos. 5,185,243, 5,679,524 and 5,573,907; EP 0 320 308 Bi; EP 0 336 731 Bi; EP 0 439 182 Bi; WO 90/01069; WO 89/126%; WO 97/31256; and WO 89/09835, and U.S. Ser. Nos. 60/078,102 and 60/073,011, all of which are incorporated by reference.

In some aspects, examples of PCR that can be used in the invention include, but is not limited to, nucleic acid sequence-based amplification (NASBA), strand displacement amplification (SDA), multiple displacement amplification (MDA), Q-beta replicase amplification, and loop-mediated isothermal amplification are used for amplification.

In some aspects, the amplification method may be specific for a certain nucleic acid such as a specific gene or a fragment thereof, or may be universal such that all or a specific type of a nucleic acid, such as mRNA, is amplified universally. In some aspect, the skilled person may design oligonucleotide primers which specifically hybridize to the nucleic acid of interest and use these primers in a PCR experiment.

In some aspects, the amplification method may use a master mix. In some aspects, the master mix may be a premixed, ready-to-use solution that may contain DNA polymerase, dNTPs, $MgCl_2$ and reaction buffers at optimal concentrations for efficient amplification of DNA templates. In some aspects, the master mix may contain DNA polymerase. In some aspects, the DNA polymerase may be a Taq DNA polymerase. In some aspects, the Taq DNA polymerase may be modified. In some aspects, the DNA polymerase may display no enzymatic activity at ambient temperature. In some aspects, the DNA polymerase may not form misprimed products and/or primer dimers prior to the first denaturation step. In some aspects, the DNA polymerase may be activated during the first denaturation step. In some aspects, the DNA polymerase may be activated after about 1 second to about 15 minutes during the first denaturation step. In some aspects, the DNA polymerase may be activated after about 5, 10, 15, 20, 25, 30, 40, 50, 60, 90, 120, 150, 180, 210, 240, 300, 350, 400, 500, 600, 700, 800, or about 900 seconds. In some aspects, the DNA polymerase may have 5'-3' polymerase activity. In some aspects, the DNA polymerase may have 5'-3' endonuclease activity. In some aspects, the DNA polymerase may have 3'-5' exonuclease activity. In some aspects, the DNA polymerase may not have 3'-5' exonuclease activity. In some aspects, the DNA polymerase may have 5'-3' polymerase activity and 5'-3' endonuclease activity, but no 3'-5' exonuclease activity. In some aspects, the DNA polymerase may have an error rate of approximately 1 error per $2.2 \times 10^5$ nucleotides incorporated. In some aspects, the DNA polymerase may have an error rate of in the range of about 1 error per $2.2 \times 10^2$ to about 1 error per $2.2 \times 10^{15}$ nucleotides incorporated.

In some aspects, the master mix may contain one or more dyes. In some aspects, the one or more dyes may be fluorescent. In some aspects, the one or more dyes may be a reference dye. In some aspects, the reference dye may be a passive reference dye. In some aspects, the reference dye may be a ROX reference dye. In some aspects, the master mix may contain $MgCl_2$. In some aspects, the master mix may not contain $MgCl_2$. In some aspects, the master mix may contain dNTPs. In some aspects, the master mix may contain stabilizers. In some aspects, the master mix may be free of contaminating DNase and/or RNase. In some aspects, the master mix may be added at a final concentration in a range of about 0.1 mM to about 50 mM. In some embodiments the master mix may be added at a concentration of about 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100 5, 10, 15, 20, 25, 30, 35, 40, 45, or about 50 mM. In some aspects, the master mix may be added at a final concentration greater than about 50 mM. In some aspects, the master mix may be added at a final concentration less than about 0.1 mM.

Detection

The act of testing a sample for a pathogen or a change in the level of a pathogen, is a "detection" even if the microorganism is determined to be not present or below the level of sensitivity. Detection may be a quantitative, semi-quantitative or non-quantitative observation and may be based on a comparison with one or more control samples. Detection may be applied to any sample wherein the presence or absence of the pathogen is to be assessed. In some aspects, and without limitation, the step of detecting a pathogen may comprise using PCR, real-time PCR, lectins, simple diffusion, lateral diffusion, immunological detection, lateral flow, or flow through methods to detect the presence of the pathogen in a culture. By way of illustration and not limitation, in particular embodiments possible detecting methods include or use the subject matter disclosed in any of U.S. Pat. Nos. 6,483,303; 6,597,176; 6,607,922; 6,927,570; and 7,323,139.

In some aspects, pathogens may be detected individually. In some aspects, multiple pathogens may be detected simultaneously. In some aspects, pathogen detection may be by a detection assay such as multiplex PCR, multiplex ELISA, DNA microarray, protein microarray or bead based assays such as a Luminex assay. In some aspects, luminex assays may use microspheres.

In some aspects, the present invention is to any detection method that allows for detecting one or more pathogens. In some aspects, the present primers, oligonucleotides probes, methods, materials, compositions, kits, and components allow for the detecting of one or more pathogens. In some aspects, the one or more pathogens may be alive. In some aspects, the one or more pathogens may be dead. In some aspects, the one or more pathogens may be alive and/or dead. In some aspects, alive pathogens may be detected to avoid high false positive results.

In some aspects, in the context of the present invention is any method that allows for detection and/or identification of a specific nucleic acid or a polypeptide, wherein the term "detection" also comprises the quantitative determination of a nucleic acid. In some aspects, the detection and/or identification may be based on specific amplification, for example, by the amplification of a specific DNA fragment using oligonucleotide primers specific for said DNA fragment in the polymerase chain reaction (PCR). In some aspects, the detection and/or identification may be based on immunoassays.

In some aspects, detection may be a quantitative, semi-quantitative or non-quantitative observation and may be based on a comparison with one or more control samples. In some embodiments and without limitation, the step of detecting a microorganism comprises using PCR, real-time PCR, lectins, multiplex PCR, PCR methods disclosed herein, simple diffusion, lateral diffusion, immunological detection, lateral flow, or flow through methods to detect the presence of the microorganism in a culture. By way of illustration and not limitation, in particular embodiments possible detecting methods include or use the subject matter disclosed in any of U.S. Pat. Nos. 6,483,303; 6,597,176; 6,607,922; 6,927,570; and 7,323,139.

The skilled person is well aware of how to design oligonucleotide primers which specifically hybridize to the nucleic acid of interest. In some aspects, the detection and/or identification may also be achieved without amplification, for example, by sequencing the nucleic acid to be analyzed or by sequence specific hybridization, for example, in the context of a microarray experiment. Sequencing techniques and microarray based analysis are well known procedures in the field. In some aspects, detection after PCR can be performed by, for example, electrophoresis, fluorescent probe method, capillary electrophoresis method, or quantitative PCR method.

In some aspects, the detection described herein comprises a detection capacity that meets and/or exceeds regulatory requirements. In some aspects, the invention described herein may detect at least 0.5 colony forming unit (CFU) in a standard overnight culture. In some aspects, a standard overnight culture can be 25 g food+225 ml media. In some aspects, the invention described herein may have a sensitivity threshold of detecting at least about 0.05 CFU/25 g. In some aspects, the invention described herein may have a sensitivity threshold of detecting at least about 0.005 CFU/25 g. In some aspects, the invention described herein may have a sensitivity threshold of detecting at least about 0.0005, 0.005, 0.05, 0.1, 0.2, 0.3, 0.4, 0.48, 0.5, 0.6, 0.7, 0.8, 0.9, 1, 1.1, 1.2, 1.5, 2, 2.5, 3 or at least 5 CFU/25 g. In some aspects, the invention described herein may have a sensitivity threshold of detecting less than about 0.05 CFU/25 g. In some aspects, the invention described herein may have a sensitivity threshold of detecting less than about 0.005 CFU/25 g.

Sequencing

Any high-throughput technique for sequencing nucleic acids can be used in the method of the invention. In some aspects, DNA sequencing techniques include dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of the separated molecules has more recently been demonstrated by sequential or single extension reactions using polymerases or ligases as well as by single or sequential differential hybridizations with libraries of probes.

Detecting

As described herein, in some embodiments, the kits and method described herein utilize detection of target sequences by detection of amplicons. In some embodiments, either direct or indirect detection of amplicon can be performed. In some embodiments, direct detection involves the incorporation of a label into the amplicon via, e.g., a labeled primer. In some embodiments, indirect detection involves incorporation of a label into, e.g., a hybridization probe. In some embodiments, for direct detection, the label(s) may be incorporated in at least four ways: (1) the primers comprise the label(s), for example attached to the base, a ribose, a phosphate, or to analogous structures in a nucleic acid analog; (2) modified nucleosides that are modified at either the base or the ribose (or to analogous structures in a nucleic acid analog) with the label(s); these label-modified nucleosides are then converted to the triphosphate form and are incorporated into the newly synthesized strand by a polymerase; (3) modified nucleotides are used that comprise a functional group that can be used to add a detectable label; or (4) modified primers are used that comprise a functional group that can be used to add a detectable label. In some embodiments, any of these methods result in a newly synthesized strand that comprises labels that can be directly detected.

In some embodiment, for indirect detection, the label may be incorporated into a hybridization probe using methods well known to one of skill in the art. In some embodiments, the label can be incorporated by attaching the label to a base, ribose, phosphate, or to analogous structures in a nucleic acid analog, or by synthesizing the hybridization probe using a modified nucleoside. In some embodiments, a modified strand of the amplicon or the hybridization probe can include a detection label. By "detection label" or "detectable label" herein is meant a moiety that allows detection. This may be a primary label or a secondary label.

In some embodiments, the detection label is a primary label. In general, labels fall into three classes: a) isotopic labels, which may be radioactive or heavy isotopes; b) magnetic, electrical, thermal labels; and c) colored or luminescent dyes. In some embodiments, labels can also include enzymes (horseradish peroxidase, etc.) and magnetic particles. In some embodiments, labels include chromophores or phosphors but in some embodiments are fluorescent dyes. In some embodiments, suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, alexa dyes, phycoerythrin, bodipy, and others described in the 6th Edition of the Molecular Probes Handbook by Richard P. Haugland, hereby expressly incorporated by reference.

In some embodiments, a secondary detectable label is used, for example, a secondary label can bind or react with a primary label for detection, or may allow the separation of the compound comprising the secondary label from unlabeled materials, etc. In some embodiments, secondary labels include, but are not limited to, one of a binding partner pair; chemically modifiable moieties; nuclease inhibitors, etc. In some embodiments, the secondary label may comprise a binding partner pair, for example, the label may be a hapten or antigen, which will bind its binding partner. In some embodiments, the binding partner can be attached to a solid support to allow separation of extended and non-extended primers, for example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. In some embodiments, nucleic acid-nucleic acid binding proteins pairs are also useful. In some embodiments, the binding partner pair comprises biotin or imino-biotin and streptavidin Imino-biotin is particularly preferred as imino-biotin disassociates from streptavidin in pH 4.0 buffer while biotin requires harsh denaturants (e.g. 6 M guanidinium HCl, pH 1.5 or 90/6 formamide at 95° C.). In some embodiment, the binding partner pair comprises a primary detection label and an antibody that will specifically bind to the primary detection label.

Probes

In some aspects, detection can be performed in a PCR mixture by using fluorescently labeled probes, each one corresponding to a unique DNA sequence, which when amplified by a DNA polymerase, emit a fluorescence signal at its specified spectral wavelength. In some aspects, the spectral frequency discrimination between different fluorophores, or reporters, attached to each probe sequence enables detection of amplicon sequences, one for each fluorescent color that can be identified.

In some aspects, in the detection method of the present invention, a process comprising the steps of mixing the above extracted DNA and/or RNA and one or more primers specific to the target pathogens to be detected, to perform multiplex PCR, is indispensable. In some aspects, the primers used are specific to target pathogens to be detected and/or an internal control. In some aspects, the primers have similar melting temperature that do not mutually produce primer dimmer, or wherein their identification bands do not interfere or overlap each other. In some aspects, primer sets include, for example, primer set specific for pathogenic Salmonella Invasion Gene A (InvA), SEQ ID NOS 9 and 10; Listeria monocytogenes gene Listeriolysin O (HlyA), SEQ ID NOS 1 and 2; and Shiga Toxin-Producing Escherichia coli genes Shiga toxin 1 (stx1), SEQ ID NOS 5 and 6; Shiga toxin 2 (stx2), SEQ ID NOS 7 and 8; encoding intimin (eaeA), SEQ ID NOS 2 and 3; and an internal control, SEQ ID NOS 16 and 17 can be exemplified respectively, and these can be used in combinations.

In some aspects, amplification is performed with the addition of labeled and or unlabeled probes. In some aspects, oligonucleotide probes include, for example, oligonucleotide probes specific for pathogenic Salmonella Invasion Gene A (InvA), SEQ ID NOS 15; Listeria monocytogenes gene Listeriolysin O (HlyA), SEQ ID NOS 11; and Shiga Toxin-Producing Escherichia coli genes Shiga toxin 1 (stx1), SEQ ID NOS 13; Shiga toxin 2 (stx2), SEQ ID NOS 14; encoding intimin (eaeA), SEQ ID NOS 12; and an internal control, SEQ ID NO 18 can be exemplified respectively, and these can be used in combinations.

In some aspects, amplification is performed with the addition of probes and primer sequences. For example, as for primer set and probe specific for pathogenic Salmonella Invasion Gene A (InvA), Primer SEQ ID NOS 9 and 10, Probe SEQ ID NOS 15; Listeria monocytogenes gene Listeriolysin O (HlyA), Primer SEQ ID NOS 1 and 2, Probe SEQ ID NOS 11; and Shiga Toxin-Producing Escherichia coli genes Shiga toxin 1 (stx1), Primer SEQ ID NOS 5 and 6, Probe SEQ ID NOS 13; Shiga toxin 2 (stx2), Primer SEQ ID NOS 7 and 8, Probe SEQ ID NOS 14; encoding intimin (eaeA), Primer SEQ ID NOS 2 and 3, Probe SEQ ID NOS 12; and an internal control, SEQ ID NO 18 can be exemplified respectively, and these can be used in combinations.

In some embodiments the quantity of primer per reaction may be at least about 0.001 nmol. In some embodiments the quantity of primer per reaction may be at least about 0.001, 0.01, 0.1, 0.3, 1, 3, 4, 10, 30, 40, 60, 100, 250, 300, 350, 400, 500, 750, 1000, 1500, 2500, or at least about 5000 nmol.

In some embodiments the quantity of probe per reaction may be at least about 0.001 nmol. In some embodiments the quantity of probe per reaction may be at least about 0.001, 0.1, 0.3, 1, 3, 4, 10, 30, 40, 60, 100, 250, 300, 350, 400, 500, 750, 1000, 1500, 2500, or at least about 5000 nmol.

In some embodiments, the quantity of internal control may be at least 25 copies of internal control reference gene per reaction. In some embodiments the quantity of internal control may be at least about 25, 500, 1000, 2000, 3000, 5000, 10000, 15000, 20000, 25000, 30000, 35000, 40000, 50000, 80000, 100000, 150000, or at least about 200,000, or at least about 300,000 copies of internal control reference gene per reaction.

In some aspects, the oligonucleotide probes are TaqMan probes. TaqMan probes are hydrolysis probes that are designed to increase the specificity of PCR assays. A standard TaqMan probe comprises a fluorophore covalently attached to the 5'-end of an oligonucleotide probe and a quencher at the 3'-end. In some aspects, during PCR amplification, the primers and fluorescently tagged probes anneal to the DNA template, and as the polymerase extends the primer sequences, the fluorescent label is cleaved from the probe strand, thereby increasing its distance from the quencher and allowing the fluorophore to emit fluorescence with greater intensity.

In some aspects, several different fluorophores (e.g. 6-carboxyfluorescein, acronym: FAM, or tetrachlorofluorescein, acronym: TET, or 6-carboxy-4',5'-dichloro-2',7'-dimethoxyfluorescein, acronym: JOE) and quenchers (e.g. tetramethylrhodamine, acronym: TAMRA or Black Hole Quencher™ 1 (BHQ1 Acronym: BHQ1) are available. Several fluorophore-quencher pairs are described in the art. See, e.g. Pesce et al, editors, *Fluorescence Spectroscopy*, Marcel Dekker, New York, (1971); White et al, *Fluorescence Analysis: A Practical Approach*, Marcel Dekker, New York, (1970); and the like. The literature also includes references providing exhaustive lists of fluorescent and non-fluorescent molecules and their relevant optical properties, e.g. Berlman, *Handbook of Fluorescence Sprectra of Aromatic Molecules*, 2nd Edition, Academic Press, New York, (1971), herein incorporated by reference. Further, there is extensive guidance in the literature for derivatizing reporter and quencher molecules for covalent attachment via common reactive groups that can be added to an oligonucleotide. See, e.g. U.S. Pat. Nos. 3,996,345; and 4,351,760. Exemplary fluorophore-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like. In some aspects, fluorophore and quencher molecules are selected from fluorescein and rhodamine dyes. These dyes and appropriate linking methodologies for attachment to oligonucleotides are known in the art. See, e.g. Marshall, *Histochemical J.* 7: 299-303 (1975); and U.S. Pat. No. 5,188,934, herein incorporated by reference.

In some aspects, multiplex PCR may be possible using non TaqMan probe reporters such as intercalating dyes by encoding intensity levels to distinguish concentration limited primer pairs alone. In some aspects, intercalating dyes, bind to double-stranded DNA sequences, and an increase in DNA product during PCR therefore leads to an increase in fluorescence intensity. In some aspects, intercalating dyes include but not limited to SYBR or PicoGreen which bind to amplified double stranded DNA. In some aspects, detection by intercalating dyes is performed by adding multiple unique primer pairs at different limiting concentrations to yield varying end point fluorescence intensities.

In some aspects, the fluorescences emitted are detected (e.g., via digital filters) and identified, and the DNA sequences corresponding to the emitted fluorescences may be similarly identified based on their correspondence.

Detecting Non-Amplified Nucleic Acid

In some embodiments, the detecting step can include lysing microorganisms in the sample, hybridizing a nucleic acid probe to a target nucleic acid sequence of the target microorganism to form a probe/target complex, wherein the probe includes a label that is stabilized by the complex, selectively degrading the label present in unhybridized probe, and detecting the presence or amount of stabilized label as a measure of the presence or amount of the target nucleic acid sequence in the sample. In some embodiments, the probe may be labeled with an acridinium ester. In some embodiments, the probe may hybridize to ribosomal RNA of the target microorganism.

In some embodiments, pathogens can be detected using, for example, a hybridization protection assay (HPA). In some embodiments, pathogens can be lysed to release nucleic acid, and an oligonucleotide probe can be hybridized to a target nucleic acid sequence of the target microorganism to form a probe/target complex wherein the probe is detected.

In some embodiments, nucleic acid analogs can be modified at the base moiety, sugar moiety, or phosphate backbone to improve, for example, stability, hybridization, or solubility of a nucleic acid. Modifications at the base moiety include substitution of deoxyuridine for deoxythymidine, and 5-methyl-2'-deoxycytidine and 5-bromo-2-deoxycytidine for deoxycytidine. In some embodiments, examples of nucleobases that can be substituted for a natural base include 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Other useful nucleobases include those disclosed, for example, in U.S. Pat. No. 3,687,808, herein incorporated by reference.

In some embodiments, modifications of the sugar moiety can include modification of the 2' hydroxyl of the ribose sugar to form 2'-O-methyl or 2'-O-allyl sugars. In some embodiments, the deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone (e.g., an aminoethylglycine backbone) and the four bases are retained. See, for example, Summerton and Weller (1997) Antisense Nucleic Acid Drug Dev. 7:187-195; and Hyrup et al. (1996) Bioorgan. Med. Chem. 4:5-23, all of which are hereby incorporated by reference. In some embodiments, the deoxyphosphate backbone can be replaced with, for example, a phosphorothioate or phosphorodithioate backbone, a phosphoroamidite, or an alkyl phosphotriester backbone. See, for example, U.S. Pat. Nos. 4,469,863, 5,235,033, 5,750,666, and 5,596,086 for methods of preparing oligonucleotides with modified backbones. In some embodiments, oligonucleotide probe can hybridize with any portion of a nucleic acid from the target microorganism, for example, an oligonucleotide can hybridize with a nucleic acid encoding a cell-wall protein or an internal cell component, such as a membrane protein, transport protein, or enzyme. In some embodiments, the oligonucleotide hybridizes with ribosomal RNA (rRNA) or a mRNA of a target microorganism. See, for example, U.S. Pat. No. 4,851,330, which is hereby incorporated by reference. For example, the oligonucleotide can hybridize with a 16S, 23S, or 5S rRNA. In some embodiments, hybridization to rRNA can increase the sensitivity of the assay as most microorganisms contain thousands of copies of each rRNA.

In some embodiments, the oligonucleotide probe is labeled with a molecule that is stabilized by the probe/target. In some embodiments, oligonucleotide probes can be between 10 and 75 (e.g., 10-14, 15-30, 25-50, 30-45, 33-40, 20-30, 31-40, 41-50, or 51-75) nucleotides in length. In some embodiments, the oligonucleotide need not be 100% complementary to that of its target nucleic acid in order for hybridization to occur. In some embodiments, the oligonucleotide has at least 80/6 (e.g., at least 85%, 90%, 95%, 99%, or 100/6) sequence identity to the complement of its target sequence. In some embodiments, hybridization of the oligonucleotide to its target can be detected based on the chemiluminescence observed after adjusting the pH to mildly alkaline conditions. In some embodiments, if hybridization occurs, chemiluminescence will be observed. In some embodiments, if hybridization does not occur, the ester bond of the AE molecule will be hydrolyzed and chemiluminescence will not be observed or will be measurably reduced.

Methods for synthesizing oligonucleotides are known.

In some embodiments, the presence, absence, or amount of unmodified label can be assessed using a luminometer (e.g., LEADER® luminometer from Gen-Probe Incorporated, San Diego, CA or the BacLite3 luminometer from 3M, St. Paul, MN, or the LUMIstar Galaxy luminometer from BMG, Durham, NC). Luminometers such as the BacLite3 luminometer and LUMIstar Galaxy luminometer have reagent dispensing capability and temperature control are particularly useful for automating the methods disclosed herein. Such luminometers can be programmed to dispense, in a predetermined order, reagents for lysing, hybridization, and detection, and allow for incubation. Automated reagent dispensing minimizes contamination issues encountered within a moist environment such as a water bath in addition to enhancing the user friendliness of the test system. It is understood that the present method is not limited by the device used to detect the label on the oligonucleotide probe.

Primer and Probe Design

In some aspects, literature and Blast searches may be performed to identify sets of genes with the potential to uniquely identify pathogenic target organisms in the context of a 5-color multiplex TaqMan-based PCR reaction. In some aspects, the genes chosen from these searches may be: Salmonella Invasion Gene A (InvA), *Listeria monocytogenes* gene Listeriolysin O (HlyA), and Shiga Toxin-Producing *Escherichia coli* genes Shiga toxin 1 (stx1), Shiga toxin 2 (stx2), and encoding intimin (eaeA).

In some embodiments, sets of multiplex PCR primers and TaqMan probes may be designed using commercial software and genomic DNA sequences. In some aspects, specificity of resulting sequences may be assessed in silico against the nr database using Blast. In some aspects, optimal PCR conditions may be identified for each of the multiplex sets. In some aspects, selection of a final set may be done in a step-wise manner. In some aspects, compatibility, sensitivity, and specificity may be initially assessed using purified genomic DNA from target organisms and with non-target bacteria DNA. In some aspects, sets may be tested using DNA prepared from bacteria cultured in the presence of various food matrices. Nucleic Acid Reagents: Primers and Probes In some embodiments, the kits and method disclosed herein use nucleic acid reagents, e.g., oligonucleotides, e.g., amplification primers and hybridization probes, for detection of the signature sequences. In some aspects, exemplary primers and probes are disclosed herein, e.g., in Table 1, and in some embodiments, the claimed kits and methods include the primers and probes disclosed in Tables 1. In some embodiments, the invention also include kits and methods using variant versions of the primers and probes disclosed herein, e.g., oligonucleotides that are shorter or longer or have at least about 80%, 81%, 82%, 83%, 84%, 85%, 86%, 88%, 89, 90%, 91%, 92%, 93%, 94%, 95%, 96%, 97%, 98%, or at least about 99% sequence identity, as long as the oligonucleotide accomplishes that same function, e.g., functions in the assay for the detection of the signature sequences.

In some embodiments, the length of a nucleic acid reagent, e.g., a primer or hybridization probe or oligonucleotide probe, will vary depending on the application. In some embodiments, the total length can be from about 5 to 80 nucleobases in length. In some embodiments, the primers, oligonucleotide probe and hybridization probes used in accordance with this invention may comprise from about 8 to about 80 nucleobases (i.e. from about 8 to about 80 linked nucleosides). One of ordinary skill in the art will appreciate that the invention embodies oligonucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length. In some embodiments, the oligonucleotides are greater than 80 nucleobases in length.

In some embodiments, the kits include nucleic acid reagents that are sets of oligonucleotides for each target sequence to be detected. Each set has PCR primers, oligonucleotide probe and or hybridization probes for each target sequence. Exemplary embodiments include the PCR primers and oligonucleotide probes disclosed in Tables 1. In some embodiments the kit includes each of the PCR primers and oligonucleotide probes listed for the respective pathogen. In some embodiments, the kit includes a subset of the disclosed primer and probes. In some embodiments, the kit includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or at least 50 of the primer pairs. In some embodiments, the kit includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or at least 50 oligonucleotide probes.

In some embodiments, the kits includes reagents for detection of less than all pathogens, e.g., for detection of at least 1, 2, 3, 4, 5, 6, 7, 8, 9, 10, 11, 12, 13, 14, 15, 16, 17, 18, 19, or at least 20 of the pathogens. In some embodiments, TaqMan probes, can be detected by methods known in the art.

Internal Controls

When testing a biological sample for contamination by a pathogen or confirming that a sample is free from a pathogen, a problem may exist with interpreting a negative result. Without appropriate controls, it may not be possible to determine whether an absence of the contaminating pathogen being detected is a result of the failure of the assay, or as a result of the absence of any contaminating pathogens in the sample. If the negative result can be attributed to the former reason, the failure of the assay could have occurred at any stage. For example, in a nucleic acid assay, the failure may have occurred during nucleic acid extraction, handling, amplification or detection steps. Generally, for example and not to be limiting, four controls may be used in PCR based methods for the detection of nucleic acids. The first control may be an internal positive control for the nucleic acid extraction step. The second control may be for the detection of the PCR products. The third control may be for the amplification step. Finally, the fourth control may be a no template control to detect contamination during the assay.

In some aspects, amplification may be performed with an internal control. In some aspects, the internal control may be a negative control. In some aspects, the internal control may be a positive control.

In some aspects, the internal control may be a polynucleotide or oligonucleotide. In some aspects, the internal control may be an exogenous sequence. In some aspects, the internal control may be used as a universal internal control as it comprises unique primer and probe sites and does not exhibit homology with any known nucleic acid sequences that may interfere with this assay, i.e. does not anneal with known nucleic acid sequences during conventional PCR techniques.

In some aspects, the internal control may be DNA and or RNA molecules of natural or synthetic origin which may be single-stranded or double-stranded, and represent the sense or antisense strand. In some aspects, the internal control may be a sequence chosen as required in an amplification reaction. In some aspects, the internal control may be a sequence selected from, e.g., sequences that are suitable to detect and/or distinguish pathogenic material such as viruses, bacteria, fungi, parasites such as *Plasmodium falciparum*, ticks, *E. coli* etc. In some aspects, the internal control may contain known nucleotide analogs or modified backbone residues or linkages, and any substrate that can be incorporated into a polymer by DNA or RNA polymerase. Examples of such analogs include phosborothioates, phosphoramidates, methyl phosphonates, chiral-methyl phosphonates, 2-O-methyl ribonucleotides, peptide-nucleic acids (PNAs), and the like. In some aspects, the internal control may be isolated. In some aspects, the internal control may be substantially isolated or purified from the genomic DNA or RNA of the species from which the nucleic acid molecule was obtained.

In some aspects, the internal control may be readily prepared by conventional methods known in the art, for example, directly synthesizing the nucleic acid sequence using methods and equipment known in the art such as automated oligonucleotide synthesizers, PCR technology, recombinant DNA techniques, and the like. WO 2003075837 A2, WO 2012114312 A2 and WO 2012114312 A2 are herein incorporated by reference.

In some aspects, an internal control probe may be used to detect the presence and or absence of the internal control. In some aspects, the internal control probe may be an internal oligonucleotide probe. In some aspects, the internal oligonucleotide probe may be labeled at the 5' end with an energy transfer donor fluorophore and labeled at the 3' ends with an energy transfer acceptor fluorophore. In some aspects, the internal oligonucleotide probe specifically anneals between the forward and reverse primers of a target sequence. In some aspects, the internal oligonucleotide probe may be cleaved by the 5' end during PCR amplification and the reporter molecule may then separate from the quencher molecule to generate a sequence specific signal. In some aspect, with each amplification cycle, additional reporter molecules may be separated from the quencher molecules. In some aspects, the intensity of a signal, such as fluorescence, may be monitored before, during, or after PCR amplification or a combination thereof.

In some aspects, the internal control may be used to distinguish a true negative result from a false negative result. As used herein, a "true negative" result correctly indicates that a sample lacks a target nucleic acid sequence. A "false negative" result incorrectly indicates the absence of a target nucleic acid sequence which may result from PCR inhibitors present in the sample or technical error.

In some embodiments, the detection methods disclose herein, may detect the presence or absence of one or more pathogens in a sample with an accurately in the range of between at least 1% to at least 99.9%. In some embodiments, the detection methods disclose herein, may detect the presence and/or absence of one or more pathogens in a sample with an accurately of at least 10%, 15%, 20%, 25%, 30%, 35%, 40%, 45%, 50%, 55%, 60%, 65%, 70%, 75%, 80%, 85%, 90%, 95%, 96%, 97%, 98% or at least 99%. In some embodiments, the detection methods disclose herein, may detect the presence and/or absence of one or more pathogens in 1/5, 215, 3/5, 4/5, or 5/5 replicates. In some embodiments, the detection methods disclose herein, may detect the presence and/or absence of one or more pathogens in 1/20, 2/20, 3/20, 4/20, 5/20, 6/20, 7/20, 8/20, 9/20, 10/20, 11/20, 12120, 13/20, 14/20, 15/20, 16/20, 17/20, 18/20, 19/20, or 20/20 replicates. In some embodiments, the detection methods disclose herein, may detect the presence and/or absence of one or more pathogens in a range of between at least 10% and 99.9% of replicates. In some embodiments, the detection methods disclose herein, may detect the presence and/or absence of one or more pathogens in at least 10%, 15%, 20%, 25%, 30%, 35%, 40%, 45%, 50%, 55%, 60%, 65%, 70%, 75%, 80%, 85%, 90%, 95%, 96%, 97%, 98% or at least 99% of replicates.

Effect

In some embodiments, the kits, devices and method disclosed herein overcome the problem of detecting multiple organisms that are considered incompatible with simultaneous enrichment. In some embodiments, the enrichment media and/or enrichment methods disclosed herein overcome the problem of detecting multiple organisms that are considered incompatible with simultaneous enrichment. In some embodiments, the lysis buffers and/or lysis methods disclosed herein overcome the problem of detecting multiple organisms that are considered incompatible with simultaneous enrichment. In some embodiments, the enrichment methods and/or enrichment media and lysis buffers and/or lysis procedures disclosed herein overcomes the problem of detecting multiple organisms that are considered incompatible with simultaneous enrichment.

In some embodiments, the enrichment media, enrichment procedures, lysis buffer, and lysis procedures may confer a synergistic effect on the sensitivity of the detection methods disclosed herein. In some embodiments, the enrichment media, enrichment procedures, lysis buffers, and lysis procedures disclosed herein may increase pathogen detection efficiency. In some embodiments, the enrichment media, enrichment procedures, lysis buffer, and lysis procedures may confer an additive effect on the sensitivity of the detection methods disclosed herein. In some embodiment, the sensitivity of the detection methods disclosed herein may increase when the enrichment media/procedure, lysis buffer/procedure, and assays disclosed herein are used in concert.

In some embodiments, the enrichment media, enrichment procedures, lysis buffer, and lysis procedures may confer a synergistic effect on the pathogen detection time of the detection methods disclosed herein. In some embodiments, the enrichment media, enrichment procedures, lysis buffers, and lysis procedures disclosed herein may decrease the pathogen detection time synergistically. In some embodiments, the enrichment media, enrichment procedures, lysis buffer, and lysis procedures may confer an additive effect on the detection time of the detection methods disclosed herein. In some embodiment, the pathogen detection time of the detection methods disclosed herein may decrease in an additive manner when the enrichment media/procedure, and lysis buffer/procedure, disclosed herein are use in concert.

TABLE 1

| SEQ ID NOS: | Sequence | Sequence Name |
|---|---|---|
| 1 | AGCTCATTTCACATCGTCCATCT | LM_HLY-BT_sense |
| 2 | TCCACCATTCCCAAGCTAAACC | LM_HLY-BT_antisens |
| 3 | GGCGGCCAGATTCAGCATAG | EC_EAE-BT_sense |
| 4 | GCTACCACCTTGCACATAAGC | EC_EAE-BT_antisense |
| 5 | TCGCCATTCGTTGACTACTTC | EC_STX1-BT_sense |
| 6 | ACATCGCTCTTGCCACAGACT | EC_STX1-BT_antisense |
| 7 | CAGTGCCCGGTGTGACAAC | EC_STX2-BT_sense |
| 8 | GACACGTTGCAGAGTGGTATAAC | EC_STX2-BT_antisense |
| 9 | CGGGCATACCATCCAGAGAA | SE_INV_BT_sense |
| 10 | CACCGTGGTCCAGTTTATCGT | SE_INV_BT_antisense |
| 11 | TTGCCAGGTAACGCAAGAA | LM_HLY-BT_probe |
| 12 | CGGAAGCCAAAGCGCAC | EC_EAE-BT_probe |
| 13 | TCTGGATTTAATGTCGCATAGCG | EC_STX1-BT_probe |
| 14 | TTCCATGACAACGGACAGC | EC_STX2-BT_probe |
| 15 | ATCGGGCCGCGACTTC | SE_INV_BT_probe |
| 16 | TGGCGGGACTATTCTGAATGAG | IC_CF10_sense |

TABLE 1-continued

| SEQ ID NOS: | Sequence | Sequence Name |
|---|---|---|
| 17 | CATCTCGCTGCTGTCTTTCTTC | IC_CF10_antisense |
| 18 | ACTACATCCTCTCCGCAGCACAC | IC_CF10_CFR610probe |
| 19 | TTTTGTGGCGGGACTATTCTGAAT GAGTACTACATCCTCTCCGC AGCACACTGCATGCACCAA GCAAAAAGATTCAAAGTTAGAGTA GGGGAACGGGACACCGAGAAGA AAGACAGCAGCGAGATGGCGCA | Synthetic template of internal control |

EXAMPLES

RTE Deli Meat (Deli Turkey) Validation (1 CFU/25 g)

All 3 target organisms were inoculated and incubated simultaneously:0.725 CU/J25 g *E. coli* 0157:1H7 (ATCC: 43895), 0.832 CFU/25 g *S. enterica* (ATCC:13076) and 1.008 CFU/25 g *L. monocytogenes* (ATCC: 13932). The samples were suspended in Buffered Listeria Enrichment Broth base (no supplements), stomached for 30 seconds, in a stomaching bag, the bag was closed and the samples were incubated for 24 hours at 37° C. The lysis buffer comprised: 8 mM EDTA, 80 mM TRIS, 4.8% Triton X-100, 27.5% Proteinase K (ready-made solution from Qiagen catalog #19133), 20 mg/ml Lysozyme (Amresco catalog #0663-10 G and 0.88 grams/ml 100 µm zirconium lysis beads (Ops Diagnostics catalog #BLBZ 100-250-14). To lyse samples, 100 µl lysis buffer solution was pipetted into each well of a deep-well block, 50 µl sterile $H_2O$ was added to each well, 50 µl of supernatant from enrichment bag was removed and add to each well. The samples were lysed at 65° C. for 15 minutes shaking at 1350 RPM.

The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 µl reaction using 1 µl of lysate at end of the lysis procedure. PCR cycle is as follows: Initial step: 98° C. for 3 minutes, 2.) 95° C. for 10 seconds, 3.) 58.5° C. for 45 seconds. Return to step 2 and repeat 49 times. Multiplex PCR was performed in 20 replicates using BioRad CFX-96 Touch instrument. Primers and probes used in multiplex PCR are disclosed in Table 1.

EAE was identified in 16/20 (80%) replicates as positive for EAE, STX-1 identified in 16/20 (80%) replicates as positive for STX-1, STX-2 was identified in 17/20 (85%) replicates as positive for STX-2, *Salmonella* spp. (1 target) was identified in 19/20 (95%) replicates as positive for *S. enterica*, *Listeria monocytogenes* (1 target) was identified in 14/20 (70%) replicates as positive for *L. monocytogenes*. FIG. 1-5.

RTE Deli Meat Validation (5 CFU/25 g)

3 target organisms inoculated simultaneously, CFU determined via plate count, *E. coli* inoculated at a measured 5.5 CFU/25 g, *S. enterica* inoculated at a measured 4.5 CFU/25 g, *L. monocytogenes* inoculated at a measured 5.15 CFU/25 g. The samples were suspended in Buffered Listeria Enrichment Broth base (no supplements), stomached for 30 seconds, in a stomaching bag, the bag was closed and the samples were incubated for 24 hours at 37° C. The lysis buffer comprised: 8 mM EDTA, 80 mM TRIS, 4.8% Triton X-100, 27.5% Proteinase K (ready-made solution from Qiagen catalog #19133), 20 mg/ml Lysozyme (Amresco catalog #0663-10 G, and 0.88 grams/ml 100 µm zirconium lysis beads (Ops Diagnostics catalog #BLBZ 100-250-14).

To lyse the samples, 100 µl lysis buffer solution was pipetted into each well of a deep-well block, 50 µl sterile $H_2O$ was added to each well, 50 µl of supernatant from enrichment bag was removed and add to each well. The samples were lysed at 65° C. for 15 minutes shaking at 1350 RPM. The samples were lysed for an additional 10 minutes at 95° C. shaking at 1350 RPM, after which, the deepwell block was cooled to room temperature. Bacterial DNA was obtained for multiplex PCR.

Multiplex amplification PCR protocol comprised 25 µl reaction using 1 µl of lysate at end of the lysis procedure. PCR cycle is as follows: Initial step: 98° C. for 3 minutes, 2.) 95° C. for 10 seconds, 3.) 58.5° C. for 45 seconds. Return to step 2 and repeat 49 times. Multiplex PCR was performed in 5 replicates using BioRad CFX-96 Touch instrument. Primers and probes used in multiplex PCR are disclosed in Table 1.

*E. coli* (STEC) targets (3 targets): EAE: identified 5/5 (100%) replicates as positive for EAE, STX-1: identified 5/5 (100%) replicates as positive for STX-1, STX-2: identified 5/5 (100%) replicates as positive for STX-2, *Salmonella* spp. (1 target): identified 5/5 (100%) replicates as positive for *S. enterica*. *L. monocytogenes* (1 target): identified 5/5 (100%) replicates as positive for *L. monocytogenes*. FIG. 6-10

RTE Meat (Hot Dog) Validation (1 CFU/25 g)

All 3 target organisms inoculated and incubated simultaneously, 0.900 CFU/25 g *E. coli* O157:H7 (ATCC:43895), 1.022CFU/25 g *S. enterica* (ATCC:13076), 0.877CFU/25 g *L. monocytogenes* (ATCC: 13932). The samples were suspended in Buffered Listeria Enrichment Broth base (no supplements), stomached for 30 seconds, in a stomaching bag, the bag was closed and the samples were incubated for 24 hours at 37° C. The lysis buffer comprised, 8 mM EDTA, 80 mM TRIS, 4.8% Triton X-100, 27.5% Proteinase K (ready-made solution from Qiagen catalog #19133), 20 mg/ml Lysozyme (Amresco catalog #0663-10 G and 0.88 grams/ml 100 µm zirconium lysis beads (Ops Diagnostics catalog #BLBZ 100-250-14).

To lyse the samples, 100 µl lysis buffer solution was pipetted into each well of a deep-well block, 50 µl sterile $H_2O$ was added to each well, 50 µl of supernatant from enrichment bag was removed and add to each well. The samples were lysed at 65° C. for 15 minutes shaking at 1350 RPM. The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 µl reaction using 1 µl of lysate at end of the lysis procedure. PCR cycle is as follows: Initial step: 98° C. for 3 minutes. 2.) 95° C. for 10 seconds. 3.) 58.5° C. for 45 seconds. Return to step 2 and repeat 49 times. Multiplex PCR was performed in 20 replicates using BioRad CFX-96 Touch instrument. Primers and probes used in multiplex PCR are disclosed in table 1

*E. coli* (STEC) targets (3 targets) EAE: identified 20/20 (100%) replicates as positive for EAE, STX-1:identified 20/20 (100%) replicates as positive for STX-1, STX-2: identified 20/20 (100%) replicates as positive for STX-2; *Salmonella* spp. (1 target): identified 20/20 (100%) replicates as positive for *S. enterica.*; *L. monocytogenes* (1 target): identified 10/20 (50%) replicates as positive for *L. monocytogenes*. FIG. 11.

RTE Meat (Hot Dog) Validation (5 CFU/25 g)

3 target organisms inoculated simultaneously, CFU determined via plate count, *E. coli* inoculated at a measured 4.5 CFU/25 g, *S. enterica* inoculated at a measured 5.11 CFU/25 g, *L. monocytogenes* inoculated at a measured 4.385 CFU/25 g. The samples were suspended in Buffered Listeria Enrichment Broth base (no supplements), stomached for 30 seconds, in a stomaching bag, the bag was closed and the samples were incubated for 24 hours at 37° C. The lysis buffer comprised: 8 mM EDTA, 80 mM TRIS, 4.8% Triton X-100, 27.5% Proteinase K (ready-made solution from Qiagen catalog #19133), 20 mg/ml Lysozyme (Amresco catalog #0663-10 G and 0.88 grams/ml 100 µm zirconium lysis beads (Ops Diagnostics catalog #BLBZ 100-250-14).

To lyse the samples, 100 µl lysis buffer solution was pipetted into each well of a deep-well block, 50 µl sterile $H_2O$ was added to each well, 50 µl of supernatant from enrichment bag was removed and add to each well. The samples were lysed at 65° C. for 15 minutes shaking at 1350 RPM. The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 µl reaction using 1 µl of lysate at end of the lysis procedure. PCR cycle is as follows: Initial step: 98° C. for 3 minutes. 2.) 95° C. for 10 seconds. 3.) 58.5° C. for 45 seconds. Return to step 2 and repeat 49 times. Multiplex PCR was performed in 5 replicates using BioRad CFX-96 Touch instrument. Primers and probes used in multiplex PCR are disclosed in Table 1.

Results: EAE: identified 5/5 (100%) replicates as positive for EAE, STX-1: identified 5/5 (100%) replicates as positive for STX-1, STX-2: identified 5/5 (100%) replicates as positive for STX-2; *Salmonella* spp. (1 target): identified 5/5 (100%) replicates as positive for *S. enterica.*; *L. monocytogenes* (1 target): identified 5/5 (100%) replicates as positive for *L. monocytogenes*. FIG. 12.

Iceberg Lettuce Validation (1 CFU/25 g)

All 3 target organisms inoculated and incubated simultaneously, 0.852 CFU/25 g *E. coli* O157:H7 (ATCC:43895), 1.04 CFU/25 g *S. enterica* (ATCC:13076), 1.064 CFU/25 g *L. monocytogenes* (ATCC: 13932).

The samples were suspended in Buffered Listeria Enrichment Broth base (no supplements), stomached for 30 seconds, in a stomaching bag, the bag was closed and the samples were incubated for 24 hours at 37° C. The lysis buffer comprised: 8 mM EDTA, 80 mM TRIS, 4.8% Triton X-100, 27.5% Proteinase K (ready-made solution from Qiagen catalog #19133), 20 mg/ml Lysozyme (Amresco catalog #0663-10 G, and 0.88 grams/ml 100 µm zirconium lysis beads (Ops Diagnostics catalog #BLBZ 100-250-14).

To lyse the samples, 100 µl lysis buffer solution was pipetted into each well of a deep-well block, 50 µl sterile $H_2O$ was added to each well, 50 µl of supernatant from enrichment bag was removed and add to each well. The samples were Lysed at 65° C. for 15 minutes shaking at 1350 RPM. The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 µl reaction using 1 µl of lysate at end of the lysis procedure. PCR cycle is as follows: Initial step: 98° C. for 3 minutes. 2.) 95° C. for 10 seconds. 3.) 58.5° C. for 45 seconds. Return to step 2 and repeat 49 times. Multiplex PCR was performed in 20 replicates using BioRad CFX-96 Touch instrument. Primers and probes used in multiplex PCR are disclosed in Table 1.

*E. coli* (STEC) targets (3 targets) EAE: identified 9/20 (45%) replicates as positive for EAE, STX-1: identified 9/20 (45) replicates as positive for STX-1, STX-2: identified 9/20 (45%) replicates as positive for STX-2; *Salmonella* spp. (1 target): identified 17/20 (85%) replicates as positive for *S. enterica.*; *L. monocytogenes* (1 target): identified 10/20 (50%) replicates as positive for *L. monocytogenes*. FIG. 13

Iceberg Lettuce Validation (5 CFU/25 g)

3 target organisms inoculated simultaneously, CFU determined via plate count, *E. coli* inoculated at a measured 4.26 CFU/25 g, *S. enterica* inoculated at a measured 5.2 CFU/25 g, *L. monocytogenes* inoculated at a measured 5.32 CFU/25 g. The samples were suspended in Buffered Listeria Enrichment Broth base (no supplements), stomached for 30 seconds, in a stomaching bag, the bag was closed and the samples were incubated for 24 hours at 37° C. The lysis buffer comprised: 8 mM EDTA: 80 mM TRIS, 4.8% Triton X-100, 27.5% Proteinase K (ready-made solution from Qiagen catalog #19133), 20 mg/ml Lysozyme (Amresco catalog #0663-10 G, and 0.88 grams/ml 100 µm zirconium lysis beads (Ops Diagnostics catalog #BLBZ 100-250-14).

To lyse the samples, 100 µl lysis buffer solution was pipetted into each well of a deep-well block, 50 µl sterile $H_2O$ was added to each well, 50 µl of supernatant from enrichment bag was removed and add to each well. The samples were lysed at 65° C. for 15 minutes shaking at 1350 RPM. The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 µl reaction using 1 µl of lysate at end of the lysis procedure. PCR cycle is as follows: Initial step: 98° C. for 3 minutes. 2.) 95° C. for 10 seconds. 3.) 58.5° C. for 45 seconds. Return to step 2 and repeat 49 times. Multiplex PCR was performed using BioRad CFX-96 Touch instrument. Primers and probes used in multiplex PCR are disclosed in Table 1.

*E. coli* (STEC) targets (3 targets), EAE: identified 5/5 (100%) replicates as positive for EAE, STX-1: identified 5/5 (100%) replicates as positive for STX-1, STX-2: identified 5/5 (100%) replicates as positive for STX-2; *Salmonella* spp. (1 target): identified 5/5 (100%) replicates as positive for *S. enterica.*; *L. monocytogenes* (1 target): 5/5 (100%) replicates as positive for *L. monocytogenes*. FIG. 14.

Raw Ground Beef Validation (1 CFU/25 g)

All 3 target organisms inoculated and incubated simultaneously: 0.852 CFU/25 g *E. coli* O157:H7 (ATCC:43895), 1.04 CFU/25 g *S. enterica* (ATCC:13076), and 1.064 CFU/25 g *L. monocytogenes* (ATCC: 13932). The samples were suspended in Buffered Listeria Enrichment Broth base (no supplements), stomached for 30 seconds, in a stomaching bag, the bag was closed and the samples were incubated for 24 hours at 37° C. The lysis buffer comprised: 8 mM EDTA, 80 mM TRIS, 4.8% Triton X-100, 27.5% Proteinase K (ready-made solution from Qiagen catalog #19133), 20 mg/ml Lysozyme (Amresco catalog #0663-10 G, 0.88 grams/ml 100 µm zirconium lysis beads (Ops Diagnostics catalog #BLBZ 100-250-14).

To lyse the samples, 100 µl lysis buffer solution was pipetted into each well of a deep-well block, 50 µl sterile $H_2O$ was added to each well, 50 µl of supernatant from enrichment bag was removed and add to each well. The samples were lysed at 65° C. for 15 minutes shaking at 1350 RPM. The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 µl reaction using 1 µl of lysate at end of the lysis procedure. PCR cycle is as follows: Initial step: 98° C. for 3 minutes. 2.) 95° C. for 10 seconds. 3.) 58.5° C. for 45 seconds. Return to step 2 and repeat 49 times. Multiplex PCR was performed in 20 replicates using BioRad CFX-96 Touch instrument. Primers and probes used in multiplex PCR are disclosed in Table 1.

*E. coli* (STEC) targets (3 targets): EAE: identified 13/20 (65%) replicates as positive for EAE, STX-1: identified 13/20 (65) replicates as positive for STX-1, STX-2: identified 13/20 (65%) replicates as positive for STX-2; *Salmonella* spp. (1 target): identified 14/20 (70%) replicates as positive for *S. enterica.*; *L. monocytogenes* (1 target): identified 8/20 (40%) replicates as positive for *L. monocytogenes*. FIG. 15.

Ground Beef Validation (5 CFU/25 g)

3 target organisms inoculated simultaneously, CFU determined via plate count: *E. coli* inoculated at a measured 4.26 CFU/25 g, *S. enterica* inoculated at a measured 5.2 CFU/25 g, and *L. monocytogenes* inoculated at a measured 5.32 CFU/25 g. The samples were suspended in Buffered Listeria Enrichment Broth base (no supplements), stomached for 30 seconds, in a stomaching bag, the bag was closed and the samples were incubated for 24 hours at 37° C. The lysis buffer comprised: 8 mM EDTA, 80 mM TRIS, 4.8% Triton X-100, 27.5% Proteinase K (ready-made solution from Qiagen catalog #19133), 20 mg/ml Lysozyme (Amresco catalog #0663-10 G, and 0.88 grams/ml 100 µm zirconium lysis beads (Ops Diagnostics catalog #BLBZ 100-250-14).

To lyse the samples, 100 µl lysis buffer solution was pipetted into each well of a deep-well block, 50 µl sterile $H_2O$ was added to each well, 50 µl of supernatant from enrichment bag was removed and add to each well. The samples were lysed at 65° C. for 15 minutes shaking at 1350 RPM. The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 µl reaction using 1 µl of lysate at end of the lysis procedure. PCR cycle is as follows: Initial step: 98° C. for 3 minutes. 2.) 95° C. for 10 seconds, 3.) 58.5° C. for 45 seconds, Return to step 2 and repeat 49 times. Multiplex PCR was performed using BioRad CFX-96 Touch instrument. Primers and probes used in multiplex PCR are disclosed in Table 1.

*E. coli* (STEC) targets (3 targets): EAE: identified 5/5 (100%) replicates as positive for EAE, STX-1: identified 5/5 (100%) replicates as positive for STX-1, STX-2: identified 5/5 (100%) replicates as positive for STX-2; *Salmonella* spp. (1 target): identified 5/5 (100%) replicates as positive for *S. enterica.*; *L. monocytogenes* (1 target): identified 5/5 (100%) replicates as positive for *L. monocytogenes*. FIG. 16.

RTE Deli Meat (Deli Turkey) Validation (1 CFU/25 g)—Internal Control

All 3 target organisms were inoculated into turkey and incubated simultaneously at 4° C. for 48 hours: 0.60 CFU/25 g *E. coli* O157:H7 (ATCC:43895), 0.48 CFU/25 g *S. enterica* (ATCC:13076) and 1.00 CFU/25 g *L. monocytogenes* (ATCC: 13932). The samples were then suspended in Buffered Listeria Enrichment Broth base (no supplements), stomached for 30 seconds, in a stomaching bag, the bag was closed and the samples were incubated for 24 hours at 37° C. Aerobic plate count (APC) performed on uninoculated control indicated $2.4 \times 10^3$ native bacteria per gram.

The lysis buffer comprised: 8 mM EDTA, 80 mM TRIS, 4.8% Triton X-100, 27.5% Proteinase K (ready-made solution from Qiagen catalog #19133), 20 mg/ml Lysozyme (Amresco catalog #0663-10 G and 0.88 grams/ml 100 μm zirconium lysis beads (Ops Diagnostics catalog #BLBZ 100-250-14). To lyse samples, 100 μl lysis buffer solution was pipetted into each well of a deep-well block, 50 μl sterile H₂O was added to each well, 50 μl of supernatant from enrichment bag was removed and add to each well. The samples were lysed at 65° C. for 15 minutes shaking at 1350 RPM.

The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 μl reactions using 1 μl of lysate at end of the lysis procedure. 30,000 copies of internal control reference gene per reaction. PCR cycle is as follows: Initial step: 98° C. for 3 minutes, 2.) 95° C. for 10 seconds, 3.) 58.5° C. for 45 seconds. Return to step 2 and repeat 49 times. Multiplex PCR was performed in 20 replicates using BioRad CFX-% Touch instrument. Primers and probes used in multiplex PCR are disclosed in Table 1. Primer quantity per reaction: 100 nmol per sequence per target. Probe quantity per reaction: 100 nmol of STX-2, Salmonella (INV), Internal Control and EAE probes per reaction; 250 nmol of STX-1 and Listeria (HLY) probes per reaction.

EAE was identified in 18/20 (90%) replicates as positive for EAE; STX-1 and STX-2 identified in 18/20 (80/6) replicates as positive for STX-1 and STX-2; *Listeria monocytogenes* was identified in 9/20 (45%) replicates as positive for *L. monocytogenes*; *S. enterica* identified 20/20 (100%) replicates as positive for *S. enterica*. Internal control identified 20/20 (100%) replicates as positive for internal control. FIG. 17-22.

RTE Deli Meat Validation (5 CFU/25 g)—Internal Control 3 target organisms inoculated into turkey simultaneously and incubated at 4° C. for 48 hours. CFU determined via plate count, *E. coli* inoculated at a measured 3 CFU/25 g, *S. enterica* inoculated at a measured 2.42 CFU/25 g, *L. monocytogenes* inoculated at a measured 5.00 CFU/25 g. The samples were then suspended in Buffered Listeria Enrichment Broth base (no supplements), stomached for 30 seconds, in a stomaching bag, the bag was closed and the samples were incubated for 24 hours at 37° C. Aerobic plate count (APC) performed on uninoculated control indicated 2.4×10³ native bacteria per gram. The lysis buffer comprised: 8 mM EDTA, 80 mM TRIS, 4.8% Triton X-100, 27.5% Proteinase K (ready-made solution from Qiagen catalog #19133), 20 mg/ml Lysozyme (Amresco catalog #0663-10 G, and 0.88 grams/ml 100 μm zirconium lysis beads (Ops Diagnostics catalog #BLBZ 100-250-14).

To lyse the samples, 100 μl lysis buffer solution was pipetted into each well of a deep-well block, 50 μl sterile H₂O was added to each well, 50 μl of supernatant from enrichment bag was removed and add to each well. The samples were lysed at 65° C. for 15 minutes shaking at 1350 RPM. The samples were lysed for an additional 10 minutes at 95° C. shaking at 1350 RPM, after which, the deepwell block was cooled to room temperature. Bacterial DNA was obtained for multiplex PCR.

Multiplex amplification PCR protocol comprised 25 μl reaction using 1 μl of lysate at end of the lysis procedure. 30,000 copies of internal control reference gene per reaction. PCR cycle is as follows: Initial step: 98° C. for 3 minutes, 2.) 95° C. for 10 seconds, 3.) 58.5° C. for 45 seconds. Return to step 2 and repeat 49 times. Multiplex PCR was performed in 5 replicates using BioRad CFX-96 Touch instrument. Primers and probes used in Table 1. Primer quantity per reaction: 100 nmol per sequence per target. Probe quantity per reaction: 100 nmol of STX-2, *Salmonella* (INV), Internal Control and EAE probes per reaction; 250 nmol of STX-1 and *Listeria* (HLY) probes per reaction.

*E. coli* (STEC) targets (3 targets): EAE: identified 5/5 (100%) replicates as positive for EAE, STX-1 and STX-2: identified 5/5 (100%) replicates as positive for STX-1 and STX-2, *Salmonella* spp. (1 target): identified 5/5 (100%) replicates as positive for *S. enterica*. *L. monocytogenes* (1 target): identified 5/5 (100%) replicates as positive for *L. monocytogenes*, Internal control identified 5/5 (100%) replicates as positive for internal control. FIG. 23-28

Lettuce Validation (1 CFU/25 g)—Internal Control

All 3 target organisms inoculated into lettuce and incubated simultaneously at 4° C. for 48 hours, 0.60 CFU/25 g *E. coli* O157:H7 (ATCC:43895), 0.48 CFU/25 g *S. enterica* (ATCC:13076), 1.00 CFU/25 g *L. monocytogenes* (ATCC: 13932).

The samples were then suspended in Buffered Listeria Enrichment Broth base (no supplements), stomached for 30 seconds, in a stomaching bag, the bag was closed and the samples were incubated for 24 hours at 37° C. Aerobic plate count (APC) performed on uninoculated control indicated 4.4×10² native bacteria per gram. The lysis buffer comprised: 8 mM EDTA, 80 mM TRIS, 4.8% Triton X-100, 27.5% Proteinase K (ready-made solution from Qiagen catalog #19133), 20 mg/ml Lysozyme (Amresco catalog #0663-10 G, and 0.88 grams/ml 100 μm zirconium lysis beads (Ops Diagnostics catalog #BLBZ 100-250-14).

To lyse the samples, 100 μl lysis buffer solution was pipetted into each well of a deep-well block, 50 μl sterile H₂O was added to each well, 50 μl of supernatant from enrichment bag was removed and add to each well. The samples were lysed at 65° C. for 15 minutes shaking at 1350 RPM. The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 μl reaction using 1 μl of lysate at end of the lysis procedure. 30,000 copies of internal control reference gene per reaction. PCR cycle is as follows: Initial step: 98° C. for 3 minutes. 2.) 95° C. for 10 seconds. 3.) 58.5° C. for 45 seconds. Return to step 2 and repeat 49 times. Multiplex PCR was performed in 20 replicates using BioRad CFX-96 Touch instrument. Primers and probes used in multiplex PCR are disclosed in Table 1. Primer quantity per reaction: 100 nmol per sequence per target. Probe quantity per reaction: 100 nmol of STX-2, *Salmonella* (INV), Internal Control and EAE probes per reaction; 250 nmol of STX-1 and *Listeria* (HLY) probes per reaction.

*E. coli* (STEC) targets (3 targets) EAE: identified 12/20 (60/6) replicates as positive for EAE, STX-1 and STX-2: identified 12/20 (60) replicates as positive for STX-1and STX-2; *Salmonella* spp. (1 target): identified 6/20 (30%) replicates as positive for *S. enterica*.; *L. monocytogenes* (1 target): identified 11/20 (60%) replicates as positive for *L. monocytogenes*. Internal control identified 20/20 (100%) replicates as positive for internal control. FIG. 29-34.

Lettuce Validation (5 CFU/25 g)—Internal Control 3 target organisms inoculated into lettuce simultaneously and incubated at 4° C. for 48 hours. CFU determined via plate count, *E. coli* inoculated at a measured 3.00 CFU/25 g, *S. enterica* inoculated at a measured 2.4 CFU/25 g, *L. monocytogenes* inoculated at a measured 5.00 CFU/25 g. The samples were then suspended in Buffered Listeria Enrichment Broth base (no supplements), stomached for 30 seconds, in a stomaching bag, the bag was closed and the samples were incubated for 24 hours at 37° C. Aerobic plate count (APC) performed on uninoculated control indicated 4.4×10² native bacteria per gram. The lysis buffer comprised: 8 mM EDTA: 80 mM TRIS, 4.8% Triton X-100, 27.5% Proteinase K (ready-made solution from Qiagen catalog #19133), 20 mg/ml Lysozyme (Amresco catalog #0663-10 G, and 0.88 grams/ml 100 μm zirconium lysis beads (Ops Diagnostics catalog #BLBZ 100-250-14).

To lyse the samples, 100 μl lysis buffer solution was pipetted into each well of a deep-well block, 50 μl sterile H₂O was added to each well, 50 μl of supernatant from enrichment bag was removed and add to each well. The samples were lysed at 65° C. for 15 minutes shaking at 1350 RPM. The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 μl reaction using 1 μl of lysate at end of the lysis procedure. 30,000 copies of internal control reference gene per reaction. PCR cycle is as follows: Initial step: 98° C. for 3 minutes. 2.) 95° C. for 10 seconds. 3.) 58.5° C. for 45 seconds. Return to step 2 and repeat 49 times. Multiplex PCR was performed using BioRad CFX-96 Touch instrument. Primers and probes used in multiplex PCR are disclosed in Table 1. Primer quantity per reaction: 100 nmol per sequence per target. Probe quantity per reaction: 100 nmol of STX-2, *Salmonella* (INV), Internal Control and EAE probes per reaction; 250 nmol of STX-1 and *Listeria* (HLY) probes per reaction.

*E. coli* (STEC) targets (3 targets), EAE: identified 4/5 (80%) replicates as positive for EAE, STX-1 and STX-2: identified 5/5 (100%) replicates as positive for STX-1 and STX-2; *Salmonella* spp. (1 target): identified 3/5 (60%) replicates as positive for *S. enterica.*; *L. monocytogenes* (1 target): 5/5 (100%) replicates as positive for *L. monocytogenes*. Internal control identified 5/5 (100%) replicates as positive for internal control. FIG. 35-40.

3 CFU Inoculation of *Listeria monocytogenes*, *Escherichia Coli* O157:H7 and *Salmonella Enterica* into Raw Beef Trim

*Listeria monocytogenes*, *Escherichia Coli* O157:H7 and *Salmonella Enterica* were inoculated into raw beef trim and incubated simultaneously at 4° C. for 48 hours: 3 CFU/25 g *Escherichia Coli* O157:H7, 3CFU/25 g *S. enterica* and 3 CFU/25 g *L. monocytogenes*. 25 gram sample were then suspended in 225 ml Media A or Media B, stomached for 30 seconds, in a stomaching bag, the bag was closed and the samples were incubated for 24 hours at 37° C.

Media A comprised: yeast extract 6 g/L (Sigma Aldrich Cat #92144), pancreatic digest of casein 17 g/L (Sigma Aldrich Cat #T9410), enzymatic digest of soy 3 g/L (Sigma Aldrich Cat #70178), dextrose 2.5 g/L (Sigma Aldrich Cat #D9434), NaCl 5 g/L (Sigma Aldrich Cat #S7653), dipotassium phosphate 2.5 G/L (Sigma Aldrich Cat #P3786), potassium phosphate 1.35 g/L (Sigma Aldrich Cat #PHR1330), disodium phosphate 9.6 g/L (Amresco Cat #0404), sodium pyruvate 1.1 g/L (Sigma Aldrich Cat #P2256). Media A pH 7.2-7.4. Media A was brought to one liter with distilled water or deionized water.

Media B comprised: yeast extract 12 g/L, pancreatic digest of casein 34 g/L, enzymatic digest of soy 6 g/L, dextrose 5 g/L, NaCl 10 g/L, dipotassium phosphate 5 g/L, potassium phosphate 2.7 g/L, disodium phosphate 19.2 g/L, sodium pyruvate 2.2 g/L. Media B pH 7.2-7.4. Media B was brought to one liter with distilled water or deionized water.

The lysis buffer comprised: 8 mM EDTA, 80 mM TRIS, 4.8% Triton X-100, 27.5% Proteinase K, 20 mg/ml Lysozyme and 0.88 grams/ml 100 μm zirconium lysis beads.

To lyse samples, 100 μl lysis buffer solution was pipetted into each well of a deep-well block, 50 μl sterile H₂O was added to each well, 50 μl of supernatant from enrichment bag was removed and add to each well. The samples were lysed at 65° C. for 15 minutes shaking at 1350 RPM.

The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 μl reactions using 1 μl of lysate at end of the lysis procedure. PCR cycle is as follows: Initial step: 98° C. for 3 minutes, 2.) 95° C. for 10 seconds, 3.) 58.5° C. for 45 seconds, 4.) Read plate. Return to step 2 and repeat 29 times. Multiplex PCR was performed in replicates using BioRad CFX-96 Touch instrument. Primers and probes used in multiplex PCR are disclosed in Table 1. Primer quantity per reaction: 100 μmol per sequence per target.

| PCR mix preparation 25 μL | |
|---|---|
| 12.5 uL | Multiplex Powermix |
| 0.2 uL | Fwd Primer (100 uM) STX-1 |
| 0.2 uL | Rev Primer (100 uM) STX-1 |
| 0.2 uL | Fwd Primer (100 uM) STX-2 |
| 0.2 uL | Rev Primer (100 uM) STX-2 |
| 0.2 uL | Fwd Primer (100 uM) EAE |
| 0.2 uL | Rev Primer (100 uM) EAE |
| 0.2 uL | Fwd Primer (100 uM) LM |
| 0.2 uL | Rev Primer (100 uM) LM |
| 0.2 uL | Fwd Primer (100 uM) SE |
| 0.2 uL | Rev Primer (100 uM) SE |
| 0.2 uL | Fwd Primer (100 uM) IC |
| 0.2 uL | Rev Primer (100 uM) IC |
| 1.0 uL | Probe (5 uM) STX-1 |
| 1.0 uL | Probe (5 uM) STX-2 |
| 1.0 uL | Probe (5 uM) EAE |
| 1.0 uL | Probe (5 uM) LM |
| 1.0 uL | Probe (5 uM) SE |
| 1.0 uL | Probe (5 uM) IC |
| 3.0 uL | PCR-grade water |
| 1.0 uL | Lysate |
| 25.0 uL | Total per reaction |

The signal for the signal for *Listeria Monocytogenes* is depicted in FIG. 41. Media A average quantitation cycle ("Cq"): 29.7; Media B average Cq: 29.8 as depicted in FIG. 41. Quantitation cycle represents the cycle at which the RFU signal exceeds the cutoff for background interference and can be considered a true signal.

15 CFU Inoculation of *Escherichia Coli* O157:H7 into Raw Spinach

*Escherichia Coli* O157:H7 was inoculated into raw spinach and incubated at 4° C. for 48 hours: 15 CFU/25 g *Escherichia Coli* O157:H7 25 gram sample were then suspended in 225 ml Media A or Media B, stomached for 30 seconds, in a stomaching bag, the bag was closed and the samples were incubated for 24 hours at 37° C.

Media A comprised: yeast extract 6 g/L, pancreatic digest of casein 17 g/L, enzymatic digest of soy 3 g/L, dextrose 2.5 g/L, NaCl 5 g/L, dipotassium phosphate 2.5 G/L, potassium phosphate 1.35 g/L, disodium phosphate 9.6 g/L, sodium pyruvate 1.1 g/L. Media A pH was within the range of 7.2-7.4. Media A was brought to one liter with distilled water or deionized water.

Media B comprised: yeast extract 12 g/L, pancreatic digest of casein 34 g/L, enzymatic digest of soy 6 g/L, dextrose 5 g/L, NaCl 10 g/L, dipotassium phosphate 5 g/L, potassium phosphate 2.7 g/L, disodium phosphate 19.2 g/L, sodium pyruvate 2.2 g/L. Media B pH was within the range of 7.2-7.4. Media B was brought to one liter with distilled water or deionized water.

The lysis buffer comprised: 8 mM EDTA, 80 mM TRIS, 4.8% Triton X-100, 27.5% Proteinase K, 20 mg/ml Lysozyme and 0.88 grams/ml 100 µm zirconium lysis beads. To lyse samples, 100 µl lysis buffer solution was pipetted into each well of a deep-well block, 50 µl sterile H$_2$O was added to each well, 50 µl of supernatant from enrichment bag was removed and add to each well. The samples were lysed at 65° C. for 15 minutes shaking at 1350 RPM.

The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 µl reactions using 1 µl of lysate at end of the lysis procedure. PCR cycle is as follows: Initial step: 98° C. for 3 minutes, 2.) 95° C. for 10 seconds, 3.) 58.5° C. for 45 seconds, 4.) Read plate. Return to step 2 and repeat 29 times. Multiplex PCR was performed in replicates using BioRad CFX-96 Touch instrument. Primers and probes used in multiplex PCR are disclosed in Table 1. Primer quantity per reaction: 100 µmol per sequence per target.

Media A average Cq: 26.0 and Media B average Cq: 25.2 as depicted in FIG. 42.

15 CFU 15 CFU Inoculation of *Listeria Monocytogenes* into Cheese

*Listeria Monocytogenes* was inoculated into cheese and incubated at 4° C. for 48 hours 15 CFU/25 g *L. monocytogenes*. 25 gram sample were then suspended in 225 ml Media A or Media B, stomached for 30 seconds, in a stomaching bag, the bag was closed and the samples were incubated for 24 hours at 37° C.

Media A comprised: yeast extract 6 g/L, pancreatic digest of casein 17 g/L, enzymatic digest of soy 3 g/L, dextrose 2.5 g/L, NaCl 5 g/L, dipotassium phosphate 2.5 G/L, potassium phosphate 1.35 g/L, disodium phosphate 9.6 g/L, sodium pyruvate 1.1 g/L. Media A pH was within the range of 7.2-7.4. Media A was brought to one liter with distilled water or deionized water.

Media B comprised: yeast extract 12 g/L, pancreatic digest of casein 34 g/L, enzymatic digest of soy 6 g/L, dextrose Sg/L, NaCl 10 g/L, dipotassium phosphate Sg/L, potassium phosphate 2.7 g/L, disodium phosphate 19.2 g/L, sodium pyruvate 2.2 g/L. Media B pH was within the range of 7.2-7.4. Media B was brought to one liter with distilled water or deionized water.

The lysis buffer comprised: 8 mM EDTA, 80 mM TRIS, 4.8% Triton X-100, 27.5% Proteinase K, 20 mg/ml Lysozyme and 0.88 grams/ml 100 µm zirconium lysis beads. To lyse samples, 100 µl lysis buffer solution was pipetted into each well of a deep-well block, 50 µl sterile H$_2$O was added to each well, 50 µl of supernatant from enrichment bag was removed and add to each well. The samples were lysed at 65° C. for 15 minutes shaking at 1350 RPM.

The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 µl reactions using 1 µl of lysate at end of the lysis procedure. PCR cycle is as follows: Initial step: 98° C. for 3 minutes, 2.) 95° C. for 10 seconds, 3.) 58.5° C. for 45 seconds, 4.) Read plate. Return to step 2 and repeat 29 times. Multiplex PCR was performed in replicates using BioRad CFX-96 Touch instrument. Primers and probes used in multiplex PCR are disclosed in Table 1. Primer quantity per reaction: 100 µmol per sequence per target. Media A average Cq: 32.1 and Media B average Cq: 29.7 as depicted in FIG. 43.

15 CFU 15 CFU Inoculation of *Listeria Monocytogenes* into Salmon

*Listeria Monocytogenes* was inoculated into salmon and incubated at 4° C. for 48 hours 15 CFU/25 g *L. monocytogenes*. 25 gram sample were then suspended in 225 ml Media A or Media B, stomached for 30 seconds, in a stomaching bag, the bag was closed and the samples were incubated for 24 hours at 37° C.

Media A comprised: yeast extract 6 g/L, pancreatic digest of casein 17 g/L, enzymatic digest of soy 3 g/L, dextrose 2.5 g/L, NaCl 5 g/L, dipotassium phosphate 2.5 G/L, potassium phosphate 1.35 g/L, disodium phosphate 9.6 g/L, sodium pyruvate 1.1 g/L. Media A pH was within the range of 7.2-7.4. Media A was brought to one liter with distilled water or deionized water.

Media B comprised: yeast extract 12 g/L, pancreatic digest of casein 34 g/L, enzymatic digest of soy 6 g/L, dextrose 5 g/L, NaCl 10 g/L, dipotassium phosphate 5 g/L, potassium phosphate 2.7 g/L, disodium phosphate 19.2 g/L, sodium pyruvate 2.2 g/L. Media B pH was within the range of 7.2-7.4. Media B was brought to one liter with distilled water or deionized water.

The lysis buffer comprised: 8 mM EDTA, 80 mM TRIS, 4.8% Triton X-100, 27.5% Proteinase K, 20 mg/ml Lysozyme and 0.88 grams/ml 100 µm zirconium lysis beads. To lyse samples, 100 µl lysis buffer solution was pipetted into each well of a deep-well block, 50 µl sterile H$_2$O was added to each well, 50 µl of supernatant from enrichment bag was removed and add to each well. The samples were lysed at 65° C. for 15 minutes shaking at 1350 RPM.

The samples were lysed for an additional 10 minutes at 95° C. shaking at 1350 RPM, after which, the deepwell block was cooled to room temperature. Bacterial DNA was obtained for multiplex PCR. Multiplex amplification PCR protocol comprised 25 µl reactions using 1 µl of lysate at end of the lysis procedure. PCR cycle is as follows: Initial step: 98° C. for 3 minutes, 2.) 95° C. for 10 seconds, 3.) 58.5° C. for 45 seconds, 4.) Read plate. Return to step 2 and repeat 29 times. Multiplex PCR was performed in replicates using BioRad CFX-96 Touch instrument. Primers and probes used in multiplex PCR are disclosed in Table 1. Primer quantity per reaction: 100 µmol per sequence per target. Media A average Cq: 31.0 and Media B average Cq: 26.6 as depicted in FIG. 44.

Raw Beef Trim Validation (3 CFU/25 g)

All 3 target organisms inoculated into raw beef trim and incubated simultaneously, 2.88 CFU/25 g *E. coli* O157:H7 (ATCC:43895), 2.80 CFU/25 g *S. enterica* (ATCC:13076), 3.90 CFU/25 g *L. monocytogenes* (ATCC: 13932).

The samples were enriched as previously described and then were incubated for 24 hours at 37° C. Aerobic plate count (APC) performed on uninoculated control indicated 1.3×10$^6$ native bacteria per gram. Sample lysis was performed and pathogens were detected as previously described.

*E. coli* (STEC) targets (3 targets) EAE: identified 7/8 (87.5%) replicates as positive for EAE, STX-1, STX-2: identified 7/8 (87.5%) replicates as positive for STX-1and STX-2; *Salmonella* spp. (1 target): identified 5/8 (62.50/6) replicates as positive for *S. enterica*.; *L. monocytogenes* (1 target): identified 8/8 (100%) replicates as positive for *L. monocytogenes*. Internal control identified detected in all replicates. FIG. 45-48.

Raw Beef Trim Validation (15 CFU/25 g)

All 3 target organisms inoculated into raw beef trim and incubated simultaneously, 7.71 CFU/25 g E. coli O157:H7 (ATCC:43895), 13.0 CFU/25 g S. enterica (ATCC:13076), 17.25 CFU/25 g L. monocytogenes (ATCC: 13932).

The samples were enriched as previously described and then were incubated for 24 hours at 37° C. Aerobic plate count (APC) performed on uninoculated control indicated $2.3 \times 10^6$ native bacteria per gram. Sample lysis was performed and pathogens were detected as previously described.

E. coli (STEC) targets (3 targets) EAE: identified 8/8 (100%) replicates as positive for EAE, STX-1, STX-2: identified 8/8 (100%) replicates as positive for STX-1and STX-2; Salmonella spp. (1 target): identified 8/8 (100%) replicates as positive for S. enterica.; L. monocytogenes (1 target): identified 8/8 (100%) replicates as positive for L. monocytogenes. Internal control identified detected in all replicates. FIG. 49-51.

Milk Validation (3 CFU/25 g)

All 3 target organisms inoculated into milk and incubated simultaneously, 2.22 CFU/25 g E. coli O157:H7 (ATCC: 43895), 2.80 CFU/25 g S. enterica (ATCC:13076), 3.80 CFU/25 g L. monocytogenes (ATCC: 13932).

The samples were enriched as previously described and then were incubated for 24 hours at 37° C. Aerobic plate count (APC) performed on uninoculated control indicated $1.3 \times 10^2$ native bacteria per gram. Sample lysis was performed and pathogens were detected as previously described.

E. coli (STEC) targets (3 targets) EAE: identified 8/8 (100%) replicates as positive for EAE, STX-1, STX-2: identified 8/8 (100%) replicates as positive for STX-1and STX-2; Salmonella spp. (1 target): identified 7/8 (87.5%) replicates as positive for S. enterica.; L. monocytogenes (1 target): identified 8/8 (100%) replicates as positive for L. monocytogenes. Internal control identified detected in all replicates. FIG. 52-55.

Milk Validation (15 CFU/25 g).

All 3 target organisms inoculated into milk and incubated simultaneously, 14.4 CFU/25 g E. coli O157:H7 (ATCC: 43895), 12.0 CFU/25 g S. enterica (ATCC:13076), 14.25 CFU/25 g L. monocytogenes (ATCC: 13932).

The samples were enriched as previously described and then were incubated for 24 hours at 37° C. Aerobic plate count (APC) performed on uninoculated control indicated $1.2 \times 10^2$ native bacteria per gram. Sample lysis was performed and pathogens were detected as previously described.

E. coli (STEC) targets (3 targets) EAE: identified 8/8 (100%) replicates as positive for EAE, STX-1, STX-2: identified 8/8 (100%) replicates as positive for STX-1and STX-2; Salmonella spp. (1 target): identified 8/8 (100%) replicates as positive for S. enterica.; L. monocytogenes (1 target): identified 8/8 (100%) replicates as positive for L. monocytogenes. Internal control identified detected in all replicates. FIG. 56-59.

Raw Spinach Validation (15 CFU/25 g)

14.4 CFU/25 g E. coli O157:H7 (ATCC:43895) was inoculated into raw spinach as previously described.

The samples were enriched as previously described and then were incubated for 24 hours at 37° C. Aerobic plate count (APC) performed on uninoculated control indicated $3.0 \times 10^7$ native bacteria per gram. Sample lysis was performed and pathogens were detected as previously described. E. coli: identified 8/8 (100%) replicates as positive for E. coli FIG. 60.

Brie de Meaux Validation (15 CFU/25 g)

12.75 CFU/25 g L. monocytogenes (ATCC:13932) was inoculated as previously described.

The samples were enriched as previously described and then were incubated for 24 hours at 37° C. Aerobic plate count (APC) performed on uninoculated control indicated $6.0 \times 10^4$ native bacteria per gram. Sample lysis was performed and pathogens were detected as previously described. L. monocytogenes was identified 8/8 (100%) replicates as positive for E. coli FIG. 61.

Smoked Salmon Validation (15 CFU/25 g)

10.8 CFU/25 g L. monocytogenes (ATCC:13932) was inoculated as previously described.

The samples were enriched as previously described and then were incubated for 24 hours at 37° C. Aerobic plate count (APC) performed on uninoculated control indicated $2.0 \times 10^1$ native bacteria per gram. Sample lysis was performed and pathogens were detected as previously described. L. monocytogenes was identified 8/8 (100%) replicates as positive for E. coli FIG. 62.

Peanut Butter Validation (15 CFU/25 g)

6.0 CFU/25 g S. enterica (ATCC:13076) was inoculated as previously described.

The samples were enriched as previously described and then were incubated for 24 hours at 37° C. Aerobic plate count (APC) performed on uninoculated control indicated $2.0 \times 10^3$ native bacteria per gram. Sample lysis was performed and pathogens were detected as previously described S. enterica was identified 8/8 (100%) replicates as positive for E. coli FIG. 63.

Raw Eggs Validation (15 CFU/25 g)

17.0 CFU/25 g S. enterica (ATCC:13076) was inoculated as previously described.

The samples were enriched as previously described and then were incubated for 24 hours at 37° C. Aerobic plate count (APC) performed on uninoculated control indicated 0.0 native bacteria per gram. Sample lysis was performed and pathogens were detected as previously described S. enterica was identified 8/8 (100%) replicates as positive for E. coli FIG. 64.

Raw Eggs Validation (15 CFU/25 g)

20.0 CFU/25 g S. enterica (ATCC:13076) was inoculated as previously described.

The samples were enriched as previously described and then were incubated for 24 hours at 37° C. Aerobic plate count (APC) performed on uninoculated control indicated $4.0 \times 10^3$ native bacteria per gram. Sample lysis was performed and pathogens were detected as previously described S. enterica was identified 8/8 (100%) replicates as positive for E. coli FIG. 65.

Disclosed herein are primers, oligonucleotides probes, methods, materials, compositions, kits, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary.

This concept applies to all aspects of this application including, but not limited to, steps in methods of making and using the disclosed methods and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It is understood that in some embodiments, the kits disclosed herein may comprise instructions to combine and or use the contents of said kits. In some embodiments, the instructions may comprise instructions of how to combine and or use a lysis buffer. In some embodiments, the instructions may comprise instructions of how to combine and or use a buffering component. In some embodiments, the instructions may comprise instructions of how to combine and or use a metal chelating agent. In some embodiments, the instructions may comprise instructions of how to combine and or use a surfactant. In some embodiments, the instructions may comprise instructions of how to combine and or use a precipitant. In some embodiments, the instructions may comprise instructions of how to combine and or use lysing moieties. In some embodiments, the instructions may comprise instructions of how to combine and or use amplification primers. In some embodiments, the instructions may comprise instructions of how to combine and or use a lysis buffer and amplification primers. In some embodiments, the instructions may comprise instructions of how to combine and or use an internal oligonucleotide probe. In some embodiments, the instructions may comprise instructions of how to combine and or use a lysis buffer, amplification primers and an internal oligonucleotide probe.

While some embodiments described herein have been shown and described herein, such embodiments are provided by way of example only. Numerous variations, changes, and substitutions will now occur to those skilled in the art without departing from the disclosure provided herein. It should be understood that various alternatives to the embodiments described herein can be employed in practicing the methods described herein.

What is claimed is:

1. A method comprising:
   a. enriching a food sample comprising a plurality of pathogens by co-culturing the plurality of pathogens together in a rich and nonselective media to form an enriched sample; wherein the rich and nonselective media comprises components to promote the growth of the plurality of pathogens; wherein the plurality of pathogens comprises at least two pathogens, wherein at least one of the plurality of pathogens is a member of the group consisting of *Listeria monocytogenes, E. coli*, and *Salmonella* spp.;
   b. conducting a first sample lysis and a second sample lysis on the enriched sample or a portion thereof, wherein the second sample lysis is performed at a temperature higher than a temperature of the first sample lysis, thereby forming an unpurified lysed sample comprising the DNA of at least one of *Listeria monocytogenes, E. coli*, and *Salmonella* spp.;
   c. conducting a multiplex amplification with amplification primers on at least a portion of the unpurified lysed sample, wherein the amplification primers comprise at least three primer pairs, wherein a first primer pair is complementary to a target nucleic acid sequence of *Listeria monocytogenes*, wherein a second primer pair is complementary to a target nucleic acid sequence of *E. coli*, wherein a third primer pair is complementary to a target nucleic acid sequence of *Salmonella* spp., and wherein the multiplex amplification is conducted in one tube; and
   d. detecting a presence or absence of each of *Listeria monocytogenes, E. coli*, and *Salmonella* spp. from a result of the multiplex amplification in the one tube; and wherein a, b, c, and d are performed in a positive total time of about 28 hrs or less;
   wherein the rich and nonselective media comprises per 1 L of water at least one of:
   (a) yeast extract at a concentration between about 12 g/L and about 20 g/L,
   (b) pancreatic digest of casein at a concentration between about 34 g/L and about 50 g/L, or
   (c) enzymatic digest of soy at a concentration between about 6 g/L and about 10 g/L.

2. The method of claim 1, wherein the rich and nonselective media further comprises, per 1 L of water:
   a. between about 1 g/L and about 10 g/L dextrose;
   b. between about 1 g/L and about 20 g/L sodium chloride;
   c. between about 1 g/L and about 10 g/L dipotassium phosphate;
   d. between about 1 g/L and about 10 g/L potassium phosphate;

e. between about 10 g/L and about 30 g/L disodium phosphate; or f. between about 1 g/L and about 10 g/L sodium pyruvate.

3. The method of claim 1, wherein the first sample lysis or the second sample lysis comprises incubating the sample with a lysis buffer.

4. The method of claim 3, wherein the lysis buffer comprises:
   a. a buffering component;
   b. a metal chelating agent;
   c. a surfactant;
   d. a precipitant;
   e. a lysing moiety; or
   f. any combination thereof.

5. The method of claim 4, wherein the lysis buffer comprises the lysing moiety, wherein the lysing moiety comprises a lysis bead or lysozyme.

6. The method of claim 4, wherein the lysis buffer comprises the metal chelating agent, wherein the metal chelating agent comprises ethylenediaminetetraacetic acid (EDTA).

7. The method of claim 1, wherein the primer pairs comprise sequences that are at least 80% homologous with sequences:
   a. SEQ ID NO: 1, SEQ ID NO: 2;
   b. SEQ ID NO: 3, SEQ ID NO: 4;
   c. SEQ ID NO: 5, SEQ ID NO: 6;
   d. SEQ ID NO: 7, SEQ ID NO: 8; or
   e. SEQ ID NO: 9, SEQ ID NO: 10.

8. The method of claim 4, wherein the precipitant comprises proteinase K.

9. The method of claim 1, wherein the temperature of the first sample lysis is from about 45° C. to about 85° C.

10. The method of claim 9, wherein the temperature of the second sample lysis is from about 85° C. to about 105° C.

11. The method of claim 1, wherein when *E. coli* is present at an amount of 0.60 CFU to 2.88 CFU/25 g of sample, the success rate of detection for *E. coli* in the sample is from 40% to 100%.

12. The method of claim 1, wherein when *Salmonella* spp. is present at an amount of 0.48 CFU to 5.2 CFU/25 g of sample, the success rate of detection for *Salmonella* spp. is from 30% to 100%.

13. The method of claim 1, wherein when *Listeria monocytogenes* is present at an amount of 0.877 CFU to 4.385 CFU/25 g of sample, the success rate of detection for *Listeria monocytogenes* is from 40% to 100%.

14. The method of claim 1, wherein the rich and nonselective media comprises, per 1 L of water, between about 2.2 g/L and about 10 g/L sodium pyruvate.

15. He method of claim 1, wherein the rich and nonselective media comprises, per 1 L of water, yeast extract at a concentration of about 12 g/L.

16. The method of claim 1, wherein the rich and nonselective media comprises, per 1 L of water, pancreatic digest of casein at a concentration of about 34 g/L.

17. The method of claim 2, wherein the rich and nonselective media comprises, per 1 L of water, enzymatic digest of soy at a concentration of about 6 g/L.

* * * * *